US012723035B2

(12) United States Patent
Arasappan et al.

(10) Patent No.: US 12,723,035 B2
(45) Date of Patent: Sep. 1, 2026

(54) CYCLOALKYL 3-OXOPIPERAZINE CARBOXAMIDES AND CYCLOHETEROALKYL 3-OXOPIPERAZINE CARBOXAMIDES AS Nav1.8 INHIBITORS

(71) Applicant: Merck Sharp & Dohme LLC, Rahway, NJ (US)

(72) Inventors: Ashok Arasappan, Bridgewater, NJ (US); Ian M. Bell, Lansdale, PA (US); Jason M. Cox, Rancho Santa Fe, CA (US); Michael J. Kelly, III, Paoli, PA (US); Mark Eric Layton, Harleysville, PA (US); Hong Liu, Hillsborough, NJ (US); Jian Liu, Norristown, PA (US); Akshay A Shah, Robbinsville, NJ (US); Michael D. VanHeyst, Harleysville, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 50 days.

(21) Appl. No.: 17/737,070

(22) Filed: May 5, 2022

(65) Prior Publication Data

US 2022/0380338 A1 Dec. 1, 2022

Related U.S. Application Data

(60) Provisional application No. 63/286,691, filed on Dec. 7, 2021, provisional application No. 63/185,637, filed on May 7, 2021.

(51) Int. Cl.

| | |
|---|---|
| ***C07D 401/12*** | (2006.01) |
| ***C07D 241/08*** | (2006.01) |
| ***C07D 405/12*** | (2006.01) |
| ***C07D 417/12*** | (2006.01) |

(52) U.S. Cl.

CPC ......... *C07D 401/12* (2013.01); *C07D 241/08* (2013.01); *C07D 405/12* (2013.01); *C07D 417/12* (2013.01); *C07B 2200/05* (2013.01)

(58) Field of Classification Search

CPC .. C07D 401/12; C07D 241/00; C07D 405/12; C07D 417/12

See application file for complete search history.

(56) References Cited

U.S. PATENT DOCUMENTS

| | | | |
|---|---|---|---|
| 8,519,137 | B2 | 8/2013 | Joshi et al. |
| 8,629,149 | B2 | 1/2014 | Pajouhesh et al. |
| 9,051,270 | B2 | 6/2015 | Hadida-Ruah et al. |
| 9,108,903 | B2 | 8/2015 | Hadida-Ruah et al. |
| 9,163,042 | B2 | 10/2015 | Anderson et al. |
| 9,783,501 | B2 | 10/2017 | Hadida-Ruah et al. |
| 2020/0140411 | A1 | 5/2020 | Arasappan et al. |
| 2024/0158446 | A1 | 5/2024 | Kawada et al. |

FOREIGN PATENT DOCUMENTS

| | | | |
|---|---|---|---|
| EP | 3470404 | A1 | 4/2019 |
| WO | 2009049180 | A2 | 4/2009 |
| WO | 2009049181 | A1 | 4/2009 |
| WO | 2009049183 | A1 | 4/2009 |
| WO | 2011026240 | A1 | 3/2011 |
| WO | 2014120808 | A1 | 8/2014 |
| WO | 2014120815 | A1 | 8/2014 |
| WO | 2014120820 | A1 | 8/2014 |
| WO | 2015010065 | A1 | 1/2015 |
| WO | 2015089361 | A1 | 6/2015 |
| WO | 2017209322 | A1 | 12/2017 |
| WO | 2018050677 | A1 | 3/2018 |
| WO | 2018213426 | A1 | 11/2018 |
| WO | 2019014352 | A1 | 1/2019 |
| WO | 2020014246 | A1 | 1/2020 |
| WO | 2020092187 | A1 | 5/2020 |

(Continued)

OTHER PUBLICATIONS

Aurora Fine Chemicals, RN 2432437-32-4, 2020, CHEMCATS, Answer 11 of 105 (Year: 2020).*

Aurora Fine Chemicals, RN 2419513-69-0, 2020, CHEMCATS, Answer 33 of 105 (Year: 2020).*

Aurora Fine Chemicals, RN 2308010-04-8, 2019, CHEMCATS, Answer 374 of 407 (Year: 2019).*

Ukrorgsyntez Ltd., RN 1956112-50-7, 2016, CHEMCATS, Answer 380 of 407 (Year: 2016).*

Ukrorgsyntez Ltd., RN 1956060-54-0, 2016, CHEMCATS, Answer 381 of 407 (Year: 2016).*

Ukrorgsyntez Ltd., RN 1949985-46-9, 2016, CHEMCATS, Answer 385 of 407 (Year: 2016).*

Enamine, RN 1428083-73-1, 2013, CHEMCATS, Answer 404 of 407 (Year: 2013).*

Price et al. "From mechanism to cure: Renewing the goal to eliminate the disease of pain", 2018, Pain Medicine, 19, pp. 1525-1549 (Year: 2018).*

(Continued)

*Primary Examiner* — Brenda L Coleman

*Assistant Examiner* — Madeline E Braun

(74) *Attorney, Agent, or Firm* — Baerbel R. Brown; Catherine D. Fitch

(57) ABSTRACT

Novel compounds of structural formula (I), and the pharmaceutically acceptable salts thereof, are inhibitors of $Na_v$1.8 channel activity and may be useful in the treatment, prevention, management, amelioration, control and suppression of diseases mediated by $Na_v$1.8 channel activity. The compounds of Formula I may be useful in the treatment, prevention or management of pain disorders, cough disorders, acute itch disorders, and chronic itch disorders.

I

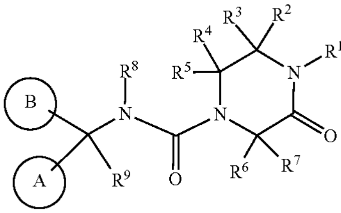

47 Claims, No Drawings

(56) References Cited

FOREIGN PATENT DOCUMENTS

| | | | |
|---|---|---|---|
| WO | 2020092667 | A1 | 5/2020 |
| WO | 2021257420 | A1 | 12/2021 |
| WO | 2021257490 | A1 | 12/2021 |
| WO | 2022192487 | A2 | 9/2022 |

OTHER PUBLICATIONS

Bagal, Sharan K. et al., Discovery and Optimization of Selective Nav1.8 Modulator Series That Demonstrate Efficacy in Preclinical Models of Pain, ACS Med. Chem. Lett., 2015, 650-654, 6.
Baker et al., Involvement of Na + Channels in Pain Pathways, Trends in Pharmacological Sciences, 2001, 27-31, 22, No. 1.
Belkouch, Mounir et al., Functional up-regulation of Nav1.8 sodium channel in Aβ afferent fibers subjected to chronic peripheral inflammation, Journal of Neuroinflammation, 2014, 1-17, 11:45.
Bennett, David L. et al., Painful and painless channelopathies, Lancet Neurol., 2014, 587-599, 13(6).
Black, Joel A. et a., Multiple Sodium Channel Isoforms and Mitogen-Activated Protein Kinases Are Present in Painful Human Neuromas, Ann Neurol, 2008, 644-653, 64(6).
Black, Joel A. et al., Sensory neuron-specific sodium channel SNS is abnormally expressed in the brains of mice with experimental allergic encephalomyelitis and humans with multiple sclerosis, Proc. Natl. Acad. Sci. USA, 2000, 11598-11602, 97(21).
Carter et al., Advances in the Management of Neuropathic Pain, Physical Medicine and Rehabilitation Clinics of North America, 2001, 447-459, 12(2).
Catterall, William A. et al., The chemical basis for electrical signaling, Nature Chemical Biology, 2017, 455-463, 13(5).
Colloca, Luana et al., Neuropathic pain, Nature Reviews Disease Primers, 2017, 1-19, 3:17002.
Coward, K et al., Immunolocalization of SNS/PN3 and NaN/SNS2 sodium channels in human pain states, Pain, 2000, 41-50, 85.
Emery, Edward C. et al., Novel SCN9A Mutations Underlying Extreme Pain Phenotypes: Unexpected Electrophysiological and Clinical Phenotype Correlations, Journal of Neuroscience, 2015, 7674-7681, 35(20).
Flaxman et al., Years Lived with Disability (YLDs) for 1160 Sequelae of 289 Diseases and Injuries 1990-2010: A Systematic Analysis for the Global Burden of Disease Study 2010, Lancet, 2012, 2163-2196, 380.
Goldin et al., Nomenclature of Voltage-Gated Sodium Channels, Neuron, 2000, 365-368, 28.
Goldin, Diveristy of Mammalian Voltage-Gated Sodium Channels, Ann NY Acad Sci., 1999, 38-50, 30, 868.
Han, Chongyang et al., The G1662S NaV1.8 mutation in small fibre neuropathy: impaired inactivation underlying DRG neuron hyperexcitability, J Neurol Neurosurg Psychiatry, 2014, 499-505, 85(5).
Han, Chongyang, et al., Sodium channel Nav1.8, Emerging links to human disease, Neurology, 2016, 473-483, 86.
Higuchi, T., et al., "Pro-drugs as NovelDelivery Systems", A.C.S. Symposium Series, 1987, 14, pp. 1-6.
Huang, Jianying et al., Small-Fiber Neuropathy Nav1.8 Mutation Shifts Activation to Hyperpolarized Potentials and Increases Excitability of Dorsal Root Ganglion Neurons, Journal of Neuroscience, 2013, 14087-14097, 33(35).
Ikoma et al., The Neurobiology of Itch, Nature Reviews, 2006, 535-547, 7.
Jarvis, Michael F. et al., A-803467, a potent and selective Nav1.8 sodium channel blocker, attenuates neuropathic and inflammatory pain in the rat, PNAS, 2007, 8520-8525, 104.
Kist, Andreas M. et al., SCN10A Mutation in a Patient with Erythromelalgia Enhances C-Fiber Activity Dependent Slowing, PLOS One, 2016, pp. 1-19, 11(9):e0161789.
Kort, Michael E. et al., Discovery and Biological Evaluation of 5-Aryl-2-furfuramides, Potent and Selective Blockers of the Nav1.8 Sodium Channel with Efficacy in Models of Neuropathic and Inflammatory Pain, J. Med. Chem., 2008, 407-416, 51.
Liu, Yang et al., VGLUT2-Dependent Glutamate Release from Nociceptors Is Required to Sense Pain and Suppress Itch, Neuron, 2010, 543-556, 68(3).
Luo, Jialie et al., Molecular and cellular mechanisms that initiate pain and itch, Cellular and Molecular Life Sciences, 2015, 3201-3223, 72.
Mcgaraughty, Steve et al., A Selective Nav1.8 Sodium Channel Blocker, A-803467 [5-(4-Chlorophenyl-N-(3,5-dimethoxyphenyl)furan-2-carboxamide], Attenuates Spinal Neuronal Activity in Neuropathic Rats, JPET, 2008, 1204-1211, 324.
Mcmahon et al., Itching for an Explanation, Trends Neuroscience, 1992, 497-501, 15.
Nair, Parameswaran et al., Airway Hyperresponsiveness in Asthma: Measurement and Clinical Relevance, J Allergy Clin Immunol Pract, 2017, 649-659, 5(3).
Payne, Claire Elizabeth et al., A novel selective and orally bioavailable NAv1.8 channel blocker, PF-01247324, attenuates nociception and sensory neuron excitability, British Journal of Pharmacology, 2015, 2654-2670, 172.
Riol-Blanco, Lorena et al., Nociceptive sensory neurons drive interleukin-23-mediated psoriasiform skin inflammation, Nature, 2014, 157-161, 510.
Roche, E.B., Bioreversible Carriers in Drug Design, Theory and Application, Pergamon Press, 1987.
Roostaei, Tina et al., Channelopathy-related SCN10A gene variants predict cerebellar dysfunction in multiple sclerosis, Neurology, 2016, 410-417, 86(5).
Schmelz et al., Specific C-Receptors for Itch in Human Skin, J. of Neuroscience, 1997, 8003-8008, 17(20).
Schreiber, Anne K. et al., Diabetic neuropathic pain: Physiopathology and treatment, World Journal of Diabetes, 2015, 432-444, 6(3).
Shields, Shannon D. et al., A Channelopathy Contributes to Cerebellar Dysfunction in a Model of Multiple Sclerosis, Ann Neurol, 2012, 186-194, 71(2).
Shields, Shannon D. et al., Oral Administration of PF-01247324, a Subtype-Selective Nav1.8 Blocker, Reverses Cerebellar Deficits in a Mouse Model of Multiple Sclerosis, PLoS One, 2015, 1-8, 10(3).
Talbot, Sebastien et al., Silencing Nociceptor Neurons Reduces Allergic Airway Inflammation, Neuron, 2015, 341-354, 87(2).
Van Loey et al., Itching Following Burns: Epidemiology and Predictors, British J. Dermatology, 2008, 95-100, 158.
Wood, John N et al., Voltage-gated sodium channels, Current Opinion in Pharmacolgoy, 2001, 17-21, 1.
Yiangou, Y. et al., SNS/PN3 and SNS2/NaN sodium channel-like immunoreactivity in human adult and neonate injured sensory nerves, FEBS Letters, 2000, 249-252, 467.
Yu et al., Overview of the Voltage-Gated Sodium Channel Family, Genome Biology, 2003, 207, 4.
Zeng, Chao et al., Relative efficacy and safety of topical non-steroidal anti-inflammatory drugs for osteoarthritis: a systematic review and network meta-analysis of randomised controlled trials and observational studies, Br J Sports Med, 2018, 642-650, 52.
Zhang, Xu-Feng et al., A-887826 is a structurally novel, potent and voltage-dependent Nav1.8 sodium channel blocker that attenuates neuropathic tactile allodynia in rats, Neuropharmacology, 2010, 201-207, 59.
CAS Registry No. 1797598-52-7; STN Entry Date Jul. 9, 2015; N-(2-Cyclobutyl-1-phenylethyl)-3-oxo-1-piperazinecarboxamide.
CAS Registry No. 1944644-73-8; STN Entry Date Jul. 4, 2016; 4-Cyclopropyl-3-oxo-N-[1-phenyl-2-(tetrahydro-3-furanyl)ethyl]-1-piperazinecarboxamide.
CAS Registry No. 1945157-34-5; STN Entry Date Jul. 4, 2016; 4-Cyclopropyl-3-oxo-N-[1-phenyl-2-(1-pyrrolidinyl)ethyl]-1-piperazinecarboxamide.
CAS Registry No. 1950125-44-6; STN Entry Date Jul. 12, 2016; N-[(4-Chlorophenyl)(4-methyl-2-morpholinyl)methyl]-2-methyl-3-oxo-1-piperazinecarboxamide.
CAS Registry No. 2126022-13-5; STN Entry Date Sep. 7, 2017; N-[Cyclopropyl(5-methyl-2-thiazolyl)methyl]-2-methyl-3-oxo-1-piperazinecarboxamide.
CAS Registry No. 2307982-25-6; STN Entry Date May 15, 2019; 2,3,6-Trimethyl-N-[2-(4-methyl-1-piperazinyl)-1-phenylethyl]-5-oxo-1-piperazinecarboxamide.

(56) References Cited

OTHER PUBLICATIONS

CAS Registry No. 2461199-17-5; STN Entry Date Aug. 26, 2020; N-(2-Cyclobutyl-1-phenylethyl)-4-methyl-3-oxo-1-piperazinecarboxamide.
Browne, Liam E. et al., Structural Determinants of Drugs Acting on the Nav1.8 Channel, J Biol Chem, 284(16), 10523-10536, 2009.
Huang, Xiaoshuang et al., Structural basis for high-voltage activation and subtype-specific inhibition of human Nav1.8, PNAS, vol. 119 No. 30 e2208211119, 1-9, 2022.

* cited by examiner

CYCLOALKYL 3-OXOPIPERAZINE CARBOXAMIDES AND CYCLOHETEROALKYL 3-OXOPIPERAZINE CARBOXAMIDES AS Nav1.8 INHIBITORS

CROSS-REFERENCE TO RELATED APPLICATIONS

This U.S. Non-provisional application claims priority from and the benefit of U.S. Provisional Application No. 63/185,637, filed May 7, 2021, and priority from and the benefit of U.S. Provisional Application No. 63/286,691, filed Dec. 7, 2021.

BACKGROUND OF THE INVENTION

Voltage-gated sodium channels (VGSC) mediate the selective influx of sodium ions in excitable cells and play a central role in initiating and propagating action potentials (Yu et al., Genome Biology 4:207 (2003)). Voltage-gated sodium channels are ubiquitous in the central and peripheral nervous system where they play a central role in the initiation and propagation of action potentials, and also in skeletal and cardiac muscle where the action potential triggers cellular contraction (Goldin et al., Ann N Y Acad Sci. 1999 Apr. 30; 868:38-50). Alterations in VGSC function or their expression can profoundly affect normal cell excitability (Huang et al., J Neurosci. 2013 Aug. 28; 33 (35):14087-97; Emery et al., J Neurosci. 2015 May 20; 35(20):7674-81; Kist et al., PLoS One. 2016 Sep. 6; 11(9):e0161789; and Schreiber et al., World J Diabetes. 2015 Apr. 15; 6(3):432-44).

Voltage-gated sodium channels are multimeric complexes characterized by one α-subunit, which forms an ion-conducting aqueous pore, and at least one β-subunit that modifies the kinetics and voltage-dependence of the channel gating. Nine different α-subunits have been identified and characterized in mammalian voltage-gated sodium channels, including $Na_v1.8$, also known as SNS, PN3 or $Na_v1.8$ (Goldin et al., Neuron. 2000 November; 28 (2):365-8).

Expression of sodium channels can be tissue specific. $Na_v1.8$ voltage-gated sodium ion channels are expressed primarily in sensory neurons, which are responsible for conveying information from the periphery (e.g. skin, muscle and joints) to the central nervous system via the spinal cord. Sodium channels are integral to this process as sodium channel activity is required for initiation and propagation of action potentials triggered by noxious stimuli (thermal, mechanical and chemical) activating peripheral nociceptors (Catterall et al., Nat Chem Biol. 2017 Apr. 13; 13(5):455-463). An increase in VGSC protein level at the cell surface or an alteration in activity of the VGSC channels can result in disease states such as migraine, neurodegeneration following ischemia, epilepsies, and chronic neuropathic and inflammatory pain states. Gain of function mutations in Nav1.7, Nav1.8, and Nav1.9 manifest in a variety of pain syndromes where patients experience spontaneous pain without an external stimulus (Bennett et al., Lancet Neurol. 2014 June; 13(6):587-99; Huang et al., J Neurosci. 2013 Aug. 28; 33(35):14087-97; Kist et al., PLoS One. 2016 Sep. 6; 11(9):e0161789; Emery et al., J Neurosci. 2015 May 20; 35(20):7674-81; and Schreiber et al., World J Diabetes. 2015 Apr. 15; 6(3):432-44).

$Na_v1.8$ voltage-gated sodium ion channels are believed to play a role in various maladies, including neuropathic pain, chronic itch, and inflammatory pain perception (Belkouch et al., J Neuroinflammation. 2014 Mar. 7; 11:45; Coward et al., Pain. 2000 March; 85(1-2):41-50; Yiangou et al., FEBS Lett. 2000 Feb. 11; 467(2-3):249-52; Black et al., Ann Neurol. 2008 December; 64(6):644-53; Bird et al., Br J Pharmacol. 2015 May; 172(10):2654-70; Liu et al., Neuron. 2010 Nov. 4; 68(3):543-56; and Zhao et al., J Clin Invest. 2013).

Large portions of the voltage gated sodium ion channels are conserved among the various subtypes; therefore there is a potential for producing serious side effects when utilizing therapeutic agents that do not demonstrate subtype selectivity. Therefore, therapeutic agents suitable for use in addressing nociception, cough, or itch disorders, require specificity in their action, for example, discriminating between action upon $Na_v1.5$ sodium ion channels, thought to be important in regulation of cardiac function, and action upon $Na_v1.8$ sodium ion channels, thought to be central in inflammatory nociception, or itch and disorders arising from dysfunctional and/or upregulated $Na_v1.8$ sodium ion channels.

Accordingly, it is believed that inhibitors of $Na_v1.8$ voltage-gated sodium ion channel activity may useful to treat or prevent diseases, disorders and conditions involving $Na_v1.8$ receptors and/or stemming specifically from dysfunction of $Na_v1.8$ voltage-gated sodium ion channels (Han et al., J Neurol Neurosurg Psychiatry 2014 May; 85(5):499-505), including but not limited to, migraine, neurodegeneration following ischemia, epilepsy, inflammatory pain, spontaneous pain, acute pain, preoperative pain, perioperative pain, post-operative pain, neuropathic pain, chronic itch, and itch disorders.

There remains a need for potent $Na_v1.8$ sodium ion channel activity inhibitors with selective activity for $Na_v1.8$ sodium ion channels. As a result, the presently disclosed compounds are useful for the treatment and prevention of diseases, disorders and conditions involving $Na_v1.8$ receptors and $Na_v1.8$ voltage-gated sodium ion channels.

The role of Nav1.8 sodium ion channels is discussed in: Bennett et al., Physical Medicine and Rehabilitation Clinics of North America, 2001, 12(2):447-459; Meissner et al., Br J Sports Med. 2018 May; 52(10):642-650; Legroux-Crespel et al., Neurology. 2016 Feb. 2; 86(5):473-83; and Flaxman et al., Lancet, 380:2163-2196 (2012).

Compounds useful to treat $Na_v1.8$ sodium ion channel related conditions are disclosed in: ACS Med. Chem. Lett. 2015, 6, 650; BJP 2015, 172, 2654; PNAS 2007, 104, 8520; J. Med. Chem. 2008, 51, 407; JPET 2008, 324, 1204; and Neuropharmacology 2010, 59, 201.

$Na_v1.8$ compounds are also disclosed in: WO 2009/049180, WO 2009/049181, WO 2009/049183, WO 2014/120808; WO 2014/120815; WO 2014/120820; WO 2015/010065; and WO 2015/089361; WO 2017/209322; U.S. Pat. Nos. 8,519,137; 9,051,270; 9,108,903; 9,163,042; 9,783,501; WO 2020/092667; WO2019/014352; WO2018/213426; U.S. Pat. No. 8,629,149; and WO2011/026240.

SUMMARY OF THE INVENTION

The present disclosure relates to novel compounds of structural formula I:

I

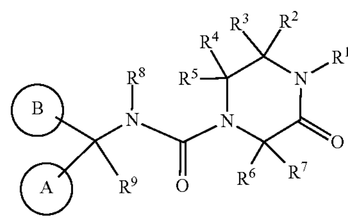

and pharmaceutically acceptable salts, hydrates and solvates thereof. The compounds of structural formula I, and embodiments thereof, are inhibitors of $Na_v1.8$ sodium ion channel activity (or $Na_v1.8$ inhibitors) and may be useful in the treatment and prevention of diseases, disorders and conditions mediated by $Na_v1.8$ sodium ion channel activity, such as nociception, osteoarthritis, peripheral neuropathy, inherited erythromelalgia, multiple sclerosis, asthma, itch, atopy, allergic or contact dermatitis, renal failure, cholestasis, pruritus, acute itch, chronic itch, migraine, neurodegeneration following ischemia, epilepsy, pain, inflammatory pain, spontaneous pain, acute pain, acute pain due to fractures, musculoskeletal damage, pancreatitis and renal colic, peri-operative pain, post-operative pain, neuropathic pain, postherpetic neuralgia, trigeminal neuralgia, diabetic neuropathy, chronic lower back pain, phantom limb pain, sciatica, pain caused by 2° or 3° burn injury, optic neuritis, pain resulting from cancer and chemotherapy, chronic pelvic pain, pain syndromes, and complex regional pain syndromes. In one embodiment, the condition, disease or disorder is a pain disorder, an acute pain disorder or chronic pain disorder. In another embodiment, the condition, disease or disorder is an acute pain disorder.

Also disclosed are pharmaceutical compositions comprising the compounds of the present of structural formula I and a pharmaceutically acceptable carrier.

Further disclosed are methods for the treatment, management, prevention, alleviation, amelioration, suppression or control of disorders, diseases, and conditions that may be responsive to inhibition of $Na_v1.8$ sodium ion channel activity in a subject in need thereof by administering the presently disclosed compounds and pharmaceutical compositions.

Further disclosed is the use of compounds of structural formula I for manufacture of a medicament useful in treating diseases, disorders and conditions that may be responsive to the inhibition of $Na_v1.8$ sodium ion channel activity.

Also disclosed is the treatment or prevention of these diseases, disorders and conditions by administering the disclosed compounds in combination with a therapeutically effective amount of another agent that may be useful to treat the disease, disorder and condition. Further described are processes for preparing the compounds of this invention.

DETAILED DESCRIPTION OF THE INVENTION

Provided are novel compounds of structural Formula I:

I

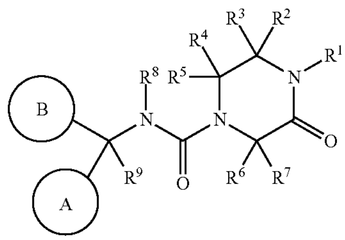

or a pharmaceutically acceptable salt thereof, wherein one of A and B is independently selected from the group consisting of:

(1) aryl, and
(2) heteroaryl, wherein aryl and heteroaryl are unsubstituted or substituted with one to five substituents selected from $R^a$, and the other of A and B is independently selected from the group consisting of:

(1) $C_{3-12}$cycloalkyl,
(2) $C_{2-11}$cycloheteroalkyl,
(3) $-C_{1-6}$alkyl-$C_{3-12}$cycloalkyl,
(4) $-C_{1-6}$alkyl-$C_{2-11}$cycloheteroalkyl,
(5) $-C_{1-6}$alkyl-O$-C_{3-12}$cycloalkyl, and
(6) $-C_{1-6}$alkyl-O$-C_{2-11}$cycloheteroalkyl, wherein alkyl, cycloalkyl and cycloheteroalkyl are unsubstituted or substituted with one to six substituents selected from $R^b$;

$R^1$ is selected from the group consisting of:

(1) hydrogen,
(2) $-C_{1-6}$alkyl,
(3) $-C_{2-6}$alkenyl,
(4) $-C_{2-6}$alkynyl,
(5) $-C_{3-6}$cycloalkyl,
(6) $-C_{2-6}$cycloheteroalkyl,
(7) $-C_{1-6}$alkyl-O$-C_{1-6}$alkyl-,
(8) $-(CH_2)_tC(O)R^j$,
(9) $-(CH_2)_tC(O)NR^eR^j$,
(10) $-(CH_2)_nNR^eC(O)R^j$,
(11) $-(CH_2)_nNR^eC(O)OR^j$,
(12) $-(CH_2)_nNR^eC(O)N(R^e)_2$,
(13) $-(CH_2)_nNR^eC(O)NR^eR^j$,
(14) $-(CH_2)_nNR^eS(O)_mR^j$,
(15) $-(CH_2)_nNR^eS(O)mN(R^e)_2$,
(16) $-(CH_2)_nNR^eS(O)mNR^eR^j$, and
(17) $-(CH_2)_nNR^eR^j$, wherein each $CH_2$, alkyl, alkenyl, alkynyl, cycloalkyl and cycloheteroalkyl is unsubstituted or substituted with one to five substituents selected from $R^c$;

$R^2$ is selected from the group consisting of:

(1) hydrogen,
(2) deuterium,
(3) $-C_{1-6}$alkyl,
(4) $-C_{2-6}$alkenyl,
(5) $-C_{2-6}$alkynyl,
(6) $-C_{3-6}$cycloalkyl,
(7) $-C_{2-6}$cycloheteroalkyl,
(8) $-C_{1-6}$alkyl-O$-C_{1-6}$alkyl-,
(9) $-(CH_2)_sC(O)R^j$,
(10) $-(CH_2)_sC(O)NR^eR^j$,
(11) $-(CH_2)_sNR^eC(O)R^j$,
(12) $-(CH_2)_sNR^eC(O)OR^j$,
(13) $-(CH_2)_sNR^eC(O)N(R^e)_2$,
(14) $-(CH_2)_sNR^eC(O)NR^eR^j$,
(15) $-(CH_2)_sNR^eS(O)_mR^j$,
(16) $-(CH_2)_sNR^eS(O)mN(R^e)_2$,
(17) $-(CH_2)_sNR^eS(O)mNR^eR^j$, and
(18) $-(CH_2)_sNR^eR^j$, wherein each $CH_2$, alkyl, alkenyl, alkynyl, cycloalkyl, and cycloheteroalkyl is unsubstituted or substituted with one to five substituents selected from $R^d$, wherein $R^2$ and $R^3$ and the carbon atoms they are connected to can form a $-C_{3-5}$cycloalkyl ring, and wherein $R^2$ and $R^4$ and the carbon atoms they are connected to can form a $-C_{3-5}$cycloalkyl ring;

$R^3$ is selected from the group consisting of:

(1) hydrogen,
(2) deuterium,
(3) $-C_{1-6}$alkyl,
(4) $-C_{2-6}$alkenyl,
(5) $-C_{2-6}$alkynyl,
(6) $-C_{3-6}$cycloalkyl, (7) —$C_{2-6}$cycloheteroalkyl,
(8) —$C_{1-6}$alkyl-O—$C_{1-6}$alkyl-,
(9) —$(CH_2)_sC(O)R^j$,
(10) —$(CH_2)_sC(O)NR^eR^j$,
(11) —$(CH_2)_sNR^eC(O)R^j$,
(12) —$(CH_2)_sNR^eC(O)OR^j$,
(13) —$(CH_2)_sNR^eC(O)N(R^e)_2$,
(14) —$(CH_2)_sNR^eC(O)NR^eR^j$,
(15) —$(CH_2)_sNR^eS(O)_mR^j$,
(16) —$(CH_2)_sNR^eS(O)mN(R^e)_2$,
(17) —$(CH_2)_sNR^eS(O)mNR^eR^j$, and
(18) —$(CH_2)_sNR^eR^j$, wherein each $CH_2$, alkyl, alkenyl, alkynyl, cycloalkyl, and cycloheteroalkyl is unsubstituted or substituted with one to five substituents selected from $R^d$;

$R^4$ is selected from the group consisting of:
(1) hydrogen,
(2) deuterium,
(3) —$C_{1-6}$alkyl,
(4) —$C_{2-6}$alkenyl,
(5) —$C_{2-6}$alkynyl,
(6) —$C_{3-6}$cycloalkyl,
(7) —$C_{2-6}$cycloheteroalkyl,
(8) —$C_{1-6}$alkyl-O—$C_{1-6}$alkyl-,
(9) —$(CH_2)_sC(O)R^j$,
(10) —$(CH_2)_sC(O)NR^eR^j$,
(11) —$(CH_2)_sNR^eC(O)R^j$,
(12) —$(CH_2)_sNR^eC(O)OR^j$,
(13) —$(CH_2)_sNR^eC(O)N(R^e)_2$,
(14) —$(CH_2)_sNR^eC(O)NR^eR^j$,
(15) —$(CH_2)_sNR^eS(O)_mR^j$,
(16) —$(CH_2)_sNR^eS(O)mN(R^e)_2$,
(17) —$(CH_2)_sNR^eS(O)mNR^eR^j$, and
(18) —$(CH_2)_sNR^eR^j$, wherein each $CH_2$, alkyl, alkenyl, alkynyl, cycloalkyl, and cycloheteroalkyl is unsubstituted or substituted with one to five substituents selected from $R^f$, and wherein $R^4$ and $R^5$ and the carbon atoms they are connected to can form a —$C_{3-5}$cycloalkyl ring;

$R^5$ is selected from the group consisting of:
(1) hydrogen,
(2) deuterium,
(3) —$C_{1-6}$alkyl,
(4) —$C_{2-6}$alkenyl,
(5) —$C_{2-6}$alkynyl,
(6) —$C_{3-6}$cycloalkyl,
(7) —$C_{2-6}$cycloheteroalkyl,
(8) —$C_{1-6}$alkyl-O—$C_{1-6}$alkyl-,
(9) —$(CH_2)_sC(O)R^j$,
(10) —$(CH_2)_sC(O)NR^eR^j$,
(11) —$(CH_2)_sNR^eC(O)R^j$,
(12) —$(CH_2)_sNR^eC(O)OR^j$,
(13) —$(CH_2)_sNR^eC(O)N(R^e)_2$,
(14) —$(CH_2)_sNR^eC(O)NR^eR^j$,
(15) —$(CH_2)_sNR^eS(O)_mR^j$,
(16) —$(CH_2)_sNR^eS(O)mN(R^e)_2$,
(17) —$(CH_2)_sNR^eS(O)mNR^eR^j$, and
(18) —$(CH_2)_sNR^eR^j$, wherein each $CH_2$, alkyl, alkenyl, alkynyl, cycloalkyl, and cycloheteroalkyl is unsubstituted or substituted with one to five substituents selected from $R^f$, and wherein $R^5$ and $R^7$ and the carbon atoms they are attached to may form a 4-, 5- or 6-membered saturated ring;

$R^6$ is selected from the group consisting of:
(1) hydrogen,
(2) deuterium,
(3) —$C_{1-6}$alkyl,
(4) —$C_{2-6}$alkenyl,
(5) —$C_{2-6}$alkynyl,
(6) —$C_{3-6}$cycloalkyl,
(7) —$C_{2-6}$cycloheteroalkyl,
(8) —$C_{1-6}$alkyl-O—$C_{1-6}$alkyl-,
(9) —$(CH_2)_sC(O)R^j$,
(10) —$(CH_2)_sC(O)NR^eR^j$,
(11) —$(CH_2)_sNR^eC(O)R^j$,
(12) —$(CH_2)_sNR^eC(O)OR^j$,
(13) —$(CH_2)_sNR^eC(O)N(R^e)_2$,
(14) —$(CH_2)_sNR^eC(O)NR^eR^j$,
(15) —$(CH_2)_sNR^eS(O)_mR^j$,
(16) —$(CH_2)_sNR^eS(O)mN(R^e)_2$,
(17) —$(CH_2)_sNR^eS(O)mNR^eR^j$, and
(18) —$(CH_2)_sNR^eR^j$, wherein each $CH_2$, alkyl, alkenyl, alkynyl, cycloalkyl, and cycloheteroalkyl is unsubstituted or substituted with one to five substituents selected from $R^g$, and wherein $R^6$ and $R^7$ and the carbon atoms they are connected to can form a —$C_{3-5}$cycloalkyl ring;

$R^7$ is selected from the group consisting of:
(1) hydrogen,
(2) deuterium,
(3) —$C_{1-6}$alkyl,
(4) —$C_{2-6}$alkenyl,
(5) —$C_{2-6}$alkynyl,
(6) —$C_{3-6}$cycloalkyl,
(7) —$C_{2-6}$cycloheteroalkyl,
(8) —$C_{1-6}$alkyl-O—$C_{1-6}$alkyl-,
(9) —$(CH_2)_sC(O)R^j$,
(10) —$(CH_2)_sC(O)NR^eR^j$,
(11) —$(CH_2)_sNR^eC(O)R^j$,
(12) —$(CH_2)_sNR^eC(O)OR^j$,
(13) —$(CH_2)_sNR^eC(O)N(R^e)_2$,
(14) —$(CH_2)_sNR^eC(O)NR^eR^j$,
(15) —$(CH_2)_sNR^eS(O)_mR^j$,
(16) —$(CH_2)_sNR^eS(O)mN(R^e)_2$,
(17) —$(CH_2)_sNR^eS(O)mNR^eR^j$, and
(18) —$(CH_2)_sNR^eR^j$, wherein each $CH_2$, alkyl, alkenyl, alkynyl, cycloalkyl, and cycloheteroalkyl is unsubstituted or substituted with one to five substituents selected from $R^g$;

$R^8$ is selected from the group consisting of:
(1) hydrogen,
(2) —$C_{1-6}$alkyl,
(3) —$C_{3-6}$cycloalkyl, and
(4) —$C_{2-6}$cycloheteroalkyl, wherein each alkyl, cycloalkyl and cycloheteroalkyl is unsubstituted or substituted with one to five substituents selected from halogen;

$R^9$ is selected from the group consisting of:
(1) hydrogen,
(2) —$C_{1-6}$alkyl,
(3) —$C_{2-6}$alkenyl, and
(4) —$C_{2-6}$alkynyl, wherein each alkyl, alkenyl and alkynyl is unsubstituted or substituted with one to five substituents selected from halogen;

each $R^a$ is independently selected from the group consisting of:
(1) CN,
(2) oxo,
(3) halogen,
(4) —$S(O)_2C_{1-6}$alkyl,
(5) —$C_{1-6}$alkyl,
(6) —$C_{2-6}$alkenyl,
(7) —$C_{2-6}$alkynyl, (8) —$C_{3-6}$cycloalkyl,
(9) —$C_{2-6}$cycloheteroalkyl,
(10) aryl,
(11) heteroaryl,
(12) —$C_{1-6}$alkyl-aryl,
(13) —$C_{1-6}$alkyl-heteroaryl,
(14) —$C_{1-6}$alkyl-$C_{3-6}$cycloalkyl,
(15) —$C_{1-6}$alkyl-$C_{2-6}$cycloheteroalkyl,
(16) —$C_{2-6}$alkenyl-$C_{3-6}$cycloalkyl,
(17) —$C_{2-6}$alkenyl-$C_{2-6}$cycloheteroalkyl,
(18) —$C_{2-6}$alkenyl-aryl,
(19) —$C_{2-6}$alkenyl-heteroaryl,
(20) —$C_{2-6}$alkynyl-$C_{3-6}$cycloalkyl,
(21) —$C_{2-6}$alkynyl$C_{2-6}$cycloheteroalkyl,
(22) —$C_{2-6}$alkynyl-aryl,
(23) —$C_{2-6}$alkynyl-heteroaryl,
(24) —OH,
(25) —$(CH_2)_p$—O—$C_{1-6}$alkyl,
(26) —$(CH_2)_p$—O—$C_{2-6}$alkenyl,
(27) —$(CH_2)_p$—O—$C_{2-6}$alkynyl,
(28) —$(CH_2)_p$—O—$C_{3-6}$cycloalkyl,
(29) —$(CH_2)_p$—O—$C_{2-6}$cycloheteroalkyl,
(30) —$(CH_2)_p$—O-aryl,
(31) —$(CH_2)_p$—O-heteroaryl,
(32) —$OC_{1-6}$alkyl-$C_{3-6}$cycloalkyl,
(33) —$OC_{1-6}$alkyl-$C_{2-6}$cycloheteroalkyl,
(34) —$OC_{1-6}$alkyl-aryl,
(35) —$OC_{1-6}$alkyl-heteroaryl,
(36) —$S(O)_rR^h$,
(37) —$C_{1-6}$alkyl-$S(O)_rR^h$,
(38) —$N(R^k)_2$,
(39) —$C(O)R^L$, and
(40) —$NR^kR^L$, wherein each $R^a$ is unsubstituted or substituted with one to six substituents selected from halogen, $CF_3$, OH, $C_{1-6}$alkyl, and —$OC_{1-6}$alkyl;

each $R^b$ is independently selected from the group consisting of:
(1) CN,
(2) oxo,
(3) halogen,
(4) —$S(O)_2C_{1-6}$alkyl,
(5) —$C_{1-6}$alkyl,
(6) —$C_{1-6}$alkenyl,
(7) —$C_{2-6}$alkynyl,
(8) —$C_{3-6}$cycloalkyl,
(9) —$C_{2-6}$cycloheteroalkyl,
(10) aryl,
(11) heteroaryl,
(12) —$C_{1-6}$alkyl-aryl,
(13) —$C_{1-6}$alkyl-heteroaryl,
(14) —$C_{1-6}$alkyl-$C_{3-6}$cycloalkyl,
(15) —$C_{1-6}$alkyl-$C_{2-6}$cycloheteroalkyl,
(16) —$C_{2-6}$alkenyl-$C_{3-6}$cycloalkyl,
(17) —$C_{2-6}$alkenyl-$C_{2-6}$cycloheteroalkyl,
(18) —$C_{2-6}$alkenyl-aryl,
(19) —$C_{2-6}$alkenyl-heteroaryl,
(20) —$C_{2-6}$alkynyl-$C_{3-6}$cycloalkyl,
(21) —$C_{2-6}$alkynyl-$C_{2-6}$cycloheteroalkyl,
(22) —$C_{2-6}$alkynyl-aryl,
(23) —$C_{2-6}$alkynyl-heteroaryl,
(24) —OH,
(25) —$(CH_2)_q$—O—$C_{1-6}$alkyl,
(26) —$(CH_2)_q$—O—$C_{2-6}$alkenyl,
(27) —$(CH_2)_q$—O—$C_{2-6}$alkynyl,
(28) —$(CH_2)_q$—O—$C_{3-6}$cycloalkyl,
(29) —$(CH_2)_q$—O—$C_{2-6}$cycloheteroalkyl,

(30) —$(CH_2)_q$—O-aryl,
(31) —$(CH_2)_q$—O-heteroaryl,
(32) —$OC_{1-6}$alkyl-$C_{3-6}$cycloalkyl,
(33) —$OC_{1-6}$alkyl-$C_{2-6}$cycloheteroalkyl,
(34) —$OC_{1-6}$alkyl-aryl,
(35) —$OC_{1-6}$alkyl-heteroaryl,
(36) —$S(O)_rR^i$,
(37) —$C_{1-6}$alkyl-$S(O)_rR^i$,
(38) —$N(R^k)_2$,
(39) —$C(O)R^L$, and
(40) —$NR^kR^L$, wherein each $R^b$ is unsubstituted or substituted with one to six substituents selected from halogen, $CF_3$, $OCF_3$, CN, $CH_2CF_3$, $CF_2CH_3$, —$C_{1-6}$alkyl, and —$OC_{1-6}$alkyl;

$R^c$ is selected from:
(1) —$C_{1-6}$alkyl,
(2) OH,
(3) halogen, and
(4) —$OC_{1-6}$alkyl, wherein alkyl is unsubstituted or substituted with one to three halogens;

$R^d$ is selected from:
(1) —$C_{1-6}$alkyl,
(2) OH,
(3) halogen, and
(4) —$OC_{1-6}$alkyl, wherein alkyl is unsubstituted or substituted with one to three halogens;

$R^e$ is selected from:
(1) hydrogen, and
(2) $C_{1-6}$alkyl;

$R^f$ is selected from:
(1) —$C_{1-6}$alkyl,
(2) OH,
(3) halogen, and
(4) —$OC_{1-6}$alkyl, wherein alkyl is unsubstituted or substituted with one to three halogens;

$R^g$ is selected from:
(1) —$C_{1-6}$alkyl,
(2) OH,
(3) halogen, and
(4) —$OC_{1-6}$alkyl, wherein alkyl is unsubstituted or substituted with one to three halogens;

$R^h$ is selected from:
(1) hydrogen,
(2) $C_{1-6}$alkyl,
(3) $C_{3-6}$cycloalkyl,
(4) aryl, and
(5) heteroaryl;

$R^i$ is selected from:
(1) hydrogen,
(2) $C_{1-6}$alkyl,
(3) $C_{3-6}$cycloalkyl,
(4) aryl, and
(5) heteroaryl;

$R^j$ is selected from:
(1) hydrogen,
(2) $C_{1-6}$alkyl,
(3) $C_{3-6}$alkenyl,
(4) $C_{3-6}$alkynyl,
(5) $C_{3-6}$cycloalkyl,
(6) $C_{2-5}$cycloheteroalkyl,
(7) aryl, and
(8) heteroaryl;

$R^k$ is selected from:

(1) hydrogen, and (2) $C_{1-6}$alkyl;

$R^L$ is selected from:

(1) hydrogen, (2) $C_{1-6}$alkyl, (3) $C_{3-6}$cycloalkyl, (4) aryl, and (5) heteroaryl;

m is independently selected from 0, 1 and 2;

n is independently selected from 2, 3, 4, 5 and 6;

p is independently selected from 0, 1, 2 and 3;

q is independently selected from 0, 1, 2 and 3;

r is independently selected from 0, 1 and 2;

s is independently selected from 0, 1, 2, 3, 4, 5, and 6; and t is independently selected from 0, 1, 2, 3, 4, 5, and 6.

The present disclosure also provides novel compounds of structural Formula I, or pharmaceutically acceptable salts thereof, wherein one of A and B is independently selected from the group consisting of:

(1) aryl, and (2) heteroaryl, wherein aryl and heteroaryl are unsubstituted or substituted with one to five substituents selected from $R^a$, and the other of A and B is independently selected from the group consisting of:

(1) $C_{3-12}$cycloalkyl, (2) $C_{2-11}$cycloheteroalkyl, (3) —$C_{1-6}$alkyl-$C_{3-12}$cycloalkyl, (4) —$C_{1-6}$alkyl-$C_{2-11}$cycloheteroalkyl, (5) —$C_{1-6}$alkyl-O—$C_{3-12}$cycloalkyl, and (6) —$C_{1-6}$alkyl-O—$C_{2-11}$cycloheteroalkyl, wherein alkyl, cycloalkyl and cycloheteroalkyl are unsubstituted or substituted with one to six substituents selected from $R^b$;

$R^1$ is selected from the group consisting of:

(1) hydrogen, (2) —$C_{1-6}$alkyl, (3) —$C_{2-6}$alkenyl, (4) —$C_{2-6}$alkynyl, (5) —$C_{3-6}$cycloalkyl, (6) —$C_{2-6}$cycloheteroalkyl, (7) —$C_{1-6}$alkyl-O—$C_{1-6}$alkyl-, (8) —$(CH_2)_tC(O)R^j$, (9) —$(CH_2)_tC(O)NR^eR^j$,

(10) —$(CH_2)_nNR^eC(O)R^j$,

(11) —$(CH_2)_nNR^eC(O)OR^j$,

(12) —$(CH_2)_nNR^eC(O)N(R^e)_2$,

(13) —$(CH_2)_nNR^eC(O)NR^eR^j$,

(14) —$(CH_2)_nNR^eS(O)_mR^j$,

(15) —$(CH_2)_nNR^eS(O)mN(R^e)_2$,

(16) —$(CH_2)_nNR^eS(O)mNR^eR^j$, and

(17) —$(CH_2)_nNR^eR^j$, wherein each $CH_2$, alkyl, alkenyl, alkynyl, cycloalkyl and cycloheteroalkyl is unsubstituted or substituted with one to five substituents selected from $R^c$;

$R^2$ is selected from the group consisting of:

(1) hydrogen, (2) —$C_{1-6}$alkyl, (3) —$C_{2-6}$alkenyl, (4) —$C_{2-6}$alkynyl, (5) —$C_{3-6}$cycloalkyl, (6) —$C_{2-6}$cycloheteroalkyl, (7) —$C_{1-6}$alkyl-O—$C_{1-6}$alkyl-, (8) —$(CH_2)_sC(O)R^j$, (9) —$(CH_2)_sC(O)NR^eR^j$,

(10) —$(CH_2)_sNR^eC(O)R^j$,

(11) —$(CH_2)_sNR^eC(O)OR^j$,

(12) —$(CH_2)_sNR^eC(O)N(R^e)_2$,

(13) —$(CH_2)_sNR^eC(O)NR^eR^j$,

(14) —$(CH_2)_sNR^eS(O)_mR^j$,

(15) —$(CH_2)_sNR^eS(O)mN(R^e)_2$,

(16) —$(CH_2)_sNR^eS(O)mNR^eR^j$, and

(17) —$(CH_2)_sNR^eR^j$, wherein each $CH_2$, alkyl, alkenyl, alkynyl, cycloalkyl, and cycloheteroalkyl is unsubstituted or substituted with one to five substituents selected from $R^d$, wherein $R^2$ and $R^3$ and the carbon atoms they are connected to can form a —$C_{3-5}$cycloalkyl ring, and wherein $R^2$ and $R^4$ and the carbon atoms they are connected to can form a —$C_{3-5}$cycloalkyl ring;

$R^3$ is selected from the group consisting of:

(1) hydrogen, (2) —$C_{1-6}$alkyl, (3) —$C_{2-6}$alkenyl, (4) —$C_{2-6}$alkynyl, (5) —$C_{3-6}$cycloalkyl, (6) —$C_{2-6}$cycloheteroalkyl, (7) —$C_{1-6}$alkyl-O—$C_{1-6}$alkyl-, (8) —$(CH_2)_sC(O)R^j$, (9) —$(CH_2)_sC(O)NR^eR^j$,

(10) —$(CH_2)_sNR^eC(O)R^j$,

(11) —$(CH_2)_sNR^eC(O)OR^j$,

(12) —$(CH_2)_sNR^eC(O)N(R^e)_2$,

(13) —$(CH_2)_sNR^eC(O)NR^eR^j$,

(14) —$(CH_2)_sNR^eS(O)_mR^j$,

(15) —$(CH_2)_sNR^eS(O)mN(R^e)_2$,

(16) —$(CH_2)_sNR^eS(O)mNR^eR^j$, and

(17) —$(CH_2)_sNR^eR^j$, wherein each $CH_2$, alkyl, alkenyl, alkynyl, cycloalkyl, and cycloheteroalkyl is unsubstituted or substituted with one to five substituents selected from $R^d$;

$R^4$ is selected from the group consisting of:

(1) hydrogen, (2) —$C_{1-6}$alkyl, (3) —$C_{2-6}$alkenyl, (4) —$C_{2-6}$alkynyl, (5) —$C_{3-6}$cycloalkyl, (6) —$C_{2-6}$cycloheteroalkyl, (7) —$C_{1-6}$alkyl-O—$C_{1-6}$alkyl-, (8) —$(CH_2)_sC(O)R^j$, (9) —$(CH_2)_sC(O)NR^eR^j$,

(10) —$(CH_2)_sNR^eC(O)R^j$,

(11) —$(CH_2)_sNR^eC(O)OR^j$,

(12) —$(CH_2)_sNR^eC(O)N(R^e)_2$,

(13) —$(CH_2)_sNR^eC(O)NR^eR^j$,

(14) —$(CH_2)_sNR^eS(O)_mR^j$,

(15) —$(CH_2)_sNR^eS(O)mN(R^e)_2$,

(16) —$(CH_2)_sNR^eS(O)mNR^eR^j$, and

(17) —$(CH_2)_sNR^eR^j$, wherein each $CH_2$, alkyl, alkenyl, alkynyl, cycloalkyl, and cycloheteroalkyl is unsubstituted or substituted with one to five substituents selected from $R^f$, and wherein $R^4$ and $R^5$ and the carbon atoms they are connected to can form a —$C_{3-5}$cycloalkyl ring;

$R^5$ is selected from the group consisting of:

(1) hydrogen, (2) —$C_{1-6}$alkyl, (3) —$C_{2-6}$alkenyl, (4) —$C_{2-6}$alkynyl, (5) —$C_{3-6}$cycloalkyl, (6) —$C_{2-6}$cycloheteroalkyl, (7) —$C_{1-6}$alkyl-O—$C_{1-6}$alkyl-, (8) $-(CH_2)_sC(O)R^j$,
(9) $-(CH_2)_sC(O)NR^eR^j$,
(10) $-(CH_2)_sNR^eC(O)R^j$,
(11) $-(CH_2)_sNR^eC(O)OR^j$,
(12) $-(CH_2)_sNR^eC(O)N(R^e)_2$,
(13) $-(CH_2)_sNR^eC(O)NR^eR^j$,
(14) $-(CH_2)_sNR^eS(O)_mR^j$,
(15) $-(CH_2)_sNR^eS(O)mN(R^e)_2$,
(16) $-(CH_2)_sNR^eS(O)mNR^eR^j$, and
(17) $-(CH_2)_sNR^eR^j$, wherein each $CH_2$, alkyl, alkenyl, alkynyl, cycloalkyl, and cycloheteroalkyl is unsubstituted or substituted with one to five substituents selected from $R^f$, and wherein $R^5$ and $R^7$ and the carbon atoms they are attached to may form a 4-, 5- or 6-membered saturated ring;

$R^6$ is selected from the group consisting of:
(1) hydrogen,
(2) $-C_{1-6}$alkyl,
(3) $-C_{2-6}$alkenyl,
(4) $-C_{2-6}$alkynyl,
(5) $-C_{3-6}$cycloalkyl,
(6) $-C_{2-6}$cycloheteroalkyl,
(7) $-C_{1-6}$alkyl-O$-C_{1-6}$alkyl-,
(8) $-(CH_2)_sC(O)R^j$,
(9) $-(CH_2)_sC(O)NR^eR^j$,
(10) $-(CH_2)_sNR^eC(O)R^j$,
(11) $-(CH_2)_sNR^eC(O)OR^j$,
(12) $-(CH_2)_sNR^eC(O)N(R^e)_2$,
(13) $-(CH_2)_sNR^eC(O)NR^eR^j$,
(14) $-(CH_2)_sNR^eS(O)_mR^j$,
(15) $-(CH_2)_sNR^eS(O)mN(R^e)_2$,
(16) $-(CH_2)_sNR^eS(O)mNR^eR^j$, and
(17) $-(CH_2)_sNR^eR^j$, wherein each $CH_2$, alkyl, alkenyl, alkynyl, cycloalkyl, and cycloheteroalkyl is unsubstituted or substituted with one to five substituents selected from $R^g$, and wherein $R^6$ and $R^7$ and the carbon atoms they are connected to can form a $-C_{3-5}$cycloalkyl ring;

$R^7$ is selected from the group consisting of:
(1) hydrogen,
(2) $-C_{1-6}$alkyl,
(3) $-C_{2-6}$alkenyl,
(4) $-C_{2-6}$alkynyl,
(5) $-C_{3-6}$cycloalkyl,
(6) $-C_{2-6}$cycloheteroalkyl,
(7) $-C_{1-6}$alkyl-O$-C_{1-6}$alkyl-,
(8) $-(CH_2)_sC(O)R^j$,
(9) $-(CH_2)_sC(O)NR^eR^j$,
(10) $-(CH_2)_sNR^eC(O)R^j$,
(11) $-(CH_2)_sNR^eC(O)OR^j$,
(12) $-(CH_2)_sNR^eC(O)N(R^e)_2$,
(13) $-(CH_2)_sNR^eC(O)NR^eR^j$,
(14) $-(CH_2)_sNR^eS(O)_mR^j$,
(15) $-(CH_2)_sNR^eS(O)mN(R^e)_2$,
(16) $-(CH_2)_sNR^eS(O)mNR^eR^j$, and
(17) $-(CH_2)_sNR^eR^j$, wherein each $CH_2$, alkyl, alkenyl, alkynyl, cycloalkyl, and cycloheteroalkyl is unsubstituted or substituted with one to five substituents selected from $R^g$;

$R^8$ is selected from the group consisting of:
(1) hydrogen,
(2) $-C_{1-6}$alkyl,
(3) $-C_{3-6}$cycloalkyl, and
(4) $-C_{2-6}$cycloheteroalkyl, wherein each alkyl, cycloalkyl and cycloheteroalkyl is unsubstituted or substituted with one to five substituents selected from halogen;

$R^9$ is selected from the group consisting of:
(1) hydrogen,
(2) $-C_{1-6}$alkyl,
(3) $-C_{2-6}$alkenyl, and
(4) $-C_{2-6}$alkynyl, wherein each alkyl, alkenyl and alkynyl is unsubstituted or substituted with one to five substituents selected from halogen;

each $R^a$ is independently selected from the group consisting of:
(1) CN,
(2) oxo,
(3) halogen,
(4) $-S(O)_2C_{1-6}$alkyl,
(5) $-C_{1-6}$alkyl,
(6) $-C_{2-6}$alkenyl,
(7) $-C_{2-6}$alkynyl,
(8) $-C_{3-6}$cycloalkyl,
(9) $-C_{2-6}$cycloheteroalkyl,
(10) aryl,
(11) heteroaryl,
(12) $-C_{1-6}$alkyl-aryl,
(13) $-C_{1-6}$alkyl-heteroaryl,
(14) $-C_{1-6}$alkyl-$C_{3-6}$cycloalkyl,
(15) $-C_{1-6}$alkyl-$C_{2-6}$cycloheteroalkyl,
(16) $-C_{2-6}$alkenyl-$C_{3-6}$cycloalkyl,
(17) $-C_{2-6}$alkenyl-$C_{2-6}$cycloheteroalkyl,
(18) $-C_{2-6}$alkenyl-aryl,
(19) $-C_{2-6}$alkenyl-heteroaryl,
(20) $-C_{2-6}$alkynyl-$C_{3-6}$cycloalkyl,
(21) $-C_{2-6}$alkynyl$C_{2-6}$cycloheteroalkyl,
(22) $-C_{2-6}$alkynyl-aryl,
(23) $-C_{2-6}$alkynyl-heteroaryl,
(24) $-OH$,
(25) $-(CH_2)_p-O-C_{1-6}$alkyl,
(26) $-(CH_2)_p-O-C_{2-6}$alkenyl,
(27) $-(CH_2)_p-O-C_{2-6}$alkynyl,
(28) $-(CH_2)_p-O-C_{3-6}$cycloalkyl,
(29) $-(CH_2)_p-O-C_{2-6}$cycloheteroalkyl,
(30) $-(CH_2)_p-$O-aryl,
(31) $-(CH_2)_p-$O-heteroaryl,
(32) $-OC_{1-6}$alkyl-$C_{3-6}$cycloalkyl,
(33) $-OC_{1-6}$alkyl-$C_{2-6}$cycloheteroalkyl,
(34) $-OC_{1-6}$alkyl-aryl,
(35) $-OC_{1-6}$alkyl-heteroaryl,
(36) $-S(O)_rR^h$,
(37) $-C_{1-6}$alkyl-$S(O)_rR^h$,
(38) $-N(R^k)_2$,
(39) $-C(O)R^L$, and
(40) $-NR^kR^L$, wherein each $R^a$ is unsubstituted or substituted with one to six substituents selected from halogen, $CF_3$, OH, $C_{1-6}$alkyl, and $-OC_{1-6}$alkyl;

each $R^b$ is independently selected from the group consisting of:
(1) CN,
(2) oxo,
(3) halogen,
(4) $-S(O)_2C_{1-6}$alkyl,
(5) $-C_{1-6}$alkyl,
(6) $-C_{1-6}$alkenyl,
(7) $-C_{2-6}$alkynyl,
(8) $-C_{3-6}$cycloalkyl,
(9) $-C_{2-6}$cycloheteroalkyl,
(10) aryl,
(11) heteroaryl,
(12) $-C_{1-6}$alkyl-aryl,

(13) —$C_{1-6}$alkyl-heteroaryl,
(14) —$C_{1-6}$alkyl-$C_{3-6}$cycloalkyl,
(15) —$C_{1-6}$alkyl-$C_{2-6}$cycloheteroalkyl,
(16) —$C_{2-6}$alkenyl-$C_{3-6}$cycloalkyl,
(17) —$C_{2-6}$alkenyl-$C_{2-6}$cycloheteroalkyl,
(18) —$C_{2-6}$alkenyl-aryl,
(19) —$C_{2-6}$alkenyl-heteroaryl,
(20) —$C_{2-6}$alkynyl-$C_{3-6}$cycloalkyl,
(21) —$C_{2-6}$alkynyl-$C_{2-6}$cycloheteroalkyl,
(22) —$C_{2-6}$alkynyl-aryl,
(23) —$C_{2-6}$alkynyl-heteroaryl,
(24) —OH,
(25) —$(CH_2)_q$—O—$C_{1-6}$alkyl,
(26) —$(CH_2)_q$—O—$C_{2-6}$alkenyl,
(27) —$(CH_2)_q$—O—$C_{2-6}$alkynyl,
(28) —$(CH_2)_q$—O—$C_{3-6}$cycloalkyl,
(29) —$(CH_2)_q$—O—$C_{2-6}$cycloheteroalkyl,
(30) —$(CH_2)_q$—O-aryl,
(31) —$(CH_2)_q$—O-heteroaryl,
(32) —$OC_{1-6}$alkyl-$C_{3-6}$cycloalkyl,
(33) —$OC_{1-6}$alkyl-$C_{2-6}$cycloheteroalkyl,
(34) —$OC_{1-6}$alkyl-aryl,
(35) —$OC_{1-6}$alkyl-heteroaryl,
(36) —$S(O)_rR^i$,
(37) —$C_{1-6}$alkyl-$S(O)_rR^i$,
(38) —$N(R^k)_2$,
(39) —$C(O)R^L$, and
(40) —$NR^kR^L$, wherein each $R^b$ is unsubstituted or substituted with one to six substituents selected from halogen, $CF_3$, $OCF_3$, CN, $CH_2CF_3$, $CF_2CH_3$, —$C_{1-6}$alkyl, and —$OC_{1-6}$alkyl;

$R^c$ is selected from:
(1) —$C_{1-6}$alkyl,
(2) OH,
(3) halogen, and
(4) —$OC_{1-6}$alkyl, wherein alkyl is unsubstituted or substituted with one to three halogens;

$R^d$ is selected from:
(1) —$C_{1-6}$alkyl,
(2) OH,
(3) halogen, and
(4) —$OC_{1-6}$alkyl, wherein alkyl is unsubstituted or substituted with one to three halogens;

$R^e$ is selected from:
(1) hydrogen, and
(2) $C_{1-6}$alkyl;

$R^f$ is selected from:
(1) —$C_{1-6}$alkyl,
(2) OH,
(3) halogen, and
(4) —$OC_{1-6}$alkyl, wherein alkyl is unsubstituted or substituted with one to three halogens;

$R^g$ is selected from:
(1) —$C_{1-6}$alkyl,
(2) OH,
(3) halogen, and
(4) —$OC_{1-6}$alkyl, wherein alkyl is unsubstituted or substituted with one to three halogens;

$R^h$ is selected from:
(1) hydrogen,
(2) $C_{1-6}$alkyl,
(3) $C_{3-6}$cycloalkyl,
(4) aryl, and
(5) heteroaryl;

$R^i$ is selected from:
(1) hydrogen,
(2) $C_{1-6}$alkyl,
(3) $C_{3-6}$cycloalkyl,
(4) aryl, and
(5) heteroaryl;

$R^j$ is selected from:
(1) hydrogen,
(2) $C_{1-6}$alkyl,
(3) $C_{3-6}$alkenyl,
(4) $C_{3-6}$alkynyl,
(5) $C_{3-6}$cycloalkyl,
(6) $C_{2-5}$cycloheteroalkyl,
(7) aryl, and
(8) heteroaryl;

$R^k$ is selected from:
(1) hydrogen, and
(2) $C_{1-6}$alkyl;

$R^L$ is selected from:
(1) hydrogen,
(2) $C_{1-6}$alkyl,
(3) $C_{3-6}$cycloalkyl,
(4) aryl, and
(5) heteroaryl;

m is independently selected from 0, 1 and 2;
n is independently selected from 2, 3, 4, 5 and 6;
p is independently selected from 0, 1, 2 and 3;
q is independently selected from 0, 1, 2 and 3;
r is independently selected from 0, 1 and 2;
s is independently selected from 0, 1, 2, 3, 4, 5, and 6; and
t is independently selected from 0, 1, 2, 3, 4, 5, and 6.

The compounds of structural formula I have numerous embodiments, which are summarized below. Included are the compounds as shown, and also individual diastereoisomers, enantiomers, and epimers of the compounds, and mixtures of diastereoisomers and/or enantiomers thereof including racemic mixtures.

In one embodiment, one of A and B is independently selected from the group consisting of: aryl and heteroaryl, wherein aryl and heteroaryl are unsubstituted or substituted with one to five substituents selected from $R^a$, and the other of A and B is independently selected from the group consisting of: —$C_{3-12}$cycloalkyl, —$C_{2-11}$cycloheteroalkyl, —$C_{1-6}$alkyl-$C_{3-12}$cycloalkyl, —$C_{1-6}$alkyl-$C_{2-11}$cycloheteroalkyl, —$C_{1-6}$alkyl-O—$C_{3-12}$cycloalkyl, and —$C_{1-6}$alkyl-O—$C_{2-11}$cycloheteroalkyl, wherein alkyl, cycloalkyl and cycloheteroalkyl are unsubstituted or substituted with one to six substituents selected from $R^b$.

In another embodiment, one of A and B is independently selected from the group consisting of: aryl, and heteroaryl, wherein aryl and heteroaryl are unsubstituted or substituted with one to five substituents selected from $R^a$, and the other of A and B is independently selected from the group consisting of: —$C_{3-10}$cycloalkyl, —$C_{2-9}$cycloheteroalkyl, —$C_{1-6}$alkyl-$C_{3-12}$cycloalkyl, —$C_{1-6}$alkyl-$C_{2-11}$cycloheteroalkyl, —$C_{1-6}$alkyl-O—$C_{3-12}$cycloalkyl, and —$C_{1-6}$alkyl-O—$C_{2-11}$cycloheteroalkyl, wherein alkyl, cycloalkyl and cycloheteroalkyl are unsubstituted or substituted with one to six substituents selected from $R^b$.

In another embodiment, one of A and B is independently selected from the group consisting of: aryl, and heteroaryl, wherein aryl and heteroaryl are unsubstituted or substituted with one to five substituents selected from $R^a$, and the other of A and B is independently selected from the group consisting of: —$C_{3-12}$cycloalkyl, and —$C_{2-11}$cycloheteroalkyl, wherein cycloalkyl and cycloheteroalkyl are unsubstituted or substituted with one to six substituents selected from $R^b$.

In another embodiment, one of A and B is independently selected from the group consisting of: aryl, and heteroaryl, wherein aryl and heteroaryl are unsubstituted or substituted with one to five substituents selected from $R^a$, and the other of A and B is independently selected from the group consisting of: $—C_{3-10}$cycloalkyl, and $—C_{2-9}$cycloheteroalkyl, wherein cycloalkyl and cycloheteroalkyl are unsubstituted or substituted with one to six substituents selected from $R^b$.

In another embodiment, one of A and B is independently selected from the group consisting of: phenyl, pyridine, and thiazole, wherein phenyl, pyridine and thiazole are unsubstituted or substituted with one to five substituents selected from $R^a$, and the other of A and B is independently selected from the group consisting of: cyclopropane, cyclobutane, cyclopentane, cyclohexane, bicyclo[3.2.1]-octane, bicyclo[3.1.0]hexane, bicyclo[2.2.2]octane, spiro[2.5]octane, bicyclo[1.1.1]pentane, spiro[3.3]heptane, spiro[2.3]hexane, spiro[2.2]pentane, piperidine, tetrahydropyran, and chromane, wherein the other of A and B is unsubstituted or substituted with one to six substituents selected from $R^b$.

In another embodiment, one of A and B is independently selected from the group consisting of phenyl, pyridine, and thiazole, wherein phenyl, pyridine and thiazole are unsubstituted or substituted with one to five substituents selected from $R^a$, and the other of A and B is independently selected from the group consisting of: cyclopropane, cyclobutane, cyclopentane, cyclohexane, bicyclo[3.2.1]-octane, bicyclo[3.1.0]hexane, bicyclo[2.2.2]octane, spiro[2.5]octane, bicyclo[1.1.1]pentane, spiro[3.3]heptane, spiro[2.3]hexane, spiro[2.2]pentane, piperidine, and tetrahydropyran, wherein the other of A and B is unsubstituted or substituted with one to six substituents selected from $R^b$.

In another embodiment, one of A and B is independently selected from the group consisting of: phenyl, and pyridine, wherein phenyl and pyridine are unsubstituted or substituted with one to four substituents selected from $R^a$, and the other of A and B is independently selected from the group consisting of cyclobutane, cyclohexane, tetrahydropyran, and chromane, wherein cyclobutane, cyclohexane and tetrahydropyran are unsubstituted or substituted with one to six substituents selected from $R^b$.

In another embodiment, one of A and B is independently selected from the group consisting of: phenyl, and pyridine, wherein phenyl and pyridine are unsubstituted or substituted with one to four substituents selected from $R^a$, and the other of A and B is independently selected from the group consisting of cyclobutane, cyclohexane, and tetrahydropyran, wherein cyclobutane, cyclohexane and tetrahydropyran are unsubstituted or substituted with one to six substituents selected from $R^b$.

In one embodiment, A is selected from the group consisting of aryl, and heteroaryl, wherein aryl and heteroaryl are unsubstituted or substituted with one to five substituents selected from $R^a$.

In another embodiment, A is selected from the group consisting of: phenyl, pyridine, and thiazole, wherein phenyl, pyridine and thiazole are unsubstituted or substituted with one to five substituents selected from $R^a$.

In another embodiment, A is selected from the group consisting of phenyl, and pyridine, wherein phenyl and pyridine are unsubstituted or substituted with one to four substituents selected from $R^a$.

In one embodiment, B is independently selected from the group consisting of: $—C_{3-12}$cycloalkyl, $—C_{2-11}$cycloheteroalkyl, $—C_{1-6}$alkyl-$C_{3-12}$cycloalkyl, $—C_{1-6}$alkyl-$C_{2-11}$cycloheteroalkyl, $—C_{1-6}$alkyl-O—$C_{3-12}$cycloalkyl, and $—C_{1-6}$alkyl-O—$C_{2-11}$cycloheteroalkyl, wherein alkyl, cycloalkyl and cycloheteroalkyl are unsubstituted or substituted with one to six substituents selected from $R^b$.

In another embodiment, B is independently selected from the group consisting of: $—C_{3-10}$cycloalkyl, $—C_{2-9}$cycloheteroalkyl, $—C_{1-6}$alkyl-$C_{3-12}$cycloalkyl, $—C_{1-6}$alkyl-$C_{2-11}$cycloheteroalkyl, $—C_{1-6}$alkyl-O—$C_{3-12}$cycloalkyl, and $—C_{1-6}$alkyl-O—$C_{2-11}$cycloheteroalkyl, wherein alkyl, cycloalkyl and cycloheteroalkyl are unsubstituted or substituted with one to six substituents selected from $R^b$.

In another embodiment, B is independently selected from the group consisting of: $—C_{3-12}$cycloalkyl, and $—C_{2-11}$cycloheteroalkyl, wherein cycloalkyl and cycloheteroalkyl are unsubstituted or substituted with one to six substituents selected from $R^b$.

In another embodiment, B is independently selected from the group consisting of: $—C_{3-10}$cycloalkyl, and $—C_{2-9}$cycloheteroalkyl, wherein cycloalkyl and cycloheteroalkyl are unsubstituted or substituted with one to six substituents selected from $R^b$.

In another embodiment, B is independently selected from the group consisting of: cyclopropane, cyclobutane, cyclopentane, cyclohexane, bicyclo[3.2.1]octane, bicyclo[3.1.0]hexane, bicyclo[2.2.2]octane, spiro[2.5]octane, bicyclo[1.1.1]pentane, spiro[3.3]heptane, spiro[2.3]hexane, spiro[2.2]pentane, piperidine, tetrahydropyran, and chromane, wherein B is unsubstituted or substituted with one to six substituents selected from $R^b$.

In another embodiment, B is independently selected from the group consisting of: cyclopropane, cyclobutane, cyclopentane, cyclohexane, bicyclo[3.2.1]octane, bicyclo[3.1.0]hexane, bicyclo[2.2.2]octane, spiro[2.5]octane, bicyclo[1.1.1]pentane, spiro[3.3]heptane, spiro[2.3]hexane, spiro[2.2]pentane, piperidine, and tetrahydropyran, wherein B is unsubstituted or substituted with one to six substituents selected from $R^b$.

In another embodiment, B is independently selected from the group consisting of: cyclobutane, cyclohexane, and tetrahydropyran, wherein cyclobutane, cyclohexane, tetrahydropyran, and chromane are unsubstituted or substituted with one to six substituents selected from $R^b$.

In another embodiment, B is independently selected from the group consisting of: cyclobutane, cyclohexane, and tetrahydropyran, wherein cyclobutane, cyclohexane and tetrahydropyran are unsubstituted or substituted with one to six substituents selected from $R^b$.

In one embodiment, $R^1$ is selected from the group consisting of: hydrogen, $—C_{1-6}$alkyl, $—C_{2-6}$alkenyl, $—C_{2-6}$alkynyl, $—C_{3-6}$cycloalkyl, $—C_{2-6}$cycloheteroalkyl, $—C_{1-6}$alkyl-O—$C_{1-6}$alkyl-, $—(CH_2)_tC(O)R^j$, $—(CH_2)_tC(O)NR^eR^j$, $—(CH_2)_nNR^eC(O)R^j$, $—(CH_2)_nNR^eC(O)OR^j$, $—(CH_2)_nNR^eC(O)N(R^e)_2$, $—(CH_2)_nNR^eC(O)NR^eR^j$, $—(CH_2)_nNR^eS(O)_mR^j$, $—(CH_2)_nNR^eS(O)mN(R^e)_2$, $—(CH_2)_nNR^eS(O)mNR^eR^j$, and $—(CH_2)_nNR^eR^j$, wherein each $CH_2$, alkyl, alkenyl, alkynyl, cycloalkyl and cycloheteroalkyl is unsubstituted or substituted with one to five substituents selected from $R^c$.

In another embodiment, $R^1$ is selected from the group consisting of: hydrogen, $—C_{1-6}$alkyl, $—C_{2-6}$alkenyl, $—C_{2-6}$alkynyl, $—C_{3-6}$cycloalkyl, and $—C_{2-6}$cycloheteroalkyl, wherein each alkyl, alkenyl, alkynyl, cycloalkyl and cycloheteroalkyl is unsubstituted or substituted with one to five substituents selected from $R^c$.

In another embodiment, $R^1$ is selected from the group consisting of: hydrogen, $—C_{1-6}$alkyl, and $—C_{3-6}$cycloalkyl, wherein each alkyl and cycloalkyl is unsubstituted or substituted with one to five substituents selected from $R^c$. In a class of this embodiment, $R^1$ is selected from the group consisting of: hydrogen, $—CH_3$, and cyclopropyl, wherein each alkyl and cycloalkyl is unsubstituted or substituted with one to three substituents selected from $R^c$.

In another embodiment, $R^1$ is selected from the group consisting of: hydrogen, and $—C_{1-6}$alkyl, wherein each alkyl is unsubstituted or substituted with one to five substituents selected from $R^c$. In a class of this embodiment, $R^1$ is selected from the group consisting of: hydrogen, and $—CH_3$, wherein $—CH_3$ is unsubstituted or substituted with one to three substituents selected from $R^c$. In another class of this embodiment, $R^1$ is hydrogen.

In another embodiment, $R^1$ is $—C_{1-6}$alkyl, wherein alkyl is unsubstituted or substituted with one to five substituents selected from $R^c$. In a class of this embodiment, $R^1$ is $—CH_3$, wherein $—CH_3$ is unsubstituted or substituted with one to three substituents selected from $R^c$.

In one embodiment, $R^2$ is selected from the group consisting of: hydrogen, $—C_{1-6}$alkyl, $—C_{2-6}$alkenyl, $—C_{2-6}$alkynyl, $—C_{3-6}$cycloalkyl, $—C_{2-6}$cycloheteroalkyl, $—C_{1-6}$alkyl-O—$C_{1-6}$alkyl-, $—(CH_2)_sC(O)R^j$, $—(CH_2)_sC(O)NR^eR^j$, $—(CH_2)_sNR^eC(O)R^j$, $—(CH_2)_sNR^eC(O)OR^j$, $—(CH_2)_sNR^eC(O)N(R^e)_2$, $—(CH_2)_sNR^eC(O)NR^eR^j$, $—(CH_2)_sNR^eS(O)_mR^j$, $—(CH_2)_sNR^eS(O)mN(R^e)_2$, $—(CH_2)_sNR^eS(O)mNR^eR^j$, and $—(CH_2)_sNR^eR^j$, wherein each $CH_2$, alkyl, alkenyl, alkynyl, cycloalkyl, and cycloheteroalkyl is unsubstituted or substituted with one to five substituents selected from $R^d$, wherein $R^2$ and $R^3$ and the carbon atoms they are connected to can form a $—C_{3-5}$cycloalkyl ring, and wherein $R^2$ and $R^4$ and the carbon atoms they are connected to can form a $—C_{3-5}$cycloalkyl ring.

In another embodiment, $R^2$ is selected from the group consisting of: hydrogen, $—C_{1-6}$alkyl, $—C_{2-6}$alkenyl, $—C_{2-6}$alkynyl, $—C_{3-6}$cycloalkyl, $—C_{2-6}$cycloheteroalkyl, $—C_{1-6}$alkyl-O—$C_{1-6}$alkyl-, $—(CH_2)_sC(O)R^j$, $—(CH_2)_sC(O)NR^eR^j$, $—(CH_2)_sNR^eC(O)R^j$, $—(CH_2)_sNR^eC(O)OR^j$, $—(CH_2)_sNR^eC(O)N(R^e)_2$, $—(CH_2)_sNR^eC(O)NR^eR^j$, $—(CH_2)_sNR^eS(O)_mR^j$, $—(CH_2)_sNR^eS(O)mN(R^e)_2$, $—(CH_2)_sNR^eS(O)mNR^eR^j$, and $—(CH_2)SNR^eR^j$, wherein each $CH_2$, alkyl, alkenyl, alkynyl, cycloalkyl, and cycloheteroalkyl is unsubstituted or substituted with one to five substituents selected from $R^d$, wherein $R^2$ and $R^3$ and the carbon atoms they are connected to can form a $—C_{3-5}$cycloalkyl ring, and wherein $R^2$ and $R^4$ and the carbon atoms they are connected to can form a $—C_{3-5}$cycloalkyl ring.

In another embodiment, $R^2$ is selected from the group consisting of: hydrogen, deuterium, $—C_{1-6}$alkyl, $—C_{2-6}$alkenyl, $—C_{2-6}$alkynyl, $—C_{3-6}$cycloalkyl, $—C_{2-6}$cycloheteroalkyl, $—C_{1-6}$alkyl-O—$C_{1-6}$alkyl-, $—(CH_2)_sC(O)R^j$, $—(CH_2)_sC(O)NR^eR^j$, $—(CH_2)_sNR^eC(O)R^j$, $—(CH_2)_sNR^eC(O)OR^j$, $—(CH_2)_sNR^eC(O)N(R^e)_2$, $—(CH_2)_sNR^eC(O)NR^eR^j$, $—(CH_2)_sNR^eS(O)_mR^j$, $—(CH_2)_sNR^eS(O)mN(R^e)_2$, $—(CH_2)_sNR^eS(O)mNR^eR^j$, and $—(CH_2)SNR^eR^j$, wherein each $CH_2$, alkyl, alkenyl, alkynyl, cycloalkyl, and cycloheteroalkyl is unsubstituted or substituted with one to five substituents selected from $R^d$, and wherein $R^2$ and $R^3$ and the carbon atoms they are connected to can form a $—C_{3-5}$cycloalkyl ring.

In another embodiment, $R^2$ is selected from the group consisting of: hydrogen, $—C_{1-6}$alkyl, $—C_{2-6}$alkenyl, $—C_{2-6}$alkynyl, $—C_{3-6}$cycloalkyl, $—C_{2-6}$cycloheteroalkyl, $—C_{1-6}$alkyl-O—$C_{1-6}$alkyl-, $—(CH_2)_sC(O)R^j$, $—(CH_2)_sC(O)NR^eR^j$, $—(CH_2)_sNR^eC(O)R^j$, $—(CH_2)_sNR^eC(O)OR^j$, $—(CH_2)_sNR^eC(O)N(R^e)_2$, $—(CH_2)_sNR^eC(O)NR^eR^j$, $—(CH_2)_sNR^eS(O)_mR^j$, $—(CH_2)_sNR^eS(O)mN(R^e)_2$, $—(CH_2)_sNR^eS(O)mNR^eR^j$, and $—(CH_2)SNR^eR^j$, wherein each $CH_2$, alkyl, alkenyl, alkynyl, cycloalkyl, and cycloheteroalkyl is unsubstituted or substituted with one to five substituents selected from $R^d$, and wherein $R^2$ and $R^3$ and the carbon atoms they are connected to can form a $—C_{3-5}$cycloalkyl ring.

In another embodiment, $R^2$ is selected from the group consisting of: hydrogen, deuterium, $—C_{1-6}$alkyl, $—C_{2-6}$alkenyl, $—C_{2-6}$alkynyl, $—C_{3-6}$cycloalkyl, $—C_{2-6}$cycloheteroalkyl, $—C_{1-6}$alkyl-O—$C_{1-6}$alkyl-, $—(CH_2)_sC(O)R^j$, $—(CH_2)_sC(O)NR^eR^j$, $—(CH_2)_sNR^eC(O)R^j$, $—(CH_2)_sNR^eC(O)OR^j$, $—(CH_2)_sNR^eC(O)N(R^e)_2$, $—(CH_2)_sNR^eC(O)NR^eR^j$, $—(CH_2)_sNR^eS(O)_mR^j$, $—(CH_2)_sNR^eS(O)mN(R^e)_2$, $—(CH_2)_sNR^eS(O)mNR^eR^j$, and $—(CH_2)SNR^eR^j$, wherein each $CH_2$, alkyl, alkenyl, alkynyl, cycloalkyl, and cycloheteroalkyl is unsubstituted or substituted with one to five substituents selected from $R^d$, and wherein $R^2$ and $R^4$ and the carbon atoms they are connected to can form a $—C_{3-5}$cycloalkyl ring.

In another embodiment, $R^2$ is selected from the group consisting of: hydrogen, $—C_{1-6}$alkyl, $—C_{2-6}$alkenyl, $—C_{2-6}$alkynyl, $—C_{3-6}$cycloalkyl, $—C_{2-6}$cycloheteroalkyl, $—C_{1-6}$alkyl-O—$C_{1-6}$alkyl-, $—(CH_2)_sC(O)R^j$, $—(CH_2)_sC(O) NR^eR^j$, $—(CH_2)_sNR^eC(O)R^j$, $—(CH_2)_sNR^eC(O)OR^j$, $—(CH_2)_sNR^eC(O)N(R^e)_2$, $—(CH_2)_sNR^eC(O)NR^eR^j$, $—(CH_2)_sNR^eS(O)_mR^j$, $—(CH_2)_sNR^eS(O)mN(R^e)_2$, $—(CH_2)_sNR^eS(O)mNR^eR^j$, and $—(CH_2)SNR^eR^j$, wherein each $CH_2$, alkyl, alkenyl, alkynyl, cycloalkyl, and cycloheteroalkyl is unsubstituted or substituted with one to five substituents selected from $R^d$, and wherein $R^2$ and $R^4$ and the carbon atoms they are connected to can form a $—C_{3-5}$cycloalkyl ring.

In another embodiment, $R^2$ is selected from the group consisting of: hydrogen, deuterium, $—C_{1-6}$alkyl, $—C_{2-6}$alkenyl, $—C_{2-6}$alkynyl, $—C_{3-6}$cycloalkyl, $—C_{2-6}$cycloheteroalkyl, $—C_{1-6}$alkyl-O—$C_{1-6}$alkyl-, $—(CH_2)_sC(O)R^j$, $—(CH_2)_sC(O)NR^eR^j$, $—(CH_2)_sNR^eC(O)R^j$, $—(CH_2)_sNR^eC(O)OR^j$, $—(CH_2)_sNR^eC(O)N(R^e)_2$, $—(CH_2)_sNR^eC(O)NR^eR^j$, $—(CH_2)_sNR^eS(O)_mR^j$, $—(CH_2)_sNR^eS(O)mN(R^e)_2$, $—(CH_2)_sNR^eS(O)mNR^eR^j$, and $—(CH_2)_sNR^eR^j$, wherein each $CH_2$, alkyl, alkenyl, alkynyl, cycloalkyl, and cycloheteroalkyl is unsubstituted or substituted with one to five substituents selected from $R^d$.

In another embodiment, $R^2$ is selected from the group consisting of: hydrogen, $—C_{1-6}$alkyl, $—C_{2-6}$alkenyl, $—C_{2-6}$alkynyl, $—C_{3-6}$cycloalkyl, $—C_{2-6}$cycloheteroalkyl, $—C_{1-6}$alkyl-O—$C_{1-6}$alkyl-, $—(CH_2)_sC(O)R^j$, $—(CH_2)_sC(O)NR^eR^j$, $—(CH_2)_sNR^eC(O)R$, $—(CH_2)_sNR^eC(O)OR^j$, $—(CH_2)_sNR^eC(O)N(R^e)_2$, $—(CH_2)_sNR^eC(O)NR^eR^j$, $—(CH_2)_sNR^eS(O)_mR^j$, $—(CH_2)_sNR^eS(O)mN(R^e)_2$, $—(CH_2)_sNR^eS(O)mNR^eR^j$, and $—(CH_2)_sNR^eR^j$, wherein each $CH_2$, alkyl, alkenyl, alkynyl, cycloalkyl, and cycloheteroalkyl is unsubstituted or substituted with one to five substituents selected from $R^d$.

In another embodiment, $R^2$ is selected from the group consisting of: hydrogen, deuterium, $—C_{1-6}$alkyl, $—C_{2-6}$alkenyl, $—C_{2-6}$alkynyl, $—C_{3-6}$cycloalkyl, and $—C_{2-6}$cycloheteroalkyl, wherein each alkyl, alkenyl, alkynyl, cycloalkyl, and cycloheteroalkyl is unsubstituted or substituted with one to five substituents selected from $R^d$.

In another embodiment, $R^2$ is selected from the group consisting of hydrogen, $—C_{1-6}$alkyl, $—C_{2-6}$alkenyl, $—C_{2-6}$alkynyl, $—C_{3-6}$cycloalkyl, and $—C_{2-6}$cycloheteroalkyl, wherein each alkyl, alkenyl, alkynyl, cycloalkyl, and cycloheteroalkyl is unsubstituted or substituted with one to five substituents selected from $R^d$.

In another embodiment, $R^2$ is selected from the group consisting of: hydrogen, deuterium, —$C_{1-6}$alkyl, and —$C_{3-6}$cycloalkyl, wherein each alkyl and cycloalkyl is unsubstituted or substituted with one to five substituents selected from $R^d$. In a class of this embodiment, $R^2$ is selected from the group consisting of: hydrogen, deuterium, —$CH_3$, and cyclopropyl, wherein each alkyl and cycloalkyl is unsubstituted or substituted with one to five substituents selected from $R^d$.

In another embodiment, $R^2$ is selected from the group consisting of hydrogen, —$C_{1-6}$alkyl, and —$C_{3-6}$cycloalkyl, wherein each alkyl and cycloalkyl is unsubstituted or substituted with one to five substituents selected from $R^d$. In a class of this embodiment, $R^2$ is selected from the group consisting of: hydrogen, —$CH_3$, and cyclopropyl, wherein each alkyl and cycloalkyl is unsubstituted or substituted with one to five substituents selected from $R^d$.

In another embodiment, $R^2$ is selected from the group consisting of: hydrogen, deuterium, and —$C_{1-6}$alkyl, wherein each alkyl and cycloalkyl is unsubstituted or substituted with one to five substituents selected from $R^d$. In a class of this embodiment, $R^2$ is selected from the group consisting of: hydrogen, deuterium, and —$CH_3$, wherein each —$CH_3$ is unsubstituted or substituted with one to three substituents selected from $R^d$. In another embodiment, $R^2$ is hydrogen. In another embodiment, $R^2$ is deuterium.

In another embodiment, $R^2$ is selected from the group consisting of hydrogen, and —$C_{1-6}$alkyl, wherein each alkyl and cycloalkyl is unsubstituted or substituted with one to five substituents selected from $R^d$. In a class of this embodiment, $R^2$ is selected from the group consisting of: hydrogen, and —$CH_3$, wherein each —$CH_3$ is unsubstituted or substituted with one to three substituents selected from $R^d$.

In another embodiment, $R^2$ is —$C_{1-6}$alkyl, wherein each alkyl and cycloalkyl is unsubstituted or substituted with one to five substituents selected from $R^d$. In a class of this embodiment, $R^2$ is —$CH_3$, wherein —$CH_3$ is unsubstituted or substituted with one to three substituents selected from $R^d$.

In one embodiment, $R^3$ is selected from the group consisting of: hydrogen, deuterium, —$C_{1-6}$alkyl, —$C_{2-6}$alkenyl, —$C_{2-6}$alkynyl, —$C_{3-6}$cycloalkyl, —$C_{2-6}$cycloheteroalkyl, —$C_{1-6}$alkyl-O—$C_{1-6}$alkyl-, —$(CH_2)_sC(O)R^j$, —$(CH_2)_sC(O)NR^eR^j$, —$(CH_2)_sNR^eC(O)R^j$, —$(CH_2)_sNR^eC(O)OR^j$, —$(CH_2)_sNR^eC(O)N(R^e)_2$, —$(CH_2)_sNR^eC(O)NR^eR^j$, —$(CH_2)_sNR^eS(O)_mR^j$, —$(CH_2)_sNR^eS(O)mN(R^e)_2$, —$(CH_2)_sNR^eS(O)mNR^eR^j$, and —$(CH_2)_sNR^eR^j$, wherein each $CH_2$, alkyl, alkenyl, alkynyl, cycloalkyl, and cycloheteroalkyl is unsubstituted or substituted with one to five substituents selected from $R^d$.

In another embodiment, $R^3$ is selected from the group consisting of: hydrogen, —$C_{1-6}$alkyl, —$C_{2-6}$alkenyl, —$C_{2-6}$alkynyl, —$C_{3-6}$cycloalkyl, —$C_{2-6}$cycloheteroalkyl, —$C_{1-6}$alkyl-O—$C_{1-6}$alkyl-, —$(CH_2)_sC(O)R^j$, —$(CH_2)_sC(O)NR^eR^j$, —$(CH_2)_sNR^eC(O)R^j$, —$(CH_2)_sNR^eC(O)OR^j$, —$(CH_2)_sNR^eC(O)N(R^e)_2$, —$(CH_2)_sNR^eC(O)NR^eR^j$, —$(CH_2)_sNR^eS(O)_mR^j$, —$(CH_2)_sNR^eS(O)mN(R^e)_2$, —$(CH_2)_sNR^eS(O)mNR^eR^j$, and —$(CH_2)_sNR^eR^j$, wherein each $CH_2$, alkyl, alkenyl, alkynyl, cycloalkyl, and cycloheteroalkyl is unsubstituted or substituted with one to five substituents selected from $R^d$.

In another embodiment, $R^3$ is selected from the group consisting of: hydrogen, deuterium, —$C_{1-6}$alkyl, —$C_{2-6}$alkenyl, —$C_{2-6}$alkynyl, —$C_{3-6}$cycloalkyl, and —$C_{2-6}$cycloheteroalkyl, wherein each alkyl, alkenyl, alkynyl, cycloalkyl, and cycloheteroalkyl is unsubstituted or substituted with one to five substituents selected from $R^d$.

In another embodiment, $R^3$ is selected from the group consisting of: hydrogen, —$C_{1-6}$alkyl, —$C_{2-6}$alkenyl, —$C_{2-6}$alkynyl, —$C_{3-6}$cycloalkyl, and —$C_{2-6}$cyclo-heteroalkyl, wherein each alkyl, alkenyl, alkynyl, cycloalkyl, and cycloheteroalkyl is unsubstituted or substituted with one to five substituents selected from $R^d$.

In another embodiment, $R^3$ is selected from the group consisting of: hydrogen, deuterium, —$C_{1-6}$alkyl, and —$C_{3-6}$cycloalkyl, wherein each alkyl, and cycloalkyl is unsubstituted or substituted with one to five substituents selected from $R^d$. In a class of this embodiment, $R^3$ is selected from the group consisting of: hydrogen, deuterium, —$CH_3$, and cyclopropyl, wherein cyclopropyl is unsubstituted or substituted with one to three substituents selected from $R^d$.

In another embodiment, $R^3$ is selected from the group consisting of hydrogen, —$C_{1-6}$alkyl, and —$C_{3-6}$cycloalkyl, wherein each alkyl, and cycloalkyl is unsubstituted or substituted with one to five substituents selected from $R^d$. In a class of this embodiment, $R^3$ is selected from the group consisting of hydrogen, —$CH_3$, and cyclopropyl, wherein cyclopropyl is unsubstituted or substituted with one to three substituents selected from $R^d$.

In another embodiment, $R^3$ is selected from the group consisting of: hydrogen, deuterium, and —$C_{1-6}$alkyl, wherein each alkyl is unsubstituted or substituted with one to five substituents selected from $R^d$. In a class of this embodiment, $R^3$ is selected from the group consisting of: hydrogen, deuterium, and —$CH_3$, wherein $CH_3$ is unsubstituted or substituted with one to three substituents selected from $R^d$. In another class of this embodiment, $R^3$ is hydrogen. In another class of this embodiment, $R^3$ is deuterium.

In another embodiment, $R^3$ is selected from the group consisting of: hydrogen, and —$C_{1-6}$alkyl, wherein each alkyl is unsubstituted or substituted with one to five substituents selected from $R^d$. In a class of this embodiment, $R^3$ is selected from the group consisting of hydrogen, and —$CH_3$, wherein $CH_3$ is unsubstituted or substituted with one to three substituents selected from $R^d$. In another class of this embodiment, $R^3$ is hydrogen.

In another embodiment, $R^3$ is —$C_{1-6}$alkyl, wherein each alkyl is unsubstituted or substituted with one to five substituents selected from $R^d$. In a class of this embodiment, $R^3$ is —$CH_3$, wherein —$CH_3$ is unsubstituted or substituted with one to three substituents selected from $R^d$.

In one embodiment, $R^4$ is selected from the group consisting of: hydrogen, deuterium, —$C_{1-6}$alkyl, —$C_{2-6}$alkenyl, —$C_{2-6}$alkynyl, —$C_{3-6}$cycloalkyl, —$C_{2-6}$cycloheteroalkyl, —$C_{1-6}$alkyl-O—$C_{1-6}$alkyl-, —$(CH_2)_sC(O)R^j$, —$(CH_2)_sC(O)NR^eR^j$, —$(CH_2)_sNR^eC(O)R^j$, —$(CH_2)_sNR^eC(O)OR^j$, —$(CH_2)_sNR^eC(O)N(R^e)_2$, —$(CH_2)_sNR^eC(O)NR^eR^j$, —$(CH_2)_sNR^eS(O)_mR^j$, —$(CH_2)_sNR^eS(O)mN(R^e)_2$, —$(CH_2)_sNR^eS(O)mNR^eR^j$, and —$(CH_2)_sNR^eR^j$, wherein each $CH_2$, alkyl, alkenyl, alkynyl, cycloalkyl, and cycloheteroalkyl is unsubstituted or substituted with one to five substituents selected from $R^f$, and wherein $R^4$ and $R^5$ and the carbon atoms they are connected to can form a —$C_{3-5}$cycloalkyl ring.

In another embodiment, $R^4$ is selected from the group consisting of: hydrogen, —$C_{1-6}$alkyl, —$C_{2-6}$alkenyl, —$C_{2-6}$alkynyl, —$C_{3-6}$cycloalkyl, —$C_{2-6}$cycloheteroalkyl, —$C_{1-6}$alkyl-O—$C_{1-6}$alkyl-, —$(CH_2)_sC(O)$ $R^j$, —$(CH_2)_sC(O)NR^eR^j$, —$(CH_2)_sNR^eC(O)R^j$, —$(CH_2)_sNR^eC(O)OR^j$, —$(CH_2)_sNR^eC(O)N(R^e)_2$, —$(CH_2)_sNR^eC(O)NR^eR^j$, —$(CH_2)_sNR^eS(O)_mR^j$, —$(CH_2)_sNR^eS(O)mN(R^e)_2$, —$(CH_2)_sNR^eS(O)mNR^eR^j$, and —$(CH_2)SNR^eR^j$, wherein each $CH_2$, alkyl, alkenyl, alkynyl, cycloalkyl, and cycloheteroalkyl is unsubstituted or substituted with one to five substituents selected from $R^f$, and wherein $R^4$ and $R^5$ and the carbon atoms they are connected to can form a $-C_{3-5}$cycloalkyl ring.

In another embodiment, $R^4$ is selected from the group consisting of: hydrogen, deuterium, $-C_{1-6}$alkyl, $-C_{2-6}$alkenyl, $-C_{2-6}$alkynyl, $-C_{3-6}$cycloalkyl, $-C_{2-6}$cycloheteroalkyl, $-C_{1-6}$alkyl-O$-C_{1-6}$alkyl-, $-(CH_2)_sC(O)R^j$, $-(CH_2)_sC(O)NR^eR^j$, $-(CH_2)_sNR^eC(O)R^j$, $-(CH_2)_sNR^eC(O)OR^j$, $-(CH_2)_sNR^eC(O)N(R^e)_2$, $-(CH_2)_sNR^eC(O)NR^eR^j$, $-(CH_2)_sNR^eS(O)_mR^j$, $-(CH_2)_sNR^eS(O)mN(R^e)_2$, $-(CH_2)_sNR^eS(O)mNR^eR^j$, and $-(CH_2)_sNR^eR^j$, wherein each $CH_2$, alkyl, alkenyl, alkynyl, cycloalkyl, and cycloheteroalkyl is unsubstituted or substituted with one to five substituents selected from $R^f$.

In another embodiment, $R^4$ is selected from the group consisting of: hydrogen, $-C_{1-6}$alkyl, $-C_{2-6}$alkenyl, $-C_{2-6}$alkynyl, $-C_{3-6}$cycloalkyl, $-C_{2-6}$cycloheteroalkyl, $-C_{1-6}$alkyl-O$-C_{1-6}$alkyl-, $-(CH_2)_sC(O)R^j$, $-(CH_2)_sC(O)NR^eR^j$, $-(CH_2)_sNR^eC(O)R$, $-(CH_2)_sNR^eC(O)OR^j$, $-(CH_2)_sNR^eC(O)N(R^e)_2$, $-(CH_2)_sNR^eC(O)NR^eR^j$, $-(CH_2)_sNR^eS(O)_mR^j$, $-(CH_2)_sNR^eS(O)mN(R^e)_2$, $-(CH_2)_sNR^eS(O)mNR^eR^j$, and $-(CH_2)_sNR^eR^j$, wherein each $CH_2$, alkyl, alkenyl, alkynyl, cycloalkyl, and cycloheteroalkyl is unsubstituted or substituted with one to five substituents selected from $R^f$.

In another embodiment, $R^4$ is selected from the group consisting of: hydrogen, deuterium, $-C_{1-6}$alkyl, $-C_{2-6}$alkenyl, $-C_{2-6}$alkynyl, $-C_{3-6}$cycloalkyl, and $-C_{2-6}$cycloheteroalkyl, wherein each alkyl, alkenyl, alkynyl, cycloalkyl, and cycloheteroalkyl is unsubstituted or substituted with one to five substituents selected from $R^f$.

In another embodiment, $R^4$ is selected from the group consisting of: hydrogen, $-C_{1-6}$alkyl, $-C_{2-6}$alkenyl, $-C_{2-6}$alkynyl, $-C_{3-6}$cycloalkyl, and $-C_{2-6}$cycloheteroalkyl, wherein each alkyl, alkenyl, alkynyl, cycloalkyl, and cycloheteroalkyl is unsubstituted or substituted with one to five substituents selected from $R^f$.

In another embodiment, $R^4$ is selected from the group consisting of: hydrogen, deuterium, $-C_{1-6}$alkyl, and $-C_{3-6}$cycloalkyl, wherein each alkyl and cycloalkyl is unsubstituted or substituted with one to five substituents selected from $R^f$. In a class of this embodiment, $R^4$ is selected from the group consisting of: hydrogen, deuterium, $-CH_3$, and cyclopropyl, wherein each $-CH_3$ and cyclopropyl is unsubstituted or substituted with one to three substituents selected from $R^f$.

In another embodiment, $R^4$ is selected from the group consisting of: hydrogen, $-C_{1-6}$alkyl, and $-C_{3-6}$cycloalkyl, wherein each alkyl and cycloalkyl is unsubstituted or substituted with one to five substituents selected from $R^f$. In a class of this embodiment, $R^4$ is selected from the group consisting of: hydrogen, $-CH_3$, and cyclopropyl, wherein each $-CH_3$ and cyclopropyl is unsubstituted or substituted with one to three substituents selected from $R^f$.

In another embodiment, $R^4$ is selected from the group consisting of: hydrogen, deuterium, and $-C_{1-6}$alkyl, wherein each alkyl is unsubstituted or substituted with one to five substituents selected from $R^f$. In a class of this embodiment, $R^4$ is hydrogen. In another class of this embodiment, $R^4$ is deuterium. In another class of this embodiment, $R^4$ is $-CH_3$, wherein $-CH_3$ is unsubstituted or substituted with one to three substituents selected from $R^f$.

In another embodiment, $R^4$ is selected from the group consisting of: hydrogen, and $-C_{1-6}$alkyl, wherein each alkyl is unsubstituted or substituted with one to five substituents selected from $R^f$. In a class of this embodiment, $R^4$ is hydrogen. In another class of this embodiment, $R^4$ is $-CH_3$, wherein $-CH_3$ is unsubstituted or substituted with one to three substituents selected from $R^f$.

In another embodiment, $R^4$ is $-C_{1-6}$alkyl, wherein each alkyl is unsubstituted or substituted with one to five substituents selected from $R^f$. In a class of this embodiment, $R^4$ is $-CH_3$, wherein $-CH_3$ is unsubstituted or substituted with one to three substituents selected from $R^f$.

In one embodiment, $R^5$ is selected from the group consisting of: hydrogen, deuterium, $-C_{1-6}$alkyl, $-C_{2-6}$alkenyl, $-C_{2-6}$alkynyl, $-C_{3-6}$cycloalkyl, $-C_{2-6}$cycloheteroalkyl, $-C_{1-6}$alkyl-O$-C_{1-6}$alkyl-, $-(CH_2)_sC(O)R^j$, $-(CH_2)_sC(O)NR^eR^j$, $-(CH_2)_sNR^eC(O)R^j$, $-(CH_2)_sNR^eC(O)OR^j$, $-(CH_2)_sNR^eC(O)N(R^e)_2$, $-(CH_2)_sNR^eC(O)NR^eR^j$, $-(CH_2)_sNR^eS(O)_mR^j$, $-(CH_2)_sNR^eS(O)mN(R^e)_2$, $-(CH_2)_sNR^eS(O)mNR^eR^j$, and $-(CH_2)_sNR^eR^j$, wherein each $CH_2$, alkyl, alkenyl, alkynyl, cycloalkyl, and cycloheteroalkyl is unsubstituted or substituted with one to five substituents selected from $R^f$, and wherein $R^5$ and $R^7$ and the carbon atoms they are attached to may form a 4-, 5- or 6-membered saturated ring.

In another embodiment, $R^5$ is selected from the group consisting of: hydrogen, $-C_{1-6}$alkyl, $-C_{2-6}$alkenyl, $-C_{2-6}$alkynyl, $-C_{3-6}$cycloalkyl, $-C_{2-6}$cycloheteroalkyl, $-C_{1-6}$alkyl-O$-C_{1-6}$alkyl-, $-(CH_2)_sC(O)R^j$, $-(CH_2)_sC(O)NR^eR^j$, $-(CH_2)_sNR^eC(O)R^j$, $-(CH_2)_sNR^eC(O)OR^j$, $-(CH_2)_sNR^eC(O)N(R^e)_2$, $-(CH_2)_sNR^eC(O)NR^eR^j$, $-(CH_2)_sNR^eS(O)_mR^j$, $-(CH_2)_sNR^eS(O)mN(R^e)_2$, $-(CH_2)_sNR^eS(O)mNR^eR^j$, and $-(CH_2)_sNR^eR^j$, wherein each $CH_2$, alkyl, alkenyl, alkynyl, cycloalkyl, and cycloheteroalkyl is unsubstituted or substituted with one to five substituents selected from $R^f$, and wherein $R^5$ and $R^7$ and the carbon atoms they are attached to may form a 4-, 5- or 6-membered saturated ring.

In another embodiment, $R^5$ is selected from the group consisting of: hydrogen, deuterium, $-C_{1-6}$alkyl, $-C_{2-6}$alkenyl, $-C_{2-6}$alkynyl, $-C_{3-6}$cycloalkyl, $-C_{2-6}$cycloheteroalkyl, $-C_{1-6}$alkyl-O$-C_{1-6}$alkyl-, $-(CH_2)_sC(O)R^j$, $-(CH_2)_sC(O)NR^eR^j$, $-(CH_2)_sNR^eC(O)R^j$, $-(CH_2)_sNR^eC(O)OR^j$, $-(CH_2)_sNR^eC(O)N(R^e)_2$, $-(CH_2)_sNR^eC(O)NR^eR^j$, $-(CH_2)_sNR^eS(O)_mR^j$, $-(CH_2)_sNR^eS(O)mN(R^e)_2$, $-(CH_2)_sNR^eS(O)mNR^eR^j$, and $-(CH_2)_sNR^eR^j$, wherein each $CH_2$, alkyl, alkenyl, alkynyl, cycloalkyl, and cycloheteroalkyl is unsubstituted or substituted with one to five substituents selected from $R^f$, and wherein $R^5$ and $R^7$ and the carbon atoms they are attached to may form a 5-membered saturated ring.

In another embodiment, $R^5$ is selected from the group consisting of: hydrogen, $-C_{1-6}$alkyl, $-C_{2-6}$alkenyl, $-C_{2-6}$alkynyl, $-C_{3-6}$cycloalkyl, $-C_{2-6}$cycloheteroalkyl, $-C_{1-6}$alkyl-O$-C_{1-6}$alkyl-, $-(CH_2)_sC(O)R^j$, $-(CH_2)_sC(O)NR^eR^j$, $-(CH_2)_sNR^eC(O)R^j$, $-(CH_2)_sNR^eC(O)OR^j$, $-(CH_2)_sNR^eC(O)N(R^e)_2$, $-(CH_2)_sNR^eC(O)NR^eR^j$, $-(CH_2)_sNR^eS(O)_mR^j$, $-(CH_2)_sNR^eS(O)mN(R^e)_2$, $-(CH_2)_sNR^eS(O)mNR^eR^j$, and $-(CH_2)_sNR^eR^j$, wherein each $CH_2$, alkyl, alkenyl, alkynyl, cycloalkyl, and cycloheteroalkyl is unsubstituted or substituted with one to five substituents selected from $R^f$, and wherein $R^5$ and $R^7$ and the carbon atoms they are attached to may form a 5-membered saturated ring.

In another embodiment, $R^5$ is selected from the group consisting of: hydrogen, deuterium, $-C_{1-6}$alkyl, $-C_{2-6}$alkenyl, $-C_{2-6}$alkynyl, $-C_{3-6}$cycloalkyl, $-C_{2-6}$cycloheteroalkyl, $-C_{1-6}$alkyl-O$-C_{1-6}$alkyl-, $-(CH_2)_sC(O)R^j$, $-(CH_2)_sC(O)NR^eR^j$, $-(CH_2)_sNR^eC(O)R^j$, $-(CH_2)_sNR^eC(O)OR^j$, $-(CH_2)_sNR^eC(O)N(R^e)_2$, $-(CH_2)_sNR^eC(O)NR^eR^j$, $-(CH_2)_sNR^eS(O)_mR^j$, $-(CH_2)_sNR^eS(O)mN(R^e)_2$, $-(CH_2)_sNR^eS(O)mNR^eR^j$, and $-(CH_2)_sNR^eR^j$, wherein each $CH_2$, alkyl, alkenyl, alkynyl, cycloalkyl, and cycloheteroalkyl is unsubstituted or substituted with one to five substituents selected from $R^f$.

In another embodiment, $R^5$ is selected from the group consisting of: hydrogen, —$C_{1-6}$alkyl, —$C_{2-6}$alkenyl, —$C_{2-6}$alkynyl, —$C_{3-6}$cycloalkyl, —$C_{2-6}$cycloheteroalkyl, —$C_{1-6}$alkyl-O—$C_{1-6}$alkyl-, —$(CH_2)_sC(O)R^j$, —$(CH_2)_sC(O)NR^eR^j$, —$(CH_2)_sNR^eC(O)R$, —$(CH_2)_sNR^eC(O)OR^j$, —$(CH_2)_sNR^eC(O)N(R^e)_2$, —$(CH_2)_sNR^eC(O)NR^eR^j$, —$(CH_2)_sNR^eS(O)_mR^j$, —$(CH_2)_sNR^eS(O)mN(R^e)_2$, —$(CH_2)_sNR^eS(O)mNR^eR^j$, and —$(CH_2)_sNR^eR^j$, wherein each $CH_2$, alkyl, alkenyl, alkynyl, cycloalkyl, and cycloheteroalkyl is unsubstituted or substituted with one to five substituents selected from $R^f$.

In another embodiment, $R^5$ is selected from the group consisting of: hydrogen, deuterium, —$C_{1-6}$alkyl, —$C_{2-6}$alkenyl, —$C_{2-6}$alkynyl, —$C_{3-6}$cycloalkyl, and —$C_{2-6}$cycloheteroalkyl, wherein each alkyl, alkenyl, alkynyl, cycloalkyl, and cycloheteroalkyl is unsubstituted or substituted with one to five substituents selected from $R^f$.

In another embodiment, $R^5$ is selected from the group consisting of: hydrogen, —$C_{1-6}$alkyl, —$C_{2-6}$alkenyl, —$C_{2-6}$alkynyl, —$C_{3-6}$cycloalkyl, and —$C_{2-6}$cycloheteroalkyl, wherein each alkyl, alkenyl, alkynyl, cycloalkyl, and cycloheteroalkyl is unsubstituted or substituted with one to five substituents selected from $R^f$.

In another embodiment, $R^5$ is selected from the group consisting of: hydrogen, deuterium, —$C_{1-6}$alkyl, and —$C_{3-6}$cycloalkyl, wherein alkyl and cycloalkyl is unsubstituted or substituted with one to five substituents selected from $R^f$. In a class of this embodiment, $R^5$ is selected from the group consisting of: hydrogen, —$CH_3$, and cyclopropyl, wherein each $CH_3$ and cyclopropyl is unsubstituted or substituted with one to three substituents selected from $R^f$.

In another embodiment, $R^5$ is selected from the group consisting of: hydrogen, —$C_{1-6}$alkyl, and —$C_{3-6}$cycloalkyl, wherein alkyl and cycloalkyl is unsubstituted or substituted with one to five substituents selected from $R^f$. In a class of this embodiment, $R^5$ is selected from the group consisting of: hydrogen, —$CH_3$, and cyclopropyl, wherein each $CH_3$ and cyclopropyl is unsubstituted or substituted with one to three substituents selected from $R^f$.

In another embodiment, $R^5$ is selected from the group consisting of: hydrogen, deuterium, and —$C_{1-6}$alkyl, wherein alkyl is unsubstituted or substituted with one to five substituents selected from $R^f$. In another embodiment, $R^5$ is hydrogen. In another embodiment, $R^5$ is deuterium.

In another embodiment, $R^5$ is selected from the group consisting of: hydrogen, and —$C_{1-6}$alkyl, wherein alkyl is unsubstituted or substituted with one to five substituents selected from $R^f$. In another embodiment, $R^5$ is hydrogen.

In another embodiment, $R^5$ is —$C_{1-6}$alkyl, wherein alkyl is unsubstituted or substituted with one to five substituents selected from $R^f$. In a class of this embodiment, $R^5$ is —$CH_3$, wherein —$CH_3$ is unsubstituted or substituted with one to three substituents selected from $R^f$.

In one embodiment, $R^6$ is selected from the group consisting of: hydrogen, deuterium, —$C_{1-6}$alkyl, —$C_{2-6}$alkenyl, —$C_{2-6}$alkynyl, —$C_{3-6}$cycloalkyl, —$C_{2-6}$cycloheteroalkyl, —$C_{1-6}$alkyl-O—$C_{1-6}$alkyl-, —$(CH_2)_sC(O)R^j$, —$(CH_2)_sC(O)NR^eR^j$, —$(CH_2)_sNR^eC(O)R^j$, —$(CH_2)_sNR^eC(O)OR^j$, —$(CH_2)_sNR^eC(O)N(R^e)_2$, —$(CH_2)_sNR^eC(O)NR^eR^j$, —$(CH_2)_sNR^eS(O)_mR^j$, —$(CH_2)_sNR^eS(O)mN(R^e)_2$, —$(CH_2)_sNR^eS(O)mNR^eR^j$, and —$(CH_2)SNR^eR^j$, wherein each $CH_2$, alkyl, alkenyl, alkynyl, cycloalkyl, and cycloheteroalkyl is unsubstituted or substituted with one to five substituents selected from $R^g$, and wherein $R^6$ and $R^7$ and the carbon atoms they are connected to can form a —$C_{3-5}$cycloalkyl ring.

In another embodiment, $R^6$ is selected from the group consisting of: hydrogen, —$C_{1-6}$alkyl, —$C_{2-6}$alkenyl, —$C_{2-6}$alkynyl, —$C_{3-6}$cycloalkyl, —$C_{2-6}$cycloheteroalkyl, —$C_{1-6}$alkyl-O—$C_{1-6}$alkyl-, —$(CH_2)_sC(O)R^j$, —$(CH_2)_sC(O)NR^eR^j$, —$(CH_2)_sNR^eC(O)R^j$, —$(CH_2)_sNR^eC(O)OR^j$, —$(CH_2)_sNR^eC(O)N(R^e)_2$, —$(CH_2)_sNR^eC(O)NR^eR^j$, —$(CH_2)_sNR^eS(O)_mR^j$, —$(CH_2)_sNR^eS(O)mN(R^e)_2$, —$(CH_2)_sNR^eS(O)mNR^eR^j$, and —$(CH_2)SNR^eR^j$, wherein each $CH_2$, alkyl, alkenyl, alkynyl, cycloalkyl, and cycloheteroalkyl is unsubstituted or substituted with one to five substituents selected from $R^g$, and wherein $R^6$ and $R^7$ and the carbon atoms they are connected to can form a —$C_{3-5}$cycloalkyl ring.

In another embodiment, $R^6$ is selected from the group consisting of: hydrogen, deuterium, —$C_{1-6}$alkyl, —$C_{2-6}$alkenyl, —$C_{2-6}$alkynyl, —$C_{3-6}$cycloalkyl, —$C_{2-6}$cycloheteroalkyl, —$C_{1-6}$alkyl-O—$C_{1-6}$alkyl-, —$(CH_2)_sC(O)R^j$, —$(CH_2)_sC(O)NR^eR^j$, —$(CH_2)_sNR^eC(O)R^j$, —$(CH_2)_sNR^eC(O)OR^j$, —$(CH_2)_sNR^eC(O)N(R^e)_2$, —$(CH_2)_sNR^eC(O)NR^eR^j$, —$(CH_2)_sNR^eS(O)_mR^j$, —$(CH_2)_sNR^eS(O)mN(R^e)_2$, —$(CH_2)_sNR^eS(O)mNR^eR^j$, and —$(CH_2)_sNR^eR^j$, wherein each $CH_2$, alkyl, alkenyl, alkynyl, cycloalkyl, and cycloheteroalkyl is unsubstituted or substituted with one to five substituents selected from $R^g$.

In another embodiment, $R^6$ is selected from the group consisting of: hydrogen, —$C_{1-6}$alkyl, —$C_{2-6}$alkenyl, —$C_{2-6}$alkynyl, —$C_{3-6}$cycloalkyl, —$C_{2-6}$cycloheteroalkyl, —$C_{1-6}$alkyl-O—$C_{1-6}$alkyl-, —$(CH_2)_sC(O)R^j$, —$(CH_2)_sC(O)NR^eR^j$, —$(CH_2)_sNR^eC(O)R^j$, —$(CH_2)_sNR^eC(O)OR^j$, —$(CH_2)_sNR^eC(O)N(R^e)_2$, —$(CH_2)_sNR^eC(O)NR^eR^j$, —$(CH_2)_sNR^eS(O)_mR^j$, —$(CH_2)_sNR^eS(O)mN(R^e)_2$, —$(CH_2)_sNR^eS(O)mNR^eR^j$, and —$(CH_2)_sNR^eR^j$, wherein each $CH_2$, alkyl, alkenyl, alkynyl, cycloalkyl, and cycloheteroalkyl is unsubstituted or substituted with one to five substituents selected from $R^g$.

In another embodiment, $R^6$ is selected from the group consisting of: hydrogen, deuterium, —$C_{1-6}$alkyl, —$C_{2-6}$alkenyl, —$C_{2-6}$alkynyl, —$C_{3-6}$cycloalkyl, and —$C_{2-6}$cycloheteroalkyl, wherein each alkyl, alkenyl, alkynyl, cycloalkyl, and cycloheteroalkyl is unsubstituted or substituted with one to five substituents selected from $R^g$. In another embodiment, $R^6$ is selected from the group consisting of: hydrogen, —$C_{1-6}$alkyl, —$C_{2-6}$alkenyl, —$C_{2-6}$alkynyl, and —$C_{3-6}$cycloalkyl, wherein each alkyl, alkenyl, alkynyl, and cycloalkyl is unsubstituted or substituted with one to five substituents selected from $R^g$.

In another embodiment, $R^6$ is selected from the group consisting of: hydrogen, —$C_{1-6}$alkyl, —$C_{2-6}$alkenyl, —$C_{2-6}$alkynyl, —$C_{3-6}$cycloalkyl, and —$C_{2-6}$cycloheteroalkyl, wherein each alkyl, alkenyl, alkynyl, cycloalkyl, and cycloheteroalkyl is unsubstituted or substituted with one to five substituents selected from $R^g$. In another embodiment, $R^6$ is selected from the group consisting of: hydrogen, —$C_{1-6}$alkyl, —$C_{2-6}$alkenyl, —$C_{2-6}$alkynyl, and —$C_{3-6}$cycloalkyl, wherein each alkyl, alkenyl, alkynyl, and cycloalkyl is unsubstituted or substituted with one to five substituents selected from $R^g$.

In another embodiment, $R^6$ is selected from the group consisting of: hydrogen, deuterium, —$C_{1-6}$alkyl, and —$C_{3-6}$cycloalkyl, wherein alkyl and cycloalkyl is unsubstituted or substituted with one to five substituents selected from $R^g$. In a class of this embodiment, $R^6$ is selected from the group consisting of: hydrogen, deuterium, —$CH_3$, —$CF_3$, —$CH_2CH_3$, —$CH_2F$, —$CH_2OH$, and cyclopropyl, wherein cyclopropyl is unsubstituted or substituted with one to five substituents selected from $R^g$. In another class of this embodiment, $R^6$ is selected from the group consisting of hydrogen, deuterium, —$CH_3$, and cyclopropyl, wherein cyclopropyl is unsubstituted or substituted with one to five substituents selected from $R^g$.

In another embodiment, $R^6$ is selected from the group consisting of hydrogen, —$C_{1-6}$alkyl, and —$C_{3-6}$cycloalkyl, wherein alkyl and cycloalkyl is unsubstituted or substituted with one to five substituents selected from $R^g$. In a class of this embodiment, $R^6$ is selected from the group consisting of hydrogen, —$CH_3$, —$CH_2CH_3$, —$CH_2F$, and cyclopropyl, wherein cyclopropyl is unsubstituted or substituted with one to five substituents selected from $R^g$. In another class of this embodiment, $R^6$ is selected from the group consisting of hydrogen, —$CH_3$, and cyclopropyl, wherein cyclopropyl is unsubstituted or substituted with one to five substituents selected from $R^g$.

In another embodiment, $R^6$ is selected from the group consisting of: hydrogen, deuterium, and $C_{1-6}$alkyl, wherein alkyl is unsubstituted or substituted with one to five substituents selected from $R^g$. In a class of this embodiment, $R^6$ is selected from the group consisting of: hydrogen, deuterium, —$CH_3$, —$CF_3$, —$CH_2CH_3$, —$CH_2OH$, and —$CH_2F$. In another class of this embodiment, $R^6$ is selected from the group consisting of: hydrogen, and —$CH_3$. In another embodiment, $R^6$ is hydrogen.

In another embodiment, $R^6$ is selected from the group consisting of: hydrogen, and —$C_{1-6}$alkyl, wherein alkyl is unsubstituted or substituted with one to five substituents selected from $R^g$. In a class of this embodiment, $R^6$ is selected from the group consisting of: hydrogen, —$CH_3$, —$CH_2CH_3$, and —$CH_2F$. In another class of this embodiment, $R^6$ is selected from the group consisting of: hydrogen, and —$CH_3$. In another embodiment, $R^6$ is hydrogen.

In another embodiment, $R^6$ is selected from the group consisting of: —$C_{1-6}$alkyl, wherein alkyl is unsubstituted or substituted with one to five substituents selected from $R^g$. In a class of this embodiment, $R^6$ is selected from the group consisting of —$CH_3$, —$CH_2CH_3$, and —$CH_2F$. In another class of this embodiment, $R^6$ is —$CH_3$.

In one embodiment, $R^7$ is selected from the group consisting of: hydrogen, deuterium, —$C_{1-6}$alkyl, —$C_{2-6}$alkenyl, —$C_{2-6}$alkynyl, —$C_{3-6}$cycloalkyl, —$C_{2-6}$cycloheteroalkyl, —$C_{1-6}$alkyl-O—$C_{1-6}$alkyl-, —$(CH_2)_sC(O)R^j$, —$(CH_2)_sC(O)NR^eR^j$, —$(CH_2)_sNR^eC(O)R^j$, —$(CH_2)_sNR^eC(O)OR^j$, —$(CH_2)_sNR^eC(O)N(R^e)_2$, —$(CH_2)_sNR^eC(O)NR^eR^j$, —$(CH_2)_sNR^eS(O)_mR^j$, —$(CH_2)_sNR^eS(O)mN(R^e)_2$, —$(CH_2)_sNR^eS(O)mNR^eR^j$, and —$(CH_2)_sNR^eR^j$, wherein each $CH_2$, alkyl, alkenyl, alkynyl, cycloalkyl, and cycloheteroalkyl is unsubstituted or substituted with one to five substituents selected from $R^g$.

In another embodiment, $R^7$ is selected from the group consisting of: hydrogen, —$C_{1-6}$alkyl, —$C_{2-6}$alkenyl, —$C_{2-6}$alkynyl, —$C_{3-6}$cycloalkyl, —$C_{2-6}$cycloheteroalkyl, —$C_{1-6}$alkyl-O—$C_{1-6}$alkyl-, —$(CH_2)_sC(O)R^j$, —$(CH_2)_sC(O)NR^eR^j$, —$(CH_2)_sNR^eC(O)R^j$, —$(CH_2)_sNR^eC(O)OR^j$, —$(CH_2)_sNR^eC(O)N(R^e)_2$, —$(CH_2)_sNR^eC(O)NR^eR^j$, —$(CH_2)_sNR^eS(O)_mR^j$, —$(CH_2)_sNR^eS(O)mN(R^e)_2$, —$(CH_2)_sNR^eS(O)mNR^eR^j$, and —$(CH_2)_sNR^eR^j$, wherein each $CH_2$, alkyl, alkenyl, alkynyl, cycloalkyl, and cycloheteroalkyl is unsubstituted or substituted with one to five substituents selected from $R^g$.

In another embodiment, $R^7$ is selected from the group consisting of: hydrogen, deuterium, —$C_{1-6}$alkyl, —$C_{2-6}$alkenyl, —$C_{2-6}$alkynyl, —$C_{3-6}$cycloalkyl, and —$C_{2-6}$cycloheteroalkyl, wherein alkyl, alkenyl, alkynyl, cycloalkyl, and cycloheteroalkyl is unsubstituted or substituted with one to five substituents selected from $R^g$.

In another embodiment, $R^7$ is selected from the group consisting of: hydrogen, —$C_{1-6}$alkyl, —$C_{2-6}$alkenyl, —$C_{2-6}$alkynyl, —$C_{3-6}$cycloalkyl, and —$C_{2-6}$cycloheteroalkyl, wherein alkyl, alkenyl, alkynyl, cycloalkyl, and cycloheteroalkyl is unsubstituted or substituted with one to five substituents selected from $R^g$.

In another embodiment, $R^7$ is selected from the group consisting of: hydrogen, deuterium, —$C_{1-6}$alkyl, —$C_{2-6}$alkenyl, —$C_{2-6}$alkynyl, and —$C_{3-6}$cycloalkyl, wherein alkyl, alkenyl, alkynyl, and cycloalkyl is unsubstituted or substituted with one to five substituents selected from $R^g$.

In another embodiment, $R^7$ is selected from the group consisting of: hydrogen, —$C_{1-6}$alkyl, —$C_{2-6}$alkenyl, —$C_{2-6}$alkynyl, and —$C_{3-6}$cycloalkyl, wherein alkyl, alkenyl, alkynyl, and cycloalkyl is unsubstituted or substituted with one to five substituents selected from $R^g$.

In another embodiment, $R^7$ is selected from the group consisting of: hydrogen, deuterium, —$C_{1-6}$alkyl, and —$C_{3-6}$cycloalkyl, wherein alkyl, and cycloalkyl is unsubstituted or substituted with one to five substituents selected from $R^g$. In a class of this embodiment, $R^7$ is selected from the group consisting of: hydrogen, deuterium, —$CH_3$, —$CF_3$, —$CH_2CH_3$, —$CH_2F$, —$CH_2OH$ and cyclopropyl, wherein cyclopropyl is unsubstituted or substituted with one to five substituents selected from $R^g$. In a class of this embodiment, $R^7$ is selected from the group consisting of: hydrogen, deuterium, —$CH_3$, —$CH_2CH_3$, —$CH_2F$ and cyclopropyl, wherein cyclopropyl is unsubstituted or substituted with one to five substituents selected from $R^g$. In another class of this embodiment, $R^7$ is selected from the group consisting of: hydrogen, deuterium, —$CH_3$, and cyclopropyl, wherein cycloalkyl is unsubstituted or substituted with one to five substituents selected from $R^g$. In another embodiment, $R^7$ is hydrogen. In another embodiment, $R^7$ is deuterium.

In another embodiment, $R^7$ is selected from the group consisting of: hydrogen, —$C_{1-6}$alkyl, and —$C_{3-6}$cycloalkyl, wherein alkyl, and cycloalkyl is unsubstituted or substituted with one to five substituents selected from $R^g$. In a class of this embodiment, $R^7$ is selected from the group consisting of: hydrogen, —$CH_3$, —$CH_2CH_3$, —$CH_2F$ and cyclopropyl, wherein cyclopropyl is unsubstituted or substituted with one to five substituents selected from $R^g$. In another class of this embodiment, $R^7$ is selected from the group consisting of: hydrogen, —$CH_3$, and cyclopropyl, wherein cycloalkyl is unsubstituted or substituted with one to five substituents selected from $R^g$. In another embodiment, $R^7$ is hydrogen.

Here In one embodiment, $R^8$ is selected from the group consisting of: hydrogen, —$C_{1-6}$alkyl, —$C_{3-6}$cycloalkyl, and —$C_{2-6}$cycloheteroalkyl, wherein each alkyl, cycloalkyl and cycloheteroalkyl is unsubstituted or substituted with one to five substituents selected from halogen.

In another embodiment, $R^8$ is selected from the group consisting of: hydrogen, and —$C_{1-6}$alkyl, wherein alkyl is unsubstituted or substituted with one to five substituents selected from halogen. In another embodiment, $R^8$ is hydrogen.

In another embodiment, $R^8$ is —$C_{1-6}$alkyl, wherein alkyl is unsubstituted or substituted with one to five substituents selected from halogen.

In one embodiment, $R^9$ is selected from the group consisting of: hydrogen, —$C_{1-6}$alkyl, —$C_{2-6}$alkenyl, and —$C_{2-6}$alkynyl, wherein each alkyl, alkenyl and alkynyl is unsubstituted or substituted with one to five substituents selected from halogen.

In another embodiment, $R^9$ is selected from the group consisting of: hydrogen, and —$C_{1-6}$alkyl, wherein alkyl is unsubstituted or substituted with one to five substituents selected from halogen. In a class of this embodiment, $R^9$ is selected from the group consisting of: hydrogen, and $CH_3$. In another embodiment, $R^9$ is hydrogen.

In another embodiment, $R^9$ is —$C_{1-6}$alkyl, wherein alkyl is unsubstituted or substituted with one to five substituents selected from halogen. In a class of this embodiment, $R^9$ is —$C_{1-6}$alkyl, $CH_3$.

In one embodiment, each $R^a$ is independently selected from the group consisting of: CN, oxo, halogen, —$S(O)_2C_{1-6}$alkyl, —$C_{1-6}$alkyl, —$C_{2-6}$alkenyl, —$C_{2-6}$alkynyl, —$C_{3-6}$cycloalkyl, —$C_{2-6}$cycloheteroalkyl, aryl, heteroaryl, —$C_{1-6}$alkyl-aryl, —$C_{1-6}$alkyl-heteroaryl, —$C_{1-6}$alkyl-$C_{3-6}$cycloalkyl, —$C_{1-6}$alkyl-$C_{2-6}$cycloheteroalkyl, —$C_{2-6}$alkenyl-$C_{3-6}$cycloalkyl, —$C_{2-6}$alkenyl-$C_{2-6}$cycloheteroalkyl, —$C_{2-6}$alkenyl-aryl, —$C_{2-6}$alkenyl-heteroaryl, —$C_{2-6}$alkynyl-$C_{3-6}$cycloalkyl, —$C_{2-6}$alkynyl$C_{2-6}$cycloheteroalkyl, —$C_{2-6}$alkynyl-aryl, —$C_{2-6}$alkynyl-heteroaryl, —OH, —$(CH_2)_p$—O—$C_{1-6}$alkyl, —$(CH_2)_p$—O—$C_{2-6}$alkenyl, —$(CH_2)_p$—O—$C_{2-6}$alkynyl, —$(CH_2)_p$—O—$C_{3-6}$cycloalkyl, —$(CH_2)_p$—O—$C_{2-6}$cycloheteroalkyl, —$(CH_2)_p$—O-aryl, —$(CH_2)_p$—O-heteroaryl, —$OC_{1-6}$alkyl-$C_{3-6}$cycloalkyl, —$OC_{1-6}$alkyl-$C_{2-6}$cycloheteroalkyl, —$OC_{1-6}$alkyl-aryl, —$OC_{1-6}$alkyl-heteroaryl, —$S(O)_rR^h$, —$C_{1-6}$alkyl-$S(O)_rR^h$, —$N(R^k)_2$, —$C(O)R^L$, and —$NR^kR^L$, wherein each $R^a$ is unsubstituted or substituted with one to six substituents selected from halogen, $CF_3$, OH, $C_{1-6}$alkyl, and —$OC_{1-6}$alkyl.

In another embodiment, each $R^a$ is independently selected from the group consisting of: CN, oxo, halogen, —$S(O)_2C_{1-6}$alkyl, —$C_{1-6}$alkyl, —$C_{2-6}$alkenyl, —$C_{2-6}$alkynyl, —$C_{3-6}$cycloalkyl, —$C_{2-6}$cycloheteroalkyl, aryl, heteroaryl, —$C_{1-6}$alkyl-aryl, —$C_{1-6}$alkyl-heteroaryl, —$C_{1-6}$alkyl-$C_{3-6}$cycloalkyl, —$C_{1-6}$alkyl-$C_{2-6}$cycloheteroalkyl, —OH, —$(CH_2)_p$—O—$C_{1-6}$alkyl, —$(CH_2)_p$—O—$C_{2-6}$alkenyl, —$(CH_2)_p$—O—$C_{2-6}$alkynyl, —$(CH_2)_p$—O—$C_{3-6}$cycloalkyl, —$(CH_2)_p$—O—$C_{2-6}$cycloheteroalkyl, —$(CH_2)_p$—O-aryl, and —$(CH_2)_p$—O-heteroaryl, wherein each $R^a$ is unsubstituted or substituted with one to six substituents selected from halogen, $CF_3$, OH, $C_{1-6}$alkyl, and —$OC_{1-6}$alkyl.

In another embodiment, each $R^a$ is independently selected from the group consisting of: CN, oxo, halogen, —$S(O)_2C_{1-6}$alkyl, —$C_{1-6}$alkyl, —$C_{2-6}$alkenyl, —$C_{2-6}$alkynyl, —$C_{3-6}$cycloalkyl, —$C_{2-6}$cycloheteroalkyl, aryl, heteroaryl, —OH, —O—$C_{1-6}$alkyl, —O—$C_{2-6}$alkenyl, —O—$C_{2-6}$alkynyl, —O—$C_{3-6}$cycloalkyl, —O—$C_{2-6}$cycloheteroalkyl, —O-aryl, and —O-heteroaryl, wherein each $R^a$ is unsubstituted or substituted with one to six substituents selected from halogen, $CF_3$, OH, $C_{1-6}$alkyl, and —$OC_{1-6}$alkyl.

In another embodiment, each $R^a$ is independently selected from the group consisting of CN, oxo, halogen, —$S(O)_2C_{1-6}$alkyl, —$C_{1-6}$alkyl, —$C_{2-6}$alkenyl, —$C_{3-6}$cycloalkyl, —$C_{2-6}$cycloheteroalkyl, aryl, heteroaryl, —OH, —O—$C_{1-6}$alkyl, —O—$C_{3-6}$cycloalkyl, and —O—$C_{2-6}$cycloheteroalkyl, wherein each $R^a$ is unsubstituted or substituted with one to six substituents selected from halogen, $CF_3$, OH, $C_{1-6}$alkyl, and —$OC_{1-6}$alkyl.

In another embodiment, each $R^a$ is independently selected from the group consisting of CN, halogen, —$C_{1-6}$alkyl, —$C_{2-6}$alkenyl, —$C_{3-6}$cycloalkyl, —$C_{2-6}$cycloheteroalkyl, aryl, heteroaryl, —O—$C_{1-6}$alkyl, —O—$C_{3-6}$cycloalkyl, and —O—$C_{2-6}$cycloheteroalkyl, wherein each $R^a$ is unsubstituted or substituted with one to six substituents selected from halogen, $CF_3$, OH, $C_{1-6}$alkyl, and $OC_{1-6}$alkyl.

In another embodiment, each $R^a$ is independently selected from the group consisting of CN, halogen, —$C_{1-6}$alkyl, —$C_{3-6}$cycloalkyl, —$C_{2-6}$cycloheteroalkyl, —O—$C_{1-6}$alkyl, —O—$C_{3-6}$cycloalkyl, and —O—$C_{2-6}$cycloheteroalkyl, wherein each $R^a$ is unsubstituted or substituted with one to six substituents selected from halogen, $CF_3$, OH, $C_{1-6}$alkyl, and $OC_{1-6}$alkyl.

In another embodiment, each $R^a$ is independently selected from the group consisting of CN, halogen, —$C_{1-6}$alkyl, and —O—$C_{1-6}$alkyl, wherein each $R^a$ is unsubstituted or substituted with one to six substituents selected from halogen, $CF_3$, OH, $C_{1-6}$alkyl, and $OC_{1-6}$alkyl.

In another embodiment, each $R^a$ is independently selected from the group consisting of halogen, —$C_{1-6}$alkyl, and —O—$C_{1-6}$alkyl, wherein each $R^a$ is unsubstituted or substituted with one to six substituents selected from halogen, $CF_3$, OH, $C_{1-6}$alkyl, and —$OC_{1-6}$alkyl. In a class of this embodiment, each $R^a$ is independently selected from the group consisting of: halogen, —$C_{1-6}$alkyl, and —O—$C_{1-6}$alkyl, wherein each alkyl is unsubstituted or substituted with one to six substituents selected from Cl, F, $CF_3$, OH, $CH_3$, and —$OCH_3$. In another class of this embodiment, each $R^a$ is independently selected from the group consisting of: Br, F, Cl, —$CF_3$, —$CH_3$, —$CHF_2$, —$CH_2CF_3$, —$CF_2CH_3$, —$OCF_3$, —$OCHF_2$, and —$OCH_2CF_3$. In another class of this embodiment, each $R^a$ is independently selected from the group consisting of: F, Cl, —$CF_3$, —$CH_3$, —$CHF_2$, —$CH_2CF_3$, —$CF_2CH_3$, —$OCF_3$, —$OCHF_2$, and —$OCH_2CF_3$. In another class of this embodiment, each $R^a$ is independently selected from the group consisting of: F, Cl, —$CF_3$, —$CH_3$, —$CHF_2$, and —$OCF_3$.

In another embodiment, each $R^a$ is independently selected from the group consisting of halogen, and —$C_{1-6}$alkyl, wherein each alkyl s unsubstituted or substituted with one to six substituents selected from halogen, $CF_3$, OH, $C_{1-6}$alkyl, and —$OC_{1-6}$alkyl. In a class of this embodiment, each $R^a$ is independently selected from the group consisting of: halogen, and —$C_{1-6}$alkyl, wherein each $R^a$ is unsubstituted or substituted with one to six substituents selected from Cl, F, $CF_3$, OH, $CH_3$, and —$OCH_3$. In another class of this embodiment, each $R^a$ is independently selected from the group consisting of: Br, F, Cl, —$CF_3$, —$CH_3$, —$CHF_2$, —$CH_2CF_3$, and —$CF_2CH_3$. In another class of this embodiment, each $R^a$ is independently selected from the group consisting of F, Cl, —$CF_3$, —$CH_3$, —$CHF_2$, —$CH_2CF_3$, and —$CF_2CH_3$. In another class of this embodiment, each $R^a$ is independently selected from the group consisting of: F, Cl, —$CF_3$, —$CH_3$, and —$CHF_2$.

In another embodiment, each $R^a$ is halogen. In a class of this embodiment, $R^a$ is F or Cl. In another embodiment, $R^a$ is —$C_{1-6}$alkyl, wherein each $R^a$ is unsubstituted or substituted with one to six substituents selected from F, Cl, $CF_3$, OH, $CH_3$, and —$OCH_3$. In a class of this embodiment, $R^a$ is —$CF_3$, —$CH_3$, or —$CHF_2$.

In one embodiment, each $R^b$ is independently selected from the group consisting of: CN, oxo, halogen, —$S(O)_2C_{1-6}$alkyl, —$C_{1-6}$alkyl, —$C_{1-6}$alkenyl, —$C_{2-6}$alkynyl, —$C_{3-6}$cycloalkyl, —$C_{2-6}$cycloheteroalkyl, aryl, heteroaryl, —$C_{1-6}$alkyl-aryl, —$C_{1-6}$alkyl-heteroaryl, —$C_{1-6}$alkyl-$C_{3-6}$cycloalkyl, —$C_{1-6}$alkyl-$C_{2-6}$cycloheteroalkyl, —$C_{2-6}$alkenyl-$C_{3-6}$cycloalkyl, —$C_{2-6}$alkenyl-$C_{2-6}$cycloheteroalkyl, —$C_{2-6}$alkenyl-aryl, —$C_{2-6}$alkenyl-heteroaryl, —$C_{2-6}$alkynyl-$C_{3-6}$cycloalkyl, —$C_{2-6}$alkynyl-$C_{2-6}$cycloheteroalkyl, —$C_{2-6}$alkynyl-aryl, —$C_{2-6}$alkynyl-heteroaryl, —OH, —$(CH_2)_q$—O—$C_{1-6}$alkyl, —$(CH_2)_q$—

O—$C_{2-6}$alkenyl, —$(CH_2)_q$—O—$C_{2-6}$alkynyl, —$(CH_2)_q$—O—$C_{3-6}$cycloalkyl, —$(CH_2)_q$—O—$C_{2-6}$cycloheteroalkyl, —$(CH_2)_q$—O-aryl, —$(CH_2)_q$—O-heteroaryl, —$OC_{1-6}$alkyl-$C_{3-6}$cycloalkyl, —$OC_{1-6}$alkyl-$C_{2-6}$cycloheteroalkyl, —$OC_{1-6}$alkyl-aryl, —$OC_{1-6}$alkyl-heteroaryl, —$S(O)_rR^i$, —$C_{1-6}$alkyl-$S(O)_rR^i$, —$N(R^k)_2$, —$C(O)R^L$, and —$NR^kR^L$, wherein each $R^b$ is unsubstituted or substituted with one to six substituents selected from halogen, $CF_3$, $OCF_3$, CN, $CH_2CF_3$, $CF_2CH_3$, —$C_{1-6}$alkyl, and O—$C_{1-6}$alkyl.

In another embodiment, each $R^b$ is independently selected from the group consisting of CN, oxo, halogen, —$S(O)_2C_{1-6}$alkyl, —$C_{1-6}$alkyl, —$C_{1-6}$alkenyl, —$C_{2-6}$alkynyl, —$C_{3-6}$cycloalkyl, —$C_{2-6}$cycloheteroalkyl, aryl, heteroaryl, —$C_{1-6}$alkyl-aryl, —$C_{1-6}$alkyl-heteroaryl, —$C_{1-6}$alkyl-$C_{3-6}$cycloalkyl, —$C_{1-6}$alkyl-$C_{2-6}$cycloheteroalkyl, —OH, —$(CH_2)_q$—O—$C_{1-6}$alkyl, —$(CH_2)_q$—O—$C_{2-6}$ alkenyl, —$(CH_2)_q$—O—$C_{2-6}$alkynyl, —$(CH_2)_q$—O—$C_{3-6}$cycloalkyl, —$(CH_2)_q$—O—$C_{2-6}$cycloheteroalkyl, —$(CH_2)_q$—O-aryl, —$(CH_2)_q$—O-heteroaryl, wherein each $R^b$ is unsubstituted or substituted with one to six substituents selected from halogen, $CF_3$, $OCF_3$, CN, $CH_2CF_3$, $CF_2CH_3$, —$C_{1-6}$alkyl, and —$OC_{1-6}$alkyl.

In another embodiment, each $R^b$ is independently selected from the group consisting of: CN, oxo, halogen, —$S(O)_2C_{1-6}$alkyl, —$C_{1-6}$alkyl, —$C_{1-6}$alkenyl, —$C_{2-6}$alkynyl, —$C_{3-6}$cycloalkyl, —$C_{2-6}$cycloheteroalkyl, aryl, heteroaryl, —$C_{1-6}$alkyl-aryl, —$C_{1-6}$alkyl-heteroaryl, —$C_{1-6}$alkyl-$C_{3-6}$cycloalkyl, —$C_{1-6}$alkyl-$C_{2-6}$cycloheteroalkyl, —OH, —O—$C_{1-6}$alkyl, —O—$C_{3-6}$cycloalkyl, and —O—$C_{2-6}$cycloheteroalkyl, wherein each $R^b$ is unsubstituted or substituted with one to six substituents selected from halogen, $CF_3$, $OCF_3$, CN, $CH_2CF_3$, $CF_2CH_3$, —$C_{1-6}$alkyl, and —$OC_{1-6}$alkyl.

In another embodiment, each $R^b$ is independently selected from the group consisting of: CN, oxo, halogen, —$S(O)_2C_{1-6}$alkyl, —$C_{1-6}$alkyl, —$C_{1-6}$alkenyl, —$C_{2-6}$alkynyl, —$C_{3-6}$cycloalkyl, —$C_{2-6}$cycloheteroalkyl, aryl, heteroaryl, —OH, —O—$C_{1-6}$alkyl, —O—$C_{3-6}$cycloalkyl, and —O—$C_{2-6}$cycloheteroalkyl, wherein each $R^b$ is unsubstituted or substituted with one to six substituents selected from halogen, $CF_3$, $OCF_3$, CN, $CH_2CF_3$, $CF_2CH_3$, —$C_{1-6}$alkyl, and —$OC_{1-6}$alkyl.

In another embodiment, each $R^b$ is independently selected from the group consisting of: CN, halogen, —$C_{1-6}$alkyl, —$C_{1-6}$alkenyl, —$C_{3-6}$cycloalkyl, —$C_{2-6}$cycloheteroalkyl, aryl, heteroaryl, —OH, —O—$C_{1-6}$alkyl, —O—$C_{3-6}$cycloalkyl, —O—$C_{2-6}$cycloheteroalkyl, wherein each $R^b$ is unsubstituted or substituted with one to six substituents selected from halogen, $CF_3$, $OCF_3$, CN, $CH_2CF_3$, $CF_2CH_3$, —$C_{1-6}$alkyl, and —$OC_{1-6}$alkyl.

In another embodiment, each $R^b$ is independently selected from the group consisting of: CN, halogen, —$C_{1-6}$alkyl, —$C_{1-6}$alkenyl, —$C_{3-6}$cycloalkyl, aryl, heteroaryl, and —O—$C_{1-6}$alkyl, wherein each $R^b$ is unsubstituted or substituted with one to six substituents selected from halogen, $CF_3$, $OCF_3$, CN, $CH_2CF_3$, $CF_2CH_3$, —$C_{1-6}$alkyl, and O—$C_{1-6}$alkyl.

In another embodiment, each $R^b$ is independently selected from the group consisting of: CN, halogen-$C_{1-6}$alkyl, —$C_{1-6}$alkenyl, —$C_{3-6}$cycloalkyl, and —$OC_{1-6}$alkyl, wherein alkyl, alkenyl and cycloalkyl is unsubstituted or substituted with one to six substituents selected from halogen, $CF_3$, $OCF_3$, CN, $CH_2CF_3$, $CF_2CH_3$, —$C_{1-6}$alkyl, and —$OC_{1-6}$alkyl.

In another embodiment, each $R^b$ is independently selected from the group consisting of: halogen, —$C_{1-6}$alkyl, —$C_{1-6}$alkenyl, —$C_{3-6}$cycloalkyl, and —O—$C_{1-6}$alkyl, wherein each $R^b$ is unsubstituted or substituted with one to six substituents selected from halogen, $CF_3$, $OCF_3$, CN, $CH_2CF_3$, $CF_2CH_3$, —$C_{1-6}$alkyl, and —$OC_{1-6}$alkyl. In a class of this embodiment, each $R^b$ is independently selected from the group consisting of: halogen, —$C_{1-6}$alkyl, —$C_{1-6}$alkenyl, —$C_{3-6}$cycloalkyl, and —O—$C_{1-6}$alkyl, wherein each alkyl, alkenyl, and cycloalkyl is unsubstituted or substituted with one to six substituents selected from F, Cl, $CF_3$, $OCF_3$, CN, $CH_2CF_3$, $CF_2CH_3$, —$CH_3$, and —$OCH_3$. In another class of this embodiment, each $R^b$ is independently selected from the group consisting of: F, Cl, —$CH_3$, —$CF_3$, —$CH_2CF_3$, —$CH(CH_3)CF_3$, —$CF_2CH_3$, =$CH_2$, cyclopropyl, —$OCH_3$, —$OCF_3$, —$OCHF_2$, —$OCH_2CF_3$, wherein cyclopropyl is unsubstituted or substituted with one to five substituents selected from F, Cl, $CF_3$, $OCF_3$, CN, $CH_2CF_3$, $CF_2CH_3$, —$CH_3$, and O—$CH_3$. In another class of this embodiment, each $R^b$ is independently selected from the group consisting of: F, Cl, —$CH_3$, —$CF_3$, —$CH_2CF_3$, —$CH(CH_3)CF_3$, =$CH_2$, cyclopropyl, —$OCH_3$, —$OCHF_2$, —$OCH_2CF_3$, wherein cyclopropyl is unsubstituted or substituted with one to five substituents selected from F, Cl, $CF_3$, $OCF_3$, CN, $CH_2CF_3$, $CF_2CH_3$, —$CH_3$, and O—$CH_3$.

In another embodiment, each $R^b$ is independently selected from the group consisting of: halogen, and —$C_{1-6}$alkyl, wherein each $R^b$ is unsubstituted or substituted with one to six substituents selected from halogen, $CF_3$, $OCF_3$, CN, $CH_2CF_3$, $CF_2CH_3$, —$C_{1-6}$alkyl, and O—$C_{1-6}$alkyl. In a class of this embodiment, each $R^b$ is independently selected from the group consisting of: halogen, and —$C_{1-6}$alkyl, wherein alkyl is unsubstituted or substituted with one to six substituents selected from F, Cl, $CF_3$, $OCF_3$, CN, $CH_2CF_3$, $CF_2CH_3$, —$CH_3$, and —$OCH_3$. In another class of this embodiment, each $R^b$ is independently selected from the group consisting of: F, Cl, —$CH_3$, —$CF_3$, —$CH_2CF_3$, —$CH(CH_3)CF_3$, and —$CF_2CH_3$. In another class of this embodiment, each $R^b$ is independently selected from the group consisting of: F, Cl, —$CH_3$, —$CF_3$, —$CH_2CF_3$, and —$CH(CH_3)CF_3$.

In another embodiment, each $R^b$ is halogen. In a class of this embodiment, $R^b$ is F or Cl. In another class of this embodiment, $R^b$ is F. In another class of this embodiment, $R^b$ is Cl.

In another embodiment, each $R^b$ is —$C_{1-6}$alkyl, wherein alkyl is unsubstituted or substituted with one to six substituents selected from F, Cl, $CF_3$, $OCF_3$, CN, $CH_2CF_3$, $CF_2CH_3$, —$CH_3$, and —$OCH_3$. In a class of this embodiment, $R^b$ is selected from: —$CH_3$, —$CF_3$, —$CH_2CF_3$, —$CH(CH_3)CF_3$, and —$CF_2CH_3$. In another class of this embodiment, $R^b$ is selected from: —$CH_3$, —$CF_3$, —$CH_2CF_3$, and —$CH(CH_3)CF_3$. In another class of this embodiment, $R^b$ is —$CF_3$.

In one embodiment, $R^c$ is selected from: —$C_{1-6}$alkyl, OH, halogen, and —$OC_{1-6}$alkyl, wherein alkyl is unsubstituted or substituted with one to three halogens.

In another embodiment, $R^c$ is selected from: —$C_{1-6}$alkyl, OH, and halogen, wherein alkyl is unsubstituted or substituted with one to three halogens. In another embodiment, $R^c$ is selected from: $C_{1-6}$alkyl, and halogen, wherein alkyl is unsubstituted or substituted with one to three halogens. In a class of this embodiment, $R^c$ is —$C_{1-6}$alkyl, wherein alkyl is unsubstituted or substituted with one to three halogens. In another class of this embodiment, $R^c$ is halogen.

In one embodiment, $R^d$ is selected from: —$C_{1-6}$alkyl, OH, halogen, and —$OC_{1-6}$alkyl, wherein alkyl is unsubstituted or substituted with one to three halogens. In another embodiment, $R^d$ is selected from: —$C_{1-6}$alkyl, OH, and halogen, wherein alkyl is unsubstituted or substituted with one to three halogens. In another embodiment, $R^d$ is selected from: —$C_{1-6}$alkyl and halogen, wherein alkyl is unsubstituted or substituted with one to three halogens. In a class of this embodiment, $R^d$ is —$C_{1-6}$alkyl or F. In another embodiment, $R^d$ is —$C_{1-6}$alkyl, wherein alkyl is unsubstituted or substituted with one to three halogens. In another embodiment, $R^d$ is halogen, wherein alkyl is unsubstituted or substituted with one to three halogens. In a class of this embodiment, $R^d$ is F.

In one embodiment, $R^e$ is selected from: hydrogen, and $C_{1-6}$alkyl. In another embodiment, $R^e$ is hydrogen. In another embodiment, $R^e$ is $C_{1-6}$alkyl.

In one embodiment, $R^f$ is selected from: —$C_{1-6}$alkyl, OH, halogen, and —$OC_{1-6}$alkyl, wherein alkyl is unsubstituted or substituted with one to three halogens. In another embodiment, $R^f$ is selected from: —$C_{1-6}$alkyl, OH, and halogen, wherein alkyl is unsubstituted or substituted with one to three halogens. In another embodiment, $R^f$ is selected from: —$C_{1-6}$alkyl and halogen, wherein alkyl is unsubstituted or substituted with one to three halogens. In a class of this embodiment, $R^f$ is —$C_{1-6}$alkyl or F. In another embodiment, $R^f$ is —$C_{1-6}$alkyl, wherein alkyl is unsubstituted or substituted with one to three halogens. In another embodiment, $R^f$ is halogen, wherein alkyl is unsubstituted or substituted with one to three halogens. In a class of this embodiment, $R^f$ is F.

In one embodiment, $R^g$ is selected from: —$C_{1-6}$alkyl, OH, halogen, and —$OC_{1-6}$alkyl, wherein alkyl is unsubstituted or substituted with one to three halogens. In another embodiment, $R^g$ is selected from: —$C_{1-6}$alkyl, OH, and halogen, wherein alkyl is unsubstituted or substituted with one to three halogens. In another embodiment, $R^g$ is selected from: —$C_{1-6}$alkyl and halogen, wherein alkyl is unsubstituted or substituted with one to three halogens. In a class of this embodiment, $R^g$ is —$C_{1-6}$alkyl or F. In another embodiment, $R^g$ is —$C_{1-6}$alkyl, wherein alkyl is unsubstituted or substituted with one to three halogens. In another embodiment, $R^g$ is halogen. In a class of this embodiment, $R^g$ is F.

In one embodiment, $R^h$ is selected from: hydrogen, $C_{1-6}$alkyl, $C_{3-6}$cycloalkyl, aryl, and heteroaryl. In another embodiment, $R^h$ is selected from: hydrogen, $C_{1-6}$alkyl, and $C_{3-6}$cycloalkyl. In another embodiment, $R^h$ is selected from: hydrogen, and $C_{1-6}$alkyl. In another embodiment, $R^h$ is hydrogen. In another embodiment, $R^h$ is $C_{1-6}$alkyl.

In one embodiment, $R^i$ is selected from: hydrogen, $C_{1-6}$alkyl, $C_{3-6}$cycloalkyl, aryl, and heteroaryl. In another embodiment, $R^i$ is selected from: hydrogen, $C_{1-6}$alkyl, and $C_{3-6}$cycloalkyl. In another embodiment, $R^i$ is selected from: hydrogen, and $C_{1-6}$alkyl. In another embodiment, $R^i$ is hydrogen. In another embodiment, $R^i$ is $C_{1-6}$alkyl.

In one embodiment, $R^i$ is selected from: hydrogen, $C_{1-6}$alkyl, $C_{3-6}$alkenyl, $C_{3-6}$alkynyl, $C_{3-6}$cycloalkyl, $C_{2-5}$cycloheteroalkyl, aryl, and heteroaryl. In another embodiment, $R^i$ is selected from: hydrogen, $C_{1-6}$alkyl, $C_{3-6}$alkenyl, $C_{3-6}$alkynyl, $C_{3-6}$cycloalkyl, and $C_{2-5}$cycloheteroalkyl, In another embodiment, $R^j$ is selected from: hydrogen, $C_{1-6}$alkyl, $C_{3-6}$cycloalkyl, and $C_{2-5}$cycloheteroalkyl. In another embodiment, $R^j$ is selected from: hydrogen, and $C_{1-6}$alkyl. In another embodiment, $R^j$ is hydrogen. In another embodiment, $R^j$ is $C_{1-6}$alkyl.

In one embodiment, $R^k$ is selected from: hydrogen, and $C_{1-6}$alkyl. In another embodiment, $R^k$ is hydrogen. In another embodiment, $R^k$ is $C_{1-6}$alkyl.

In one embodiment, $R^L$ is selected from: hydrogen, $C_{1-6}$alkyl, $C_{3-6}$cycloalkyl, aryl, and heteroaryl. In another embodiment, $R^L$ is selected from: hydrogen, $C_{1-6}$alkyl, and $C_{3-6}$cycloalkyl. In another embodiment, $R^L$ is selected from: hydrogen, and $C_{1-6}$alkyl. In a class of this embodiment, $R^L$ is hydrogen. In another class of this embodiment, $R^L$ is $C_{1-6}$alkyl. In one embodiment, m is 0, 1 or 2. In another embodiment, m is 0 or 1. In another embodiment, m is 0 or 2. In another embodiment, m is 0. In another embodiment, m is 1. In another embodiment, m is 2.

In one embodiment, n is 2, 3, 4, 5 or 6. In another embodiment, n is 2, 3, 4, or 5. In another embodiment, n is 2, 3, or 4. In another embodiment, n is 2 or 3. In another embodiment, n is 2 or 4. In another embodiment, n is 2, 3, 4, or 5. In another embodiment, n is 3. In another embodiment, n is 4. In another embodiment, n is 5. In another embodiment, n is 6.

In one embodiment, p is 0, 1, 2 or 3. In another embodiment, p is 0, 1 or 2. In another embodiment, p is 0, 1 or 3. In another embodiment, p is 1, 2 or 3. In another embodiment, p is 1 or 2. In another embodiment, p is 1 or 3. In another embodiment, p is 0 or 1. In another embodiment, p is 0 or 2. In another embodiment, p is 0 or 3. In another embodiment, p is 0. In another embodiment, p is 1. In another embodiment, p is 2. In another embodiment, p is 3.

In one embodiment, q is 0, 1, 2 or 3. In another embodiment, q is 0, 1 or 2. In another embodiment, q is 0, 1 or 3. In another embodiment, q is 1, 2 or 3. In another embodiment, q is 1 or 2. In another embodiment, q is 1 or 3. In another embodiment, q is 0 or 1. In another embodiment, q is 0 or 2. In another embodiment, q is 0 or 3. In another embodiment, q is 0. In another embodiment, q is 1. In another embodiment, q is 2. In another embodiment, q is 3.

In one embodiment, r is 0, 1 or 2. In another embodiment, r is 0 or 1. In another embodiment, r is 0 or 2. In another embodiment, r is 0. In another embodiment, r is 1. In another embodiment, r is 2.

In one embodiment, s is 0, 1, 2, 3, 4, 5 or 6. In another embodiment, s is 0, 1, 2, 3, 4, or 5. In another embodiment, s is 1, 2, 3, 4, 5 or 6. In another embodiment, s is 1, 2, 3, 4 or 5. In another embodiment, s is 0, 1, 2, 3, or 4. In another embodiment, s is 1, 2, 3, or 4. In another embodiment, s is 0, 1, 2, or 3. In another embodiment, s is 1, 2, or 3. In another embodiment, s is 0, 1 or 2. In another embodiment, s is 1 or 2. In another embodiment, s is 0. In another embodiment, s is 1. In another embodiment, s is 2. In another embodiment, s is 3. In another embodiment, s is 4. In another embodiment, s is 5. In another embodiment, s is 6.

In one embodiment, t is 0, 1, 2, 3, 4, 5 or 6. In another embodiment, t is 0, 1, 2, 3, 4, or 5. In another embodiment, t is 1, 2, 3, 4, 5 or 6. In another embodiment, t is 1, 2, 3, 4 or 5. In another embodiment, t is 0, 1, 2, 3, or 4. In another embodiment, t is 1, 2, 3, or 4. In another embodiment, t is 0, 1, 2, or 3. In another embodiment, t is 1, 2, or 3. In another embodiment, t is 0, 1 or 2. In another embodiment, t is 1 or 2. In another embodiment, t is 0. In another embodiment, t is 1. In another embodiment, t is 2. In another embodiment, t is 3. In another embodiment, t is 4. In another embodiment, t is 5. In another embodiment, t is 6.

In another embodiment, provided are compounds of structural formula Ia:

Ia

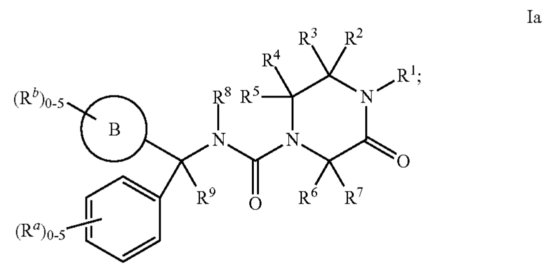

or a pharmaceutically acceptable salt thereof.

In another embodiment, provided are compounds of structural formula Ib:

Ib

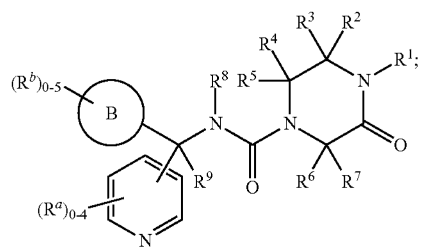

or a pharmaceutically acceptable salt thereof.

In a class of this embodiment, the pyridyl is:

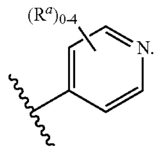

In another class of this embodiment, the pyridyl is:

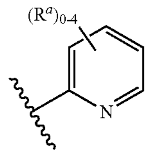

In another class of this embodiment, the pyridyl is:

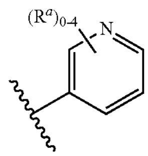

In another embodiment, provided are compounds of structural formula Ic:

Ic

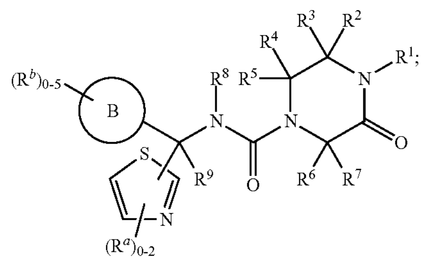

or a pharmaceutically acceptable salt thereof.

In another embodiment, provided are compounds of structural formula Id:

Id

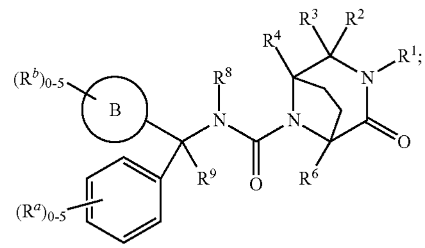

or a pharmaceutically acceptable salt thereof.

In another embodiment, provided are compounds of structural formula Ie:

Ie

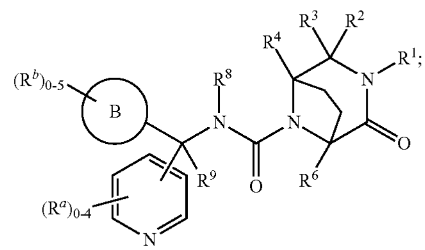

or a pharmaceutically acceptable salt thereof.

In a class of this embodiment, the pyridyl is:

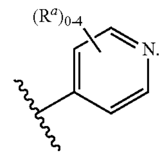

In another class of this embodiment, the pyridyl is:

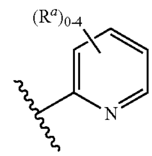

In another class of this embodiment, the pyridyl is:

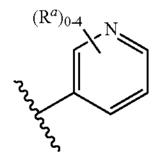

In another embodiment, provided are compounds of structural formula If:

If

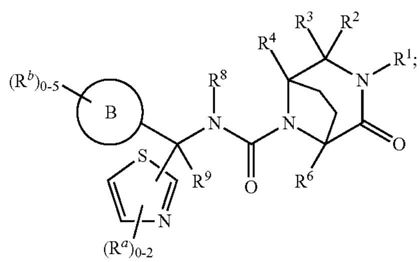

or a pharmaceutically acceptable salt thereof.

The compound of structural formula I, includes the compounds of structural formulas Ia, Ib, 1c, Id, Ie and If, and pharmaceutically acceptable salts, hydrates and solvates thereof.

Another embodiment relates to compounds of structural formula I wherein:

A is selected from the group consisting of:
(1) aryl, and
(2) heteroaryl,
wherein aryl and heteroaryl are unsubstituted or substituted with one to five substituents selected from $R^a$;
B is independently selected from the group consisting of:
(1) —$C_{3-12}$cycloalkyl,
(2) —$C_{2-11}$cycloheteroalkyl,
(3) —$C_{1-6}$alkyl-$C_{3-12}$cycloalkyl,
(4) —$C_{1-6}$alkyl-$C_{2-11}$cycloheteroalkyl,
(5) —$C_{1-6}$alkyl-O—$C_{3-12}$cycloalkyl, and
(6) —$C_{1-6}$alkyl-O—$C_{2-11}$cycloheteroalkyl,
wherein alkyl, cycloalkyl and cycloheteroalkyl are unsubstituted or substituted with one to six substituents selected from $R^b$; and
$R^1$, $R^2$, $R^3$, $R^4$, $R^5$, $R^6$, $R^7$, $R^8$, $R^9$, $R^a$, $R^b$, $R^c$, $R^d$, $R^e$, $R^f$, $R^g$, $R^h$, $R^i$, $R^j$, $R^k$, $R^L$, m, n, p, q, r, s and t are as defined above;
or a pharmaceutically acceptable salt thereof.

Another embodiment relates to compounds of structural formula I wherein:

A is selected from the group consisting of:
(1) phenyl,
(2) pyridine, and
(3) thiazole,
wherein phenyl, pyridine and thiazole are unsubstituted or substituted with one to five substituents selected from $R^a$;
B is independently selected from the group consisting of:
(1) cyclopropane,
(2) cyclobutane,
(3) cyclopentane,
(4) cyclohexane,
(5) bicyclo[3.2.1]octane,
(6) bicyclo[3.1.0]hexane,
(7) bicyclo[2.2.2]octane,
(8) spiro[2.5]octane,
(9) bicyclo[1.1.1]pentane,
(10) spiro[3.3]heptane,
(11) spiro[2.3]hexane,
(12) spiro[2.2]pentane,
(13) piperidine,
(14) tetrahydropyran, and
(15) chromane,
wherein B is unsubstituted or substituted with one to six substituents selected from $R^b$.
$R^1$ is selected from the group consisting of:
(1) hydrogen, and
(2) —$C_{1-6}$alkyl, and
wherein each alkyl is unsubstituted or substituted with one to five substituents selected from $R^c$;
$R^2$ is selected from the group consisting of:
(1) hydrogen,
(2) deuterium,
(3) —$C_{1-6}$alkyl, and
(4) —$C_{3-6}$cycloalkyl,
wherein each alkyl and cycloalkyl is unsubstituted or substituted with one to five substituents selected from $R^d$;
$R^3$ is selected from the group consisting of:
(1) hydrogen,
(2) deuterium,
(3) —$C_{1-6}$alkyl, and
(4) —$C_{3-6}$cycloalkyl,
wherein each alkyl and cycloalkyl is unsubstituted or substituted with one to five substituents selected from $R^d$;
$R^4$ is selected from the group consisting of:
(1) hydrogen,
(2) deuterium,
(3) —$C_{1-6}$alkyl, and
(4) —$C_{3-6}$cycloalkyl,
wherein each alkyl and cycloalkyl is unsubstituted or substituted with one to five substituents selected from $R^f$;
$R^5$ is selected from the group consisting of:
(1) hydrogen,
(2) deuterium,
(3) —$C_{1-6}$alkyl, and
(4) —$C_{3-6}$cycloalkyl,
wherein alkyl and cycloalkyl is unsubstituted or substituted with one to five substituents selected from $R^f$;
$R^6$ is selected from the group consisting of:
(1) hydrogen,
(2) —$C_{1-6}$alkyl, and
(3) —$C_{3-6}$cycloalkyl,
wherein alkyl and cycloalkyl is unsubstituted or substituted with one to five substituents selected from $R^g$;
$R^7$ is selected from the group consisting of:
(1) hydrogen,
(2) —$C_{1-6}$alkyl, and
(3) —$C_{3-6}$cycloalkyl,
wherein alkyl, and cycloalkyl is unsubstituted or substituted with one to five substituents selected from $R^g$;
$R^8$ is selected from the group consisting of:
(1) hydrogen, and
(2) —$C_{1-6}$alkyl,
wherein alkyl is unsubstituted or substituted with one to five substituents selected from halogen;
$R^9$ is selected from the group consisting of:
(1) hydrogen, and
(2) —$C_{1-6}$alkyl,
wherein alkyl is unsubstituted or substituted with one to five substituents selected from halogen;
$R^a$ is independently selected from the group consisting of:
(1) CN,
(2) oxo,
(3) halogen,
(4) —$S(O)_2C_{1-6}$alkyl,
(5) —$C_{1-6}$alkyl,
(6) —$C_{2-6}$alkenyl,
(7) —$C_{3-6}$cycloalkyl,
(8) —$C_{2-6}$cycloheteroalkyl,
(9) aryl,

(10) heteroaryl,
(11) —OH,
(12) —O—$C_{1-6}$alkyl,
(13) —O—$C_{3-6}$cycloalkyl, and
(14) —O—$C_{2-6}$cycloheteroalkyl, wherein each $R^a$ is unsubstituted or substituted with one to six substituents selected from halogen, $CF_3$, OH, $C_{1-6}$alkyl, and —$OC_{1-6}$alkyl; and each $R^b$ is independently selected from the group consisting of:
(1) CN,
(2) oxo,
(3) halogen,
(4) —$S(O)_2C_{1-6}$alkyl,
(5) —$C_{1-6}$alkyl,
(6) —$C_{1-6}$alkenyl,
(7) —$C_{2-6}$alkynyl,
(8) —$C_{3-6}$cycloalkyl,
(9) —$C_{2-6}$cycloheteroalkyl,
(10) aryl,
(11) heteroaryl,
(12) —OH,
(13) —O—$C_{1-6}$alkyl,
(14) —O—$C_{3-6}$cycloalkyl, and
(15) —O—$C_{2-6}$cycloheteroalkyl, wherein each $R^b$ is unsubstituted or substituted with one to six substituents selected from halogen, $CF_3$, $OCF_3$, CN, $CH_2CF_3$, $CF_2CH_3$, —$C_{1-6}$alkyl, and —$OC_{1-6}$alkyl; and $R^c$, $R^d$, $R^e$, $R^f$, $R^g$, $R^h$, $R^i$, $R^j$, $R^k$, $R^L$, m, n, p, q, r, s and t are as defined above;

or a pharmaceutically acceptable salt thereof.

Another embodiment relates to compounds of structural formula I wherein:

A is selected from the group consisting of:
(1) phenyl,
(2) pyridine, and
(3) thiazole, wherein phenyl, pyridine and thiazole are unsubstituted or substituted with one to five substituents selected from $R^a$;

B is independently selected from the group consisting of:
(1) cyclopropane,
(2) cyclobutane,
(3) cyclopentane,
(4) cyclohexane,
(5) bicyclo[3.2.1]octane,
(6) bicyclo[3.1.0]hexane,
(7) bicyclo[2.2.2]octane,
(8) spiro[2.5]octane,
(9) bicyclo[1.1.1]pentane,
(10) spiro[3.3]heptane,
(11) spiro[2.3]hexane,
(12) spiro[2.2]pentane
(13) piperidine, and
(14) tetrahydropyran, wherein B is unsubstituted or substituted with one to six substituents selected from $R^b$.

$R^1$ is selected from the group consisting of:
(1) hydrogen, and
(2) —$C_{1-6}$alkyl, and wherein each alkyl is unsubstituted or substituted with one to five substituents selected from $R^c$;

$R^2$ is selected from the group consisting of:
(1) hydrogen,
(2) —$C_{1-6}$alkyl, and
(3) —$C_{3-6}$cycloalkyl, wherein each alkyl and cycloalkyl is unsubstituted or substituted with one to five substituents selected from $R^d$;

$R^3$ is selected from the group consisting of:
(1) hydrogen,
(2) —$C_{1-6}$alkyl, and
(3) —$C_{3-6}$cycloalkyl, wherein each alkyl and cycloalkyl is unsubstituted or substituted with one to five substituents selected from $R^d$;

$R^4$ is selected from the group consisting of:
(1) hydrogen,
(2) —$C_{1-6}$alkyl, and
(3) —$C_{3-6}$cycloalkyl, wherein each alkyl and cycloalkyl is unsubstituted or substituted with one to five substituents selected from $R^f$;

$R^5$ is selected from the group consisting of:
(1) hydrogen,
(2) —$C_{1-6}$alkyl, and
(3) —$C_{3-6}$cycloalkyl, wherein alkyl and cycloalkyl is unsubstituted or substituted with one to five substituents selected from $R^f$;

$R^6$ is selected from the group consisting of:
(1) hydrogen,
(2) —$C_{1-6}$alkyl, and
(3) —$C_{3-6}$cycloalkyl, wherein alkyl and cycloalkyl is unsubstituted or substituted with one to five substituents selected from $R^g$;

$R^7$ is selected from the group consisting of:
(1) hydrogen,
(2) —$C_{1-6}$alkyl, and
(3) —$C_{3-6}$cycloalkyl, wherein alkyl, and cycloalkyl is unsubstituted or substituted with one to five substituents selected from $R^g$;

$R^8$ is selected from the group consisting of:
(1) hydrogen, and
(2) —$C_{1-6}$alkyl, wherein alkyl is unsubstituted or substituted with one to five substituents selected from halogen;

$R^9$ is selected from the group consisting of:
(1) hydrogen, and
(2) —$C_{1-6}$alkyl, wherein alkyl is unsubstituted or substituted with one to five substituents selected from halogen;

$R^a$ is independently selected from the group consisting of:
(1) CN,
(2) oxo,
(3) halogen,
(4) —$S(O)_2C_{1-6}$alkyl,
(5) —$C_{1-6}$alkyl,
(6) —$C_{2-6}$alkenyl,
(7) —$C_{3-6}$cycloalkyl,
(8) —$C_{2-6}$cycloheteroalkyl,
(9) aryl,
(10) heteroaryl,
(11) —OH,
(12) —O—$C_{1-6}$alkyl,
(13) —O—$C_{3-6}$cycloalkyl, and
(14) —O—$C_{2-6}$cycloheteroalkyl, wherein each $R^a$ is unsubstituted or substituted with one to six substituents selected from halogen, $CF_3$, OH, $C_{1-6}$alkyl, and —$OC_{1-6}$alkyl;

each $R^b$ is independently selected from the group consisting of:
(1) CN,
(2) oxo, (3) halogen,
(4) $—S(O)_2C_{1-6}$alkyl,
(5) $—C_{1-6}$alkyl,
(6) $—C_{1-6}$alkenyl,
(7) $—C_{2-6}$alkynyl,
(8) $—C_{3-6}$cycloalkyl,
(9) $—C_{2-6}$cycloheteroalkyl,
(10) aryl,
(11) heteroaryl,
(12) —OH,
(13) $—O—C_{1-6}$alkyl,
(14) $—O—C_{3-6}$cycloalkyl, and
(15) $—O—C_{2-6}$cycloheteroalkyl, wherein each $R^b$ is unsubstituted or substituted with one to six substituents selected from halogen, $CF_3$, $OCF_3$, CN, $CH_2CF_3$, $CF_2CH_3$, $—C_{1-6}$alkyl, and $—OC_{1-6}$alkyl; and $R^c$, $R^d$, $R^e$, $R^f$, $R^g$, $R^h$, $R^i$, $R^j$, $R^k$, $R^L$, m, n, p, q, r, s and t are as defined above; or a pharmaceutically acceptable salt thereof.

Another embodiment relates to compounds of structural formula I wherein:

A is selected from the group consisting of:
(1) phenyl, and
(2) pyridine, wherein phenyl and pyridine are unsubstituted or substituted with one to four substituents selected from $R^a$;

B is independently selected from the group consisting of:
(1) $—C_{3-12}$cycloalkyl, and
(2) $—C_{2-11}$cycloheteroalkyl, wherein cycloalkyl and cycloheteroalkyl are unsubstituted or substituted with one to six substituents selected from $R^b$;

$R^1$ is hydrogen;

$R^2$, $R^3$, $R^4$ and $R^5$ are deuterium or hydrogen;

$R^6$ and $R^7$ are $CH_3$ or hydrogen;

$R^8$ and $R^9$ are hydrogen;

each $R^a$ is independently selected from the group consisting of:
(1) halogen,
(2) $—C_{1-6}$alkyl, and
(3) $—O—C_{1-6}$alkyl, wherein each $R^a$ is unsubstituted or substituted with one to six substituents selected from halogen, $CF_3$, OH, $C_{1-6}$alkyl, and $—OC_{1-6}$alkyl;

each $R^b$ is independently selected from the group consisting of:
(1) halogen,
(2) $—C_{1-6}$alkyl,
(3) $—C_{1-6}$alkenyl,
(4) $—C_{3-6}$cycloalkyl, and
(5) $—O—C_{1-6}$alkyl, wherein each $R^b$ is unsubstituted or substituted with one to six substituents selected from halogen, $CF_3$, $OCF_3$, CN, $CH_2CF_3$, $CF_2CH_3$, $—C_{1-6}$alkyl, and $—OC_{1-6}$alkyl; and $R^c$, $R^d$, $R^e$, $R^f$, $R^g$, $R^h$, $R^i$, $R^j$, $R^k$, $R^L$, m, n, p, q, r, s and t are as defined above;

or a pharmaceutically acceptable salt thereof.

Another embodiment relates to compounds of structural formula I wherein:

A is selected from the group consisting of:
(1) phenyl, and
(2) pyridine, wherein phenyl and pyridine are unsubstituted or substituted with one to four substituents selected from $R^a$;

B is independently selected from the group consisting of:
(1) $—C_{3-12}$cycloalkyl, and
(2) $—C_{2-11}$cycloheteroalkyl, wherein cycloalkyl and cycloheteroalkyl are unsubstituted or substituted with one to six substituents selected from $R^b$;

$R^1$, $R^2$, $R^3$, $R^4$, $R^5$, $R^6$, $R^7$, $R^8$ and $R^9$ are hydrogen;

each $R^a$ is independently selected from the group consisting of
(1) halogen,
(2) $—C_{1-6}$alkyl, and
(3) $—O—C_{1-6}$alkyl, wherein each $R^a$ is unsubstituted or substituted with one to six substituents selected from halogen, $CF_3$, OH, $C_{1-6}$alkyl, and $—OC_{1-6}$alkyl;

each $R^b$ is independently selected from the group consisting of
(1) halogen,
(2) $—C_{1-6}$alkyl,
(3) $—C_{1-6}$alkenyl,
(4) $—C_{3-6}$cycloalkyl, and
(5) $—O—C_{1-6}$alkyl, wherein each $R^b$ is unsubstituted or substituted with one to six substituents selected from halogen, $CF_3$, $OCF_3$, CN, $CH_2CF_3$, $CF_2CH_3$, $—C_{1-6}$alkyl, and $—OC_{1-6}$alkyl; and $R^c$, $R^d$, $R^e$, $R^f$, $R^g$, $R^h$, $R^i$, $R^j$, $R^k$, $R^L$, m, n, p, q, r, s and t are as defined above;

or a pharmaceutically acceptable salt thereof.

Illustrative, but non-limiting, examples of the compounds that are useful as inhibitors of $Na_v1.8$ channel activity are the following compounds:

(1) N-((R)-3-chloro-4-fluorophenyl)(trans-4-(trifluoromethyl)cyclohexyl)methyl)-3-oxopiperazine-1-carboxamide;
(2) N-((S)-3-chloro-4-fluorophenyl)(trans-4-(trifluoromethyl)cyclohexyl)methyl)-3-oxopiperazine-1-carboxamide;
(3) N-((R)-(3-chloro-4-fluorophenyl)(8,8-difluorobicyclo[3.2.1]octan-3-yl)methyl)-3-oxopiperazine-1-carboxamide;
(4) N-((S)-(3-chloro-4-fluorophenyl)(8,8-difluorobicyclo[3.2.1]octan-3-yl)methyl)-3-oxopiperazine-1-carboxamide;
(5) (2R)-N-((R)-(3-chloro-4-fluorophenyl)(8,8-difluorobicyclo[3.2.1]octan-3-yl)methyl)-2-methyl-3-oxopiperazine-1-carboxamide;
(6) (2R)-N-((S)-(3-chloro-4-fluorophenyl)(8,8-difluorobicyclo[3.2.1]octan-3-yl)methyl)-2-methyl-3-oxopiperazine-1-carboxamide;
(7) N-((R)-(4-chlorophenyl)(trans-4-(trifluoromethyl)cyclohexyl)methyl)-3-oxopiperazine-1-carboxamide;
(8) N-((R)-(4-chlorophenyl)(trans-4-(trifluoromethyl)cyclohexyl)methyl)-3-oxopiperazine-1-carboxamide;
(9) N-((S)-(4-chlorophenyl)(trans-4-(trifluoromethyl)cyclohexyl)methyl)-3-oxopiperazine-1-carboxamide;
(10) (2R)-N-((R)-(3-chloro-4-fluorophenyl)(trans-4-(trifluoromethyl)cyclohexyl)methyl)-2-methyl-3-oxopiperazine-1-carboxamide;
(11) (2R)-N-((S)-(3-chloro-4-fluorophenyl)(trans-4-(trifluoromethyl)cyclohexyl)methyl)-2-methyl-3-oxopiperazine-1-carboxamide;
(12) (R)-2-methyl-3-oxo-N-((R)-(trans-4-(trifluoromethyl)cyclohexyl)(3,4,5-trifluorophenyl)methyl)piperazine-1-carboxamide;
(13) (R)-2-methyl-3-oxo-N-((S)-(trans-4-(trifluoromethyl)cyclohexyl)(3,4,5-trifluorophenyl)methyl)piperazine-1-carboxamide;

(14) (2R)-N-((R)-(3-chloro-4-fluorophenyl)((1R,3s,5S)-6,6-difluorobicyclo[3.1.0]hexan-3-yl)methyl)-2-methyl-3-oxopiperazine-1-carboxamide;

(15) (2R)-N-((S)-(3-chloro-4-fluorophenyl)((1R,3s,5S)-6,6-difluorobicyclo[3.1.0]hexan-3-yl)methyl)-2-methyl-3-oxopiperazine-1-carboxamide;

(16) (2R)-N-((R)-(3,4-difluorophenyl)(trans-4-(trifluoromethyl)cyclohexyl)methyl)-2-methyl-3-oxopiperazine-1-carboxamide;

(17) (2R)-N-((S)-(3,4-difluorophenyl)(trans-4-(trifluoromethyl)cyclohexyl)methyl)-2-methyl-3-oxopiperazine-1-carboxamide;

(18) (2R)-N-((R)-(3-chloro-2,4-difluorophenyl)(trans-4-(trifluoromethyl)cyclohexyl)methyl)-2-methyl-3-oxopiperazine-1-carboxamide;

(19) (2R)-N-((S)-(3-chloro-2,4-difluorophenyl)(trans-4-(trifluoromethyl)cyclohexyl)methyl)-2-methyl-3-oxopiperazine-1-carboxamide;

(20) N-((R)-(3-chloro-2,4-difluorophenyl)(trans-4-(trifluoromethyl)cyclohexyl)methyl)-3-oxopiperazine-1-carboxamide;

(21) N-((S)-(3-chloro-2,4-difluorophenyl)(trans-4-(trifluoromethyl)cyclohexyl)methyl)-3-oxopiperazine-1-carboxamide;

(22) (R)-N-((R)-(3-chloro-2,4-difluorophenyl)((1R,3s,5S)-6,6-difluorobicyclo[3.1.0]hexan-3-yl)methyl)-2-methyl-3-oxopiperazine-1-carboxamide;

(23) (R)-N-((S)-(3-chloro-2,4-difluorophenyl)((1R,3s,5S)-6,6-difluorobicyclo[3.1.0]hexan-3-yl)methyl)-2-methyl-3-oxopiperazine-1-carboxamide;

(24) N-((R)-(3-chloro-4-fluorophenyl)(4-(trifluoromethyl)bicyclo[2.2.2]octan-1-yl)methyl)-3-oxopiperazine-1-carboxamide;

(25) N-((S)-(3-chloro-4-fluorophenyl)(4-(trifluoromethyl)bicyclo[2.2.2]octan-1-yl)methyl)-3-oxopiperazine-1-carboxamide;

(26) (2R)-N-((R)-(3-chloro-2,4-difluorophenyl)(4,4-difluorocyclohexyl)methyl)-2-methyl-3-oxopiperazine-1-carboxamide;

(27) (2R)-N-((S)-(3-chloro-2,4-difluorophenyl)(4,4-difluorocyclohexyl)methyl)-2-methyl-3-oxopiperazine-1-carboxamide;

(28) (2R)-N-((R)-(3-chloro-4-fluorophenyl)(4,4-difluorocyclohexyl)methyl)-2-methyl-3-oxopiperazine-1-carboxamide;

(29) (2R)-N-((S)-(3-chloro-4-fluorophenyl)(4,4-difluorocyclohexyl)methyl)-2-methyl-3-oxopiperazine-1-carboxamide;

(30) (2R)-N-((R)-(3-chloro-4-fluorophenyl)(1-(2,2,2-trifluoroethyl)piperidin-4-yl)methyl)-2-methyl-3-oxopiperazine-1-carboxamide;

(31) (2R)-N-((S)-(3-chloro-4-fluorophenyl)(1-(2,2,2-trifluoroethyl)piperidin-4-yl)methyl)-2-methyl-3-oxopiperazine-1-carboxamide;

(32) (2R)-N-((R)-(4-chlorophenyl)(1-(2,2,2-trifluoroethyl)piperidin-4-yl)methyl)-2-methyl-3-oxopiperazine-1-carboxamide;

(33) (2R)-N-((S)-(4-chlorophenyl)(1-(2,2,2-trifluoroethyl)piperidin-4-yl)methyl)-2-methyl-3-oxopiperazine-1-carboxamide;

(34) N-((R)-(3-chloro-4-fluorophenyl)(1-(2,2,2-trifluoroethyl)piperidin-4-yl)methyl)-3-oxopiperazine-1-carboxamide;

(35) N-((S)-(3-chloro-4-fluorophenyl)(1-(2,2,2-trifluoroethyl)piperidin-4-yl)methyl)-3-oxopiperazine-1-carboxamide;

(36) (2R)-N-((R)-(3-chloro-4-fluorophenyl)(1-(R)-(1,1,1-trifluoropropan-2-yl)piperidin-4-yl)methyl)-3-oxopiperazine-1-carboxamide;

(37) (2R)-N-((R)-(3-chloro-4-fluorophenyl)(1-(S)-(1,1,1-trifluoropropan-2-yl)piperidin-4-yl)methyl)-3-oxopiperazine-1-carboxamide;

(38) (2R)-N-((S)-(3-chloro-4-fluorophenyl)(1-(R)-(1,1,1-trifluoropropan-2-yl)piperidin-4-yl)methyl)-3-oxopiperazine-1-carboxamide;

(39) (2R)-N-((S)-(3-chloro-4-fluorophenyl)(1-(S)-(1,1,1-trifluoropropan-2-yl)piperidin-4-yl)methyl)-3-oxopiperazine-1-carboxamide;

(40) (2R)-N-((R)-(3-chloro-4-fluorophenyl)(trans-1,1-difluorospiro[2.5]octan-6-yl)methyl)-2-methyl-3-oxopiperazine-1-carboxamide;

(41) (2R)-N-((S)-(3-chloro-4-fluorophenyl)(trans-1,1-difluorospiro[2.5]octan-6-yl)methyl)-2-methyl-3-oxopiperazine-1-carboxamide;

(42) (2R)-N-((R)-(3-chloro-4-fluorophenyl)(cis-1,1-difluorospiro[2.5]octan-6-yl)methyl)-2-methyl-3-oxopiperazine-1-carboxamide;

(43) (2R)-N-((S)-(3-chloro-4-fluorophenyl)(cis-1,1-difluorospiro[2.5]octan-6-yl)methyl)-2-methyl-3-oxopiperazine-1-carboxamide;

(44) (R)-N-((S)-(3-chloro-2,4-difluorophenyl)(trans-3-(trifluoromethyl)cyclobutyl)methyl)-2-methyl-3-oxopiperazine-1-carboxamide;

(45) (R)-N-((R)-(3-chloro-2,4-difluorophenyl)(trans-3-(trifluoromethyl)cyclobutyl)methyl)-2-methyl-3-oxopiperazine-1-carboxamide;

(46) (R)-N-((S)-(3-chloro-2,4-difluorophenyl)(cis-3-(trifluoromethyl)cyclobutyl)methyl)-2-methyl-3-oxopiperazine-1-carboxamide;

(47) (R)-N-((R)-(3-chloro-2,4-difluorophenyl)(cis-3-(trifluoromethyl)cyclobutyl)methyl)-2-methyl-3-oxopiperazine-1-carboxamide;

(48) (2R)-N-((R)-(3-chloro-2,4-difluorophenyl)(trans-3-cyclopropylcyclobutyl)methyl)-2-methyl-3-oxopiperazine-1-carboxamide;

(49) (2R)-N-((R)-(3-chloro-2,4-difluorophenyl)(cis-3-cyclopropylcyclobutyl)methyl)-2-methyl-3-oxopiperazine-1-carboxamide;

(50) (2R)-N-((S)-(3-chloro-2,4-difluorophenyl)(trans-3-cyclopropylcyclobutyl)methyl)-2-methyl-3-oxopiperazine-1-carboxamide;

(51) (2R)-N-((S)-(3-chloro-2,4-difluorophenyl)(cis-3-cyclopropylcyclobutyl)methyl)-2-methyl-3-oxopiperazine-1-carboxamide;

(52) (2R)-N-((R)-(3-chloro-2,4-difluorophenyl)(trans-1,1-difluorospiro[2.3]hexan-5-yl)methyl)-2-methyl-3-oxopiperazine-1-carboxamide;

(53) (2R)-N-((R)-(3-chloro-2,4-difluorophenyl)(cis-1,1-difluorospiro[2.3]hexan-5-yl)methyl)-2-methyl-3-oxopiperazine-1-carboxamide;

(54) (2R)-N-((S)-(3-chloro-2,4-difluorophenyl)(trans-1,1-difluorospiro[2.3]hexan-5-yl)methyl)-2-methyl-3-oxopiperazine-1-carboxamide;

(55) (2R)-N-((S)-(3-chloro-2,4-difluorophenyl)(cis-1,1-difluorospiro[2.3]hexan-5-yl)methyl)-2-methyl-3-oxopiperazine-1-carboxamide;

(56) (2R)-N-((R)-(3-chloro-2,4-difluorophenyl)(6,6-difluorospiro[3.3]heptan-2-yl)methyl)-2-methyl-3-oxopiperazine-1-carboxamide;

(57) 2R)-N-((S)-(3-chloro-2,4-difluorophenyl)(6,6-difluorospiro[3.3]heptan-2-yl)methyl)-2-methyl-3-oxopiperazine-1-carboxamide;

(58) (2R)-N-((R)-(3-chloro-2,4-difluorophenyl)(3,3-difluorocyclobutyl)methyl)-2-methyl-3-oxopiperazine-1-carboxamide;
(59) (2R)-N-((S)-(3-chloro-2,4-difluorophenyl)(3,3-difluorocyclobutyl)methyl)-2-methyl-3-oxopiperazine-1-carboxamide;
(60) (2R)-N-((R)-(3-chloro-2,4-difluorophenyl)(3-methylenecyclobutyl)methyl)-2-methyl-3-oxopiperazine-1-carboxamide;
(61) (2R)-N-((S)-(3-chloro-2,4-difluorophenyl)(3-methylenecyclobutyl)methyl)-2-methyl-3-oxopiperazine-1-carboxamide;
(62) N-((S)-(3-chloro-2,4-difluorophenyl)(trans-3-(trifluoromethyl)cyclobutyl)methyl)-3-oxopiperazine-1-carboxamide;
(63) (R)-N-((S)-(3-chloro-2,4-difluorophenyl)(trans-3-(trifluoromethyl)cyclobutyl)methyl)-2-cyclopropyl-3-oxopiperazine-1-carboxamide;
(64) (S)-N-((S)-(3-chloro-2,4-difluorophenyl)(trans-3-(trifluoromethyl)cyclobutyl)methyl)-2-cyclopropyl-3-oxopiperazine-1-carboxamide;
(65) (2R)-N-((R)-(3-chloro-2,4-difluorophenyl)(spiro[2.3]hexan-5-yl)methyl)-2-methyl-3-oxopiperazine-1-carboxamide;
(66) (2R)-N-((S)(3-chloro-2,4-difluorophenyl)(spiro[2.3]hexan-5-yl)methyl)-2-methyl-3-oxopiperazine-1-carboxamide;
(67) (2R)-N-((R)-(3-chloro-2,4-difluorophenyl)(trans-3-(difluoromethyl)cyclobutyl)methyl)-2-methyl-3-oxopiperazine-1-carboxamide;
(68) (2R)-N-((S)-(3-chloro-2,4-difluorophenyl)(trans-3-(difluoromethyl)cyclobutyl)methyl)-2-methyl-3-oxopiperazine-1-carboxamide;
(69) (2R)-N-((R)-(3-chloro-2,4-difluorophenyl)(3-(trifluoromethyl)bicyclo[1.1.1]pentan-1yl)methyl)-2-methyl-3-oxopiperazine-1-carboxamide;
(70) (2R)-N-((S)-(3-chloro-2,4-difluorophenyl)(3-(trifluoromethyl)bicyclo[1.1.1]pentan-1-yl)methyl)-2-methyl-3-oxopiperazine-1-carboxamide;
(71) (2R)-N-((R)-(3-chloro-2,4-difluorophenyl)(3,3-dimethylcyclobutyl)methyl)-2-methyl-3-oxopiperazine-1-carboxamide;
(72) (2R)-N-((S)-(3-chloro-2,4-difluorophenyl)(3,3-dimethylcyclobutyl)methyl)-2-methyl-3-oxopiperazine-1-carboxamide;
(73) N-((R)-(3-chloro-2,4-difluorophenyl)(3,3-dimethylcyclobutyl)methyl)-3-oxopiperazine-1-carboxamide;
(74) N-((S)-(3-chloro-2,4-difluorophenyl)(3,3-dimethylcyclobutyl)methyl)-3-oxopiperazine-1-carboxamide;
(75) (2R)-N-((R)-(3,3-dimethylcyclobutyl)(6-(trifluoromethyl)pyridin-3-yl)methyl)-2-methyl-3-oxopiperazine-1-carboxamide;
(76) (2R)-N-((S)-(3,3-dimethylcyclobutyl)(6-(trifluoromethyl)pyridin-3-yl)methyl)-2-methyl-3-oxopiperazine-1-carboxamide;
(77) N-((R)-(3-chloro-4-fluorophenyl)(3-(trifluoromethyl)bicyclo[1.1.1]pentan-1-yl)methyl)-3-oxopiperazine-1-carboxamide;
(78) N-((S)-(3-chloro-4-fluorophenyl)(3-(trifluoromethyl)bicyclo[1.1.1]pentan-1-yl)methyl)-3-oxopiperazine-1-carboxamide;
(79) (2R)-N-((R)-(3-chloro-4-fluorophenyl)(3-(trifluoromethyl)bicyclo[1.1.1]pentan-1-yl)methyl)-2-methyl-3-oxopiperazine-1-carboxamide;
(80) (2R)-N-((S)-(3-chloro-4-fluorophenyl)(3-(trifluoromethyl)bicyclo[1.1.1]pentan-1-yl)methyl)-2-methyl-3-oxopiperazine-1-carboxamide;
(81) (2R)-N-((R)-(4-fluoro-3-methylphenyl)(trans-4-(trifluoromethyl)cyclohexyl)methyl)-2-methyl-3-oxopiperazine-1-carboxamide;
(82) (2R)-N-((S)-(4-fluoro-3-methylphenyl)(trans-4-(trifluoromethyl)cyclohexyl)methyl)-2-methyl-3-oxopiperazine-1-carboxamide;
(83) (2R)-N-((R)-(4-fluoro-3-methylphenyl)(cis-4-(trifluoromethyl)cyclohexyl)methyl)-2-methyl-3-oxopiperazine-1-carboxamide;
(84) (2R)-N-((S)-(4-fluoro-3-methylphenyl)(cis-4-(trifluoromethyl)cyclohexyl)methyl)-2-methyl-3-oxopiperazine-1-carboxamide;
(85) (2R)-N-((R)-(4-chloro-3-(difluoromethyl)phenyl)(cis-4-(trifluoromethyl) cyclohexyl)methyl)-2-methyl-3-oxopiperazine-1-carboxamide;
(86) (2R)-N-((R)-(4-chloro-3-(difluoromethyl)phenyl)(trans-4-(trifluoromethyl) cyclohexyl)methyl)-2-methyl-3-oxopiperazine-1-carboxamide;
(87) (2R)-N-((S)-(4-chloro-3-(difluoromethyl)phenyl)(cis-4-(trifluoromethyl) cyclohexyl)methyl)-2-methyl-3-oxopiperazine-1-carboxamide;
(88) (2R)-N-((S)-(4-chloro-3-(difluoromethyl)phenyl)(trans-4-(trifluoromethyl) cyclohexyl)methyl)-2-methyl-3-oxopiperazine-1-carboxamide;
(89) (2R)-N-((R)-(3-chloro-4-fluorophenyl)(trans-3-(difluoromethoxy)cyclobutyl)methyl)-2-methyl-3-oxopiperazine-1-carboxamide;
(90) (2R)-N-((R)-(3-chloro-4-fluorophenyl)(cis-3-(difluoromethoxy)cyclobutyl)methyl)-2-methyl-3-oxopiperazine-1-carboxamide;
(91) (2R)-N-((S)-(3-chloro-4-fluorophenyl)(cis-3-(difluoromethoxy)cyclobutyl)methyl)-2-methyl-3-oxopiperazine-1-carboxamide;
(92) (2R)-N-((S)-(3-chloro-4-fluorophenyl)(trans-3-(difluoromethoxy)cyclobutyl)methyl)-2-methyl-3-oxopiperazine-1-carboxamide;
(93) (2R)-N-((R)-(3-chloro-2,4-difluorophenyl)(trans-3-(difluoromethoxy)cyclobutyl)methyl)-2-methyl-3-oxopiperazine-1-carboxamide;
(94) (2R)-N-((R)-(3-chloro-2,4-difluorophenyl)(cis-3-(difluoromethoxy)cyclobutyl)methyl)-2-methyl-3-oxopiperazine-1-carboxamide;
(95) (2R)-N-((S)-(3-chloro-2,4-difluorophenyl)(cis-3-(difluoromethoxy)cyclobutyl)methyl)-2-methyl-3-oxopiperazine-1-carboxamide;
(96) (2R)-N-((S)-(3-chloro-2,4-difluorophenyl)(trans-3-(difluoromethoxy)cyclobutyl)methyl)-2-methyl-3-oxopiperazine-1-carboxamide;
(97) (2R)-N-((R)-(3-chloro-2,4-difluorophenyl)(trans-3-methoxycyclobutyl)methyl)-2-methyl-3-oxopiperazine-1-carboxamide;
(98) (2R)-N-((R)-(3-chloro-2,4-difluorophenyl)(cis-3-methoxycyclobutyl)methyl)-2-methyl-3-oxopiperazine-1-carboxamide;
(99) (2R)-N-((S)-(3-chloro-2,4-difluorophenyl)(cis-3-methoxycyclobutyl)methyl)-2-methyl-3-oxopiperazine-1-carboxamide;
(100) (2R)-N-((S)-(3-chloro-2,4-difluorophenyl)(trans-3-methoxycyclobutyl)methyl)-2-methyl-3-oxopiperazine-1-carboxamide;
(101) (2R)-N-((R)-(3-chloro-2,4-difluorophenyl)((R)-spiro[2.2]pentan-1-yl)methyl)-2-methyl-3-oxopiperazine-1-carboxamide;
(102) (2R)-N-((R)-(3-chloro-2,4-difluorophenyl)((S)-spiro[2.2]pentan-1-yl)methyl)-2-methyl-3-oxopiperazine-1-carboxamide;

(103) (2R)-N-((S)-(3-chloro-2,4-difluorophenyl)(R)-spiro[2.2]pentan-1-yl)methyl)-2-methyl-3-oxopiperazine-1-carboxamide;

(104) (2R)-N-((S)-(3-chloro-2,4-difluorophenyl)((S)-spiro[2.2]pentan-1-yl)methyl)-2-methyl-3-oxopiperazine-1-carboxamide;

(105) (2R)-N-((R)-(3-chloro-2,4-difluorophenyl)((R)-3,3-difluorocyclopentyl)methyl)-2-methyl-3-oxopiperazine-1-carboxamide;

(106) (2R)-N-((R)-(3-chloro-2,4-difluorophenyl)((S)-3,3-difluorocyclopentyl)methyl)-2-methyl-3-oxopiperazine-1-carboxamide;

(107) (2R)-N-((S)-(3-chloro-2,4-difluorophenyl)((R)-(3,3-difluorocyclopentyl)methyl)-2-methyl-3-oxopiperazine-1-carboxamide;

(108) (2R)-N-((S)-(3-chloro-2,4-difluorophenyl)((S)-3,3-difluorocyclopentyl)methyl)-2-methyl-3-oxopiperazine-1-carboxamide;

(109) (2R)-N-((R)-(3-chloro-4-fluorophenyl)(trans-3-(trifluoromethyl)cyclobutyl)methyl)-2-methyl-3-oxopiperazine-1-carboxamide;

(110) (2R)-N-((R)-(3-chloro-4-fluorophenyl)(cis-3-(trifluoromethyl)cyclobutyl)methyl)-2-methyl-3-oxopiperazine-1-carboxamide;

(111) (2R)-N-((S)-(3-chloro-4-fluorophenyl)(trans-3-(trifluoromethyl)cyclobutyl)methyl)-2-methyl-3-oxopiperazine-1-carboxamide;

(112) (2R)-N-((S)-(3-chloro-4-fluorophenyl)(cis-3-(trifluoromethyl)cyclobutyl)methyl)-2-methyl-3-oxopiperazine-1-carboxamide;

(113) (2R)-N-((R)-(3-chloro-4-fluorophenyl)(cis-3-(2,2,2-trifluoroethoxy)cyclobutyl)-methyl)-2-methyl-3-oxopiperazine-1-carboxamide;

(114) (2R)-N-((S)-(3-chloro-4-fluorophenyl)(cis-3-(2,2,2-trifluoroethoxy)cyclobutyl)-methyl)-2-methyl-3-oxopiperazine-1-carboxamide;

(115) (2R)-N-((R)-(3-chloro-4-fluorophenyl)(trans-3-(2,2,2-trifluoroethoxy)cyclobutyl)-methyl)-2-methyl-3-oxopiperazine-1-carboxamide;

(116) (2R)-N-((S)-(3-chloro-4-fluorophenyl)(trans-3-(2,2,2-trifluoroethoxy)cyclobutyl)-methyl)-2-methyl-3-oxopiperazine-1-carboxamide;

(117) N-((R)-(5-chloro-6-(trifluoromethyl)pyridin-2-yl)(trans-4-(trifluoromethyl)cyclohexyl)methyl)-3-oxopiperazine-1-carboxamide;

(118) N-((S)-(5-chloro-6-(trifluoromethyl)pyridin-2-yl)(trans-4-(trifluoromethyl)cyclo-hexyl)methyl)-3-oxopiperazine-1-carboxamide;

(119) (2R)-N-((R)-(5-chloro-6-(trifluoromethyl)pyridin-2-yl)(4,4-difluorocyclohexyl)-methyl)-2-methyl-3-oxopiperazine-1-carboxamide;

(120) (2R)-N-((S)-(5-chloro-6-(trifluoromethyl)pyridin-2-yl)(4,4-difluorocyclohexyl)-methyl)-2-methyl-3-oxopiperazine-1-carboxamide;

(121) (2R)-N-((R or S)-(5-chloro-6-(trifluoromethyl)pyridin-2-yl)(cis-3-(trifluoromethyl)-cyclobutyl)methyl)-2-methyl-3-oxopiperazine-1-carboxamide;

(122) (2R)-N-((R or S)-(5-chloro-6-(trifluoromethyl)pyridin-2-yl)(trans-3-(trifluoromethyl)-cyclobutyl)methyl)-2-methyl-3-oxopiperazine-1-carboxamide;

(123) (2R)-N-((S or R)-(5-chloro-6-(trifluoromethyl)pyridin-2-yl)(trans-3-(trifluoromethyl)-cyclobutyl)methyl)-2-methyl-3-oxopiperazine-1-carboxamide;

(124) (2R)-N-((S or R)-(5-chloro-6-(trifluoromethyl)pyridin-2-yl)(cis-3-(trifluoromethyl)-cyclobutyl)methyl)-2-methyl-3-oxopiperazine-1-carboxamide;

(125) (2R)-N-((R or S)-1-(3-chloro-4-fluorophenyl)-1-(cis-3-(trifluoromethyl)cyclobutyl)ethyl)-2-methyl-3-oxopiperazine-1-carboxamide;

(126) (2R)-N-((R or S)-1-(3-chloro-4-fluorophenyl)-1-(trans-3-(trifluoromethyl)cyclobutyl)-ethyl)-2-methyl-3-oxopiperazine-1-carboxamide;

(127) (2R)-N-((S or R)-1-(3-chloro-4-fluorophenyl)-1-(cis-3-(trifluoromethyl)cyclobutyl)-ethyl)-2-methyl-3-oxopiperazine-1-carboxamide;

(128) (2R)-N-((S or R)-1-(3-chloro-4-fluorophenyl)-1-(trans-3-(trifluoromethyl)cyclobutyl)-ethyl)-2-methyl-3-oxopiperazine-1-carboxamide;

(129) (2R)-N-((R)-(3-fluoro-4-(trifluoromethoxy)phenyl)(trans-3-(trifluoromethyl)cyclo-butyl)methyl)-2-methyl-3-oxopiperazine-1-carboxamide;

(130) (2R)-N-((S)-(3-fluoro-4-(trifluoromethoxy)phenyl)(trans-3-(trifluoromethyl)cyclo-butyl)methyl)-2-methyl-3-oxopiperazine-1-carboxamide;

(131) ((2R)-N-((R)-(2-fluoro-4-(trifluoromethoxy)phenyl)(trans-3-(trifluoromethyl)cyclo-butyl)-methyl)-2-methyl-3-oxopiperazine-1-carboxamide;

(132) (2R)-N-((S)-(2-fluoro-4-(trifluoromethoxy)phenyl)(trans-3-(trifluoromethyl)cyclo-butyl)methyl)-2-methyl-3-oxopiperazine-1-carboxamide;

(133) (2R)-N-((R)-(4-fluoro-3-(trifluoromethyl)phenyl)(trans-3-(trifluoromethyl)cyclo-butyl)methyl)-2-methyl-3-oxopiperazine-1-carboxamide;

(134) (2R)-N-((S)-(4-fluoro-3-(trifluoromethyl)phenyl)(trans-3-(trifluoromethyl)-cyclo-butyl)methyl)-2-methyl-3-oxopiperazine-1-carboxamide;

(135) N-((R)-(4-fluoro-3-(trifluoromethyl)phenyl)(trans-3-(trifluoro methyl)cyclobutyl)-methyl)-3-oxopiperazine-1-carboxamide;

(136) N-((S)-(4-fluoro-3-(trifluoromethyl)phenyl)(trans-3-(trifluoro methyl)cyclobutyl)-methyl)-3-oxopiperazine-1-carboxamide;

(137) (2R)-N-((R)-(3-chloro-2-fluorophenyl)(trans-3-(trifluoromethyl)cyclobutyl)methyl)-2-methyl-3-oxopiperazine-1-carboxamide;

(138) (2R)-N-((S)-(3-chloro-2-fluorophenyl)(trans-3-(trifluoromethyl)cyclobutyl)methyl)-2-methyl-3-oxopiperazine-1-carboxamide;

(139) (2R)-N-((R)-(3-chloro-4-(trifluoromethoxy)phenyl)(3-(trifluoromethyl)cyclobutyl)-methyl)-2-methyl-3-oxopiperazine-1-carboxamide;

(140) (2R)-N-((S)-(3-chloro-4-(trifluoromethoxy)phenyl)(3-(trifluoromethyl)cyclobutyl)-methyl)-2-methyl-3-oxopiperazine-1-carboxamide;

(141) (2R)-2-methyl-3-oxo-N-((trans-4-(trifluoromethyl)cyclohexyl)((R)-2-(trifluoro-methyl)thiazol-4-yl)methyl)piperazine-1-carboxamide;

(142) (2R)-2-methyl-3-oxo-N-((trans-4-(trifluoromethyl)cyclohexyl)((S)-2-(trifluoro-methyl)thiazol-4-yl)methyl)piperazine-1-carboxamide;

(143) (2R)-N-((R)-(3-chloro-2,4-difluorophenyl)((3R,6R)-6-(trifluoromethyl)tetrahydro-2H-pyran-3-yl)methyl)-2-methyl-3-oxopiperazine-1-carboxamide;

(144) (2R)-N-((R)-(3-chloro-2,4-difluorophenyl)((3S,6S)-6-(trifluoromethyl)tetrahydro-2H-pyran-3-yl)methyl)-2-methyl-3-oxopiperazine-1-carboxamide;

(145) (2R)-N-((S)-(3-chloro-2,4-difluorophenyl)((3R,6R)-6-(trifluoromethyl)tetrahydro-2H-pyran-3-yl)methyl)-2-methyl-3-oxopiperazine-1-carboxamide;

(146) (2R)-N-((S)-(3-chloro-2,4-difluorophenyl)((3S,6S)-6-(trifluoromethyl)tetrahydro-2H-pyran-3-yl)methyl)-2-methyl-3-oxopiperazine-1-carboxamide;

(147) (2R)-N-(R)-(3-chloro-2,4-difluorophenyl)(trans-2-(trifluoromethyl)cyclopropyl)-methyl)-2-methyl-3-oxopiperazine-1-carboxamide;

(148) (2R)-N-(R)-(3-chloro-2,4-difluorophenyl)(trans-2-(trifluoromethyl)cyclopropyl)-methyl)-2-methyl-3-oxopiperazine-1-carboxamide;

(149) (2R)-N-(S)-(3-chloro-2,4-difluorophenyl)(trans-2-(trifluoromethyl)cyclopropyl)-methyl)-2-methyl-3-oxopiperazine-1-carboxamide;

(150) (2R)-N-(S)-(3-chloro-2,4-difluorophenyl)(trans-2-(trifluoromethyl)cyclopropyl)-methyl)-2-methyl-3-oxopiperazine-1-carboxamide;

(151) (2R)-N-((R or S)-(3-chloro-2,4-difluorophenyl)(cis-3-(trifluoromethyl)cyclopentyl)-methyl)-2-methyl-3-oxopiperazine-1-carboxamide;

(152) (2R)-N-((R or S)-(3-chloro-2,4-difluorophenyl)(cis-3-(trifluoromethyl)cyclopentyl)-methyl)-2-methyl-3-oxopiperazine-1-carboxamide;

(153) (2R)-N-((R or S)-(3-chloro-2,4-difluorophenyl)(trans-3-(trifluoromethyl)cyclopentyl)-methyl)-2-methyl-3-oxopiperazine-1-carboxamide; and (154) (2R)-N-((R or S)-(3-chloro-2,4-difluorophenyl)(trans-3-(trifluoromethyl)cyclopentyl)-methyl)-2-methyl-3-oxopiperazine-1-carboxamide;

or a pharmaceutically acceptable salt thereof.

Illustrative, but non-limiting, examples of the compounds that are useful as inhibitors of $Na_v1.8$ channel activity are the following compounds:

(1) (R)-N-((S)-(3-chloro-2,4-difluorophenyl)((1r,3S)-3-(trifluoromethyl)cyclobutyl)-methyl)-2-methyl-3-oxopiperazine-5,5,6,6-d4-1-carboxamide;

(2) (S)-N-((S)-(3-chloro-2,4-difluorophenyl)((1r,3S)-3-(trifluoromethyl)cyclobutyl)-methyl)-2-methyl-3-oxopiperazine-5,5,6,6-d4-1-carboxamide;

(3) (2R)-N-((1(R or S))-(4-fluoro-3-(trifluoromethyl)phenyl)-trans-(6-(trifluoromethyl)-tetrahydro-2H-pyran-3-yl)methyl)-2-methyl-3-oxopiperazine-1-carboxamide;

(4) (2R)-N-((1(R or S))-(4-fluoro-3-(trifluoromethyl)phenyl)-trans-(6-(trifluoromethyl)-tetrahydro-2H-pyran-3-yl)methyl)-2-methyl-3-oxopiperazine-1-carboxamide;

(5) (S)-N-((S)-(3-chloro-2,4-difluorophenyl)((1r,3S)-3-(trifluoromethyl)cyclobutyl)-methyl)-2-(fluoromethyl)-3-oxopiperazine-2-d-1-carboxamide;

(6) (R)-N-((R)-(3-chloro-2,4-difluorophenyl)((R)-chroman-3-yl)methyl)-2-methyl-3-oxopiperazine-1-carboxamide; s (7) (R)-N-((S)-(3-chloro-2,4-difluorophenyl)((R)-chroman-3-yl)methyl)-2-methyl-3-oxopiperazine-1-carboxamide;

(8) (R)-N-((R)-(3-chloro-2,4-difluorophenyl)((S)-chroman-3-yl)methyl)-2-methyl-3-oxopiperazine-1-carboxamide;

(9) (R)-N-((S)-(3-chloro-2,4-difluorophenyl)((S)-chroman-3-yl)methyl)-2-methyl-3-oxopiperazine-1-carboxamide;

(10) (R)-N-((S)-(3-chloro-2,4-difluorophenyl)((1r,3S)-3-(trifluoromethyl)cyclobutyl)-methyl)-3-oxo-2-(trifluoromethyl)piperazine-1-carboxamide;

(11) (S)-N-((S)-(3-chloro-2,4-difluorophenyl)((1r,3S)-3-(trifluoromethyl)cyclobutyl)-methyl)-3-oxo-2-(trifluoromethyl)piperazine-1-carboxamide; and

(12) (R)-N-((S)-(3-chloro-2,4-difluorophenyl)((1r,3S)-3-(trifluoromethyl)cyclobutyl)-methyl)-2-(hydroxymethyl)-3-oxopiperazine-1-carboxamide;

or a pharmaceutically acceptable salt thereof.

Illustrative, but non-limiting, examples of the compounds that are useful as inhibitors of $Na_v1.8$ channel activity are the following compounds:

(1) N-((R)-3-chloro-4-fluorophenyl)(trans-4-(trifluoromethyl)cyclohexyl)methyl)-3-oxopiperazine-1-carboxamide;

(2) N-((S)-3-chloro-4-fluorophenyl)(trans-4-(trifluoromethyl)cyclohexyl)methyl)-3-oxopiperazine-1-carboxamide;

(3) (R)-N-((S)-(3-chloro-2,4-difluorophenyl)(trans-3-(trifluoromethyl)cyclobutyl)methyl)-2-methyl-3-oxopiperazine-1-carboxamide;

(4) (R)-N-((R)-(3-chloro-2,4-difluorophenyl)(trans-3-(trifluoromethyl)cyclobutyl)methyl)-2-methyl-3-oxopiperazine-1-carboxamide;

(5) (R)-N-((S)-(3-chloro-2,4-difluorophenyl)(cis-3-(trifluoromethyl)cyclobutyl)methyl)-2-methyl-3-oxopiperazine-1-carboxamide;

(6) (R)-N-((R)-(3-chloro-2,4-difluorophenyl)(cis-3-(trifluoromethyl)-cyclobutyl)methyl)-2-methyl-3-oxopiperazine-1-carboxamide;

(7) N-((S)-(3-chloro-2,4-difluorophenyl)(trans-3-(trifluoromethyl)cyclobutyl)methyl)-3-oxopiperazine-1-carboxamide;

(8) (2R)-N-((R or S)-(5-chloro-6-(trifluoromethyl)pyridin-2-yl)(cis-3-(trifluoromethyl)-cyclobutyl)methyl)-2-methyl-3-oxopiperazine-1-carboxamide;

(9) (2R)-N-((R or S)-(5-chloro-6-(trifluoromethyl)pyridin-2-yl)(trans-3-(trifluoromethyl)-cyclobutyl)methyl)-2-methyl-3-oxopiperazine-1-carboxamide;

(10) (2R)-N-((S or R)-(5-chloro-6-(trifluoromethyl)pyridin-2-yl)(trans-3-(trifluoromethyl)-cyclobutyl)methyl)-2-methyl-3-oxopiperazine-1-carboxamide;

(11) (2R)-N-((S or R)-(5-chloro-6-(trifluoromethyl)pyridin-2-yl)(cis-3-(trifluoromethyl)-cyclobutyl)methyl)-2-methyl-3-oxopiperazine-1-carboxamide;

(12) (2R)-N-((R)-(3-chloro-2,4-difluorophenyl)((3R,6R)-6-(trifluoromethyl)tetrahydro-2H-pyran-3-yl)methyl)-2-methyl-3-oxopiperazine-1-carboxamide;

(13) (2R)-N-((R)-(3-chloro-2,4-difluorophenyl)((3S,6S)-6-(trifluoromethyl)tetrahydro-2H-pyran-3-yl)methyl)-2-methyl-3-oxopiperazine-1-carboxamide;

(14) (2R)-N-((S)-(3-chloro-2,4-difluorophenyl)((3R,6R)-6-(trifluoromethyl)tetrahydro-2H-pyran-3-yl)methyl)-2-methyl-3-oxopiperazine-1-carboxamide; and

(15) (2R)-N-((S)-(3-chloro-2,4-difluorophenyl)((3S,6S)-6-(trifluoromethyl)tetrahydro-2H-pyran-3-yl)methyl)-2-methyl-3-oxopiperazine-1-carboxamide;

or a pharmaceutically acceptable salt thereof.

Illustrative, but non-limiting, examples of the compounds that are useful as inhibitors of $Na_v1.8$ channel activity are the following compounds:

(1) N-((R)-3-chloro-4-fluorophenyl)(trans-4-(trifluoromethyl)cyclohexyl)methyl)-3-oxopiperazine-1-carboxamide;

(2) N-((S)-3-chloro-4-fluorophenyl)(trans-4-(trifluoromethyl)cyclohexyl)methyl)-3-oxopiperazine-1-carboxamide;

(3) (R)-N-((S)-(3-chloro-2,4-difluorophenyl)(trans-3-(trifluoromethyl)cyclobutyl)methyl)-2-methyl-3-oxopiperazine-1-carboxamide;

(4) (R)-N-((R)-(3-chloro-2,4-difluorophenyl)(trans-3-(trifluoromethyl)cyclobutyl)methyl)-2-methyl-3-oxopiperazine-1-carboxamide;

(5) (R)-N-((S)-(3-chloro-2,4-difluorophenyl)(cis-3-(trifluoromethyl)cyclobutyl)methyl)-2-methyl-3-oxopiperazine-1-carboxamide;

(6) (R)-N-((R)-(3-chloro-2,4-difluorophenyl)(cis-3-(trifluoromethyl)-cyclobutyl)methyl)-2-methyl-3-oxopiperazine-1-carboxamide;

(7) N-((S)-(3-chloro-2,4-difluorophenyl)(trans-3-(trifluoromethyl)cyclobutyl)methyl)-3-oxopiperazine-1-carboxamide;

(8) (2R)-N-((R or S)-(5-chloro-6-(trifluoromethyl)pyridin-2-yl)(cis-3-(trifluoromethyl)-cyclobutyl)methyl)-2-methyl-3-oxopiperazine-1-carboxamide;

(9) (2R)-N-((R or S)-(5-chloro-6-(trifluoromethyl)pyridin-2-yl)(trans-3-(trifluoromethyl)-cyclobutyl)methyl)-2-methyl-3-oxopiperazine-1-carboxamide;

(10) (2R)-N-((S or R)-(5-chloro-6-(trifluoromethyl)pyridin-2-yl)(trans-3-(trifluoromethyl)-cyclobutyl)methyl)-2-methyl-3-oxopiperazine-1-carboxamide;

(11) (2R)-N-((S or R)-(5-chloro-6-(trifluoromethyl)pyridin-2-yl)(cis-3-(trifluoromethyl)-cyclobutyl)methyl)-2-methyl-3-oxopiperazine-1-carboxamide;

(12) (2R)-N-((R)-(3-chloro-2,4-difluorophenyl)((3R,6R)-6-(trifluoromethyl)tetrahydro-2H-pyran-3-yl)methyl)-2-methyl-3-oxopiperazine-1-carboxamide;

(13) (2R)-N-((R)-(3-chloro-2,4-difluorophenyl)((3S,6S)-6-(trifluoromethyl)tetrahydro-2H-pyran-3-yl)methyl)-2-methyl-3-oxopiperazine-1-carboxamide;

(14) (2R)-N-((S)-(3-chloro-2,4-difluorophenyl)((3R,6R)-6-(trifluoromethyl)tetrahydro-2H-pyran-3-yl)methyl)-2-methyl-3-oxopiperazine-1-carboxamide; and

(15) (2R)-N-((S)-(3-chloro-2,4-difluorophenyl)((3S,6S)-6-(trifluoromethyl)tetrahydro-2H-pyran-3-yl)methyl)-2-methyl-3-oxopiperazine-1-carboxamide;

(16) (R)-N-((S)-(3-chloro-2,4-difluorophenyl)((1r,3S)-3-(trifluoromethyl)cyclobutyl)methyl)-2-methyl-3-oxopiperazine-5,5,6,6-d4-1-carboxamide; and

(17) (S)-N-((S)-(3-chloro-2,4-difluorophenyl)((1r,3S)-3-(trifluoromethyl)cyclobutyl)methyl)-2-methyl-3-oxopiperazine-5,5,6,6-d4-1-carboxamide;

or a pharmaceutically acceptable salt thereof.

Although the specific stereochemistries described above are preferred, other stereoisomers, including diastereoisomers, enantiomers, epimers, and mixtures of these may also have utility in treating $Na_v1.8$ mediated diseases.

Synthetic methods for making the compounds are disclosed in the Examples shown below. Where synthetic details are not provided in the examples, the compounds are readily made by a person of ordinary skill in the art of medicinal chemistry or synthetic organic chemistry by applying the synthetic information provided herein. Where a stereochemical center is not defined, the structure represents a mixture of stereoisomers at that center. For such compounds, the individual stereoisomers, including enantiomers, diastereoisomers, and mixtures of these are also compounds of structural formula I.

Definitions

"Ac" is acetyl, which is $CH_3C(=O)$—.

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched, or combinations thereof, unless otherwise defined. Examples of alkenyl include vinyl, allyl, isopropenyl, pentenyl, hexenyl, heptenyl, 1-propenyl, 2-butenyl, 2-methyl-2-butenyl, and the like. In certain embodiments, alkenyl is $—C_1$alkenyl or $=CH_2$.

"Alkynyl" means carbon chains which contain at least one carbon-carbon triple bond, and which may be linear or branched, or combinations thereof, unless otherwise defined. Examples of alkynyl include ethynyl, propargyl, 3-methyl-1-pentynyl, 2-heptynyl and the like.

"Cycloalkyl" means a saturated monocyclic, bicyclic, spirocyclic or bridged carbocyclic ring, having a specified number of carbon atoms. The cycloalkyl ring may be fused to a phenyl ring. $C_{3-12}$cycloalkyl means a saturated monocyclic, bicyclic, spirocyclic or bridged carbocyclic ring, with three to twelve carbon atoms. The $C_{3-12}$cycloalkyl may be fused to a phenyl ring. $C_{3-10}$cycloalkyl means a saturated monocyclic, bicyclic, spirocyclic or bridged carbocyclic ring, with three to ten carbon atoms. The $C_{3-10}$cycloalkyl may be fused to a phenyl ring. Examples of cycloalkyl include cyclopropyl, cyclobutyl, cyclopentyl, cyclohexyl, cycloheptyl, and the like. In one embodiment, cycloalkyl is cyclopropyl. In another embodiment, cycloalkyl is selected from: cyclopropane, cyclobutane, cyclopentane, and cyclohexane. In another embodiment, cycloalkyl is selected from: cyclopropane, cyclobutane, cyclopentane, cyclohexane, bicyclo[3.2.1]octane, bicyclo[3.1.0]-hexane, bicyclo[2.2.2]octane, spiro[2.5]octane, bicyclo[1.1.1]pentane, spiro[3.3]heptane, spiro[2.3]hexane, and spiro[2.2]pentane. In another embodiment, cycloalkyl is selected from: cyclobutane, and cyclohexane. In another embodiment, cycloalkyl is cyclopropane.

"Cycloheteroalkyl" means a saturated or partly unsaturated non-aromatic monocyclic, bicyclic, spirocyclic or bridged ring or ring system having a specified number of carbon atoms and containing at least one ring heteroatom selected from N, NH, S (including SO and $SO_2$) and O. The cycloheteroalkyl ring may be fused to a phenyl ring. The cycloheteroalkyl ring may be substituted on the ring carbons and/or the ring nitrogen or sulfur. $C_{2-11}$cycloheteroalkyl means a saturated or partly unsaturated non-aromatic monocyclic, bicyclic, spirocyclic or bridged ring or ring system with two to eleven carbon atoms and containing at least one ring heteroatom selected from N, NH, S (including SO and $SO_2$) and O. The cycloheteroalkyl ring may be substituted on the ring carbons and/or the ring nitrogen or sulfur. The $C_{2-11}$cycloheteroalkyl may be fused to a phenyl ring. $C_{2-9}$ cycloheteroalkyl means a saturated or partly unsaturated non-aromatic monocyclic, bicyclic, spirocyclic or bridged ring or ring system with two to nine carbon atoms and containing at least one ring heteroatom selected from N, NH, S (including SO and $SO_2$) and O. The cycloheteroalkyl ring may be substituted on the ring carbons and/or the ring nitrogen or sulfur. The $C_{2-9}$ cycloheteroalkyl may be fused to a phenyl ring. Examples of cycloheteroalkyl include tetrahydrofuran, pyrrolidine, tetrahydrothiophene, azetidine, piperazine, piperidine, morpholine, oxetane and tetrahydropyran. In one embodiment, cycloheteroalkyl is selected from: azetidine, piperidine, pyrrolidine, tetrahydropyran, and tetrahydrofuran. In another embodiment, cycloheteroalkyl is selected from: piperidine, and tetrahydropyran. In another embodiment, cycloheteroalkyl is tetrahydropyran. In another embodiment, cycloheteroalkyl is chromane.

"Aryl" means a monocyclic, bicyclic or tricyclic carbocyclic aromatic ring or ring system containing 6-14 carbon atoms, wherein at least one of the rings is aromatic. Examples of aryl include phenyl and naphthyl. In one embodiment, aryl is phenyl. In another embodiment, aryl is selected from phenyl and naphthalene.

"Heteroaryl" means a monocyclic, bicyclic or tricyclic ring or ring system containing 5-14 ring atoms and containing at least one ring heteroatom selected from N, NH, S (including SO and $SO_2$) and O, wherein at least one of the heteroatom containing rings is aromatic. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzothiophenyl, quinolyl, indolyl, isoquinolyl, quinazolinyl, dibenzofuranyl, and the like. In one embodiment, heteroaryl is selected from pyridine and thiazole. In another embodiment, heteroaryl is pyridine. In another embodiment, heteroaryl is thiazole. In another embodiment, heteroaryl is selected from: pyridine, pyrimidine, pyrazine, pyridazine, imidazole, pyrazole, thiazole, oxazole, benzofuran, benzoxazole, benzothiazole, indole, indazole, imidazopyridine, thiophene, and thiazolopyridine. In another embodiment, heteroaryl is pyridine.

"Halogen" includes fluorine, chlorine, bromine and iodine. In one embodiment, halogen is fluorine, chorine or bromine. In another embodiment, halogen is fluorine or chlorine. In another embodiment, halogen is fluorine or bromine. In another embodiment, halogen is fluorine. In another embodiment, halogen is chlorine. In another embodiment, halogen is bromine.

"Me" represents methyl.

"Oxo" represents =O.

"Saturated" means containing only single bonds.

"Unsaturated" means containing at least one double or triple bond. In one embodiment, unsaturated means containing at least one double bond. In another embodiment, unsaturated means containing one double bond. In another embodiment, unsaturated means containing at least one triple bond. In another embodiment, unsaturated means containing one triple bond.

When any variable (e.g., $R^1$, $R^a$, etc.) occurs more than one time in any constituent or in structural formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to:

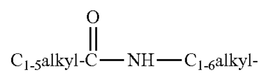

In choosing compounds, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The phrase "pharmaceutically acceptable" is employed herein to refer to those compounds, materials, compositions, salts and/or dosage forms which are, using sound medical judgment, and following all applicable government regulations, safe and suitable for administration to a human being or an animal.

Compounds of structural formula I may contain one or more asymmetric centers and can thus occur as racemates and racemic mixtures, single enantiomers, diastereomeric mixtures and individual diastereomers. The present disclosure is meant to encompass all such isomeric forms of the compounds of structural formula I.

The independent syntheses of optical isomers and diastereoisomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration or sufficient heavy atoms to make an absolute assignment.

If desired, racemic mixtures of the compounds may be separated so that the individual enantiomers are isolated. The separation can be carried out by methods well-known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of structural formula I.

In the compounds of general structural formula I, the atoms may exhibit their natural isotopic abundances, or one or more of the atoms may be artificially enriched in a particular isotope having the same atomic number, but an atomic mass or mass number different from the atomic mass or mass number predominately found in nature. The present disclosure is meant to include all suitable isotopic variations of the compounds of structural formula I. For example, different isotopic forms of hydrogen (H) include protium ($^1H$), deuterium ($^2H$), and tritium ($^3H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Tritium is radioactive and may therefore provide for a radiolabeled compound, useful as a tracer in metabolic or kinetic studies. Isotopically-enriched compounds within structural formula I, can be prepared without undue experimentation by conventional techniques well known to those skilled in the art or by processes analogous to those described in the Schemes and Examples herein using appropriate isotopically-enriched reagents and/or intermediates.

Furthermore, some of the crystalline forms for compounds may exist as polymorphs and as such are intended to be included in the present disclosure. In addition, some of the compounds of structural formula I may form solvates with water or common organic solvents. Such solvates are encompassed within the scope of this disclosure.

It is generally preferable to administer compounds as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Salts

It will be understood that, as used herein, references to the compounds are meant to also include the pharmaceutically acceptable salts, and also salts that are not pharmaceutically acceptable when they are used as precursors to the free compounds or their pharmaceutically acceptable salts or in other synthetic manipulations.

The compounds may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this disclosure which are generally prepared by reacting the free base with a suitable organic or inorganic acid. Representative salts of basic compounds include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide, trifluoroacetate and valerate. Furthermore, where the compounds of structural formula I carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

The term "prodrug" means compounds that are rapidly transformed, for example, by hydrolysis in blood, in vivo to the parent compound, e.g., conversion of a prodrug of structural formula I to a compound of structural formula I, or to a salt thereof; a thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference. This disclosure includes prodrugs of the novel compounds of structural formula I.

Solvates, and in particular, the hydrates of the compounds are included in the present disclosure as well.

Utilities

The compound are selective inhibitors of $Na_v1.8$ sodium ion channel activity or have selective activity as $Na_v1.8$ sodium ion channel blockers. In one embodiment, the compounds exhibit at least 10-fold selectivity for $Na_v1.8$ sodium channels over $Na_v1.5$ sodium channels, and in some embodiments exhibit at least 100-fold selectivity for $Na_v1.8$ sodium channels over $Na_v1.5$ sodium channels based on functional potency ($IC_{50}$ values) for each channel in Qube® assay system.

The compounds are potent inhibitors of $Na_v1.8$ channel activity. The compounds, and pharmaceutically acceptable salts thereof, may be efficacious in the treatment of diseases, disorders and conditions that are mediated by the inhibition of $Na_v1.8$ sodium ion channel activity and/or $Na_v1.8$ receptors.

Diseases, disorders or conditions mediated by $Na_v1.8$ sodium ion channel activity and/or $Na_v1.8$ receptors, include but are not limited to nociception, osteoarthritis, peripheral neuropathy, inherited erythromelalgia, multiple sclerosis, asthma, pruritus, acute itch, chronic itch, migraine, neurodegeneration following ischemia, epilepsy, inflammatory pain, spontaneous pain, acute pain, peri-operative pain, post-operative pain, neuropathic pain, postherpetic neuralgia, trigeminal neuralgia, diabetic neuropathy, chronic lower back pain, phantom limb pain, pain resulting from cancer and chemotherapy, chronic pelvic pain, pain syndromes, and complex regional pain syndromes.

One or more of these conditions or diseases may be treated, managed, prevented, reduced, alleviated, ameliorated or controlled by the administration of a therapeutically effective amount of a compound, or a pharmaceutically acceptable salt thereof, to a patient in need of treatment. Also, the compounds may be used for the manufacture of a medicament which may be useful for treating, preventing, managing, alleviating, ameliorating or controlling one or more of these conditions, diseases or disorders: nociception, osteoarthritis, peripheral neuropathy, inherited erythromelalgia, multiple sclerosis, asthma, pruritus, acute itch, chronic itch, migraine, neurodegeneration following ischemia, epilepsy, inflammatory pain, spontaneous pain, acute pain, pen-operative pain, post-operative pain, neuropathic pain, postherpetic neuralgia, trigeminal neuralgia, diabetic neuropathy, chronic lower back pain, phantom limb pain, pain resulting from cancer and chemotherapy, chronic pelvic pain, pain syndromes, and complex regional pain syndromes.

Preferred uses of the compounds may be for the treatment of one or more of the following diseases by administering a therapeutically effective amount to a patient in need of treatment. The compounds may be used for manufacturing a medicament for the treatment of one or more of these diseases:

(1) pain conditions, (2) pruritic conditions, and (3) cough conditions.

In one embodiment, the pain condition is an acute pain or chronic pain disorder. In another embodiment, the pain condition is an acute pain disorder.

The compounds may be effective in treating nociception. Nociception or pain is essential for survival and often serves a protective function. However, the pain associated with surgical procedures and current therapies to relieve that pain, can delay recovery after surgery and increase the length of hospital stays. As many as 80% of surgical patients experience post-operative pain due to tissue damage, and damage to peripheral nerves and subsequent inflammation. Approximately 10-50% of surgical patients will develop chronic pain after surgery often because the nerve damage results in lasting neuropathic pain once the wound has healed.

The compounds of structural formula I may be effective in treating osteoarthritis. Osteoarthritis is type of arthritis caused by inflammation, breakdown, and eventual loss of cartilage in the joints. The standards of care for pain associated with osteoarthritis are non-steroidal anti-inflammatory drugs (NSAIDs), for example celecoxib and diclofenac (reviewed in Zeng et al., 2018). Patients that do not respond to NSAID therapies are typically treated with low dose opiates, such as hydrocodone. Patients that are refractory to the above therapies will usually opt for total joint replacement.

The compounds of structural formula I may be effective in treating peripheral neuropathy. Peripheral neuropathy is nerve damage caused by chronically high blood sugar and diabetes. It leads to numbness, loss of sensation, and sometimes pain in distal limbs such as feet, legs, or hands. It is the most common complication of diabetes. The standards of care for the treatment of painful diabetic neuropathy are gabapentinoids, for example gabapentin and pregabalin. Some patients will respond well to tricyclic antidepressants such as amitriptyline, while other patients get significant relief using SRI/NRI drugs such as duloxetine (Schreiber et al., World J Diabetes. 2015 Apr. 15; 6(3):432-44). Many options are available, however side-effects are common (e.g. dizziness, nausea) which limit their full potential.

The compounds of structural formula I may be effective in treating inherited erythromelalgia. Inherited erythromelalgia (IEM) is a chronic pain syndrome which has been linked to mutations in several voltage-gated sodium channels, including Nav1.8 (Kist et al., PLoS One. 2016 Sep. 6; 11(9):e0161789). Patients present with the classic “gloves and stocking” flare pattern on distal regions such as hands and feet, typically brought on with warm temperatures and exercise. Some patients find relief from the burning pain associated with flares by cold water immersion. Although medications that affect voltage-gated sodium channels (eg, lidocaine and mexiletine) show promise, there is no current standard of care to treat IEM.

The compounds of structural formula I may be effective in treating neuropathic pain. Neuropathic pain is pain caused by damage or disease affecting the somatosensory nervous system. It has been demonstrated in human patients, as well as in animal models of neuropathic pain, that damage to primary afferent sensory neurons can lead to neuroma formation and spontaneous activity, as well as evoked activity in response to normally innocuous stimuli. (Colloca et al., Nat Rev Dis Primers. 2017 Feb. 16; 3:17002; Coward et al., Pain. 2000 March; 85(1-2):41-50; Yiangou et al., FEBS Lett. 2000 Feb. 11; 467(2-3):249-52; Carter et al., Phys Med Rehabil Clin N Am. 2001 May; 12(2):447-59). Some nerve injuries result in an increase in Nav1.8 expression, which is believed to be an underlying mechanism for pathological pain. (Black et al., Ann Neurol. 2008 December; 64(6):644-53; Bird et al., Br J Pharmacol. 2015 May; 172(10):2654-70). Injuries of the peripheral nervous system often result in neuropathic pain persisting long after an initial injury resolves. Examples of neuropathic pain include, but are not limited to, post herpetic neuralgia, trigeminal neuralgia, diabetic neuropathy, chronic lower back pain, lumbar radiculopathy, phantom limb pain, pain resulting from cancer and chemotherapy, chronic pelvic pain, complex regional pain syndrome and related neuralgias, and painful conditions that arise due to gain-of-function mutations in Nav1.8 (Huang et al., J Neurosci. 2013 Aug. 28; 33(35): 14087-97; Kist et al., PLoS One. 2016 Sep. 6; 11(9): e0161789; Emery et al., J Neurosci. 2015 May 20; 35(20): 7674-81; and Schreiber et al., World J Diabetes. 2015 Apr. 15; 6(3):432-44.

The ectopic activity of normally silent sensory neurons is thought to contribute to the generation and maintenance of neuropathic pain, which is generally assumed to be associated with an increase in sodium channel activity in the injured nerve. (Wood et al., Curr Opin Pharmacol. 2001 February; 1(1):17-21; Baker et al., TRENDS in Pharmacological Sciences, 2001, 22(1): 27-31). Standards of care for neuropathic pain vary considerably depending on the particular condition, but first line therapies are typically pregabalin, gabapentin, tricyclic antidepressants (e.g. amitriptyline), and SRI/NRI drugs (e.g. duloxetine). Patients refractory to these therapies are usually prescribed low dose opiates (e.g. hydrocodone).

The compounds of structural formula I may be effective in treating multiple sclerosis.

Recent evidence points to a potential role for $Na_v1.8$ in multiple sclerosis. $Na_v1.8$ expression in cerebellum has been identified in tissues taken from animal models of multiple sclerosis (EAE model) and in postmortem brains from patients suffering from multiple sclerosis (MS) (Shields et al., Ann Neurol. 2012 February; 71(2):186-94; Black et al., Proc Natl Acad Sci U.S.A. 2000 Oct. 10; 97(21):11598-602). Also, two SCN10A polymorphisms showed significant association with MS (Roostaei et al., Neurology. 2016 Feb. 2; 86 (5):410-7). When Nav1.8 is overexpressed in cerebellum, mice develop ataxic-related motor deficits which are ameliorated with oral delivery of a selective small molecule Nav1.8 antagonist (Shields et al., PLoS One. 2015 Mar. 6; 10(3)). These studies suggest that a Nav1.8 antagonist may be a useful therapy to treat symptoms related to multiple sclerosis.

The compounds of structural formula I may be effective in treating asthma. Asthma is caused by airway inflammation in which a person's airways become hyper-responsive, narrow and swollen, which makes it difficult to breathe. These symptoms are typically triggered through an allergic reaction (Nair P et al., J Allergy Clin Immunol Pract. 2017 May-June; 5(3):649-659). In a preclinical model of asthma, deletion of Nav1.8-containing neurons, or inhibition of nerve fibers via small molecules reduces airway inflammation and immune cell infiltration (Talbot et al., Neuron. 2015 Jul. 15; 87(2):341-54). Selective Nav1.8 antagonists may be a useful therapy to prevent airway hypersensitivity caused by immune cell infiltration.

The compounds of structural formula I may be effective in treating pruritus. Pruritus, also commonly known as itch, affects approximately 4% of the global population is an unpleasant sensation that elicits the desire or reflex to scratch, and is regarded as closely related to pain (Luo et al., Cell Mol Life Sci. 2015 September; 72 (17): 3201-23). Theories on the origin of itch implicate the subtle, low-frequency activation of nociceptors (pain-sensing neurons); however, it has been described that some afferents preferentially respond to histamine, which induces itch (Schmelz et al., J Neurosci. 1997 Oct. 15; 17(20):8003-8). At the same time, it has been found that histamine-responding neurons also respond to capsaicin which produces pain (McMahon et al., Trends in Neuroscience 1992, 15:497-501). Members of the transient receptor potential (TRP) family, and nerve growth factor (NGF) are both known to play a role in itch and pain, and clinically, both maladies are treated with therapeutic agents such as gabapentin and antidepressants. Therefore, it continues to be accepted that the underlying mechanisms of pain and itch are highly interwoven and complex, and distinguishing pan-selective or itch-selective pathways remains ambiguous (Ikoma et al., Nat Rev Neurosci. 2006 July; 7(7):535-47). A role for Nav1.8 in pruritis was studied using a mouse transgenically expressing a constitutively active form of the serine/threonine kinase BRAF was expressed in Nav1.8-expressing neurons. This resulted in enhanced pruriceptor excitability, and heightened evoked and spontaneous scratching behavior (Zhao et al., 2013). In skin, pruritogens are released from keratinocytes, lymphocytes, mast cells, and eosinophils during inflammation. These molecules act directly on free nerve endings which express Nav1.8 to induce itch (Riol-Blanco et al., Nature. 2014 Jun. 5; 510 (7503):157-61). Chronic and acute itch can arise from many different insults, diseases and disorders, and may be classified as dermal or pruriceptive, neurogenic, neuropathic, or psychogenic: itch can arise from both systemic disorders, skin disorders, as well as physical or chemical insult to the dermis. Pathologically, conditions such as dry skin, eczema, psoriasis, varicella zoster, urticaria, scabies, renal failure, cirrhosis, lymphoma, iron deficiency, diabetes, menopause, polycythemia, uremia, and hyperthyroidism can cause itch, as can diseases of the nervous system such as tumors, multiple sclerosis, peripheral neuropathy, nerve compression, and delusions related to obsessive-compulsive disorders. Medicines such as opioids and chloroquine can also trigger itch (Ikoma et al., Nat Rev Neurosci. 2006 July; 7(7):535-47). Itching following burn is also an extremely serious clinical problem as it hampers the healing process, resulting in permanent scaring, and negatively impacting quality of life (Van Loey et al., Br J Dermatol. 2008 January; 158(1):95-100).

Also within the scope of this disclosure are pharmaceutically acceptable salts of the compounds, and pharmaceutical compositions comprising the compounds and a pharmaceutically acceptable carrier.

The compounds, or pharmaceutically acceptable salts thereof, may be useful in treating pain conditions, pruritic conditions, and cough conditions.

A compound of structural formula I, or a pharmaceutically acceptable salt thereof, may be used in the manufacture of a medicament for the treatment of pain conditions, pruritic conditions, and cough conditions in a human or other mammalian patient.

A method of treating a pain conditions comprises the administration of a therapeutically effective amount of a compound of structural formula I, or a pharmaceutically acceptable salt thereof, or a pharmaceutical composition comprising the compound, to a patient in need of treatment. A method of treating a pruritic condition comprises the administration of a therapeutically effective amount of a compound of structural formula I, or a pharmaceutically acceptable salt thereof, or a pharmaceutical composition comprising the compound, to a patient in need of treatment. A method of treating a cough condition comprises the administration of a therapeutically effective amount of a compound of structural formula I, or a pharmaceutically acceptable salt thereof, or a pharmaceutical composition comprising the compound, to a patient in need of treatment. Other medical uses of the compounds of structural formula I are described herein.

The term "pain condition" as used herein includes, but are not limited to, acute pain, peri-operative pain, pre-operative pain, post-operative pain, neuropathic pain, post herpetic neuralgia, trigeminal neuralgia, diabetic neuropathy, chronic lower back pain, phantom limb pain, chronic pelvic pain, vulvodynia, complex regional pain syndrome and related neuralgias, pain associated with cancer and chemotherapy, pain associated with HIV, and HIV treatment-induced neuropathy, nerve injury, root avulsions, painful traumatic mononeuropathy, painful polyneuropathy, erythromyelalgia, paroxysmal extreme pain disorder, small fiber neuropathy, burning mouth syndrome, central pain syndromes (potentially caused by virtually any lesion at any level of the nervous system), postsurgical pain syndromes (e.g., post mastectomy syndrome, post thoracotomy syndrome, stump pain)), bone and joint pain (osteoarthritis), repetitive motion pain, dental pain, myofascial pain (muscular injury, fibromyalgia), perioperative pain (general surgery, gynecological), chronic pain, dysmennorhea, pain associated with angina, inflammatory pain of varied origins (e.g. osteoarthritis, rheumatoid arthritis, rheumatic disease, teno-synovitis and gout), shoulder tendonitis or bursitis, gouty arthritis, and aolymyalgia rheumatica, primary hyperalgesia, secondary hyperalgesia, primary allodynia, secondary allodynia, or other pain caused by central sensitization, complex regional pain syndrome, chronic arthritic pain and related neuralgias acute pain, migraine, migraine headache, headache pain, cluster headache, non-vascular headache, traumatic nerve injury, nerve compression or entrapment, and neuroma pain, The term "pruritic condition" or "pruritic disorder" as used herein includes, but is not limited to, conditions with an unpleasant sensation that provokes the desire to scratch, such as chronic itch.

The term "cough condition" or "cough disorder" as used herein includes, but is not limited to, chronic cough, neuropathic cough or cough due to neurological conditions.

Treatment of a disease, disorder or condition mediated by $Na_v1.8$ sodium ion channel activity or $Na_v1.8$ receptors refers to the administration of the compounds of structural formula I to a subject with the disease, disorder or condition. One outcome of treatment may be reducing the disease, disorder or condition mediated by $Na_v1.8$ sodium ion channel activity or $Na_v1.8$ receptors. Another outcome of treatment may be alleviating the disease, disorder or condition mediated by $Na_v1.8$ sodium ion channel activity or $Na_v1.8$ receptors. Another outcome of treatment may be ameliorating the disease, disorder or condition mediated by $Na_v1.8$ sodium ion channel activity or $Na_v1.8$ receptors. Another outcome of treatment may be suppressing the disease, disorder or condition mediated by $Na_v1.8$ sodium ion channel activity or $Na_v1.8$ receptors. Another outcome of treatment may be managing the disease, disorder or condition mediated by $Na_v1.8$ sodium ion channel activity or $Na_v1.8$ receptors.

Another outcome of treatment may be preventing the disease, disorder or condition mediated by $Na_v1.8$ sodium ion channel activity or $Na_v1.8$ receptors.

Prevention of the disease, disorder or condition mediated by $Na_v1.8$ sodium ion channel activity or $Na_v1.8$ receptors refers to the administration of the compounds of the present disclosure to a subject at risk of the disease, disorder or condition. One outcome of prevention may be reducing the disease, disorder or condition mediated by $Na_v1.8$ sodium ion channel activity or $Na_v1.8$ receptors in a subject at risk of the disease, disorder or condition. Another outcome of prevention may be suppressing the disease, disorder or condition mediated by $Na_v1.8$ sodium ion channel activity or $Na_v1.8$ receptors in a subject at risk of the disease, disorder or condition. Another outcome of prevention may be ameliorating the disease, disorder or condition mediated by $Na_v1.8$ sodium ion channel activity or $Na_v1.8$ receptors in a subject at risk of the disease, disorder or condition. Another outcome of prevention may be alleviating the disease, disorder or condition mediated by $Na_v1.8$ sodium ion channel activity or $Na_v1.8$ receptors in a subject at risk of the disease, disorder or condition. Another outcome of prevention may be managing the disease, disorder or condition mediated by $Na_v1.8$ sodium ion channel activity or $Na_v1.8$ receptors in a subject at risk of the disease, disorder or condition.

One outcome of treatment may be reducing the amount of pain experienced by a subject relative to that subject's pain immediately before the administration of the compounds of structural formula I. Another outcome of treatment may be alleviating the amount of pain experienced by a subject relative to that subject's pain immediately before the administration of the compounds of structural formula I. Another outcome of treatment may be ameliorating the amount of pain experienced by a subject relative to that subject's pain immediately before the administration of the compounds of structural formula I. Another outcome of treatment may be suppressing the amount of pain experienced by a subject relative to that subject's pain immediately before the administration of the compounds of structural formula I. Another outcome of treatment may be managing the amount of pain experienced by a subject relative to that subject's pain immediately before the administration of the compounds of structural formula I. Another outcome of treatment may be ameliorating the amount of pain experienced by a subject relative to that subject's pain immediately before the administration of the compounds of structural formula I.

Another outcome of treatment may be preventing further pain experienced by a subject after the administration of the compounds of structural formula I.

Prevention of pain refers to the administration of the compounds of structural formula I to reduce the pain of a subject at risk of pain. Prevention includes, but is not limited to, the administration to a subject prior to surgery or other expected painful event. One outcome of prevention may be reducing pain in a subject at risk of pain. Another outcome of prevention may be suppressing pain in a subject at risk of pain. Another outcome of prevention may be ameliorating pain in a subject at risk of pain. Another outcome of prevention may be alleviating pain in a subject at risk of pain. Another outcome of prevention may be managing pain in a subject at risk of pain.

The terms "administration of" and or "administering a" compound should be understood to mean providing a compound of structural formula I or a prodrug thereof to the individual or mammal in need of treatment.

The administration of the compound of structural formula I in order to practice the present methods of therapy is carried out by administering an effective amount of the compound of structural formula I to the mammal in need of such treatment or prophylaxis. The need for a prophylactic administration according to the methods provided herein is determined via the use of well known risk factors. The effective amount of an individual compound is determined, in the final analysis, by the physician or veterinarian in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The usefulness of the present compounds in these diseases or disorders may be demonstrated in animal disease models that have been reported in the literature.

Administration and Dose Ranges

Any suitable route of administration may be employed for providing a mammal, especially a human, with an effective dose of a compound of structural formula I. For example, oral, intravenous, infusion, subcutaneous, transcutaneous, intramuscular, intradermal, transmucosal, intramucosal, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of structural formula I are administered orally.

In the treatment or prevention of disorders, diseases and/or conditions which require inhibition of $Na_v1.8$ sodium ion channel activity, a suitable dosage level will generally be about 0.0001 to 500 mg per kg patient body weight per day which can be administered in single or multiple doses. In one embodiment, a suitable dosage level may be about 0.001 to 500 mg per kg patient body weight per day. In another embodiment, a suitable dosage level may be about 0.001 to about 250 mg/kg per day. In another embodiment, a suitable dosage level may be about 0.01 to about 250 mg/kg per day. In another embodiment, a suitable dosage level may be about 0.1 to about 100 mg/kg per day. In another embodiment, a suitable dosage level may be about 0.05 to 100 mg/kg per day. In another embodiment, a suitable dosage level may be about 0.1 to 50 mg/kg per day. In another embodiment, a suitable dosage level may be about 0.05 to 0.5 mg/kg per day. In another embodiment, a suitable dosage level may be about 0.5 to 5 mg/kg per day. In another embodiment, a suitable dosage level may be about 5 to 50 mg/kg per day. For oral administration, the compositions are preferably provided in the form of tablets containing 0.01 to 1000 mg of the active ingredient, particularly 0.01, 0.025, 0.05, 0.075, 0.1, 0.25, 0.5, 0.75, 1.0, 2.5, 5.0, 7.5, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 8 times per day; preferably, 1 to 4 times a day; more preferably once or twice per day. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of structural formula I may be used in pharmaceutical compositions comprising (a) the compound (s) or pharmaceutically acceptable salts thereof, and (b) a pharmaceutically acceptable carrier. The compounds of structural formula I may be used in pharmaceutical compositions that include one or more other active pharmaceutical ingredients. The compounds of this disclosure may also be used in pharmaceutical compositions in which the compound of structural formula I or a pharmaceutically acceptable salt thereof is the only active ingredient.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions disclosed herein encompass any composition made by admixing a compound of structural formula I and a pharmaceutically acceptable carrier.

Compounds of structural formula I may be used in combination with other drugs that may also be useful in the treatment or amelioration of the diseases or conditions for which compounds of structural formula I are useful. Such other drugs may be administered, by a route and in an amount commonly used therefor, contemporaneously or sequentially with a compound of structural formula I. In the treatment of patients who have pain conditions, pruritic conditions and cough conditions, more than one drug is commonly administered. The compounds of Formula I may generally be administered to a patient who is already taking one or more other drugs for these conditions. Often the compounds will be administered to a patient who is already being treated with one or more anti-pain compounds when the patient's pain is not adequately responding to treatment.

The combination therapy also includes therapies in which the compound of structural formula I and one or more other drugs are administered on different overlapping schedules. It is also contemplated that when used in combination with one or more other active ingredients, the compound of structural formula I and the other active ingredients may be used in lower doses than when each is used singly. Accordingly, the pharmaceutical compositions disclosed herein include those that contain one or more other active ingredients, in addition to a compound of structural formula I.

Examples of other active ingredients that may be administered in combination with a compound of structural formula I, and either administered separately or in the same pharmaceutical composition, include but are not limited to:

(i) an opioid agonist;
(ii) an opioid antagonist;
(iii) a calcium channel antagonist;
(iv) a NMDA receptor agonist;
(v) a NMDA receptor antagonist;
(vi) a COX-2 selective inhibitor;
(vii) a NSAID (non-steroidal anti-inflammatory drug);
(viii) an analgesic;
(ix) a sodium channel inhibitor;
(x) an anti-NGF antibody;
(xi) a $Na_v1.7$ inhibitor;
(xii) a HCN inhibitor;
(xiii) a TRPV1 antagonist;
(xiv) a $Na_v1.7$ biological; and
(xv) a $Na_v1.8$ biological; and pharmaceutically acceptable salts thereof.

In another embodiment, the pharmaceutical composition comprises:

(1) compound of Claim 1 or a pharmaceutically acceptable salt thereof;
(2) one or more compounds, or pharmaceutically acceptable salts thereof, selected from the group consisting of:

(i) an opioid agonist;
(ii) an opioid antagonist;
(iii) a calcium channel antagonist;
(iv) a NMDA receptor agonist;
(v) a NMDA receptor antagonist;
(vi) a COX-2 selective inhibitor;
(vii) a NSAID (non-steroidal anti-inflammatory drug);
(viii) an analgesic;
(ix) a sodium channel inhibitor;
(x) an anti-NGF antibody;
(xi) a $Na_v1.7$ inhibitor;
(xii) a HCN inhibitor;
(xiii) a TRPV1 antagonist;
(xiv) a $Na_v1.7$ biological; and
(xv) a $Na_v1.8$ biological; and pharmaceutically acceptable salts thereof; and (3) a pharmaceutically acceptable carrier.

A $Na_v$ 1.7 biological means a protein, including, but not limited to, antibodies, nanobodies and peptides, that inhibits the function of the $Na_v1.7$ channel. A $Na_v$ 1.8 biological means a protein, including, but not limited to, antibodies, nanobodies and peptides, that inhibits the function of the $Na_v1.8$ channel.

Specific compounds of use in combination with a compound of structural formula I include: sodium channel inhibitors, including but not limited to, lidocaine including the lidocaine patch; tricyclic antidepressants including, but not limited to, amitriptyline; and SRI/NRI drugs, including but not limited to, duloxetine.

Suitable opioid agonists include, but are not limited to, codeine, fentanyl, hydrocodone, hydromorphone, levorphanol, meperidine, methadone, morphine, oxycodone, oxymorphone, buprenorphine, butorphanol, dezocine, nalbuphine, pentazocine, and tramadol.

Suitable opioid antagonists include, but are not limited to, naltrexone and naloxone.

Suitable calcium channel antagonists include, but are not limited to, Amlodipine, Diltiazem, Felodipine, gabapentin, Isradipine, Nicardipine, Nifedipine, Nisoldipine, pregabalin, Verapamil, and ziconitide.

Suitable NMDA receptor antagonists include, but are not limited to, ketamine, methadone, memantine, amantadine, and dextromethorphan.

Suitable COX-2 inhibitors include, but are not limited to, celecoxib, etoricoxib and parecoxib.

Suitable NSAIDs or non-steroidal anti-inflammatory drugs include, but are not limited to, aspirin, diclofenac, diflunisal, etodolac, fenoprofin, flurbiprofen, ibuprofen, indomethacin, ketoprofen, meclofenamic acid, mefenamic acid, meloxicam, naproxen, naproxen sodium, oxaprozin, piroxicam, sulindac, and tolmetin.

Suitable analgesics include, but are not limited to, acetaminophen and duloxetine.

The above combinations include combinations of a compound of structural formula I not only with one other active compound, but also with two or more other active compounds. Non-limiting examples include combinations of compounds with two or more active compounds selected from: opioid agonists; opioid antagonists; calcium channel antagonists; NMDA receptor agonists; NMDA receptor antagonists; COX-2 selective inhibitors; NSAIDs (non-steroidal anti-inflammatory drugs); and an analgesic.

The compounds of structural formula I, or a pharmaceutically acceptable salt thereof, may also be used in combination with spinal cord stimulation therapy and cutaneous stimulation therapy.

Also provided is a method for the treatment or prevention of a $Na_v1.8$ sodium ion channel activity mediated disease, disorder or condition, which method comprises administration to a patient in need of such treatment or at risk of developing a $Na_v1.8$ sodium ion channel activity mediated disease with a therapeutically effective amount of a $Na_v1.8$ sodium ion channel activity inhibitor and an amount of one or more active ingredients, such that together they give effective relief.

In a further aspect, there is provided a pharmaceutical composition comprising a $Na_v1.8$ sodium ion channel activity inhibitor and one or more active ingredients, together with at least one pharmaceutically acceptable carrier or excipient.

Thus, there is provided the use of a $Na_v1.8$ sodium ion channel activity inhibitor and one or more active ingredients for the manufacture of a medicament for the treatment or prevention of a $Na_v1.8$ sodium ion channel activity mediated disease, disorder or condition. In a further or alternative aspect of the present disclosure, there is therefore provided a product comprising a $Na_v1.8$ sodium ion channel activity inhibitor and one or more active ingredients as a combined preparation for simultaneous, separate or sequential use in the treatment or prevention of a $Na_v1.8$ sodium ion channel activity mediated disease, disorder or condition. Such a combined preparation may be, for example, in the form of a twin pack.

It will be appreciated that for the treatment or prevention of pain conditions, pruritic conditions and cough conditions, a compound of structural formula I may be used in conjunction with another pharmaceutical agent effective to treat that disease, disorder or condition.

Also provided is a method for the treatment or prevention of pain conditions, pruritic conditions and cough conditions, which method comprises administration to a patient in need of such treatment an amount of a compound of structural formula I and an amount of another pharmaceutical agent effective to threat that disorder, disease or condition, such that together they give effective relief.

Further provided is a method for the treatment or prevention of pain conditions, pruritic conditions and cough conditions, which method comprises administration to a patient in need of such treatment an amount of a compound of structural formula I and an amount of another pharmaceutical agent useful in treating that particular condition, disorder or disease, such that together they give effective relief.

The term "therapeutically effective amount" means the amount the compound of structural formula I that will elicit the biological or medical response of a cell, tissue, system, animal or human that is being sought by the researcher, veterinarian, medical doctor or other clinician, which includes alleviation of the symptoms of the disorder being treated. The novel methods of treatment provided herein are for disorders known to those skilled in the art. The term "mammal" includes humans, and companion animals such as dogs and cats.

The weight ratio of the compound of structural formula I to the second active ingredient may be varied and will depend upon the effective dose of each ingredient. Generally, an effective dose of each will be used. Thus, for example, when a compound of structural formula I is combined with a COX-2 inhibitor the weight ratio of the compound of structural formula I to the COX-2 inhibitor will generally range from about 1000:1 to about 1:1000, preferably about 200:1 to about 1:200. Combinations of a compound of structural formula I and other active ingredients will generally also be within the aforementioned range, but in each case, an effective dose of each active ingredient should be used.

Methods of Synthesis

The following reaction schemes and Examples illustrate methods which may be employed for the synthesis of the compounds of structural formula I described herein. These reaction schemes and Examples are provided for illustration and are not to be construed as limiting the invention in any manner. All substituents are as defined above unless indicated otherwise. Several strategies based upon synthetic transformations known in the literature of organic synthesis may be employed for the preparation of the compounds of structural formula I.

Instrumentation

Reverse phase chromatography was carried out on a Gilson GX-281 equipped with a column selected from the following: Phenomenex Synergi C18 (150 mm×30 mm×4 micron), YMC-Actus Pro C18 (150 mm×30 mm×5 micron), Xtimate C18 (150 mm×25 mm×5 micron), Boston Green ODS (150 mm×30 mm×5 micron), XSELECT C18 (150 mm×30 mm×5 micron), and Waters XSELECT C18 (150 mm×30 mm×5 micron). Conditions included either high pH (0-100% acetonitrile/water eluent comprising 0.1% v/v 10 mM $NH_4CO_3$ or 0.05% $NH_4OH$) or low pH (0-95% acetonitrile/water eluent comprising 0.1% v/v TFA) and are noted for some examples.

SFC chiral resolution was carried out on a Sepiate Prep SFC 100, Multigram II (MG II), THAR80 prep SFC, or a Waters SFC (80, 200, or 350).

LC/MS determinations were carried out on a Waters Classing Aquity system equipped with UV and MS detectors and a Waters SQD mass spectrometer, a Shimadzu 20 UV 254 and 220 nM with Shimadzu 2010 or 2020 mass spectrometer, or an Agilent 1200 HPLC quipped with DAD/ELSD and G6110 MSD using one of the following conditions: 1) Ascentis Express C18 (3×50 mm) 2.7 μm column using mobile phase containing A: 0.05% TFA in water and B: 0.05% TFA in acetonitrile with a gradient from 90:10 (A:B) to 5:95 (A:B) over 6 min at a flow rate of 1.8 mL/min, UV detection at 210 nm; 2) Aquity BEH C18, (1.0×50 mm) 1.7 μm column using mobile phase containing A: 0.05% TFA in water and B: 0.05% TFA in acetonitrile with a gradient from 90:10 (A:B) to 5:95 (A:B) over 2 min at a flow rate of 0.3 mL/min, UV detection at 215 nm; 3) Agilent YMC J'Sphere H-80 (3×50 mm) 5 μm column using mobile phase containing A: 0.1% TFA in water and B: acetonitrile with a gradient from 95:5 (A:B) to 0:100 (A:B) over 3.6 min and 0:100 (A:B) for 0.4 min at a flow rate of 1.4 mL/min, UV detection at 254 and 220 nm and Agilent 1100 quadrupole mass spectrometer; 4) an Agilent TC-C18 (2.1×50 mm) 5 μm column using mobile phase containing A: 0.0375% TFA in water and B: 0.01875% TFA in acetonitrile with a gradient from 90:10 (A:B) for 0.4 min to 90:10 to 0:100 (A:B) over 3 min and 10:90 (A:B) for 0.6 min at a flow rate of 0.8 mL/min, UV detection at 254 and 220 nm and Agilent 6110 quadrupole mass spectrometer.

Proton or 1H NMR was acquired using a Varian Unity-Inova 400 MHz NMR spectrometer equipped with a Varian 400 ATB PFG 5 mm, Nalorac DBG 400-5 or a Nalorac IDG 400-5 probe, a Varian-400 MHz MR spectrometer equipped with an Auto X ID PFG Probe 5 mm, a Varian 400 MHz VNMRS spectrometer equipped with a PFG 4Nuc Probe 5 mm, or a Bruker AvanceIII 500 MHz spectrometer equipped with a PABBO Probe 5 mm in accordance with standard analytical techniques, unless specified otherwise, and results of spectral analysis are reported. Chemical shift (6) values are reported in delta (6) units, parts per million (ppm). Chemical shifts for 1H NMR spectra are given relative to signals for residual non-deuterated solvent ($CDCl_3$ referenced at δ 7.26 ppm; DMSO d-6 referenced at δ 2.50 ppm and $CD_3OD$ referenced at δ 3.31 ppm). Multiples are reported by the following abbreviations: s=singlet, d=doublet, t=triplet, q=quartet, dd=doublet of doublets, m=multiplet or overlap of nonequivalent resonances. Coupling constants (J) are reported in Hertz (Hz).

Abbreviations

AcOH is acetic acid; Boc is tert-butoxycarbonyl; Calc'd is calculated; CDI is 1,1'-carbonyldiimidazole, DAST is diethylaminosulfur trifluoride; DCE is dichloroethane; DCM is dichloromethane; DEA is diethanolamine; DIBAL-H is diisobutylaluminum hydride; DIPEA or DIEA is N,N-diisopropylethylamine; DMA is dimethylacetamide; DMF is dimethylformamide; DMSO is dimethylsulfoxide; dppf is 1,1'-bis(diphenylphosphino)ferrocene; EDC is 1-ethyl-3-(3-dimethylaminopropyl)carbodiimide; EDCI is 1-ethyl-3-(3-dimethylaminopropyl)carbodiimide; $Et_2O$ is diethyl ether; EtOAc is ethyl acetate; EtOH is ethanol; $Et_3N$ or $NEt_3$ is triethyl amine; g is grams; h or hr(s) is hour(s); HATU is 1-[bis(dimethylamino)-methylene]-1H-1,2,3-triazolo[4,5-b]pyridinium-3-oxidehexafluoro-phosphate; Hex is hexanes; HOAt is 1-Hydroxy-7-azabenzotriazole; HPLC is high-performance liquid chromatography; IPA is isopropyl alcohol; iPrMgCl or i-PrMgCl is isopropylmagnesium chloride; iPrMgCl—LiCl is isopropylmagnesium chloride lithium chloride complex; L is liter; LAH is lithium aluminum hydride; LC/MS is liquid chromatography/mass spectrometry; LRMS is low resolution mass spectrometry; M is molar; Me is methyl; MeOH is methanol; MeCN is acetonitrile; MeMgBr is methylmagnesium bromide; mg is milligrams; mL is milliliter; mmol is millimole(s); Ms-Cl is methanesulfonyl Chloride; N is normal; NaHMDS is Sodium bis(trimethylsilyl)amide; $NH_4OAc$ is ammonium acetate, NMO is 4-Methylmorpholine N-oxide; NMP is N-methylpyrrolidone; mPa is millipascal(s); mol % is mole percent; PCC is pyridinium chloro-chromate; Pd/C is palladium on carbon; $Pd(dppf)Cl_2$ is [1,1-bis(diphenyl-phosphino)-ferrocene]dichloropalladium(II); $Pd(PPh_3)_4$ is tetrakis(triphenyl-phosphine)-palladium(O); $Pd(tBu_3P)_2$ is Bis (tri-tert-butylphosphine)-palladium(O); pet. ether or PE is petroleum ether; PG is protecting group; $PPh_3$ is triphenylphosphine; ppm is milligrams per liter; Prep. or prep is preparative; psi is pounds per square inch; rt or RT is room temperature; SFC is Supercritical Fluid Chromatography;s TBAF is tetrabutylammonium fluoride; tBuXPhos Pd G3 is [(2-Di-tert-butylphosphino-2',4',6'-triisopropyl-1,1'-biphenyl)-2-(2'-amino-1,1'-biphenyl)] palladium(II) methanesulfonate; TEA is triethylamine; TFA is trifluoro acetic acid; THF is tetrahydrofuran; $Ti(OEt)_4$ is titanium (IV) ethoxide; $Ti(OiPr)_4$ is titanium (IV) isopropoxide; TLC is thin layer chromatography; UV is ultraviolet; and v/v is volume per volume.

As illustrated in Scheme A, compounds of structural formula I can be prepared by condensation between an appropriately functionalized aldehyde A-1 and tert-butanesulfinamide, utilizing dehydrating agents such as $Ti(OEt)_4$ or $Ti(OiPr)_4$, to afford intermediate A-2. Intermediate A-2 can then be reacted with a variety of organometallic nucleophiles A-3 to give intermediate A-4, which can be deprotected under acidic conditions to give amines of formula A-5. Amine A-5 can then be brought together with piperazine A-6 under urea coupling conditions (using triphosgene or CDI as coupling regents) to deliver compounds of formula A-7. In some embodiments, a protecting group (such as Boc) may need to be removed throughout the course of synthesis. Aldehydes of type A-1 and organometallics of type A-3 are commercially available or may be synthesized from appropriate starting materials and reagents.

Scheme A

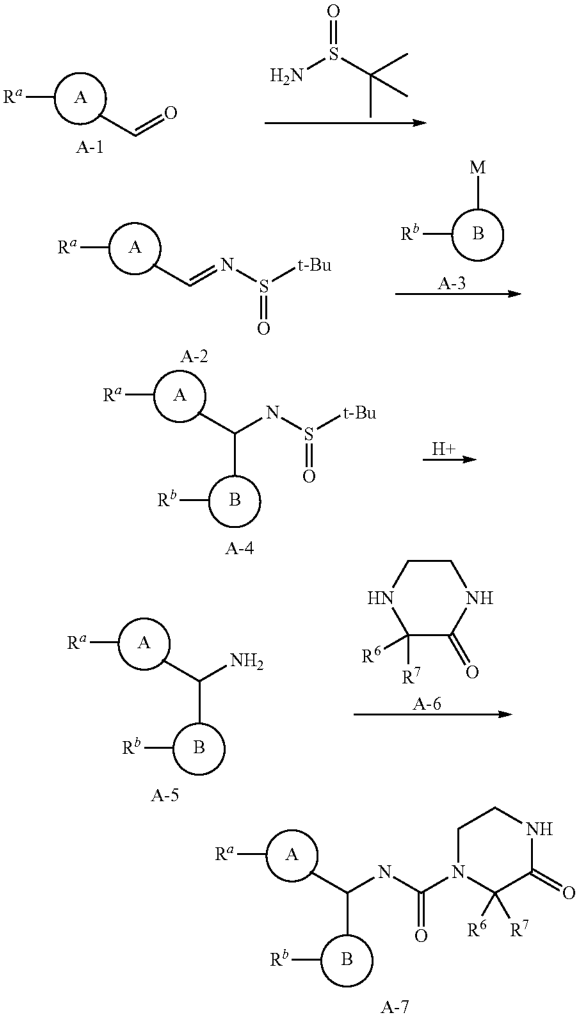

As illustrated in Scheme B, the compounds of structural formula I can be prepared by activation of appropriately functionalized carboxylic acid B-1 with either $(COCl)_2$ or amide coupling with amine B-2 to give intermediate B-3. This intermediate is then suitable to for reaction with a variety of organometallic nucleophiles A-3 to give intermediate B-4. Intermediate B-4 can then undergo reductive amination reaction in the presence of an amine source and reductant to yield intermediate A-5. In some cases, tert-butanesulfinamide was used as the amine source and would require deprotection (in an acidic environment) following reductive amination. Amine A-5 can then be brought together with piperazine A-6 under urea coupling conditions (using triphosgene or CDI as coupling regents) to deliver compounds of formula A-7. In some embodiments, a protecting group, such as Boc, may need to be removed throughout the course of synthesis. Carboxylic acids of type B-1 and organometallics of type A-3 are commercially available or may be synthesized from appropriate starting materials and reagents.

Scheme B

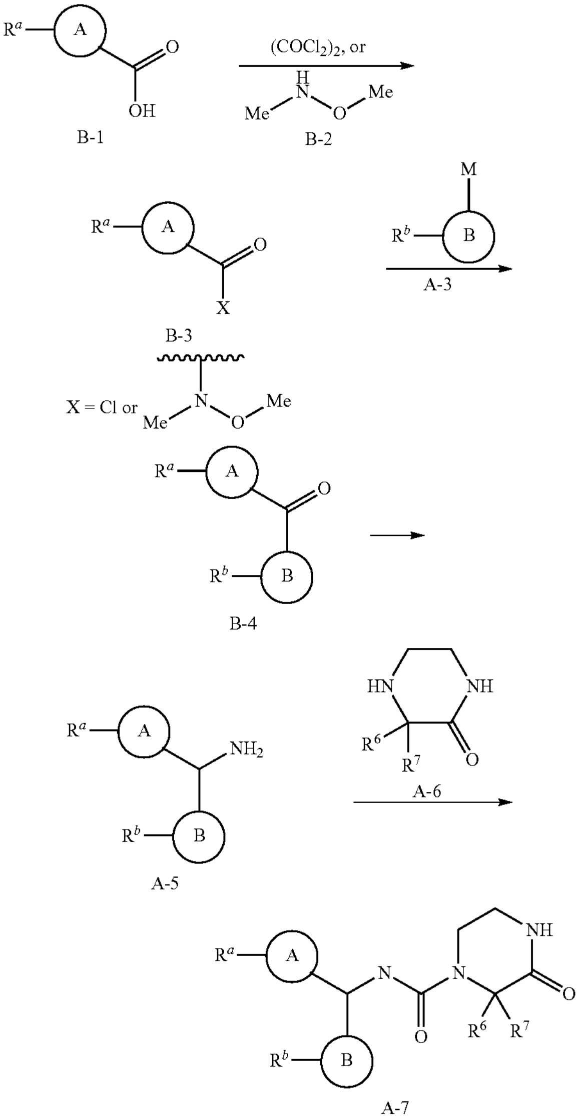

EXAMPLES

Examples 1A and 1B

N-((R)-3-chloro-4-fluorophenyl)(trans-4-(trifluoromethyl)cyclohexyl)methyl)-3-oxopiperazine-1-carboxamide and N-((S)-3-chloro-4-fluorophenyl)(trans-4-(trifluoromethyl)cyclohexyl)-methyl)-3-oxopiperazine-1-carboxamide

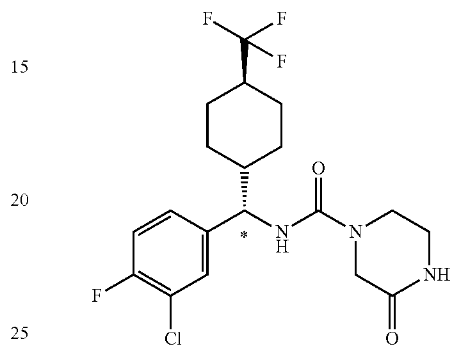

Step 1: (3-chloro-4-fluorophenyl)(-4-(trifluoromethyl)cyclohexyl)methanone To a solution of trans-4-(trifluoromethyl)cyclohexanecarboxylic acid (571 mg, 2.91 mmol) in $CH_2Cl_2$ (5 mL) at 0° C. was added oxalyl chloride in DCM (2 M, 3.64 mL, 7.28 mmol) and one drop of DMF. The mixture was warmed to RT, stirred for 4 hours, then heated to 40° C. and stirred for 30 minutes. The mixture was then concentrated under reduced pressure to give a residue, which was dissolved in THF (4 mL, solution A). In a different flask, copper(I) cyanide (652 mg, 7.28 mmol) was suspended in THF (4 mL) and cooled to 0° C., followed by the addition of 3-chloro-4-fluorophenylmagnesium bromide in THF (0.5 M, 11.64 mL, 5.82 mmol). The mixture was stirred at 0° C. for 1 hour, then solution A was added and the mixture was stirred at 0° C. for 4 hours. The reaction was quenched with 30 ml of saturated aqueous $NH_4Cl$ and extracted with ethyl acetate (2×30 mL). The combined organic layers were dried over $Na_2SO_4$, filtered and concentrated under reduced pressure to give the title compound. LCMS m/z (M+H): calculated 308.7, observed 309.2.

Step 2: (3-chloro-4-fluorophenyl)(trans-4-(trifluoromethyl)cyclohexyl)methanamine A microwave tube was charged with (3-chloro-4-fluorophenyl)(trans-4-(trifluoromethyl) cyclohexyl)methanone (1281 mg, 4.15 mmol), ammonium acetate (2559 mg, 33.2 mmol) and ethanol (15 mL). The mixture was microwaved at 130° C. for 20 minutes and cooled to RT, followed by the addition of sodium cyanoborohydride (287 mg, 4.56 mmol). The reaction mixture was microwaved at 125° C. for 20 minutes and then cooled to RT. The reaction was quenched by the addition of 10% aqueous $K_2CO_3$ (30 mL), and extracted with ethyl acetate (2×30 mL). The combined organic layers were dried over $Na_2SO_4$, filtered and concentrated under reduced pressure to give the title compound. LCMS m/z (M+H): calculated 413.9, observed 414.4.

Step 3: Examples 1A and 1B To a solution of (3-chloro-4-fluorophenyl)(trans-4-(trifluoro-methyl)cyclohexyl)methanamine (333 mg, 1.075 mmol) in DCM (3 mL) at 0° C. was added $Et_3N$ (0.749 mL, 5.38 mmol) and triphosgene (319 mg, 1.075 mmol). The mixture was stirred at 0° C. for 1 hour and then piperazin-2-one (215 mg, 2.150 mmol) was added. After stirring at 0° C. for 1 hour, the reaction was warmed to RT, stirred at RT for 1 hour, and then concentrated under reduced pressure. The resulting residue was purified by column chromatography on silica gel, eluting with (0-4% MeOH/DCM) to give a mixture of isomers, which was further separated by SFC (OD-H column, 25% EtOH+ 0.25% DIPEA co-solvent) to give Examples 1A (second eluted fraction) and 1B (first eluted fraction)

Example 1A: LRMS m/z (M+H): calculated 435.8, observed 436.4. $^{1}$H NMR δ (ppm) (500 MHz, DMSO-d6): 8.01 (s, 1H), 7.53 (dd, J=7.3, 2.0 Hz, 1H), 7.35 (t, J=8.9 Hz, 1H), 7.32-7.27 (m, 1H), 6.88 (d, J=8.6 Hz, 1H), 4.37 (t, J=9.1 Hz, 1H), 3.96-3.77 (m, 2H), 3.54-3.41 (m, 2H), 3.14 (td, J=5.3, 2.6 Hz, 2H), 2.19 (d, J=8.6 Hz, 1H), 2.06 (d, J=12.5 Hz, 1H), 1.93 (d, J=12.4 Hz, 1H), 1.78 (d, J=12.7 Hz, 1H), 1.65 (q, J=11.8 Hz, 1H), 1.28-0.87 (m, 5H). Example 1B: LRMS m/z (M+H): calculated 435.8, observed 436.4. $^{1}$H NMR δ (ppm) (500 MHz, DMSO-d6): 8.01 (s, 1H), 7.53 (dd, J=7.3, 2.0 Hz, 1H), 7.38-7.26 (m, 2H), 6.87 (d, J=8.6 Hz, 1H), 4.44-4.31 (m, 1H), 4.00-3.80 (m, 2H), 3.57-3.42 (m, 2H), 2.51 (p, J=1.8 Hz, 2H), 2.25-2.13 (m, 1H), 2.08 (s, 1H), 1.93 (d, J=11.9 Hz, 1H), 1.83-1.74 (m, 1H), 1.71-1.57 (m, 1H), 1.27-0.94 (m, 5H).

TABLE 1

The following examples were prepared according to the synthetic procedure for Examples 1A and 1B, using the appropriate starting materials and reagents.

| Example | Compound | Name | Calc'd [M + H]$^+$ | Observed [M + H]$^+$ | Conditions |
|---|---|---|---|---|---|
| 2A | 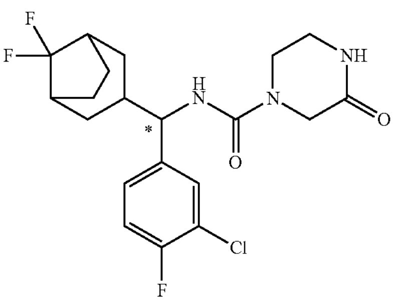 [SMILES: O=C1CN(C(=O)NC(c2ccc(F)c(Cl)c2)C2CC3CCC(C2)C3(F)F)CCN1] | N-((R or S)-(3-chloro-4-fluoro-phenyl)(8,8-difluoro-bicyclo[3.2.1]octan-3-yl)methyl)-3-oxopiperazine-1-carboxamide | 429.8 | 430.4 | SFC: OD-H Co-solvent: 25% (IPA + 0.2% DIPEA) peak 1 |
| 2B | 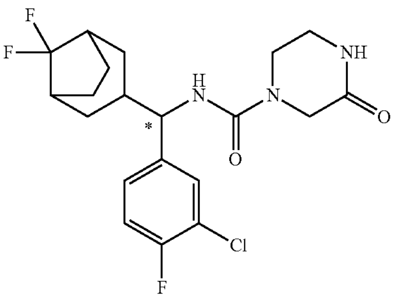 [SMILES: O=C1CN(C(=O)NC(c2ccc(F)c(Cl)c2)C2CC3CCC(C2)C3(F)F)CCN1] | N-((S or R)-(3-chloro-4-fluoro-phenyl)(8,8-difluroo-bicyclo[3.2.1]octan-3-yl)methyl)-3-oxopiperazine-1-carboxamide | 429.8 | 430.4 | SFC: OD-H Co-solvent 25% (IPA + 0.2% DIPEA) peak 2 |
| 3A | 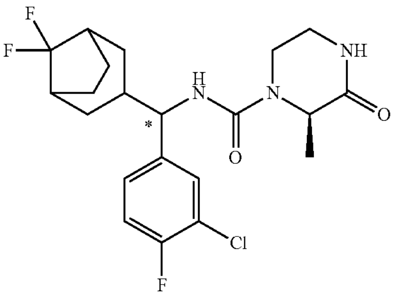 [SMILES: C[C@@H]1C(=O)NCCN1C(=O)NC(c1ccc(F)c(Cl)c1)C1CC2CCC(C1)C2(F)F] | (2R)-N-((R or S)-(3-chloro-4-fluoro-phenyl)(8,8-difluoro-bicyclo[3.2.1]octan-3-yl)methyl)-2-methyl-3-oxo-piperazine-1-carboxamide | 443.9 | 444.4 | SFC: OJ-H Co-solvent: 20% MeOH peak 1 |

TABLE 1-continued

The following examples were prepared according to the synthetic procedure for Examples 1A and 1B, using the appropriate starting materials and reagents.

| Example | Compound | Name | Calc'd $[M + H]^+$ | Observed $[M + H]^+$ | Conditions |
|---|---|---|---|---|---|
| 3B | 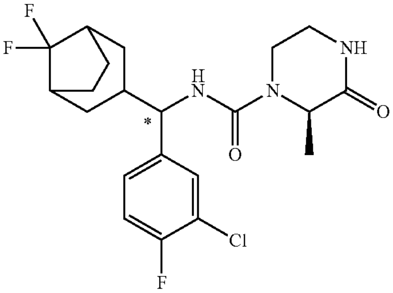 [SMILES: C[C@@H]1C(=O)NCCN1C(=O)NC(c1ccc(F)c(Cl)c1)C1CC2CCC(C1)C2(F)F] | (2R)-N-((S or R)-(3-chloro-4-fluoro-phenyl)(8,8-difluoro-bicyclo[3.2.1]octan-3-yl)methyl)-2-methyl-3-oxo-piperazine-1-carboxamide | 443.9 | 444.4 | SFC: OJ-H Co-solvent: 20% MeOH peak 2 |
| 4A | 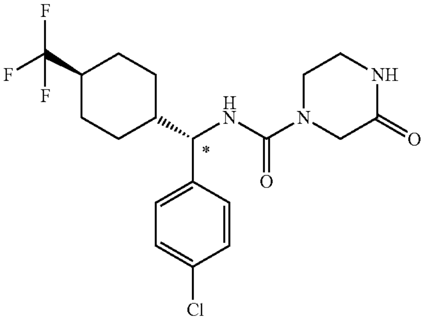 | N-((R or S)-(4-chlorophenyl)(trans-4-(trifluoromethyl)-cyclohexyl)methyl)-3-oxopiperazine-1-carboxamide | 417.8 | 418.4 | SFC: OJ-H Co-solvent: 30% (MeOH/CH3CN 1:1) peak 2 |
| 4B | 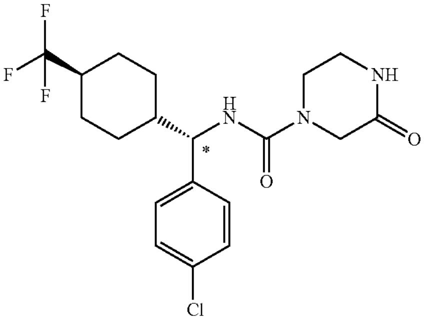 | N-((S or R)-(4-chlorophenyl)(trans-4-(trifluoromethyl)-cyclohexyl)methyl)-3-oxopiperazine-1-carboxamide | 417.8 | 418.4 | SFC: OJ-H Co-solvent: 30% (MeOH/$CH_3CN$ 1:1) peak 1 |
| 5A | 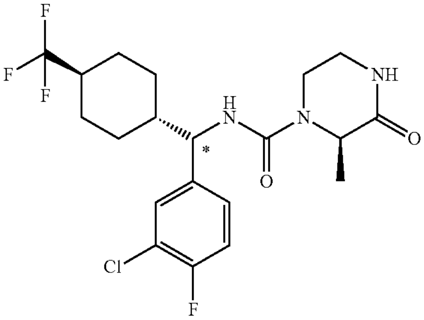 [SMILES: C[C@@H]1C(=O)NCCN1C(=O)NC(c1ccc(F)c(Cl)c1)[C@H]1CC[C@H](C(F)(F)F)CC1] | (2R)-N-((R or S)-(3-chloro-4-fluoro-phenyl)(trans-4-(trifluoromethyl)cyclo-hexyl)methyl)-2-methyl-3-oxo-piperazine-1-carboxamide | 449.8 | 450.4 | SFC: OJ-H Co-solvent: 30% (MeOH/$CH_3CN$ 1:1) peak 1 |

TABLE 1-continued

The following examples were prepared according to the synthetic procedure for Examples 1A and 1B, using the appropriate starting materials and reagents.

| Example | Compound | Name | Calc'd $[M + H]^+$ | Observed $[M + H]^+$ | Conditions |
|---|---|---|---|---|---|
| 5B | 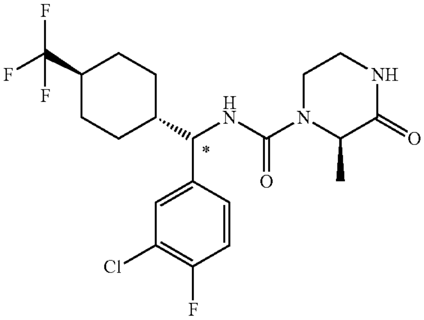 [SMILES: C[C@@H]1C(=O)NCCN1C(=O)NC(c1ccc(F)c(Cl)c1)[C@H]1CC[C@H](C(F)(F)F)CC1] | (2R)-N-((S or R)-(3-chloro-4-fluoro-phenyl)(trans-4-(tri-fluoromethyl)cyclo-hexyl)methyl)-2-methyl-3-oxo-piperazine-1-carboxamide | 449.8 | 450.4 | SFC: OJ-H Co-solvent: 30% (MeOH/ $CH_3CN$ 1:1): peak 2 |
| 6A | 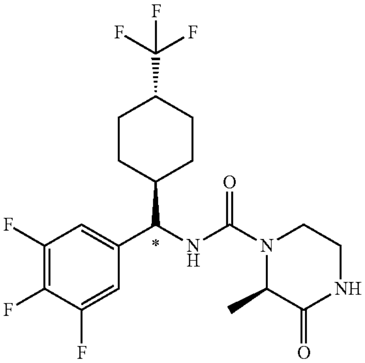 [SMILES: C[C@@H]1C(=O)NCCN1C(=O)NC(c1cc(F)c(F)c(F)c1)[C@H]1CC[C@H](C(F)(F)F)CC1] | (R)-2-methyl-3-oxo-N-((R or S)-(trans-4-(trifluoromethyl)cyclo-hexyl)(3,4,5-tri-fluorophenyl)methyl) piperazine-1-carboxamide | 451.4 | 452.3 | SFC: OJ-H Co-solvent: 25% EtOH peak 1 |
| 6B | 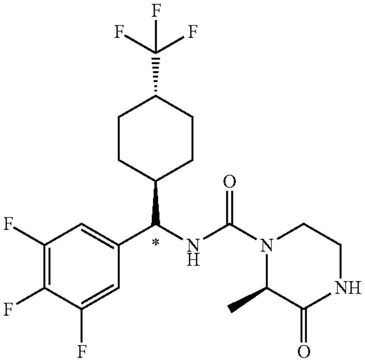 [SMILES: C[C@@H]1C(=O)NCCN1C(=O)NC(c1cc(F)c(F)c(F)c1)[C@H]1CC[C@H](C(F)(F)F)CC1] | (R)-2-methyl-3-oxo-N-((S or R)-(trans-4-(trifluoromethyl)cyclo-hexyl)(3,4,5-tri-fluorophenyl)methyl) piperazine-1-carboxamide | 451.4 | 452.3 | SFC: OJ-H Co-solvent: 25% EtOH peak 2 |
| 7A | 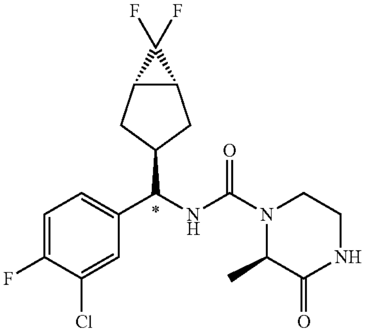 [SMILES: C[C@@H]1C(=O)NCCN1C(=O)NC(c1ccc(F)c(Cl)c1)[C@@H]1C[C@@H]2[C@H](C1)C2(F)F] | (2R)-N-((R or S)-(3-chloro-4-fluoro-phenyl)((1R,3s,5S)-6,6-difluoro-bicyclo[3.1.0]hexan-3-yl)methyl)-2-methyl-3-oxo-piperazine-1-carboxamide | 415.8 | 416.3 | SFC: OJ-H Co-solvent: 30% (EtOH + 0.2% DIPEA) peak 1 |

TABLE 1-continued

The following examples were prepared according to the synthetic procedure for Examples 1A and 1B, using the appropriate starting materials and reagents.

| Example | Compound | Name | Calc'd [M + H]+ | Observed [M + H]+ | Conditions |
|---|---|---|---|---|---|
| 7B | 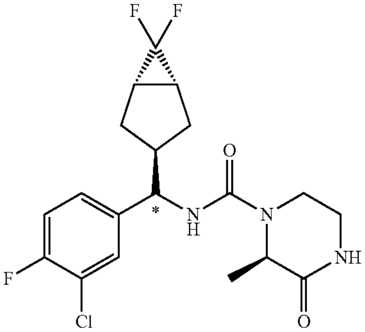 [SMILES: C[C@@H]1C(=O)NCCN1C(=O)NC(c1ccc(F)c(Cl)c1)[C@@H]1C[C@@H]2[C@H](C1)C2(F)F] | (2R)-N-((S or R)-(3-chloro-4-fluoro-phenyl)((1R,3s,5S)-6,6-difluoro-bicyclo[3.1.0]hexan-3-yl)methyl)-2-methyl-3-oxo-piperazine-1-carboxamide | 415.8 | 416.3 | SFC: OJ-H Co-solvent: 30% (EtOH + 0.2% DIPEA) peak 1 |
| 8A | 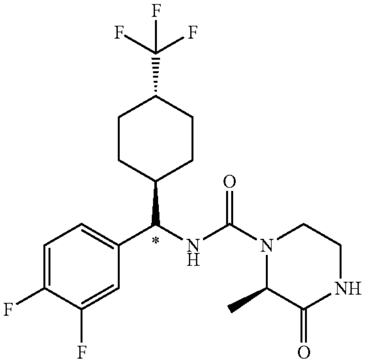 [SMILES: C[C@@H]1C(=O)NCCN1C(=O)NC(c1ccc(F)c(F)c1)[C@H]1CC[C@H](C(F)(F)F)CC1] | (2R)-N-((R or S)-(3,4-difluoro-phenyl)(trans-4-(trifluoromethyl)cyclo-hexyl)methyl)-2-methyl-3-oxo-piperazine-1-carboxamide | 433.4 | 434.4 | SFC: OJ-H Co-solvent: 30% EtOH peak 1 |
| 8B | 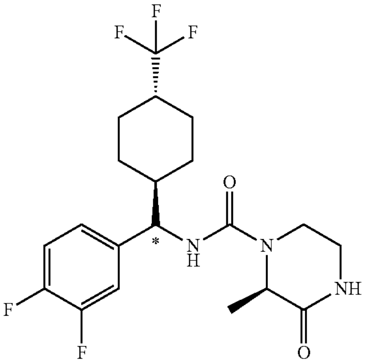 [SMILES: C[C@@H]1C(=O)NCCN1C(=O)NC(c1ccc(F)c(F)c1)[C@H]1CC[C@H](C(F)(F)F)CC1] | (2R)-N-((S or R)-(3,4-difluoro-phenyl)(trans-4-(trifluoromethyl)cyclo-hexyl)methyl)-2-methyl-3-oxo-piperazine-1-carboxamide | 433.4 | 434.4 | SFC: OJ-H Co-solvent: 30% EtOH peak 2 |
| 9A | 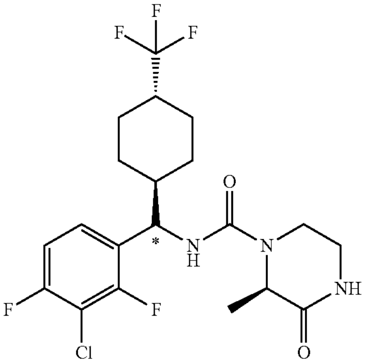 [SMILES: C[C@@H]1C(=O)NCCN1C(=O)NC(c1ccc(F)c(Cl)c1F)[C@H]1CC[C@H](C(F)(F)F)CC1] | (2R)-N-((R or S)-(3-chloro-2,4-difluoro-phenyl)(trans-4-(trifluoromethyl)cyclo-hexyl)methyl)-2-methyl-3-oxo-piperazine-1-carboxamide | 467.9 | 468.4 | SFC: OJ-H Co-solvent: 15% EtOH peak 1 |

TABLE 1-continued

| The following examples were prepared according to the synthetic procedure for Examples 1A and 1B, using the appropriate starting materials and reagents. | | | | | |
|---|---|---|---|---|---|
| Example | Compound | Name | Calc'd $[M + H]^+$ | Observed $[M + H]^+$ | Conditions |
| 9B | 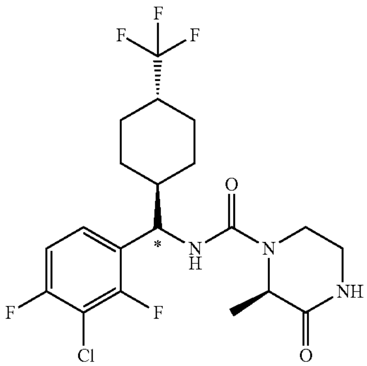 [SMILES: C[C@@H]1C(=O)NCCN1C(=O)NC(c1ccc(F)c(Cl)c1F)[C@H]1CC[C@H](C(F)(F)F)CC1] | (2R)-N-((S or R)-(3-chloro-2,4-difluoro-phenyl)(trans-4-(trifluoromethyl)cyclo-hexyl)methyl)-2-methyl-3-oxo-piperazine-1-carboxamide | 467.9 | 468.4 | SFC: OJ-H Co-solvent: 15% EtOH peak 2 |
| 10A | 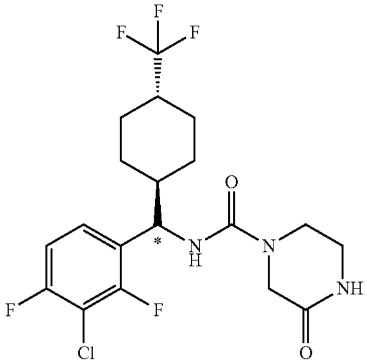 [SMILES: O=C1CN(C(=O)NC(c2ccc(F)c(Cl)c2F)[C@H]2CC[C@H](C(F)(F)F)CC2)CCN1] | N-((R or S)-(3-chloro-2,4-difluoro-phenyl)(trans-4-(trifluoromethyl)cyclo-hexyl)methyl)-3-oxopiperazine-1-carboxamide | 453.8 | 454.4 | SFC: OJ-H Co-solvent: 15% EtOH peak 1 |
| 10B | 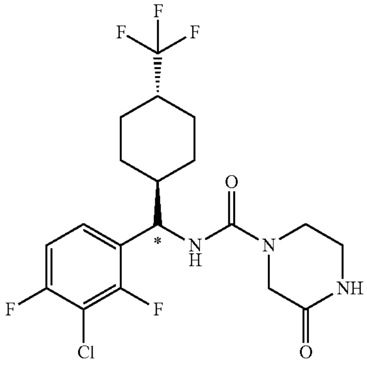 [SMILES: O=C1CN(C(=O)NC(c2ccc(F)c(Cl)c2F)[C@H]2CC[C@H](C(F)(F)F)CC2)CCN1] | N-((S or R)-(3-chloro-2,4-di-fluorophenyl)(trans-4-(trifluoromethyl)-cyclohexyl)methyl)-3-oxopiperazine-1-carboxamide | 453.8 | 454.4 | SFC: OJ-H Co-solvent: 15% EtOH peak 2 |
| 11A | 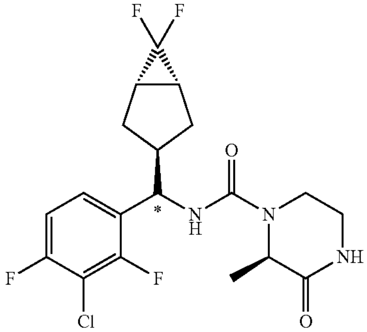 [SMILES: C[C@@H]1C(=O)NCCN1C(=O)NC(c1ccc(F)c(Cl)c1F)[C@@H]1C[C@@H]2[C@H](C1)C2(F)F] | (R)-N-((R or S)-(3-chloro-2,4-difluoro-phenyl)((1R,3s,5S)-6,6-difluoro-bicyclo[3.1.0]hexan-3-yl)methyl)-2-methyl-3-oxo-piperazine-1-carboxamide | 433.8 | 434.3 | SFC: OJ-H Co-solvent: 25% EtOH peak 1 |

TABLE 1-continued

The following examples were prepared according to the synthetic procedure for Examples 1A and 1B, using the appropriate starting materials and reagents.

| Example | Compound | Name | Calc'd $[M + H]^+$ | Observed $[M + H]^+$ | Conditions |
|---|---|---|---|---|---|
| 11B | 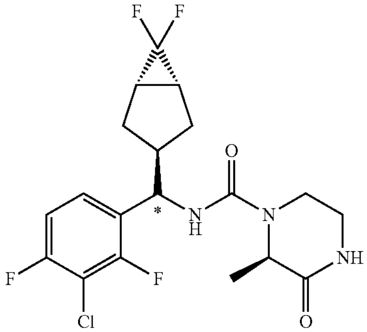 [SMILES: C[C@@H]1C(=O)NCCN1C(=O)NC(c1ccc(F)c(Cl)c1F)[C@@H]1C[C@@H]2[C@H](C1)C2(F)F] | (R)-N-((S or R)-(3-chloro-2,4-difluoro-phenyl)((1R,3s,5S)-6,6-difluoro-bicyclo[3.1.0]hexan-3-yl)methyl)-2-methyl-3-oxo-piperazine-1-carboxamide | 433.8 | 434.3 | SFC: OJ-H Co-solvent: 25% EtOH peak 2 |
| 12A | 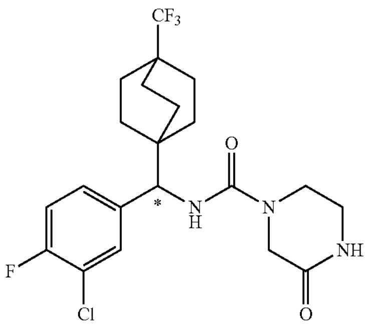 [SMILES: O=C1CN(C(=O)NC(c2ccc(F)c(Cl)c2)C23CCC(C(F)(F)F)(CC2)CC3)CCN1] | N-((R or S)-(3-chloro-4-fluoro-phenyl)(4-(trifluoro-methyl)bicyclo[2.2.2]octan-1-yl)methyl)-3-oxopiperazine-1-carboxamide | 461.9 | 462.4 | SFC: AD-H Co-solvent: 25% MeOH + 0.2% DIPEA peak 1 |
| 12B | 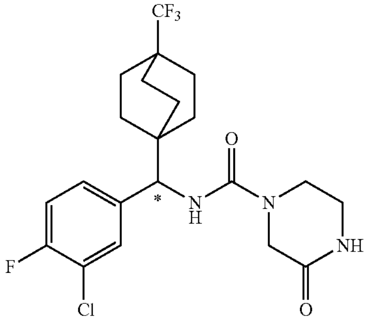 [SMILES: O=C1CN(C(=O)NC(c2ccc(F)c(Cl)c2)C23CCC(C(F)(F)F)(CC2)CC3)CCN1] | N-((S or R)-(3-chloro-4-fluoro-phenyl)(4-(trifluoro-methyl)bicyclo[2.2.2]octan-1-yl)methyl)-3-oxopiperazine-1-carboxamide | 461.9 | 462.4 | SFC: AD-H Co-solvent: 25% MeOH + 0.2% DIPEA peak 2 |
| 13A | 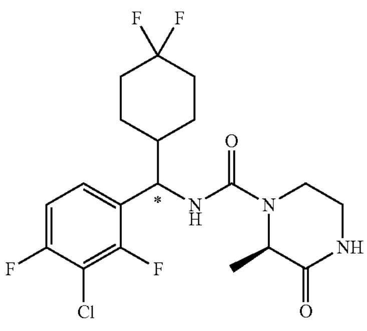 [SMILES: C[C@@H]1C(=O)NCCN1C(=O)NC(c1ccc(F)c(Cl)c1F)C1CCC(F)(F)CC1] | (2R)-N-((R or S)-(3-chloro-2,4-difluoro-phenyl)(4,4-difluoro-cyclohexyl)methyl)-2-methyl-3-oxo-piperazine-1-carboxamide | 435.1 | 436.2 | SFC: AS-H Co-solvent: 45% EtOH + 0.1% $NH_3H_2O$ peak 1 |

TABLE 1-continued

The following examples were prepared according to the synthetic procedure for Examples 1A and 1B, using the appropriate starting materials and reagents.

| Example | Compound | Name | Calc'd $[M + H]^+$ | Observed $[M + H]^+$ | Conditions |
|---|---|---|---|---|---|
| 13B | 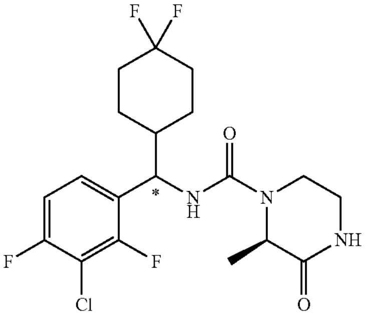 [SMILES: C[C@@H]1C(=O)NCCN1C(=O)NC(c1ccc(F)c(Cl)c1F)C1CCC(F)(F)CC1] | (2R)-N-((S or R)-(3-chloro-2,4-difluoro-phenyl)(4,4-difluoro-cyclohexyl)methyl)-2-methyl-3-oxo-piperazine-1-carboxamide | 435.1 | 436.2 | SFC: AS-H Co-solvent: 45% EtOH + 0.1% $NH_3H_2O$ peak 2 |
| 14A | 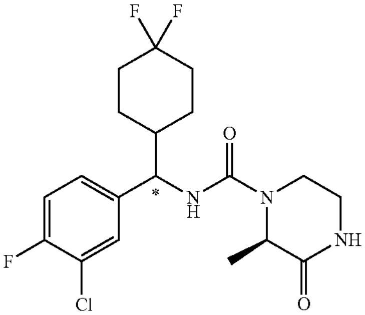 [SMILES: C[C@@H]1C(=O)NCCN1C(=O)NC(c1ccc(F)c(Cl)c1)C1CCC(F)(F)CC1] | (2R)-N-((R or S)-(3-chloro-4-fluoro-phenyl)(4,4-difluoro-cyclohexyl)methyl)-2-methyl-3-oxo-piperazine-1-carboxamide | 417.1 | 418.2 | SFC: AS-H Co-solvent: 45% EtOH + 0.1% $NH_3H_2O$ peak 1 |
| 14B | 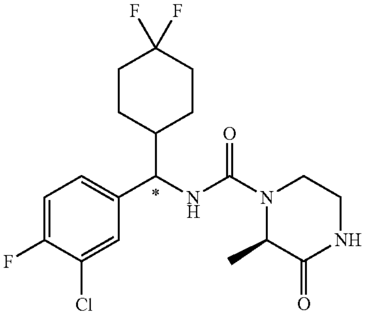 [SMILES: C[C@@H]1C(=O)NCCN1C(=O)NC(c1ccc(F)c(Cl)c1)C1CCC(F)(F)CC1] | (2R)-N-((S or R)-(3-chloro-4-fluoro-phenyl)(4,4-difluoro-cyclohexyl)methyl)-2-methyl-3-oxo-piperazine-1-carboxamide | 417.1 | 418.2 | SFC: AS-H Co-solvent: 45% EtOH + 0.1% $NH_3H_2O$ peak 2 |

Examples 15A and 15B (2R)-N-((R)-(3-chloro-4-fluorophenyl)(1-(2,2,2-trifluoroethyl)piperidin-4-yl)methyl)-2-methyl-3-oxopiperazine-1-carboxamide and (2R)-N-((S)-(3-chloro-4-fluorophenyl)(1-(2,2,2-trifluoroethyl) piperidin-4-yl)methyl)-2-methyl-3-oxopiperazine-1-carboxamide

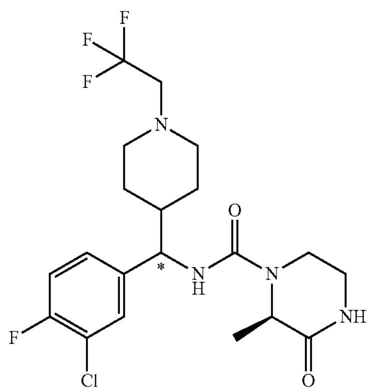 [SMILES: C[C@@H]1C(=O)NCCN1C(=O)NC(c1ccc(F)c(Cl)c1)C1CCN(CC(F)(F)F)CC1]

Step 1: 1-(2,2,2-trifluoroethyl)piperidine-4-carbonitrile To a solution of 4-cyanopiperidine (517 mg, 4.69 mmol) in anhydrous $CH_2Cl_2$ (8 mL) was added 2,2,2-trifluoroethyl-trifluoromethane-sulfonate (0.744 mL, 5.16 mmol) and $Et_3N$ (0.850 mL, 6.10 mmol). The mixture was stirred at RT for 3 days and then partitioned between diethyl ether and saturated aqueous $NaHCO_3$. The separated organic layer was dried over $Na_2SO_4$, filtered and concentrated under reduced pressure to give the title compound. LRMS m/z (M+H): calculated 192.2, observed 193.1.

Step 2: (3-chloro-4-fluorophenyl)(1-(2,2,2-trifluoroethyl) piperidin-4-yl)methanamine A microwave tube was charged with 1-(2,2,2-trifluoroethyl)piperidine-4-carbonitrile (380 mg, 1.977 mmol), 0.5 M 3-chloro-4-fluorophenyl magnesium bromide in THF (5.93 mL, 2.97 mmol) and THF (3 mL). The mixture was microwaved at 100° C. for 15 minutes and cooled to RT, followed by addition of MeOH (2 mL) and $NaBH_4$ (224 mg, 5.93 mmol). The reaction was stirred at RT for 3 hours, then quenched with saturated aqueous $NH_4Cl$ (30 mL) and extracted with ethyl acetate (2×30 mL). The combined organic layers were dried over $Na_2SO_4$, filtered and concentrated under reduced pressure. The resulting residue was purified by column chromatography on silica gel, eluting with (0-5% MeOH/DCM) to give the title compound. LRMS m/z (M+H): calculated 324.7, observed 325.2.

Step 3: Examples 15A and 15B To a solution of (3-chloro-4-fluorophenyl)(1-(2,2,2-trifluoro-ethyl)piperidin-4-yl) methanamine (150 mg, 0.462 mmol) in $CH_2Cl_2$ (3 mL) at 0° C. were added $Et_3N$ (0.322 mL, 2.309 mmol) and triphosgene (137 mg, 0.462 mmol). The mixture was stirred at 0° C. for 1 hour and then (R)-3-methylpiperazin-2-one (105 mg, 0.924 mmol) was added. After stirring at 0° C. for 1 hour, the reaction warmed to RT for 1 hour and concentrated under reduced pressure. The resulting residue was purified by column chromatography on silica gel, eluting with (0-4% MeOH/DCM) to give a mixture, which was further separated by SFC (OD-H column, 25% EtOH co-solvent) to give example 15A (first eluted fraction) and example 15B (second eluted fraction).

Example 15A: LRMS m/z (M+H): calculated 464.9, observed 465.4. $^1$H NMR δ (ppm) (500 MHz, Chloroform-d): 7.31 (s, 1H), 7.15-7.10 (m, 2H), 6.54 (s, 1H), 5.34 (s, 1H), 4.74 (d, J=6.5 Hz, 1H), 4.63 (d, J=6.8 Hz, 1H), 4.27 (d, J=13.2 Hz, 1H), 3.48 (dt, J=11.6, 5.7 Hz, 1H), 3.30 (d, J=11.9 Hz, 1H), 3.16-3.08 (m, 1H), 3.05 (d, J=10.5 Hz, 1H), 2.97 (q, J=9.6 Hz, 3H), 2.30 (td, J=11.2, 3.3 Hz, 2H), 1.69 (d, J=25.0 Hz, 4H), 1.52 (d, J=7.0 Hz, 3H).

Example 15B: LRMS m/z (M+H): calculated 464.9, observed 465.4. $^1$H NMR δ (ppm) (500 MHz, Chloroform-d): 7.35 (d, J=6.7 Hz, 1H), 7.16-7.09 (m, 2H), 6.07 (s, 1H), 5.10 (s, 1H), 4.61 (t, J=8.2 Hz, 1H), 4.44 (q, J=6.9 Hz, 1H), 4.27 (d, J=12.8 Hz, 1H), 3.46 (td, J=11.5, 4.1 Hz, 1H), 3.30 (d, J=12.0 Hz, 1H), 3.19-3.11 (m, 1H), 2.99 (tt, J=23.4, 12.5 Hz, 4H), 2.41-2.26 (m, 2H), 1.82 (d, J=11.5 Hz, 1H), 1.64 (d, J=21.0 Hz, 4H), 1.55 (d, J=7.0 Hz, 3H).

TABLE 2

The following examples were prepared according to the synthetic procedure for examples 15A and 15B, using appropriate starting material and reagents

| Example | Compound | Name | Calc'd $[M + H]^+$ | Observed $[M + H]^+$ | Conditions |
|---|---|---|---|---|---|
| 16A | 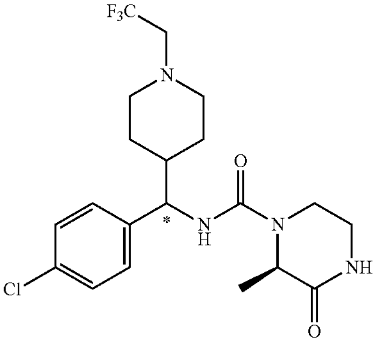 [SMILES: C[C@@H]1C(=O)NCCN1C(=O)NC(c1ccc(Cl)cc1)C1CCN(CC(F)(F)F)CC1] | (2R)-N-((R or S)-(4-chlorophenyl)(1-(2,2,2-trifluoroethyl)piperidin-4-yl)methyl)-2-methyl-3-oxopiperazine-1-carboxamide | 446.9 | 447.4 | SFC: AS-H Co-solvent: 25% (IPA + 0.2% DIPEA) peak 1 |

TABLE 2-continued

| The following examples were prepared according to the synthetic procedure for examples 15A and 15B, using appropriate starting material and reagents | | | | | |
|---|---|---|---|---|---|
| Example | Compound | Name | Calc'd [M + H]+ | Observed [M + H]+ | Conditions |
| 16B | 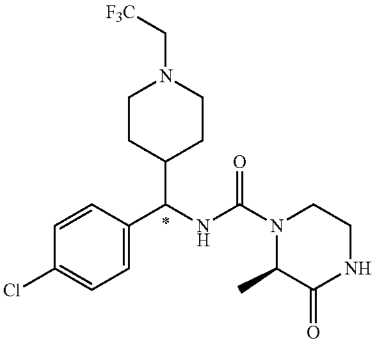 [SMILES: C[C@@H]1C(=O)NCCN1C(=O)NC(c1ccc(Cl)cc1)C1CCN(CC(F)(F)F)CC1] | (2R)-N-((S or R)-(4-chlorophenyl)(1-(2,2,2-trifluoroethyl)piperidin-4-yl)methyl)-2-methyl-3-oxopiperazine-1-carboxamide | 446.9 | 447.4 | SFC: AS-H Co-solvent 25% (IPA + 0.2% DIPEA) peak 2 |
| 17A | 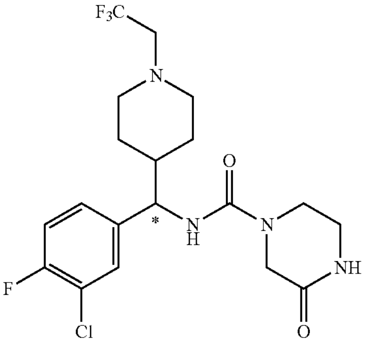 [SMILES: O=C1CN(C(=O)NC(c2ccc(F)c(Cl)c2)C2CCN(CC(F)(F)F)CC2)CCN1] | N-((R or S)-(3-chloro-4-flurophenyl)(1-(2,2,2-trifluoroethyl)piperidin-4-yl)methyl)-3-oxopiperazine-1-carboxamide | 450.9 | 451.4 | SFC: OD-H Co-solvent; 25% (IPA + 0.2% DIPEA) peak 1 |
| 17B | 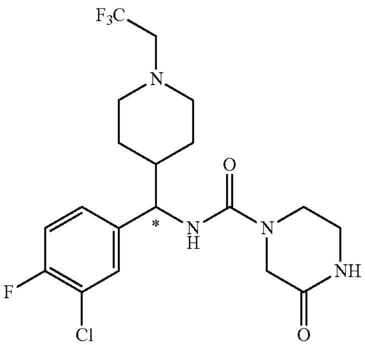 [SMILES: O=C1CN(C(=O)NC(c2ccc(F)c(Cl)c2)C2CCN(CC(F)(F)F)CC2)CCN1] | N-((S or R)-(3-chloro-4-fluorophenyl)(1-(2,2,2-trifluoroethyl)piperidin-4-yl)methyl)-3-oxopiperazine-1-carboxamide | 450.9 | 451.4 | SFC: OD-H Co-solvent: 25% (IPA + 0.2% DIPEA) peak 2 |

Examples 18A, 18B, 18C and 18D (2R)-N-((R)-(3-chloro-4-fluorophenyl)(1-(R)-(1,1,1-trifluoropropan-2-yl)piperidin-4-yl)methyl)-3-oxopiperazine-1-carboxamide, (2R)-N-((R)-(3-chloro-4-fluorophenyl)(1-(S)-(1,1,1-trifluoropropan-2-yl)piperidin-4-yl)methyl)-3-oxopiperazine-1-carboxamide, (2R)-N-((S)-(3-chloro-4-fluorophenyl)(1-(R)-(1,1,1-trifluoropropan-2-yl)piperidin-4-yl)methyl)-3-oxopiperazine-1-carboxamide and (2R)-N-((S)-(3-chloro-4-fluorophenyl)(1-(S)-(1,1,1-trifluoropropan-2-yl)piperidin-4-yl)methyl)-3-oxopiperazine-1-carboxamide

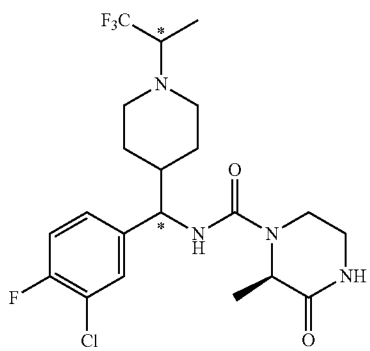 [SMILES: CC(N1CCC(C(NC(=O)N2CCNC(=O)[C@H]2C)c2ccc(F)c(Cl)c2)CC1)C(F)(F)F]

Step 1: tert-butyl 4-(3-chloro-4-fluorobenzoyl)piperidine-1-carboxylate To a solution of tert-butyl 4-(methoxy(methyl)carbamoyl)piperidine-1-carboxylate (542 mg, 1.990 mmol) in THF (8 mL) at 0° C. was added 3-chloro-4-fluorophenylmagnesium bromide in THF (0.5 M, 7.96 mL, 3.98 mmol). The mixture was stirred at 0° C. for 30 minutes, then warmed to RT for 2 hours. The reaction was then quenched with saturated aqueous $NH_4Cl$ and extracted with diethyl ether. The separated organic layer was dried over $Na_2SO_4$, filtered and concentrated under reduced pressure to give the title compound. LRMS m/z (M+H): calculated 341.8, observed 342.4.

Step 2: (3-chloro-4-fluorophenyl)(piperidin-4-yl)methanone hydrochloride To a solution of tert-butyl 4-(3-chloro-4-fluorobenzoyl)piperidine-1-carboxylate (680 mg, 1.989 mmol) in $CH_2Cl_2$ (3 mL) and MeOH (1 mL) was added HCl in 1,4-dioxane (4 M, 3 mL, 12.00 mmol). The mixture was stirred at RT for 3 hours and then concentrated under reduced pressure to give the title compound. LRMS m/z (M+H): calculated 241.7, observed 242.2.

Step 3: (3-chloro-4-fluorophenyl)(1-(1,1,1-trifluoropropan-2-yl)piperidin-4-yl)methanone To a solution of (3-chloro-4-fluorophenyl)(piperidin-4-yl)methanone hydrochloride in DMF (5 mL) were added 1,1,1-trifluoropropan-2-yl trifluoromethanesulfonate (636 mg, 2.58 mmol) and $Et_3N$ (1.108 mL, 7.95 mmol). The mixture was heated to 50° C. for 20 hours, then cooled to RT, quenched with $H_2O$ and extracted with ethyl acetate. The separated organic layer was dried over $Na_2SO_4$, filtered and concentrated under reduced pressure. The resulting residue was purified by column chromatography on silica gel, eluting with (0-40% ethyl acetate/hexane) to give the title compound. LRMS m/z (M+H): calculated 337.7, observed 338.3.

Step 4: (S)-N-((Z)-(3-chloro-4-fluorophenyl)(1-(1,1,1-trifluoropropan-2-yl)piperidin-4-yl)-methylene)-2-methylpropane-2-sulfinamide A microwave tube was charged with (3-chloro-4-fluorophenyl)(1-(1,1,1-trifluoropropan-2-yl)piperidin-4-yl)methanone (188 mg, 0.557 mmol), (S)-(−)-2-methyl-2-propane sulfinamide (135 mg, 1.113 mmol) and titanium(IV) isopropoxide (1 mL, 3.38 mmol). The mixture was microwaved at 120° C. for 30 minutes. Then saturated aqueous $NaHCO_3$ (10 mL) and 30 mL ethyl acetate (30 mL). The mixture was stirred at RT for 20 min, and then filtered through a Celite® pad. The separated organic layer was dried over $Na_2SO_4$, filtered and concentrated under reduced pressure. The resulting residue was purified by column chromatography on silica gel, eluting with (0-20% ethyl acetate/hexane) to give the title compound. LRMS m/z (M+H): calculated 440.9, observed 441.4.

Step 5: (S)-N-((3-chloro-4-fluorophenyl)(1-(1,1,1-trifluoropropan-2-yl)piperidin-4-yl)methyl)-2-methylpropane-2-sulfinamide (isomers A and B) To a solution of (S)-N-((Z)-(3-chloro-4-fluorophenyl)(1-(1,1,1-trifluoropropan-2-yl)piperidin-4-yl)methylene)-2-methylpropane-2-sulfinamide (174 mg, 0.395 mmol) in THF (1 mL) and MeOH (500 μL) was added $NaBH_4$ (59.7 mg, 1.578 mmol) at RT. The mixture was stirred at RT for 3 hours and then partitioned between ethyl acetate and saturated aqueous $NaHCO_3$. The organic layer was separated and then washed with brine. The separated organic layer was dried over $Na_2SO_4$, filtered and concentrated under reduced pressure. The resulting residue was purified by preparative TLC, eluting with (40% ethyl acetate in hexane) to give the title compounds: Isomer A (first eluted fraction): LRMS m/z (M+H): calculated 442.9, observed 443.4; and Isomer B (second eluted fraction): LRMS m/z (M+H): calculated 442.9, observed 443.4.

Step 6: (3-chloro-4-fluorophenyl)(1-(1,1,1-trifluoropropan-2-yl)piperidin-4-yl)methanamine hydrochloride To a solution of (S)-N-((3-chloro-4-fluorophenyl)(1-(1,1,1-trifluoropropan-2-yl)piperidin-4-yl)methyl)-2-methylpropane-2-sulfinamide (Isomer A, 48 mg, 0.108 mmol) in $CH_2Cl_2$ (500 μL) and MeOH (500 μL) was added HCl in 1,4-dioxane (4 M, 1 mL, 4.00 mmol). The mixture was stirred at RT for 2 hours and then concentrated under reduced pressure. The resulting residue was washed with hexane (2×10 mL), filtered to remove the solvent and dried under reduced pressure to give the title compound. LRMS m/z (M+H): calculated 338.8, observed 339.3.

Step 7: Examples 18A and 18B To a solution of (3-chloro-4-fluorophenyl)(1-(1,1,1-trifluoropropan-2-yl)piperidin-4-yl)methanamine HCl (41.5 mg, 0.111 mmol) in $CH_2Cl_2$ (2 mL) at 0° C. were added $Et_3N$ (0.092 mL, 0.664 mmol) and triphosgene (32.8 mg, 0.111 mmol). The mixture was stirred at 0° C. for 1 hour and then (R)-3-methylpiperazin-2-one (18.94 mg, 0.166 mmol) was added. After stirring at 0° C. for 1 hour, the reaction warmed to RT for 1 hour and concentrated under reduced pressure. The resulting residue was purified by column chromatography on silica gel, eluting with (0-4% MeOH/DCM) to give a mixture, which was separated by SFC (OJ-H column, 20% (EtOH+0.2% DIPEA) co-solvent) to give Examples 18A (first eluted fraction) and 18B (second eluted fraction).

Example 18A: LRMS m/z (M+H): calculated 478.9, observed 479.4. $^1H$ NMR δ (ppm) (500 MHz, Chloroform-d): 7.31 (s, 1H), 7.12 (d, J=6.9 Hz, 2H), 6.39 (s, 1H), 5.12 (s, 1H), 4.66 (s, 1H), 4.51 (s, 1H), 4.24 (d, J=13.3 Hz, 1H), 3.57-3.46 (m, 1H), 3.31 (d, J=11.4 Hz, 1H), 3.23-3.07 (m, 2H), 2.94 (s, 2H), 2.56 (s, 1H), 2.36 (s, 1H), 1.76 (d, J=11.6 Hz, 1H), 1.63 (s, 2H), 1.49 (d, J=7.0 Hz, 3H), 1.37 (s, 2H), 1.23 (s, 3H). Example 18B: LRMS m/z (M+H): calculated 478.9, observed 479.4. $^1H$ NMR δ (ppm) (500 MHz, Chloroform-d): 7.30 (s, 1H), 7.12 (d, J=6.9 Hz, 2H), 6.25 (s, 1H), 5.01 (s, 1H), 4.66 (s, 1H), 4.47 (s, 1H), 4.24 (d, J=12.9 Hz, 1H), 3.52 (t, J=7.8 Hz, 1H), 3.31 (d, J=9.6 Hz, 1H), 3.23-3.08 (m, 2H), 2.99 (s, 1H), 2.86 (s, 1H), 2.55 (s, 1H), 2.38 (s, 1H), 1.79 (d, J=12.2 Hz, 1H), 1.63 (s, 2H), 1.50 (d, J=7.0 Hz, 3H), 1.36 (s, 2H), 1.24 (s, 3H).

Step 8: Examples 18C and 18D Examples 18C and 18D were prepared according to the synthetic procedure for Examples 18A and 18B by using isomer B from Step 5. Example 18C (first eluted fraction) and Example 18D (second eluted fraction) were separated by SFC (OD-H column, 15% (EtOH+0.2% DIPEA) co-solvent). Example 18C: LRMS m/z (M+H): calculated 478.9, observed 479.4. $^1$H NMR δ (ppm) (500 MHz, Chloroform-d): 7.40 (dd, J=7.0, 2.0 Hz, 1H), 7.19-7.13 (m, 1H), 7.09 (t, J=8.6 Hz, 1H), 6.27 (d, J=3.3 Hz, 1H), 5.38 (d, J=6.5 Hz, 1H), 4.59 (t, J=7.9 Hz, 1H), 4.52 (d, J=6.9 Hz, 1H), 4.29 (d, J=12.5 Hz, 1H), 3.45 (td, J=11.6, 4.2 Hz, 1H), 3.33-3.25 (m, 1H), 3.21-3.09 (m, 2H), 2.95 (d, J=10.0 Hz, 1H), 2.89 (d, J=9.2 Hz, 1H), 2.58 (t, J=10.7 Hz, 1H), 2.33 (s, 1H), 1.83 (d, J=12.3 Hz, 1H), 1.66 (d, J=8.9 Hz, 2H), 1.54 (d, J=7.0 Hz, 3H), 1.40-1.30 (m, 2H), 1.22 (d, J=6.2 Hz, 3H).

Example D: LRMS m/z (M+H): calculated 478.9, observed 479.4. $^1$H NMR δ (ppm) (500 MHz, Chloroform-d): 7.39 (d, J=6.6 Hz, 1H), 7.19-7.13 (m, 1H), 7.10 (t, J=8.6 Hz, 1H), 6.27 (s, 1H), 5.34 (d, J=16.6 Hz, 1H), 4.60 (d, J=7.7 Hz, 1H), 4.52 (s, 1H), 4.29 (d, J=12.8 Hz, 1H), 3.46 (dt, J=11.4, 5.8 Hz, 1H), 3.29 (d, J=12.1 Hz, 1H), 3.22-3.10 (m, 2H), 3.00 (s, 1H), 2.84 (s, 1H), 2.54 (s, 1H), 2.39 (t, J=10.4 Hz, 1H), 1.86 (d, J=13.1 Hz, 1H), 1.73-1.57 (m, 2H), 1.55 (d, J=7.0 Hz, 3H), 1.28 (t, J=7.1 Hz, 2H), 1.24 (d, J=6.1 Hz, 3H).

Examples 19A, 19B, 19C and 19D (2R)-N-((R)-(3-chloro-4-fluorophenyl)(trans-1,1-difluorospiro[2.5]octan-6-yl)methyl)-2-methyl-3-oxopiperazine-1-carboxamide, (2R)-N-((S)-(3-chloro-4-fluorophenyl)(trans-1,1-difluorospiro[2.5]octan-6-yl)methyl)-2-methyl-3-oxopiperazine-1-carboxamide, (2R)-N-((R)-(3-chloro-4-fluorophenyl)(cis-1,1-difluorospiro[2.5]octan-6-yl)methyl)-2-methyl-3-oxopiperazine-1-carboxamide and (2R)-N-((S)-(3-chloro-4-fluorophenyl)(cis-1,1-difluorospiro[2.5]octan-6-yl)methyl)-2-methyl-3-oxopiperazine-1-carboxamide

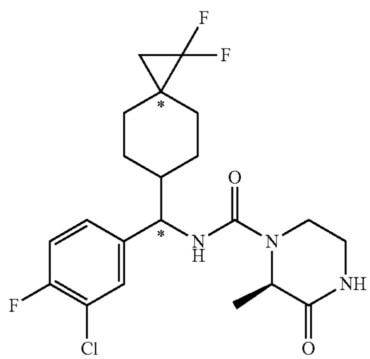 [SMILES: C[C@@H]1C(=O)NCCN1C(=O)NC(c1ccc(F)c(Cl)c1)C1CCC2(CC1)CC2(F)F]

Step 1: (3-chloro-4-fluorophenyl)(1,1-difluorospiro[2.5]octan-6-yl)methanone To a solution of 1,1-difluorospiro[2.5]octane-6-carboxylic acid (318 mg, 1.672 mmol) in $CH_2Cl_2$ (4 mL) at 0° C. was added $(COCl)_2$ in DCM (2 M, 1.672 mL, 3.34 mmol) and one drop of DMF. The mixture was warmed to RT and stirred for 4 hours, followed by heating to 40° C. for 30 minutes. The mixture was then concentrated under reduced pressure. The resulting residue was redissolved in THF (4 mL) to prepare solution A. In a separate reaction flask, copper(I) cyanide (374 mg, 4.18 mmol) was suspended in THF (4 mL) and cooled to 0° C., followed by the addition of (3-chloro-4-fluorophenyl) magnesium bromide in THF (0.5 M, 6.69 mL, 3.34 mmol). The mixture was stirred at 0° C. for 1 hour, then added to solution A and stirred at 0° C. for 2 hours, then warmed to RT for 2 hours. The reaction mixture was partitioned between ethyl acetate and saturated aqueous $NH_4Cl$, and filtered thorough a Celite® pad. The separated organic layer was dried over $Na_2SO_4$, filtered and concentrated under reduced pressure to give the title compound. LRMS m/z (M+H): calculated 302.7, observed 302.9.

Step 2: (3-chloro-4-fluorophenyl)(1,1-difluorospiro[2.5]octan-6-yl)methanamine hydrochloride A microwave tube was charged with (3-chloro-4-fluorophenyl)(1,1-difluorospiro[2.5]octan-6-yl)methanone (506 mg, 1.672 mmol), ammonium acetate (1031 mg, 13.37 mmol) and ethanol (10 mL). The mixture was microwaved at 125° C. for 15 min and cooled to RT, followed by addition of sodium cyanoborohydride (126 mg, 2.006 mmol). The reaction was microwaved at 125° C. for 15 min, then cooled to RT and quenched with 30 mL of 10% aqueous $K_2CO_3$ and extracted with ethyl acetate (2×30 mL). The combined organic layers were dried over $Na_2SO_4$, filtered and concentrated under reduced pressure. The resulting residue was treated with HCl (2 M, 2 mL) in diethy ether and the resulting solid was filtered off to give the title compound.

LRMS m/z (M+H): calculated 303.7, observed 304.0.

Step 3: examples 19A, 19B, 19C and 19D To a suspension of (3-chloro-4-fluorophenyl)(1,1-difluorospiro[2.5]octan-6-yl)methanamine hydrochloride (160 mg, 0.527 mmol) in $CH_2Cl_2$ (3 mL) at 0° C. were added triphosgene (156 mg, 0.527 mmol) and $Et_3N$ (0.367 mL, 2.63 mmol). The mixture was stirred at 0° C. for 1 hour, then (R)-3-methylpiperazin-2-one (90 mg, 0.790 mmol) was added. The reaction was stirred at 0° C. for 1 hour, then warmed to RT for 1 hour and concentrated under reduced pressure. The resulting residue was purified by column chromatography on silica gel, eluting with (0-4% MeOH/DCM) to give a mixture, which was separated by SFC (AD-H column, 20% (EtOH+0.2% DIPEA) co-solvent) to give Examples 19A (first eluted fraction), 19B (second eluted fraction), 19C (third eluted fraction) and 19D (fourth eluted fraction).

Example 19A: LRMS m/z (M+H): calculated 443.9, observed 444.3. $^1$H NMR δ (ppm) (500 MHz, Chloroform-d): 7.31 (d, J=6.8 Hz, 1H), 7.15-7.11 (m, 2H), 6.19 (d, J=15.9 Hz, 1H), 4.92 (s, 1H), 4.64 (t, J=8.2 Hz, 1H), 4.43 (s, 1H), 4.22 (d, J=12.7 Hz, 1H), 3.51 (td, J=11.5, 4.2 Hz, 1H), 3.37-3.29 (m, 1H), 3.14 (ddd, J=14.4, 11.2, 3.6 Hz, 1H), 2.02-1.93 (m, 1H), 1.72-1.60 (m, 4H), 1.48 (dd, J=7.0, 4.2 Hz, 3H), 1.29-1.18 (m, 3H), 1.07 (dt, J=20.4, 7.7 Hz, 3H).

Example 19B: LRMS m/z (M+H): calculated 443.9, observed 444.3. $^1$H NMR δ (ppm) (500 MHz, Chloroform-d): 7.31 (d, J=6.5 Hz, 1H), 7.16-7.11 (m, 2H), 6.02 (s, 1H), 4.81 (s, 1H), 4.66 (t, J=8.4 Hz, 1H), 4.39 (d, J=6.5 Hz, 1H), 4.22 (d, J=14.6 Hz, 1H), 3.56-3.47 (m, 1H), 3.36-3.29 (m, 1H), 3.15 (ddd, J=14.5, 11.2, 3.7 Hz, 1H), 1.98 (d, J=12.6 Hz, 1H), 1.73-1.59 (m, 4H), 1.48 (d, J=7.1 Hz, 3H), 1.29-1.21 (m, 4H), 0.99 (td, J=7.9, 3.8 Hz, 2H).

Example 19C: LRMS m/z (M+H): calculated 443.9, observed 444.3. $^1$H NMR δ (ppm) (500 MHz, Chloroform-d): 7.34 (d, J=6.9 Hz, 1H), 7.18-7.05 (m, 2H), 5.99 (s, 1H), 4.96 (s, 1H), 4.68 (t, J=8.0 Hz, 1H), 4.41 (d, J=6.8 Hz, 1H), 4.28 (d, J=12.9 Hz, 1H), 3.47 (td, J=11.6, 4.3 Hz, 1H), 3.30 (d, J=11.8 Hz, 1H), 3.16 (ddd, J=14.5, 11.3, 3.7 Hz, 1H), 1.92 (d, J=13.1 Hz, 1H), 1.77-1.58 (m, 4H), 1.56 (d, J=7.1 Hz, 3H), 1.51 (d, J=15.2 Hz, 1H), 1.30-1.08 (m, 3H), 1.06 (t, J=8.6 Hz, 2H).

Example 19D: LRMS m/z (M+H): calculated 443.9, observed 444.3. $^1$H NMR δ (ppm) (500 MHz, Chloroform-d): 7.38 (s, 1H), 7.19-7.09 (m, 2H), 6.06 (s, 1H), 5.12 (s, 1H), 4.66 (s, 1H), 4.43 (s, 1H), 4.29 (d, J=12.3 Hz, 1H), 3.47 (t, J=11.0 Hz, 1H), 3.30 (d, J=11.5 Hz, 1H), 3.16 (t, J=12.1 Hz, 1H), 1.97 (d, J=12.6 Hz, 1H), 1.80-1.58 (m, 4H), 1.55 (d, J=6.9 Hz, 3H), 1.29-1.20 (m, 4H), 0.99 (t, J=8.6 Hz, 2H).

Examples 20A, 20B, 20C and 20D (R)-N-((S)-(3-chloro-2,4-difluorophenyl)(trans-3-(trifluoromethyl)cyclobutyl)methyl)-2-methyl-3-oxopiperazine-1-carboxamide (20A), (R)-N-((R)-(3-chloro-2,4-difluorophenyl)(trans-3-(trifluoromethyl)cyclobutyl)methyl)-2-methyl-3-oxopiperazine-1-carboxamide (20B), (R)-N-((S)-(3-chloro-2,4-difluorophenyl)(cis-3-(trifluoromethyl)cyclobutyl)methyl)-2-methyl-3-oxopiperazine-1-carboxamide (20C) and (R)-N-((R)-(3-chloro-2,4-difluorophenyl)(cis-3-(trifluoromethyl)cyclobutyl)methyl)-2-methyl-3-oxopiperazine-1-carboxamide (20D)

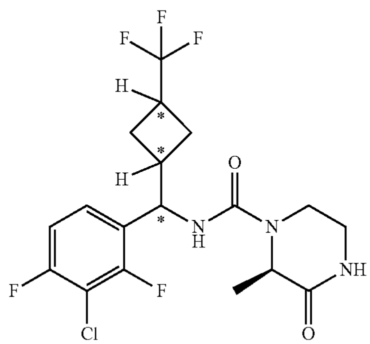 [SMILES: C[C@@H]1C(=O)NCCN1C(=O)NC(c1ccc(F)c(Cl)c1F)C1CC(C(F)(F)F)C1]

Step 1: (3-chloro-2,4-difluorophenyl)(3-(trifluoromethyl)cyclobutyl)methanone To a solution of 3-(trifluoromethyl)cyclobutane-1-carboxylic acid (1.00 g, 5.95 mmol) in $CH_2Cl_2$ (15 mL) at 0° C. was added $(COCl)_2$ in DCM (2 M, 3.57 mL, 7.14 mmol) and one drop of DMF. The mixture was warmed to RT and stirred at RT for 4 hours. Then the mixture was concentrated under reduced pressure, and the resulting residue was redissolved in THF (6 mL) to prepare solution A. In a separate flask, 2-chloro-1,3-difluoro-4-iodobenzene (2.449 g, 8.92 mmol) was dissolved in THF (20 mL), cooled to −20° C., followed by the addition of isopropylmagnesium chloride-lithium chloride complex in THF (1.3 M, 6.86 mL, 8.92 mmol). The mixture was stirred at −20° C. for 2 hours, then warmed to 0° C., followed by the addition of copper(I) cyanide (1.066 g, 11.90 mmol). The mixture was stirred at 0° C. for 30 minutes, then solution A was added. The reaction was maintained at 0° C. for 2 hours, warmed to RT for 1 hour, and then partitioned between ethyl acetate and saturated aqueous $NH_4Cl$, and filtered thorough a Celite® pad. The separated organic layer was dried over $Na_2SO_4$, filtered and concentrated under reduced pressure to give the title compound. LRMS m/z (M+H): calculated 298.6, observed 299.1.

Step 2: (R,E)-N-((3-chloro-2,4-difluorophenyl)(3-(trifluoromethyl)cyclobutyl)methylene)-2-methylpropane-2-sulfinamide A microwave tube was charged with (3-chloro-2,4-difluorophenyl)(3-(trifluoromethyl)cyclobutyl)methanone (1.7 g, 5.69 mmol), (R)-(+)-2-methyl-2-propanesulfinamide (1.035 g, 8.54 mmol) and tetraethoxytitanium (10.46 mL, 11.39 mmol). The reaction mixture was microwaved at 105° C. for 1 hour, then cooled to RT and poured into $H_2O$ (30 mL) and 50 ml ethyl acetate (50 mL). The mixture was stirred for 10 min, and then filtered through a Celite® pad. The separated organic layer was dried over $Na_2SO_4$, filtered and concentrated under reduced pressure to give the title compound. LRMS m/z (M+H): calculated 401.8, observed 402.3.

Step 3: (R)-N-((S)-(3-chloro-2,4-difluorophenyl)(trans-3-(trifluoromethyl)cyclobutyl)methyl)-2-methylpropane-2-sulfinamide (isomer A), (R)-N-((S)-(3-chloro-2,4-difluorophenyl)(cis-3-(trifluoromethyl)cyclobutyl)methyl)-2-methylpropane-2-sulfinamide (isomer B-1), (R)-N-((R)-(3-chloro-2,4-difluorophenyl)(cis-3-(trifluoromethyl)cyclobutyl)methyl)-2-methylpropane-2-sulfinamide (isomer B-2) and (R)-N-((R)-(3-chloro-2,4-difluorophenyl)(trans-3-(trifluoro-methyl)cyclobutyl)methyl)-2-methylpropane-2-sulfinamide (isomer C) To a solution of (R,E)-N-((3-chloro-2,4-difluorophenyl)(3-(trifluoromethyl)cyclobutyl)methylene)-2-methylpropane-2-sulfinamide (2.2 g, 5.48 mmol) in THF (10 mL) and MeOH (2 mL) at 0° C. was added $NaBH_4$ (0.207 g, 5.48 mmol). The mixture was stirred at 0° C. for 1 hour, then warmed to RT for 1 hour and partitioned between ethyl acetate and saturated aqueous $NaHCO_3$. The separated organic layer was dried over $Na_2SO_4$, filtered and concentrated under reduced pressure. The resulting residue was purified by column chromatography on silica gel, eluting with (0-40% ethyl acetate/hexane) to give a mixture which was separated by SFC (AD-H column, 10% MeOH co-solvent) to give isomer A (first eluted fraction), isomer B (second eluted fraction) and isomer C (third eluted fraction). Isomer B was further separated by SFC (IF-H column, 30% EtOH with 0.25% DIPEA co-solvent) to give isomer B-1 (first eluted fraction) and isomer B-2 (second eluted fraction).

Step 4: (S)-(3-chloro-2,4-difluorophenyl)(trans-3-(trifluoromethyl)cyclobutyl)methanamine hydrochloride A solution of (R)-N-((S)-(3-chloro-2,4-difluorophenyl)(trans-3-(trifluoromethyl)-cyclobutyl)-methyl)-2-methyl propane-2-sulfinamide (isomer A, 125 mg, 0.310 mmol) in $CH_2Cl_2$ (1 mL) was cooled to 0° C., followed by the addition of HCl in 1,4-dioxane (4 M, 1 mL, 4 mmol). The mixture was stirred at 0° C. for 2 hours and then concentrated under reduced pressure. The resulting residue was washed with diethyl ether (2×5 mL) and filtered to give the title compound. LRMS m/z (M+H): calculated 299.7, observed 300.2.

Step 5: Example 20A To a suspension of (S)-(3-chloro-2,4-difluorophenyl)(trans-3-(trifluoro-methyl)cyclobutyl)methanamine hydrochloride (59 mg, 0.197 mmol) in $CH_2Cl_2$ (4 mL) at 0° C. was added triphosgene (58.4 mg, 0.197 mmol) and $Et_3N$ (0.082 ml, 0.591 mmol). The mixture was stirred at 0° C. for 1 hour, then (R)-3-methylpiperazin-2-one (29.2 mg, 0.256 mmol) was added. The reaction mixture was stirred at 0° C. for 1 hour, then warmed to RT for 1 hour and concentrated under reduced pressure. The resulting residue was purified by column chromatography on silica gel, eluting with (0-4% MeOH/DCM) to give example 20A. LRMS m/z (M+H): calculated 439.8, observed 440.3. $^1$H NMR δ (ppm) (500 MHz, Chloroform-d): 7.22 (q, J=8.0 Hz, 1H), 6.97 (t, J=8.2 Hz, 1H), 6.57 (d, J=28.5 Hz, 1H), 5.37-5.21 (m, 1H), 5.01 (dd, J=10.7, 8.4 Hz, 1H), 4.56-4.43

(m, 1H), 4.18 (d, J=13.2 Hz, 1H), 3.54-3.43 (m, 1H), 3.32 (d, J=11.1 Hz, 1H), 3.20-3.08 (m, 1H), 3.00-2.82 (m, 2H), 2.36 (d, J=5.9 Hz, 1H), 2.28-2.17 (m, 1H), 2.09 (q, J=9.9, 6.9 Hz, 1H), 1.97-1.88 (m, 1H), 1.45 (d, J=7.0 Hz, 3H).

Step 6: Examples 20B, 20C and 20D Examples 20B, 20C and 20D were prepared according to the synthetic procedure for Example 20A by using the different isomers obtained in Step 3 as starting materials.

Isomer C gave Example 20B: LRMS m/z (M+H): calculated 439.8, observed 440.3. $^1$H NMR δ (ppm) (500 MHz, Chloroform-d): 7.22 (q, J=7.5 Hz, 1H), 6.97 (t, J=8.3 Hz, 1H), 6.38 (d, J=28.8 Hz, 1H), 5.24 (s, 1H), 5.03 (dd, J=10.9, 8.2 Hz, 1H), 4.44 (d, J=6.6 Hz, 1H), 4.22 (d, J=13.4 Hz, 1H), 3.45 (td, J=11.5, 3.7 Hz, 1H), 3.30 (d, J=11.7 Hz, 1H), 3.21-3.11 (m, 1H), 3.00-2.84 (m, 2H), 2.37 (dt, J=12.8, 6.5 Hz, 1H), 2.28-2.18 (m, 1H), 2.11 (q, J=10.1, 7.1 Hz, 1H), 1.99-1.88 (m, 1H), 1.50 (d, J=7.0 Hz, 3H).

Isomer B-1 gave Example 20C: LRMS m/z (M+H): calculated 439.8, observed 440.3. $^1$H NMR δ (ppm) (500 MHz, Chloroform-d): 7.21 (td, J=8.2, 6.0 Hz, 1H), 7.02-6.92 (m, 1H), 6.34 (s, 1H), 4.98 (d, J=8.0 Hz, 1H), 4.94-4.87 (m, 1H), 4.39 (q, J=7.1 Hz, 1H), 4.17 (d, J=13.6 Hz, 1H), 3.51 (td, J=11.5, 4.2 Hz, 1H), 3.32 (dq, J=11.7, 3.6 Hz, 1H), 3.15 (ddd, J=14.2, 11.1, 3.6 Hz, 1H), 2.83 (dt, J=17.6, 8.8 Hz, 1H), 2.72 (p, J=8.9 Hz, 1H), 2.35 (dtd, J=11.9, 8.3, 3.7 Hz, 1H), 2.16-2.06 (m, 1H), 2.06-1.98 (m, 1H), 1.93-1.85 (m, 1H), 1.48 (d, J=7.1 Hz, 3H).

Isomer B-2 gave example 20D: LRMS m/z (M+H): calculated 439.8, observed 440.3. $^1$H NMR δ (ppm) (500 MHz, Chloroform-d): 7.25-7.19 (m, 1H), 7.00-6.93 (m, 1H), 6.35 (s, 1H), 5.19 (s, 1H), 4.97 (t, J=8.8 Hz, 1H), 4.42 (q, J=6.9 Hz, 1H), 4.24 (d, J=12.8 Hz, 1H), 3.46 (td, J=11.6, 4.2 Hz, 1H), 3.34-3.27 (m, 1H), 3.16 (ddd, J=14.3, 11.2, 3.6 Hz, 1H), 2.83 (dt, J=17.6, 8.8 Hz, 1H), 2.74 (p, J=9.0 Hz, 1H), 2.31 (dtd, J=11.9, 8.2, 3.8 Hz, 1H), 2.16-2.09 (m, 1H), 2.04 (ddd, J=12.0, 8.1, 3.8 Hz, 1H), 1.97-1.88 (m, 1H), 1.52 (d, J=7.1 Hz, 3H).

TABLE 3

The following examples were prepared according to the synthetic procedure for Examples 20A, 20B, 20C and 20D, using the appropriate starting materials and reagents

| Example | Compound | Name | Calc'd [M + H]$^+$ | Observed [M + H]$^+$ | Conditions |
|---|---|---|---|---|---|
| 21A | 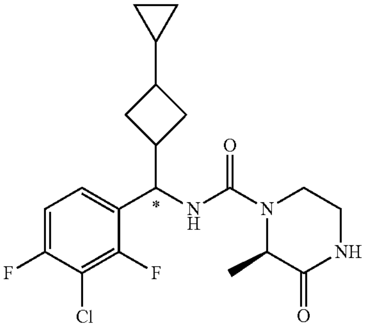 [SMILES: C[C@@H]1C(=O)NCCN1C(=O)NC(c1ccc(F)c(Cl)c1F)C1CC(C2CC2)C1] | (2R)-N-((R or S)-(3-chloro-2,4-difluoro-phenyl)(trans or cis-3-cyclopropylcyclobutyl) methyl)-2-methyl-3-oxopiperazine-1-carboxamide | 411.9 | 412.4 | In step 3 SFC: AD-H Co-solvent: 25% EtOH then 10% (IPA + 0.2% DIPEA) peak 1 |
| 21B | 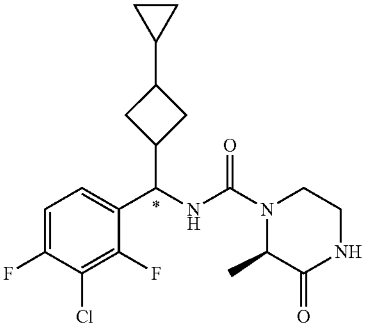 [SMILES: C[C@@H]1C(=O)NCCN1C(=O)NC(c1ccc(F)c(Cl)c1F)C1CC(C2CC2)C1] | (2R)-N-((R or S)-(3-chloro-2,4-difluoro-phenyl)(cis or trans-3-cyclopropylcyclobutyl) methyl)-2-methyl-3-oxopiperazine-1-carboxamide | 411.9 | 412.4 | In step 3 SFC: AD-H Co-solvent: 25% EtOH then 10% (IPA + 0.2% DIPEA) peak 2 |
| 21C | 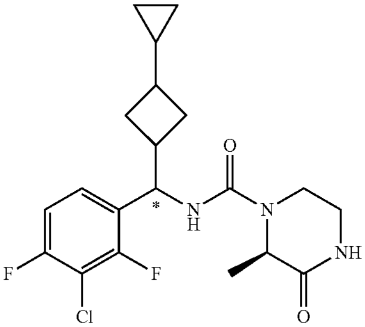 [SMILES: C[C@@H]1C(=O)NCCN1C(=O)NC(c1ccc(F)c(Cl)c1F)C1CC(C2CC2)C1] | (2R)-N-((S or R)-(3-chloro-2,4-difluoro-phenyl)(trans or cis-3-cyclopropyl-cyclobutyl)-methyl)-2-methyl-3-oxopiperazine-1-carboxamide | 411.9 | 412.4 | In step 3 SFC: AD-H Co-solvent: 25% EtOH then 10% (IPA + 0.2% DIPEA) peak 3 |

TABLE 3-continued

The following examples were prepared according to the synthetic procedure for Examples 20A, 20B, 20C and 20D, using the appropriate starting materials and reagents

| Example | Compound | Name | Calc'd [M + H]+ | Observed [M + H]+ | Conditions |
|---|---|---|---|---|---|
| 21D | 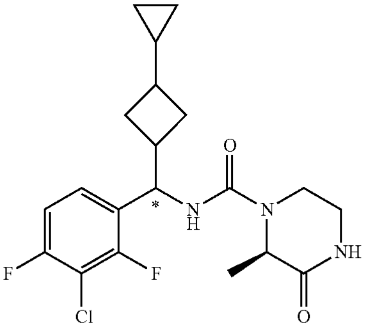 [SMILES: C[C@@H]1C(=O)NCCN1C(=O)NC(c1ccc(F)c(Cl)c1F)C1CC(C2CC2)C1] | (2R)-N-((S or R)-(3-chloro-2,4-difluoro-phenyl)(cis or trans-3-cyclopropyl-cyclobutyl)-methyl)-2-methyl-3-oxopiperazine-1-carboxamide | 411.9 | 412.4 | In step 3 SFC: AD-H Co-solvent: 25% EtOH then 10% (IPA + 0.2% DIPEA) peak 4 |
| 22A | 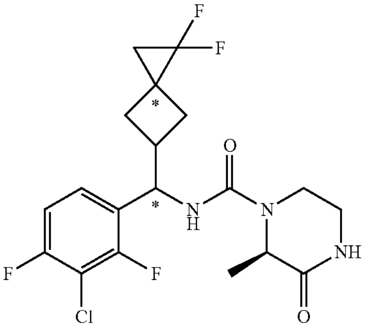 [SMILES: C[C@@H]1C(=O)NCCN1C(=O)NC(c1ccc(F)c(Cl)c1F)C1CC2(C1)CC2(F)F] | (2R)-N-((R or S)-(3-chloro-2,4-difluoro-phenyl)(trans or cis-1,1-difluoro-spiro[2,3]-hexan-5-yl)methyl)-2-methyl-3-oxopiperazine-1-carboxamide | 433.8 | 434.4 | In step 3 SFC: AD-H Co-solvent; 10% MeOH peak 1 |
| 22B | 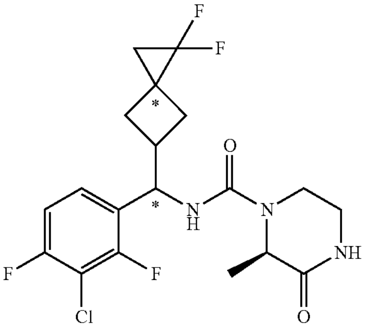 [SMILES: C[C@@H]1C(=O)NCCN1C(=O)NC(c1ccc(F)c(Cl)c1F)C1CC2(C1)CC2(F)F] | (2R)-N-((R or S)-(3-chloro-2,4-difluoro-phenyl)(cis or trans-1,1-difluoro-spiro[2,3]-hexan-5-yl)methyl)-2-methyl-3-oxopiperazine-1-carboxamide | 433.8 | 434.4 | In step 3 SFC: AD-H Co-solvent: 10% MeOH peak 2 |
| 22C | 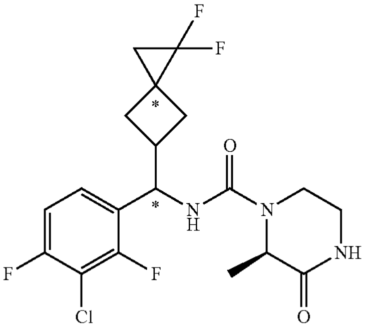 [SMILES: C[C@@H]1C(=O)NCCN1C(=O)NC(c1ccc(F)c(Cl)c1F)C1CC2(C1)CC2(F)F] | (2R)-N-((S or R)-(3-chloro-2,4-difluoro-phenyl)(trans or cis-1,1-difluoro-spiro[2.3]-hexan-5-yl)methyl)-2-methyl-3-oxopiperazine-1-carboxamide | 433.8 | 434.4 | In step 3 SFC: AD-H Co-solvent: 10% MeOH peak 3 |

TABLE 3-continued

The following examples were prepared according to the synthetic procedure for Examples 20A, 20B, 20C and 20D, using the appropriate starting materials and reagents

| Example | Compound | Name | Calc'd $[M + H]^+$ | Observed $[M + H]^+$ | Conditions |
| --- | --- | --- | --- | --- | --- |
| 22D | 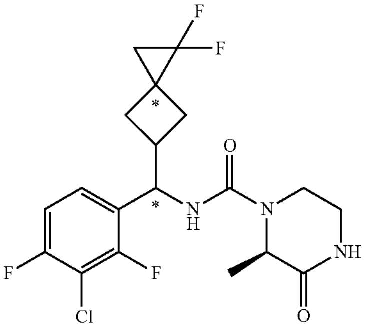 [SMILES: C[C@@H]1C(=O)NCCN1C(=O)NC(c1ccc(F)c(Cl)c1F)C1CC2(C1)CC2(F)F] | (2R)-N-((So or R)-(3-chloro-2,4-difluoro-phenyl)(cis or trans-1,1-difluoro-spiro[2.3]-hexan-5-yl)methyl)-2-methyl-3-oxopiperazine-1-carboxamide | 433.8 | 434.4 | In step 3 SFC: AD-H Co-solvent: 10% MeOH peak 4 |
| 23 | 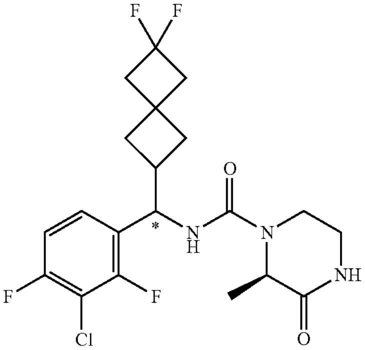 [SMILES: C[C@@H]1C(=O)NCCN1C(=O)NC(c1ccc(F)c(Cl)c1F)C1CC2(C1)CC(F)(F)C2] | (2R)-N-((R or S)-(3-chloro-2,4-difluoro-phenyl)(6,6-difluoro-spiro[3.3]heptan-2-yl)methyl)-2-methyl-3-oxopiperazine-1-carboxamide | 447.8 | 448.4 | In step 3 SFC: AD-H Co-solvent: 20% MeOH peak 1 |
| 24A | 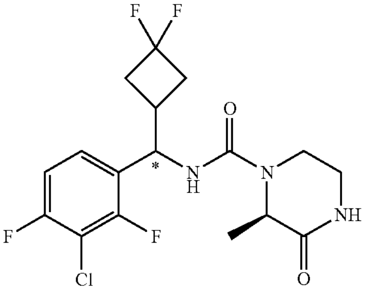 [SMILES: C[C@@H]1C(=O)NCCN1C(=O)NC(c1ccc(F)c(Cl)c1F)C1CC(F)(F)C1] | (2R)-N-((R or S)-(3-chloro-2,4-difluoro-phenyl)(3,3-difluoro-cyclobutyl)methyl)-2-methyl-3-oxopiperazine-1-carboxamide | 407.8 | 408.3 | In step 5 SFC: OJ-H Co-solvent: 30% EtOH peak 1 |
| 24B | 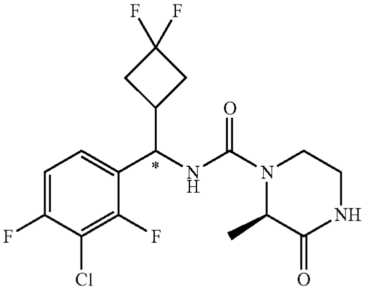 [SMILES: C[C@@H]1C(=O)NCCN1C(=O)NC(c1ccc(F)c(Cl)c1F)C1CC(F)(F)C1] | (2R)-N-((S or R)-(3-chloro-2,4-difluoro-phenyl)(3,3-difluoro-cyclobutyl)methyl)-2-methyl-3-oxopiperazine-1-carboxamide | 407.8 | 408.3 | In step 5 SFC: OJ-H Co-solvent: 30% EtOH peak 2 |

TABLE 3-continued

| The following examples were prepared according to the synthetic procedure for Examples 20A, 20B, 20C and 20D, using the appropriate starting materials and reagents | | | | | |
|---|---|---|---|---|---|
| Example | Compound | Name | Calc'd $[M + H]^+$ | Observed $[M + H]^+$ | Conditions |
| 25A | 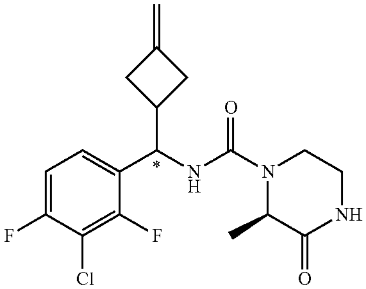 [SMILES: C=C1CC(C(NC(=O)N2CCNC(=O)[C@H]2C)c2ccc(F)c(Cl)c2F)C1] | (2R)-N-((R or S)-(3-chloro-2,4-difluoro-phenyl)(3-methylene-cyclobutyl)methyl)-2-methyl-3-oxopiperazine-1-carboxamide | 383.8 | 384.3 | In step 3 SFC: AD-H Co-solvent; 35% MeOH peak 1 |
| 25B | 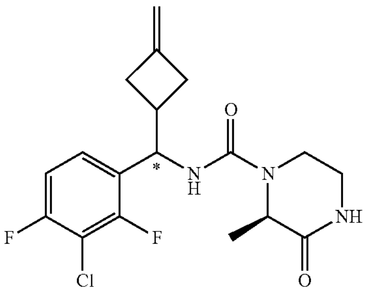 [SMILES: C=C1CC(C(NC(=O)N2CCNC(=O)[C@H]2C)c2ccc(F)c(Cl)c2F)C1] | (2R)-N-((S or R)-(3-chloro-2,4-difluoro-phenyl)(3-methylene-scyclobutyl)methyl)-2-methyl-3-oxopiperazine-1-carboxamide | 383.8 | 384.3 | In step 3 SFC: AD-H Co-solvent: 35% MeOH peak 2 |

Example 26

N-((S)-(3-chloro-2,4-difluorophenyl)(trans-3-(trifluoromethyl)cyclobutyl)methyl)-3-oxopiperazine-1-carboxamide

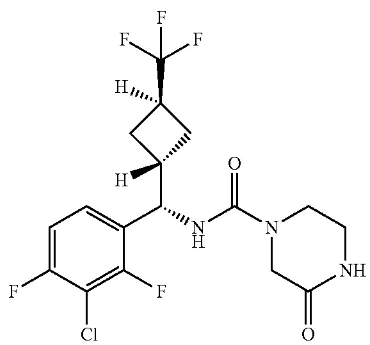 [SMILES: O=C1CN(C(=O)N[C@H](c2ccc(F)c(Cl)c2F)[C@H]2C[C@@H](C(F)(F)F)C2)CCN1]

To a solution of (S)-(3-chloro-2,4-difluorophenyl)(trans-3-(trifluoromethyl)cyclobutyl) methanamine hydrochloride (70 mg, 0.208 mmol) in $CH_2Cl_2$ (3 ml) at 0° C. were added $Et_3N$ (0.116 mL, 0.833 mmol) and triphosgene (61.8 mg, 0.208 mmol). The mixture was stirred at 0° C. for 1 hour, and piperazin-2-one (27.1 mg, 0.271 mmol) was added. Then the reaction mixture was stirred at 0° C. for 1 hour, warmed to RT for 1 hour and concentrated under reduced pressure. The resulting residue was purified by column chromatography on silica gel, eluting with (0-4% MeOH/DCM) to give Example 26. LRMS m/z (M+H): calculated 425.8, observed 426.4. $^1H$ NMR δ (ppm) (500 MHz, Chloroform-d): 7.22 (q, J=8.1 Hz, 1H), 6.98 (t, J=8.3 Hz, 1H), 6.51 (d, J=23.9 Hz, 1H), 5.03 (dd, J=10.8, 7.9 Hz, 1H), 4.08 (s, 2H), 3.68 (t, J=5.1 Hz, 2H), 3.43 (s, 2H), 3.04-2.84 (m, 2H), 2.37 (q, J=9.7, 6.5 Hz, 1H), 2.28-2.18 (m, 1H), 2.09 (d, J=13.5 Hz, 1H), 2.00-1.83 (m, 2H).

Examples 27A and 27B (R or S)-N-((S)-(3-chloro-2,4-difluorophenyl)(trans-3-(trifluoromethyl)cyclobutyl)methyl)-2-cyclopropyl-3-oxopiperazine-1-carboxamide and (S or R)-N-((S)-(3-chloro-2,4-difluorophenyl)(trans-3-(trifluoromethyl)cyclobutyl)methyl)-2-cyclopropyl-3-oxopiperazine-1-carboxamide

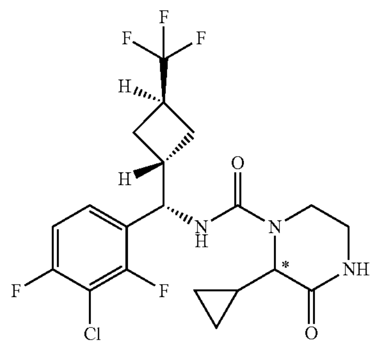 [SMILES: O=C1NCCN(C(=O)N[C@H](c2ccc(F)c(Cl)c2F)[C@H]2C[C@@H](C(F)(F)F)C2)C1C1CC1]

To a solution of (S)-(3-chloro-2,4-difluorophenyl)(trans-3-(trifluoromethyl)cyclobutyl) methanamine hydrochloride (95.8 mg, 0.285 mmol) in $CH_2Cl_2$ (4 mL) at 0° C. were added $Et_3N$ (0.199 mL, 1.425 mmol) and triphosgene (85 mg, 0.285 mmol). The mixture was stirred at 0° C. for 1 hour and 3-cyclopropylpiperazin-2-one (51.9 mg, 0.371 mmol) was added. After stirring at 0° C. for 1 hour, the reaction was warmed to RT for 1 hour and concentrated under reduced pressure. The resulting residue was purified by column chromatography on silica gel, eluting with (0-4% MeOH/DCM) to give a mixture of isomers, which was further separated by SFC (OD-H column, 30% MeOH co-solvent) to give Examples 27A (first eluted fraction) and 27B (second eluted fraction).

Example 27A: LRMS m/z (M+H): calculated 465.8, observed 466.4. $^1$H NMR δ (ppm) (500 MHz, Chloroform-d): 7.21 (td, J=8.2, 6.0 Hz, 1H), 6.98 (t, J=8.3 Hz, 1H), 6.52 (s, 1H), 5.11 (d, J=8.3 Hz, 1H), 5.03-4.96 (m, 1H), 4.15 (d, J=6.8 Hz, 1H), 4.03 (d, J=13.2 Hz, 1H), 3.51-3.43 (m, 1H), 3.42-3.30 (m, 2H), 2.94 (dq, J=9.9, 5.1 Hz, 1H), 2.86 (dt, J=16.5, 8.5 Hz, 1H), 2.37 (d, J=6.3 Hz, 1H), 2.28-2.17 (m, 1H), 2.11 (s, 1H), 1.94-1.84 (m, 1H), 1.27-1.21 (m, 1H), 0.66 (dt, J=9.5, 4.7 Hz, 1H), 0.57 (ddt, J=12.9, 8.5, 4.9 Hz, 2H), 0.47 (q, J=7.4, 5.3 Hz, 1H).

Example 27B: LRMS m/z (M+H): calculated 465.8, observed 466.4. $^1$H NMR δ (ppm) (500 MHz, Chloroform-d): 7.20 (td, J=8.2, 6.0 Hz, 1H), 7.01-6.92 (m, 1H), 6.66 (s, 1H), 5.22 (d, J=8.0 Hz, 1H), 5.04 (dd, J=11.0, 8.0 Hz, 1H), 4.18-4.08 (m, 2H), 3.47-3.39 (m, 1H), 3.38-3.31 (m, 2H), 2.95 (ddt, J=14.7, 9.8, 5.0 Hz, 1H), 2.86 (dt, J=16.7, 8.7 Hz, 1H), 2.36 (dt, J=12.8, 6.5 Hz, 1H), 2.29-2.20 (m, 1H), 2.11 (dq, J=13.4, 7.0, 6.2 Hz, 1H), 1.99-1.88 (m, 1H), 1.32-1.27 (m, 1H), 0.74-0.67 (m, 1H), 0.61 (ddt, J=21.8, 8.3, 4.3 Hz, 2H), 0.51 (dq, J=10.1, 5.1 Hz, 1H).

Examples 28A and 28B (2R)-N-((R)-(3-chloro-2,4-difluorophenyl)(spiro[2.3]hexan-5-yl)methyl)-2-methyl-3-oxopiperazine-1-carboxamide and (2R)-N-((S)(3-chloro-2,4-difluorophenyl)(spiro[2.3]hexan-5-yl)methyl)-2-methyl-3-oxopiperazine-1-carboxamide

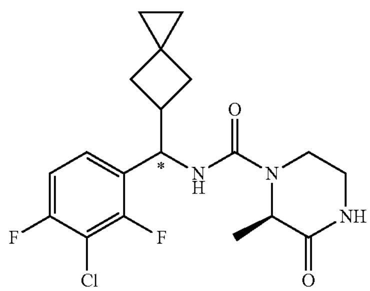 [SMILES: C[C@@H]1C(=O)NCCN1C(=O)NC(c1ccc(F)c(Cl)c1F)C1CC2(CC2)C1]

Example 28A: (2R)-N-((R or S)-(3-chloro-2,4-difluorophenyl)(spiro[2.3]hexan-5-yl)methyl)-2-methyl-3-oxopiperazine-1-carboxamide To a 0° C. solution of diethylzinc in hexane (1 M, 2.215 mL, 2.215 mmol) in $CH_2Cl_2$ (5 mL) was added dropwise TFA (0.171 mL, 2.215 mmol) in $CH_2Cl_2$ (500 μL). The mixture was stirred 1 hour, then diiodomethane (0.179 mL, 2.215 mmol) was added. Then after 40 minutes, (2R)-N-((R or S)(3-chloro-2,4-difluorophenyl)(3-methylene-cyclobutyl)methyl)-2-methyl-3-oxopiperazine-1-carboxamide (Example 25A, 170 mg, 0.443 mmol) in $CH_2Cl_2$ (1 mL) was added. The reaction was stirred for 2 hours and then quenched with saturated aqueous $NH_4Cl$. The separated organic layer was dried ($MgSO_4$), filtered and concentrated under reduced pressure. The resulting residue was purified by column chromatography on silica gel, eluting with (0-3% MeOH/$CH_2Cl_2$) to give Example 28A. LRMS m/z (M+H): calculated 397.9, observed 398.3. $^1$H NMR δ (ppm) (500 MHz, Chloroform-d): 7.21 (q, J=8.1 Hz, 1H), 6.95 (t, J=8.4 Hz, 1H), 6.35 (s, 1H), 5.00 (dq, J=15.4, 7.6 Hz, 2H), 4.38 (q, J=7.1 Hz, 1H), 4.18 (d, J=15.3 Hz, 1H), 3.56-3.45 (m, 1H), 3.35-3.27 (m, 1H), 3.14 (ddd, J=14.2, 11.2, 3.6 Hz, 1H), 2.86 (h, J=7.1 Hz, 1H), 2.28-2.15 (m, 1H), 2.08 (d, J=8.3 Hz, 1H), 2.01-1.94 (m, 1H), 1.83 (dd, J=11.5, 6.6 Hz, 1H), 1.48 (t, J=7.0 Hz, 3H), 0.53-0.35 (m, 4H).

Example 28B: (2R)-N-((S or R)-(3-chloro-2,4-difluorophenyl)(spiro[2.3]hexan-5-yl)methyl)-2-methyl-3-oxopiperazine-1-carboxamide Example 28B was prepared according to a the synthetic procedure for Example 28A using Example 25B as the starting material. LRMS m/z (M+H): calculated 397.9, observed 398.3. $^1$H NMR δ (ppm) (500 MHz, Chloroform-d): 7.25-7.19 (m, 1H), 6.95 (q, J=8.3, 7.6 Hz, 1H), 6.46 (s, 1H), 5.07 (d, J=6.5 Hz, 2H), 4.39 (q, J=6.9 Hz, 1H), 4.23 (d, J=13.4 Hz, 1H), 3.45 (td, J=11.5, 4.2 Hz, 1H), 3.31-3.26 (m, 1H), 3.19-3.12 (m, 1H), 2.87 (d, J=8.1 Hz, 1H), 2.24-2.17 (m, 1H), 2.13-2.07 (m, 1H), 2.02-1.94 (m, 1H), 1.87 (dd, J=11.5, 6.7 Hz, 1H), 1.51 (d, J=7.1 Hz, 3H), 0.44 (t, J=9.5 Hz, 4H).

Examples 29A and 29B (2R)-N-((R)-(3-chloro-2,4-difluorophenyl)(trans-3-(difluoromethyl)cyclobutyl)methyl)-2-methyl-3-oxopiperazine-1-carboxamide and (2R)-N-((S)-(3-chloro-2,4-difluorophenyl)(trans-3-(difluoromethyl)cyclobutyl)methyl)-2-methyl-3-oxopiperazine-1-carboxamide

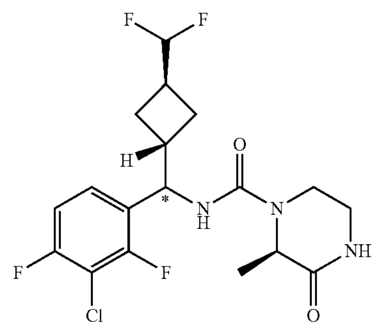 [SMILES: C[C@@H]1C(=O)NCCN1C(=O)NC(c1ccc(F)c(Cl)c1F)[C@H]1C[C@H](C(F)F)C1]

Step 1: (3-chloro-2,4-difluorophenyl)(trans-3-(difluoromethyl)cyclobutyl)methanone To a solution of 3-(difluoromethyl)cyclobutane-1-carboxylic acid (1.00 g, 6.66 mmol) in $CH_2Cl_2$ (15 mL) at 0° C. was added $(COCl)_2$ in $CH_2Cl_2$ (2 M, 3.66 mL, 7.33 mmol) and one drop of DMF. The mixture was warmed to RT for 4 hours and then concentrated under reduced pressure. The resulting residue was dissolved in THF (6 mL) to prepare solution A. In a separate flask, a solution of 2-chloro-1,3-difluoro-4-iodobenzene (2.74 g, 9.99 mmol) in THF (20 mL) was cooled to −20° C., followed by the addition of isopropyl magnesium chloride-lithium chloride complex in THF (1.3 M, 7.69 mL, 9.99 mmol). The resulting mixture was stirred at −20° C. for 2 hours, then warmed to 0° C., followed by addition of copper(I) cyanide (1.193 g, 13.32 mmol). The mixture was stirred at 0° C. for 30 minutes, followed by the addition of solution A. The reaction was maintained at 0° C. for 2 hours, then warmed to RT for 1 hour, and quenched with saturated aqueous $NH_4Cl$ (40 mL) and extracted with ethyl acetate (2×30 mL). The combined organic layers were dried over $Na_2SO_4$, filtered and concentrated under reduced pressure. The resulting residue was purified by column chromatography on silica gel, eluting with (0-20% ethyl acetate/hexane) to give a trans/cis mixture, which was separated by SFC (AD-H column, 10% MeOH co-solvent) to give the title compound (trans isomer, second eluted fraction from SFC). LRMS m/z (M+H): calculated 280.6, observed 281.3.

Step 2: (R)—N-((E)-(3-chloro-2,4-difluorophenyl)(trans-3-(difluoromethyl)cyclobutyl) methylene)-2-methylpropane-2-sulfinamide A microwave tube was charged with (3-chloro-2,4-difluorophenyl)(trans-3-(difluoromethyl) cyclobutyl)methanone (180 mg, 0.641 mmol), (R)-2-methyl-2 propanesulfinamide (117 mg, 0.962 mmol), tetraethoxytitanium (0.403 mL, 1.924 mmol) and toluene (1.5 mL). The mixture was microwaved at 105° C. for 1 hour, and then cooled to RT, followed by the addition of $H_2O$ (20 mL) and ethyl acetate (20 mL). The mixture was stirred for 10 minutes, then filtered through a Celite® pad. The separated organic layer was dried over $Na_2SO_4$, filtered and concentrated under reduced pressure to give the title compound. LRMS m/z (M+H): calculated 383.8, observed 384.3.

Step 3: (R)—N-((3-chloro-2,4-difluorophenyl)(trans-3-(difluoromethyl)cyclobutyl)methyl)-2-methylpropane-2-sulfinamide To a solution of (R)—N-((E)-(3-chloro-2,4-difluorophenyl)(trans-3-(difluoromethyl)cyclobutyl) methylene)-2-methylpropane-2-sulfinamide (246 mg, 0.641 mmol) in THF (4 mL) and water (200 μL) at −78° C. was added $NaBH_4$ (72.7 mg, 1.923 mmol). The mixture was stirred at −78° C. for 3 h, then gradually warmed to RT and partitioned between ethyl acetate and saturated aqueous $NaHCO_3$. The separated organic layer was dried over $Na_2SO_4$, filtered and concentrated under reduce pressure to give the title compound. LRMS m/z (M+H): calculated 385.8, observed 386.4.

Step 4: (3-chloro-2,4-difluorophenyl)(trans-3-(difluoromethyl)cyclobutyl)methanamine hydrochloride To a solution of (R)—N-((3-chloro-2,4-difluorophenyl)(trans-3-(difluoromethyl)cyclobutyl) methyl)-2-methylpropane-2-sulfinamide (167 mg, 0.433 mmol) in $CH_2Cl_2$ (1 mL) at 0° C. was added HCl in 1,4-dixoane (4 M, 1 mL, 4.00 mmol). The mixture was stirred at 0° C. for 2 hours and then rconcentrated under reduced pressure. The resulting residue was washed with diethyl ether (2×8 mL), and filtered to give the title compound. LRMS m/z (M+H): calculated 281.7, observed 282.3.

Step 5: Examples 29A and 29B To a solution of (3-chloro-2,4-difluorophenyl)(trans-3-(difluoromethyl)cyclobutyl) methanamine hydrochloride (130 mg, 0.462 mmol) in DCM (5 mL) at 0° C. were added $Et_3N$ (0.257 mL, 1.846 mmol) and triphosgene (137 mg, 0.462 mmol). The mixture was stirred at 0° C. for 1 hour, then (R)-3-methylpiperazin-2-one (52.7 mg, 0.462 mmol) was added. The reaction was stirred at 0° C. for 1 hour, then warmed to RT over 1 hour, and concentrated the reaction mixture under reduced pressure. The resulting residue was purified by column chromatography on silica gel, eluting with (0-4% MeOH/DCM) to give a mixture of isomers which was further separated by SFC (AD-H column, 20% EtOH co-solvent) to give Examples 29A (first eluted fraction) and 29B (second eluted fraction).

Example 29A: LRMS m/z (M+H): calculated 421.8, observed 422.5. $^1H$ NMR δ (ppm) (500 MHz, DMSO-d6): 7.20 (d, J=5.6 Hz, 1H), 6.97 (t, J=8.3 Hz, 1H), 5.86 (td, J=57.1, 3.7 Hz, 1H), 4.96 (s, 1H), 4.37 (s, 1H), 4.20-4.15 (m, 1H), 3.51 (td, J=11.3, 4.0 Hz, 1H), 3.36-3.29 (m, 1H), 3.16 (t, J=12.2 Hz, 1H), 2.75 (d, J=40.6 Hz, 2H), 2.28 (d, J=6.0 Hz, 1H), 2.19-2.09 (m, 1H), 2.01 (s, 1H), 1.90-1.78 (m, 1H), 1.48 (d, J=7.0 Hz, 3H).

Example 29B: LRMS m/z (M+H): calculated 421.8, observed 422.5. $^1H$ NMR δ (ppm) (500 MHz, DMSO-d6): 7.21 (q, J=7.0 Hz, 1H), 6.97 (t, J=8.3 Hz, 1H), 6.24 (s, 1H), 5.86 (td, J=57.1, 3.7 Hz, 1H), 5.05-4.99 (m, 1H), 4.39 (s, 1H), 4.22 (d, J=13.4 Hz, 1H), 3.54-3.41 (m, 1H), 3.30 (d, J=9.8 Hz, 1H), 3.17 (t, J=10.9 Hz, 1H), 2.87-2.63 (m, 2H), 2.28 (dt, J=12.2, 6.0 Hz, 1H), 2.12 (dd, J=17.8, 10.9 Hz, 1H), 2.01 (s, 1H), 1.90-1.81 (m, 1H), 1.73 (s, 1H), 1.51 (d, J=7.0 Hz, 3H).

Examples 30A and 30B (2R)-N-((R)-(3-chloro-2,4-difluorophenyl)(3-(trifluoromethyl)bicyclo[1.1.1]pentan-1-yl)methyl)-2-methyl-3-oxopiperazine-1-carboxamide and (2R)-N-((S)-(3-chloro-2,4-difluorophenyl)(3-(trifluoromethyl)bicyclo[1.1.1]pentan-1-yl)methyl)-2-methyl-3-oxopiperazine-1-carboxamide

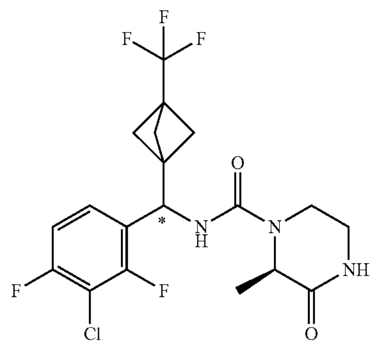 [SMILES: C[C@@H]1C(=O)NCCN1C(=O)NC(c1ccc(F)c(Cl)c1F)C12CC(C(F)(F)F)(C1)C2]

Step 1: N-methoxy-N-methyl-3-(trifluoromethyl)bicyclo[1.1.1]pentane-1-carboxamide To a mixture of 3-(trifluoromethyl)bicyclo[1.1.1]pentane-1-carboxylic acid (300 mg, 1.666 mmol) in DCM (12 mL) was added CDI (540 mg, 3.33 mmol) under $N_2$ at 25° C. The mixture was stirred at 25° C. for 1 hour under $N_2$, then N,O-dimethylhydroxylamine hydrochloride (244 mg, 2.498 mmol) and triethylamine (0.696 mL, 5.00 mmol) were added. The reaction mixture was stirred at 25° C. for 12 hours under $N_2$, then concentrated under reduced pressure. The resulting residue was purified by flash silica gel chromatography (ISCO®; 12 g SepaFlash® Silica Flash Column, eluent of 10-50% ethyl acetate/pet. ether) to give the title compound. $^1H$ NMR ($CDCl_3$, 400 MHz) δ 3.67 (s, 3H), 3.18 (s, 3H), 2.48-2.07 (m, 6H).

Step 2: (3-chloro-2,4-difluorophenyl)(3-(trifluoromethyl) bicyclo[1.1.1]pentan-1-yl)methanone To a mixture of 1-bromo-3-chloro-2,4-difluorobenzene (856 mg, 3.76 mmol) in THF (2 mL) was added isopropyl magnesium chloride (2.90 mL, 3.76 mmol, 1.3 M toluene solution) at 0° C. under $N_2$ over 2 hours. Then N-methoxy-N-methyl-3-(trifluoromethyl)bicyclo[1.1.1]pentane-1-carboxamide (280 mg, 1.255 mmol) was added at 0° C. and the reaction stirred at 20° C. under $N_2$ for 16 hours. The reaction mixture was then dissolved in water (20 mL) and EtOAc (20 mL). The organic layer was separated and the aqueous layer was back extracted with EtOAc (3×20 mL). The combined organic layers were washed with brine (20 mL), dried over anhydrous $Na_2SO_4$, filtered and the filtrate was evaporated in vacuo. The resulting residue was purified by Prep-TLC (silica gel, pet. ether/ethyl acetate=9/1) to give the title compound. $^{1}$H NMR (500 MHz, $CDCl_3$) δ 7.62-7.67 (m, 1H), 7.07-7.11 (m, 1H), 2.41 (s, 6H).

Step 3: (3-chloro-2,4-difluorophenyl)(3-(trifluoromethyl) bicyclo[1.1.1]pentan-1-yl)methanamine To a mixture of (3-chloro-2,4-difluorophenyl)(3-(trifluoromethyl)bicyclo [1.1.1]pentan-1-yl)methanone (120 mg, 0.386 mmol) and ammonium acetate (447 mg, 5.79 mmol) in EtOH (2 mL) was added sodium cyanoborohydride (36.4 mg, 0.579 mmol) at 25° C. The reaction was stirred under microwave at 130° C. for 10 minutes. Then the reaction mixture was concentrated to remove most of the EtOH, treated with 2 N NaOH until pH>10, and extracted with EtOAc (2×20 mL). The combined organic layers were dried over anhydrous $Na_2SO_4$, filtered, and concentrated under reduced pressure to give the title compound. LRMS m/z (M-16): calculated 311.1, observed 294.9.

Step 4: Examples 30A and 30B A mixture of CDI (62.4 mg, 0.385 mmol) and (3-chloro-2,4-difluorophenyl)(3-(trifluoromethyl) bicyclo[1.1.1]pentan-1-yl)methanamine (100 mg crude) in DCM (2 mL) was stirred at 20° C. for 1 hour. Then (R)-3-methylpiperazin-2-one (47.6 mg, 0.417 mmol) was added. The resulting mixture was stirred at 20° C. for 16 hours. Then the mixture was purified by reverse phase HPLC (75:25 to 45:55; water (0.1% TFA):MeCN (0.1% TFA)) to give a mixture of isomers, which were further separated by SFC (AD-H column, 5%-40% EtOH with 0.05% DEA co-solvent) to give Examples 30A (first eluted fraction) and 30B (second eluted fraction).

Example 30A: LRMS m/z (M+H): calculated 451.1, observed 452.0. $^{1}$H NMR δ (ppm) (500 MHz, $CD_3OD$-d4): 7.27-7.42 (m, 1H), 7.11-7.15 (m, 1H), 6.66-6.68 (m, 1H), 5.34-5.36 (m, 1H), 4.65 (d, J=7.0 Hz, 1H), 3.94-4.14 (m, 1H), 3.20-3.42 (m, 3H), 1.89 (s, 6H), 1.41 (d, J=7.0 Hz, 3H).

Example 30B: LRMS m/z (M+H): calculated 451.1, observed 452.0. $^{1}$H NMR δ (ppm) (500 MHz, $CD_3OD$-d4): 7.24-7.41 (m, 1H), 7.14 (t, J=8.4 Hz, 1H), 5.35 (s, 1H), 4.42-4.69 (m, 1H), 3.90-4.13 (m, 1H), 3.34-3.43 (m, 1H), 3.24-3.30 (m, 2H), 1.90 (s, 6H), 1.41 (d, J=7.0 Hz, 3H).

TABLE 4

The following examples were prepared according to the synthetic procedure for Examples 30A and 30B, using the appropriate starting materials and reagents

| Example | Compound | Name | Calc'd $[M + H]^+$ | Observed $[M + H]^+$ | Conditions |
|---|---|---|---|---|---|
| 31A | 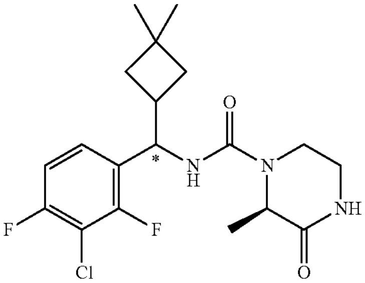 [SMILES: C[C@@H]1C(=O)NCCN1C(=O)NC(c1ccc(F)c(Cl)c1F)C1CC(C)(C)C1] | (2R)-N-((R or S)-(3-chloro-2,4-difluoro-phenyl)(3,3-dimethyl-cyclobutyl)methyl)-2-methyl-3-oxopiperazine-1-carboxamide | 399.2 | 400.2 | SFC: AD-H Co-solvent: 20% EtOH with 0.1% $NH_3H_2O$ peak 1 |
| 31B | 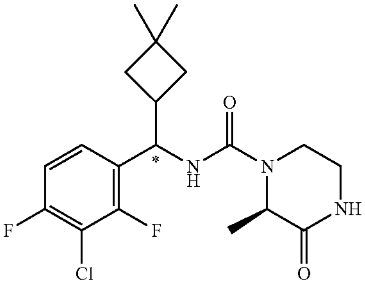 [SMILES: C[C@@H]1C(=O)NCCN1C(=O)NC(c1ccc(F)c(Cl)c1F)C1CC(C)(C)C1] | (2R)-N-((S or R)-(3-chloro-2,4-difluoro-phenyl)(3,3-dimethyl-cyclobutyl)methyl)-2-methyl-3-oxopiperazine-1-carboxamide | 399.2 | 400.2 | SFC: AD-H Co-solvent: 20% EtOH with 0.1% $NH_3H_2O$ peak 2 |
| 32A | 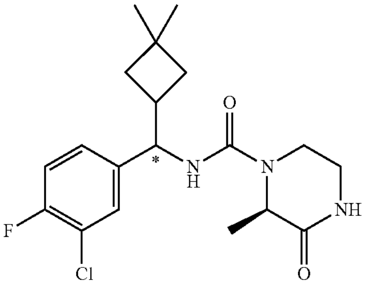 [SMILES: C[C@@H]1C(=O)NCCN1C(=O)NC(c1ccc(F)c(Cl)c1)C1CC(C)(C)C1] | N-((R or S)-(3-chloro-2,4-difluorophenyl)(3,3-dimethylcyclobutyl)methyl)-3-oxopiperazine-1-carboxamide | 385.1 | 386.1 | SFC: AD-H Co-solvent: 20% EtOH with 0.1% $NH_3H_2O$ peak 1 |

TABLE 4-continued

The following examples were prepared according to the synthetic procedure for Examples 30A and 30B, using the appropriate starting materials and reagents

| Example | Compound | Name | Calc'd $[M+H]^+$ | Observed $[M+H]^+$ | Conditions |
|---|---|---|---|---|---|
| 32B | 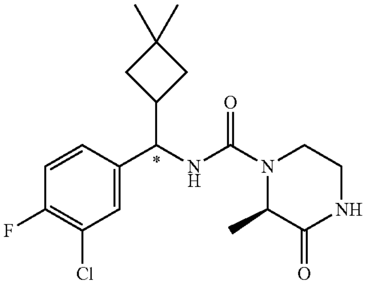 [SMILES: C[C@@H]1C(=O)NCCN1C(=O)NC(c1ccc(F)c(Cl)c1)C1CC(C)(C)C1] | N-((S or R)-(3-chloro-2,4-difluorophenyl)(3,3-dimethylcyclobutyl)methyl)-3-oxopiperazine-1-carboxamide | 385.1 | 386.1 | SFC: AD-H Co-solvent: 20% EtOH with 0.1% $NH_3H_2O$ peak 2 |
| 33A | 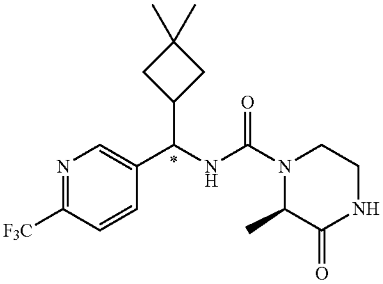 | (2R)-N-((R or S)-(3,3-dimethylcyclobutyl)(6-(trifluoromethyl)pyridin-3-yl)methyl)-2-methyl-3-oxopiperazine-1-carboxamide | 398.2 | 399.2 | SFC: AD-H Co-solvent: 30% EtOH with 0.1% $NH_3H_2O$ peak 1 |
| 33B | 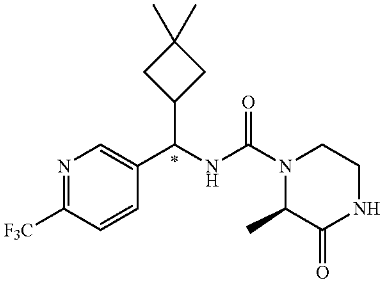 [SMILES: C[C@@H]1C(=O)NCCN1C(=O)NC(c1ccc(C(F)(F)F)nc1)C1CC(C)(C)C1] | (2R)-N-((S or R)-(3,3-dimethylcyclobutyl)(6-(trifluoromethyl)pyridin-3-yl)methyl)-2-methyl-3-oxopiperazine-1-carboxamide | 398.2 | 399.2 | SFC: AD-H Co-solvent: 30% EtOH with 0.1% $NH_3H_2O$ peak 2 |
| 34A | 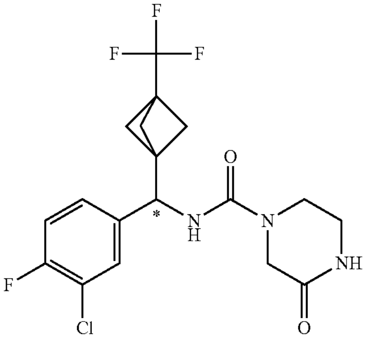 [SMILES: O=C1CN(C(=O)NC(c2ccc(F)c(Cl)c2)C23CC(C(F)(F)F)(C2)C3)CCN1] | N-((R or S)-(3-chloro-4-fluorophenyl)(3-(trifluoromethyl)bicyclo[1.1.1]pentan-1-yl)methyl)-3-oxopiperazine-1-carboxamide | 419.1 | 420.2 | SFC: OJ-3 Co-solvent: 5%-40% EtOH with 0.05% DEA peak 1 |

TABLE 4-continued

| The following examples were prepared according to the synthetic procedure for Examples 30A and 30B, using the appropriate starting materials and reagents | | | | | |
|---|---|---|---|---|---|
| Example | Compound | Name | Calc'd [M + H]$^+$ | Observed [M + H]$^+$ | Conditions |
| 34B | 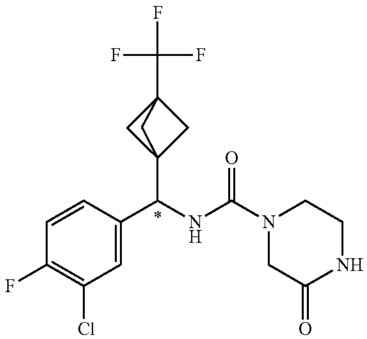 [SMILES: O=C1CN(C(=O)NC(c2ccc(F)c(Cl)c2)C23CC(C(F)(F)F)(C2)C3)CCN1] | N-((S or R)-(3-chloro-4-fluorophenyl)(3-(trifluoromethyl)bicyclo[1.1.1]pentan-1-yl)methyl)-3-oxopiperazine-1-carboxamide | 419.1 | 420.2 | SFC: OJ-3 Co-solvent: 5%-40% EtOH with 0.05% DEA peak 2 |
| 35A | 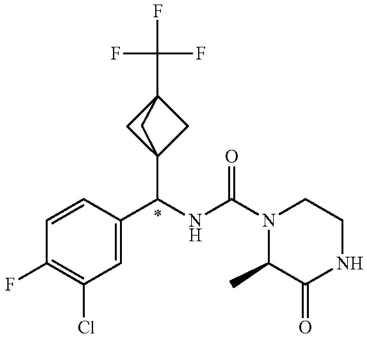 [SMILES: C[C@@H]1C(=O)NCCN1C(=O)NC(c1ccc(F)c(Cl)c1)C12CC(C(F)(F)F)(C1)C2] | (2R)-N-((R or S)-(3-chloro-4-fluoro-phenyl)(3-(trifluoro-methyl)bicyclo[1.1.1]pen-tan-1-yl)methyl)-2-methyl-3-oxopiperazine-1-carboxamide | 433.1 | 434.1 | SFC: AD-3 Co-solvent: 5%-40% EtOH with 0.05% DEA peak 1 |
| 35B | 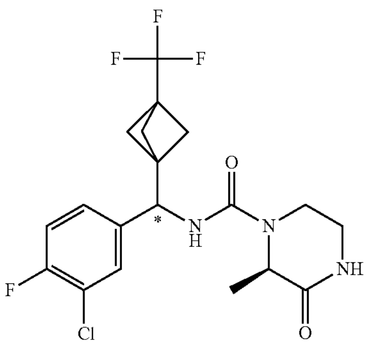 [SMILES: C[C@@H]1C(=O)NCCN1C(=O)NC(c1ccc(F)c(Cl)c1)C12CC(C(F)(F)F)(C1)C2] | (2R)-N-((S or R)-(3-chloro-4-fluoro-phenyl)(3-(trifluoro-methyl)bicyclo[1.1.1]pen-tan-1-yl)methyl)-2-methyl-3-oxopiperazine-1-carboxamide | 433.1 | 434.1 | SFC: AD-3 Co-solvent: 5%-40% EtOH with 0.05% DEA peak 2 |

Examples 36A, 36B, 36C and 36D (2R)-N-((R)-(4-fluoro-3-methylphenyl)(trans-4-(trifluoromethyl)cyclohexyl)methyl)-2-methyl-3-oxopiperazine-1-carboxamide, (2R)-N-((S)-(4-fluoro-3-methylphenyl)(trans-4-(trifluoromethyl)cyclohexyl)methyl)-2-methyl-3-oxopiperazine-1-carboxamide, (2R)-N-((R)-(4-fluoro-3-methylphenyl)(cis-4-(trifluoromethyl)cyclohexyl)methyl)-2-methyl-3-oxopiperazine-1-carboxamide and (2R)-N-((S)-(4-fluoro-3-methylphenyl)(cis-4-(trifluoromethyl)cyclohexyl)-methyl)-2-methyl-3-oxopiperazine-1-carboxamide

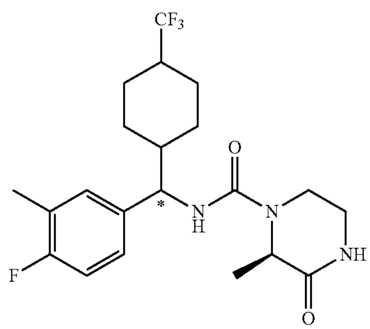 [SMILES: Cc1cc(C(NC(=O)N2CCNC(=O)[C@H]2C)C2CCC(C(F)(F)F)CC2)ccc1F]

Step 1: N-methoxy-N-methyl-4-(trifluoromethyl)cyclohexane-1-carboxamide To a mixture of 4-(trifluoromethyl) cyclohexane-1-carboxylic acid 1 (4 g, 20.39 mmol) and HATU (11.63 g, 30.6 mmol) in DMF (40 mL) was added N,O-dimethylhydroxylamine hydrochloride (2.98 g, 30.6 mmol) at 0° C. The resulting mixture was stirred at 20° C. for 2 hours. Then water (300 mL) was added and the mixture was extracted with ethyl acetate (3×20 mL). The combined organic layers were washed with brine (100 mL), dried over $Na_2SO_4$, and filtered. The filtrate was evaporated under reduced pressure, and the resulting crude product was purified by flash silica gel chromatography (ISCO®; 12 g SepaFlash® Silica Flash Column, Eluent of 13% petroleum ether/ethyl acetate) to give the title compound. LRMS m/z (M+H): calculated 339.1, observed 240.1.

Step 2: (4-fluoro-3-methylphenyl)(4-(trifluoromethyl)cyclohexyl)methanone To a mixture of N-methoxy-N-methyl-4-(trifluoromethyl)cyclohexane-1-carboxamide (500 mg, 2.090 mmol) in THF (3 mL) was added (4-fluoro-3-methylphenyl) magnesium bromide (13.79 ml, 6.90 mmol) at 0° C. The resulting mixture was stirred at 20° C. for 18 hours. Then water (15 mL) was added and the mixture was extracted with ethyl acetate (2×8 mL). The combined organic layers were washed with brine (15 mL), dried over $Na_2SO_4$, filtered and the filtrate was evaporated under reduced pressure. The resulting crude product was purified by flash silica gel chromatography (ISCO®; 12 g Sepa-Flash® Silica Flash Column, Eluent of 4% petroleum ether/ethyl acetate) to give the title compound. LRMS m/z (M+H): calculated 288.1, observed 289.1.

Step 3: (4-fluoro-3-methylphenyl)(4-(trifluoromethyl)cyclohexyl)methanamine $NH_4OAc$ (802 mg, 10.41 mmol) and $NaBH_3CN$ (65.4 mg, 1.041 mmol) were added to a solution of (4-fluoro-3-methylphenyl)(4-(trifluoromethyl)cyclohexyl)methanone (200 mg, 0.694 mmol) in EtOH (4 mL) in a microwave vial. The reaction mixture was stirred and heated at 130° C. for 15 min in a microwave reactor. Then the reaction mixture was concentrated to remove most of the EtOH, treated with 2 N NaOH until pH>10, and extracted with ethyl acetate (2×20 mL). The combined organic layers were dried over $Na_2SO_4$, filtered, and concentrated under reduced pressure to give the title compound. LRMS m/z (M+H): calculated 289.1, observed 290.1.

Step 4: Examples 36A, 36B, 36C and 36D A mixture of (4-fluoro-3-methylphenyl)(4-(trifluoromethyl)cyclohexyl) methanamine (150 mg crude), CDI (168 mg, 1.037 mmol) and DIEA (0.272 mL, 1.555 mmol) in DMF (1 mL) was stirred at 20° C. for 1 hour, followed by the addition of (R)-3-methylpiperazin-2-one (71.0 mg, 0.622 mmol) in DMF (0.5 mL). The resulting mixture was stirred at 20° C. for 1 hour, and then purified by reverse phase HPLC (53:47 to 33:67; water (0.1% TFA):MeCN (0.1% TFA)), followed by lyophilization to give a mixture of isomers which was separated by SFC (OD-H column, 40% EtOH co-solvent) to give Examples 36A (first eluted fraction), 36B (second eluted fraction), 36C (third fraction) and 36D (fourth eluted fraction).

Examples 36A: LRMS m/z (M+H): calculated 429.2, observed 430.3. $^1$H NMR δ (ppm) (500 MHz, Chloroform-d): 7.89 (br s, 1H), 7.16-7.18 (m, 1H), 7.09-7.15 (m, 1H), 6.99-7.06 (m, 1H), 6.77 (d, J=8.4 Hz, 1H), 4.46 (q, J=7.2 Hz, 1H), 4.31 (t, J=9.6 Hz, 1H), 3.88-3.95 (m, 1H), 2.93-3.15 (m, 3H), 2.19 (m, 4H), 2.00-2.05 (m, 1H), 1.89-1.93 (m, 1H), 1.70-1.76 (m, 1H), 1.59-1.63 (m, 1H), 0.82-1.26 (m, 8H).

Examples 36B: LRMS m/z (M+H): calculated 429.2, observed 430.3. $^1$H NMR δ (ppm) (500 MHz, Chloroform-d): 7.19-7.24 (m, 1H), 7.18 (t, J=6.5 Hz, 1H), 6.99 (t, J=9.0 Hz, 1H), 4.83-4.89 (m, 2H), 4.56 (q, J=7.0 Hz, 1H), 4.01-4.61 (m, 1H), 3.17-3.32 (m, 3H), 2.28 (s, 3H), 2.19-2.23 (m, 1H), 2.10 (td, J=4.5, 11.5 Hz, 1H), 1.88-1.97 (m, 1H), 1.72-1.81 (m, 2H), 1.64-1.72 (m, 1H), 1.55-1.64 (m, 2H), 1.42 (d, J=7.0 Hz, 3H), 1.30-1.40 (m, 1H), 1.26 (dd, J=4.5, 13.5 Hz, 1H).

Example 36C: LRMS m/z (M+H): calculated 429.2, observed 430.3. $^1$H NMR δ (ppm) (500 MHz, Chloroform-d): 7.19-7.24 (m, 1H), 7.16-7.19 (m, 1H), 7.00 (t, J=9.0 Hz, 1H), 4.84-4.89 (m, 2H), 4.54 (q, J=7.0 Hz, 1H), 3.99-4.08 (m, 1H), 3.28-3.31 (m, 1H), 3.16-3.27 (m, 2H), 2.28 (s, 3H), 2.19-2.22 (m, 1H), 2.11 (m, 1H), 1.88-1.96 (m, 1H), 1.71-1.81 (m, 2H), 1.63-1.70 (m, 1H), 1.55-1.63 (m, 2H), 1.35 (d, J=7.0 Hz, 4H).

Example 36D: LRMS m/z (M+H): calculated 429.2, observed 430.3. $^1$H NMR δ (ppm) (500 MHz, Chloroform-d): 7.05 (d, J=7.5 Hz, 1H), 6.99-7.02 (m, 1H), 6.86 (t, J=9.0 Hz, 1H), 4.43 (q, J=7.0 Hz, 1H), 4.29 (d, J=10.0 Hz, 1H), 3.88-3.96 (m, 1H), 3.16-3.21 (m, 1H), 3.05-3.16 (m, 2H), 2.15 (s, 3H), 2.04-2.08 (m, 1H), 1.93-2.03 (m, 1H), 1.86-1.93 (m, 1H), 1.72-1.78 (m, 1H), 1.56-1.66 (m, 1H), 1.25 (d, J=7.0 Hz, 5H), 0.93-1.14 (m, 2H), 0.79-0.84 (m, 1H)

TABLE 5

The following examples were prepared according to the synthetic procedure for Examples 36A, 36B, 36C and 36D, using the appropriate starting materials and reagents

| Example | Compound | Name | Calc'd $[M + H]^+$ | Observed $[M + H]^+$ | Conditions |
|---|---|---|---|---|---|
| 37A | 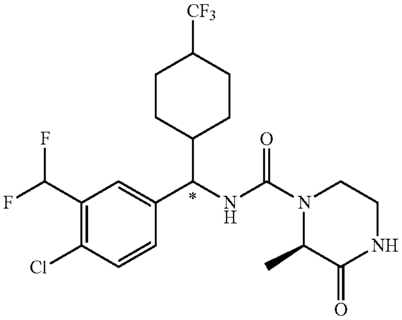 [SMILES: C[C@@H]1C(=O)NCCN1C(=O)NC(c1ccc(Cl)c(C(F)F)c1)C1CCC(C(F)(F)F)CC1] | (2R)-N-((R or S)-(4-chloro-3-(difluoro-methyl)phenyl)(cis-4-(trifluoromethyl) cyclohexyl)methyl)-2-methyl-3-oxopiperazine-1-carboxamide | 481.2 | 482.2 | SFC: OD-H Co-solvent: 40% EtOH with 0.05% DEA peak 1 |
| 37B | 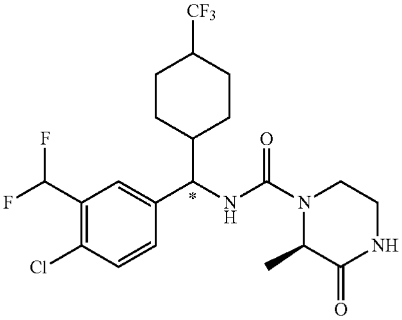 [SMILES: C[C@@H]1C(=O)NCCN1C(=O)NC(c1ccc(Cl)c(C(F)F)c1)C1CCC(C(F)(F)F)CC1] | (2R)-N-((R or S)-(4-chloro-3-(difluoro-methyl)phenyl)(trans-4-(trifluoromethyl) cyclohexyl)methyl)-2-methyl-3-oxopiperazine-1-carboxamide | 481.2 | 482.2 | SFC: OD-H Co-solvent: 40% EtOH with 0.05% DEA peak 2 |
| 37C | 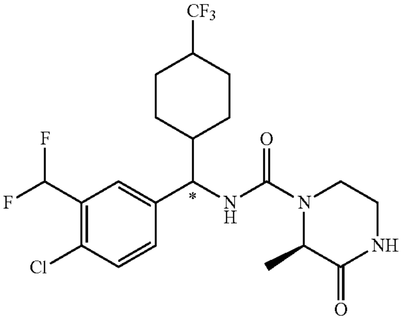 [SMILES: C[C@@H]1C(=O)NCCN1C(=O)NC(c1ccc(Cl)c(C(F)F)c1)C1CCC(C(F)(F)F)CC1] | (2R)-N-((S or R)-(4-chloro-3-(difluoro-methyl)phenyl)(cis-4-(trifluoromethyl) cyclohexyl)methyl)-2-methyl-3-oxopiperazine-1-carboxamide | 481.2 | 482.2 | SFC: OD-H Co-solvent: 40% EtOH with 0.05% DEA peak 3 |
| 37D | 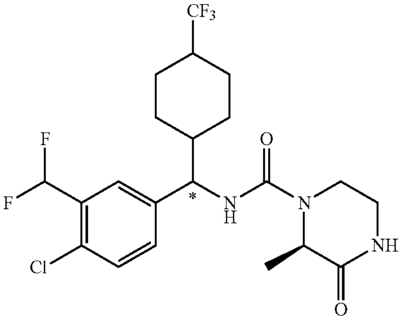 [SMILES: C[C@@H]1C(=O)NCCN1C(=O)NC(c1ccc(Cl)c(C(F)F)c1)C1CCC(C(F)(F)F)CC1] | (2R)-N-((S or R)-(4-chloro-3-(difluoro-methyl)phenyl)(trans-4-(trifluoromethyl) cyclohexyl)methyl)-2-methyl-3-oxopiperazine-1-carboxamide | 481.2 | 482.2 | SFC: OD-H Co-solvent: 40% EtOH with 0.05% DEA peak 4 |

TABLE 5-continued

The following examples were prepared according to the synthetic procedure for Examples 36A, 36B, 36C and 36D, using the appropriate starting materials and reagents

| Example | Compound | Name | Calc'd $[M + H]^+$ | Observed $[M + H]^+$ | Conditions |
|---|---|---|---|---|---|
| 38A | 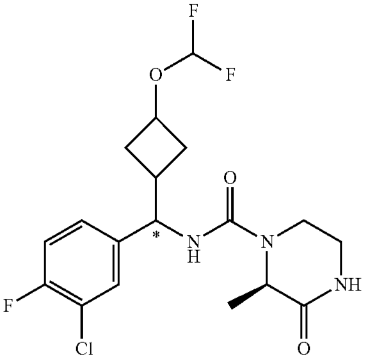 [SMILES: C[C@@H]1C(=O)NCCN1C(=O)NC(c1ccc(F)c(Cl)c1)C1CC(OC(F)F)C1] | (2R)-N-((R or S)-(3-chloro-4-fluoro-phenyl)-(trans-3-(difluoro-methoxy)cyclobutyl)-methyl)-2-methyl-3-oxopiperazine-1-carboxamide | 419.1 | 420.1 | SFC: OJ-3 Co-solvent: 5%-40% EtOH with 0.05% DEA peak 1 |
| 38B | 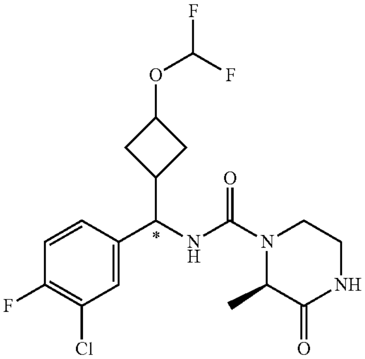 [SMILES: C[C@@H]1C(=O)NCCN1C(=O)NC(c1ccc(F)c(Cl)c1)C1CC(OC(F)F)C1] | (2R)-N-((R or S)-(3-chloro-4-fluorophenyl)(cis-3-(difluoromethoxy)cyclobutyl)methyl)-2-methyl-3-oxopiperazine-1-carboxamide | 419.1 | 420.1 | SFC: OJ-3 Co-solvent: 5%-40% EtOH with 0.05% DEA peak 2 |
| 38C | 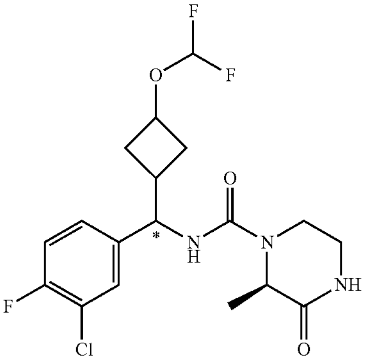 [SMILES: C[C@@H]1C(=O)NCCN1C(=O)NC(c1ccc(F)c(Cl)c1)C1CC(OC(F)F)C1] | (2R)-N-((S or R)-(3-chloro-4-fluorophenyl)(cis-3-(difluoromethoxy)cyclobutyl)methyl)-2-methyl-3-oxopiperazine-1-carboxamide | 419.1 | 420.1 | SFC: OJ-3 Co-solvent: 5%-40% EtOH with 0.05 DEA peak 3 |
| 38D | 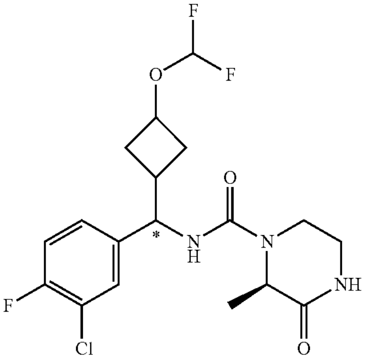 [SMILES: C[C@@H]1C(=O)NCCN1C(=O)NC(c1ccc(F)c(Cl)c1)C1CC(OC(F)F)C1] | (2R)-N-((S or R)-(3-chloro-4-fluorophenyl)-(trans-3-(difluoro-methoxy)cyclobutyl)-methyl)-2-methyl-3-oxopiperazine-1-carboxamide | 419.1 | 420.1 | SFC: OJ-3 Co-solvent: 5%-40% EtOH with 0.05% DEA peak 4 |

TABLE 5-continued

The following examples were prepared according to the synthetic procedure for Examples 36A, 36B, 36C and 36D, using the appropriate starting materials and reagents

| Example | Compound | Name | Calc'd $[M + H]^+$ | Observed $[M + H]^+$ | Conditions |
|---|---|---|---|---|---|
| 39A | 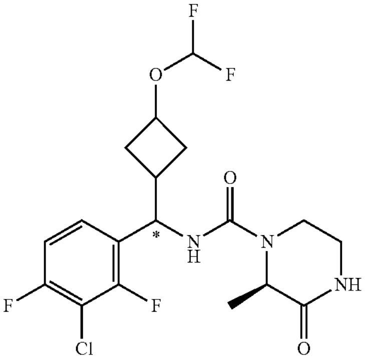 [SMILES: C[C@@H]1C(=O)NCCN1C(=O)NC(c1ccc(F)c(Cl)c1F)C1CC(OC(F)F)C1] | (2R)-N-((R or S)-(3-chloro-2,4-difluoro-phenyl)(trans-3-(difluoromethoxy)-cyclobutyl)methyl)-2-methyl-3-oxopiperazine-1-carboxamide | 437.1 | 438.1 | SFC: OJ-3 Co-solvent: 5%-40% MeOH with 0.05% DEA peak 1 |
| 39B | 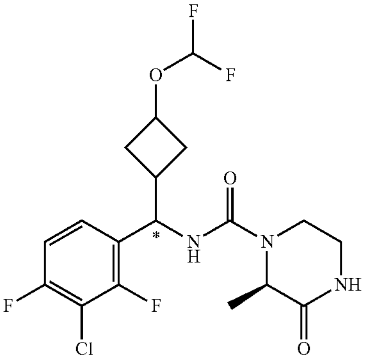 [SMILES: C[C@@H]1C(=O)NCCN1C(=O)NC(c1ccc(F)c(Cl)c1F)C1CC(OC(F)F)C1] | (2R)-N-((R or S)-(3-chloro-2,4-difluoro-phenyl)(cis-3-(difluoro-methoxy)cyclobutyl)-methyl)-2-methyl-3-oxopiperazine-1-carboxamide | 437.1 | 438.1 | SFC: OJ-3 Co-solvent: 5%-40% MeOH with 0.05% DEA peak 2 |
| 39C | 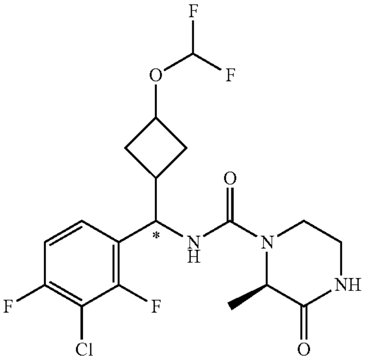 [SMILES: C[C@@H]1C(=O)NCCN1C(=O)NC(c1ccc(F)c(Cl)c1F)C1CC(OC(F)F)C1] | (2R)-N-((S or R)-(3-chloro-2,4-difluoro-phenyl)(cis-3-(difluoro-methoxy)cyclobutyl)-methyl)-2-methyl-3-oxopiperazine-1-carboxamide | 437.1 | 438.1 | SFC: OJ-3 Co-solvent: 5%-40% MeOH with 0.05% DEA peak 3 |
| 39D | 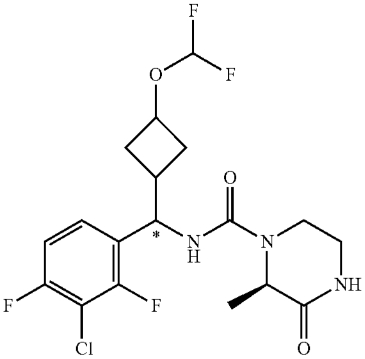 [SMILES: C[C@@H]1C(=O)NCCN1C(=O)NC(c1ccc(F)c(Cl)c1F)C1CC(OC(F)F)C1] | (2R)-N-((S or R)-(3-chloro-2,4-difluoro-phenyl)(trans-3-(difluoro-methoxy)cyclobutyL)-methyl)-2-methyl-3-oxopiperazine-1-carboxamide | 437.1 | 438.1 | SFC: OJ-3 Co-solvent: 5%-40% MeOH with 0.05% DEA peak 4 |

TABLE 5-continued

| The following examples were prepared according to the synthetic procedure for Examples 36A, 36B, 36C and 36D, using the appropriate starting materials and reagents | | | | | |
|---|---|---|---|---|---|
| Example | Compound | Name | Calc'd $[M + H]^+$ | Observed $[M + H]^+$ | Conditions |
| 40A | 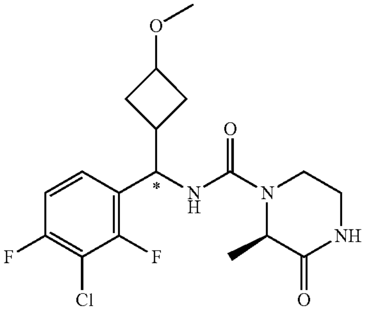 [SMILES: COC1CC(C(NC(=O)N2CCNC(=O)[C@H]2C)c2ccc(F)c(Cl)c2F)C1] | (2R)-N-((R or S)-(3-chloro-2,4-difluoro-phenyl)(trans-3-methoxy-cyclobutyl)methyl)-2-methyl-3-oxopiperazine-1-carboxamide | 401.1 | 402.1 | SFC: OD-H Co-solvent: 5%-40% EtOH with 0.05% DEA peak 1 |
| 40B | 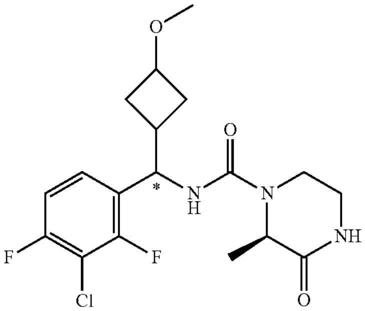 [SMILES: COC1CC(C(NC(=O)N2CCNC(=O)[C@H]2C)c2ccc(F)c(Cl)c2F)C1] | (2R)-N-((R or S)-(3-chloro-2,4-difluoro-phenyl)(cis-3-methoxy-cyclobutyl)methyl)-2-methyl-3-oxopiperazine-1-carboxamide | 401.1 | 402.1 | SFC: OD-H Co-solvent: 5%-40% EtOH with 0.05% DEA peak 2 |
| 40C | 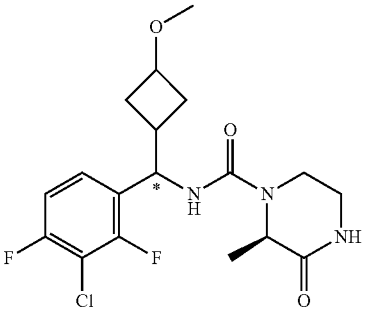 [SMILES: COC1CC(C(NC(=O)N2CCNC(=O)[C@H]2C)c2ccc(F)c(Cl)c2F)C1] | (2R)-N-((S or R)-(3-chloro-2,4-difluoro-phenyl)(cis-3-methoxycyclobutyl)-methyl)-2-methyl-3-oxopiperazine-1-carboxamide | 401.1 | 402.1 | SFC: OD-H Co-solvent: 5%-40% EtOH with 0.05% DEA peak 3 |
| 40D | 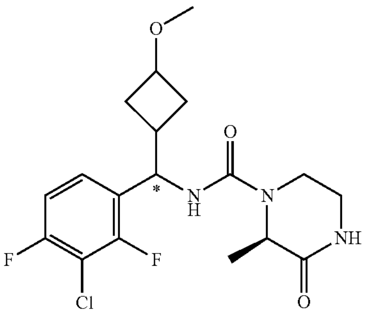 [SMILES: COC1CC(C(NC(=O)N2CCNC(=O)[C@H]2C)c2ccc(F)c(Cl)c2F)C1] | (2R)-N-((S or R)-(3-chloro-2,4-difluoro-phenyl)(trans-3-methoxycyclobutyl)-methyl)-2-methyl-3-oxopiperazine-1-carboxamide | 401.1 | 402.1 | SFC: OD-H Co-solvent: 5%-40% EtOH with 0.05% DEA peak 4 |

TABLE 5-continued

The following examples were prepared according to the synthetic procedure for Examples 36A, 36B, 36C and 36D, using the appropriate starting materials and reagents

| Example | Compound | Name | Calc'd $[M + H]^+$ | Observed $[M + H]^+$ | Conditions |
|---|---|---|---|---|---|
| 41A | 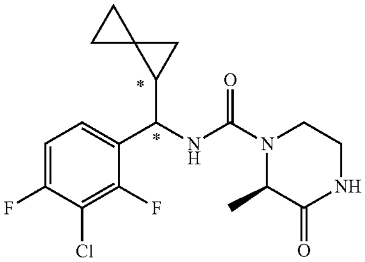 [SMILES: C[C@@H]1C(=O)NCCN1C(=O)NC(c1ccc(F)c(Cl)c1F)C1CC12CC2] | (2R)-N-((R or S)-(3-chloro-2,4-difluoro-phenyl)((R or S)-spiro[2.2]pentan-1-yl)methyl)-2-methyl-3-oxopiperazine-1-carboxamide | 383.1 | 384.2 | SFC: OJ-H Co-solvent: 30% EtOH with 0.05% DEA peak 1 |
| 41B | 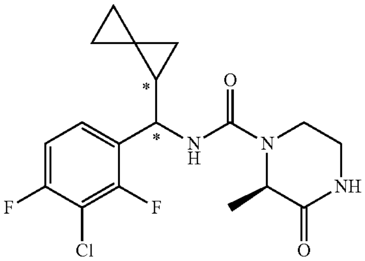 [SMILES: C[C@@H]1C(=O)NCCN1C(=O)NC(c1ccc(F)c(Cl)c1F)C1CC12CC2] | (2R)-N-((S or R)-(3-chloro-2,4-difluoro-phenyl)((R or S)-spiro[2.2]pentan-1-yl)methyl)-2-methyl-3-oxopiperazine-1-carboxamide | 383.1 | 384.2 | SFC: OJ-H Co-solvent: 30% EtOH with 0.05% DEA peak 2 |
| 41C | 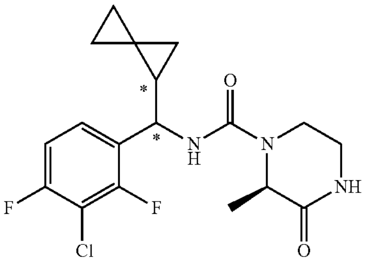 [SMILES: C[C@@H]1C(=O)NCCN1C(=O)NC(c1ccc(F)c(Cl)c1F)C1CC12CC2] | (2R)-N-((R or S)-(3-chloro-2,4-difluoro-phenyl)(S or R)-spiro[2.2]pentan-1-yl)methyl)-2-methyl-3-oxopiperazine-1-carboxamide | 383.1 | 384.2 | SFC: OJ-H Co-solvent: 30% EtOH with 0.05% DEA peak 3 |
| 41D | 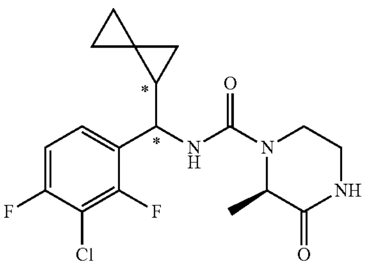 [SMILES: C[C@@H]1C(=O)NCCN1C(=O)NC(c1ccc(F)c(Cl)c1F)C1CC12CC2] | (2R)-N-((S or R)-(3-chloro-2,4-difluoro-phenyl)((S or R)-spiro[2.2]pentan-1-yl)methyl)-2-methyl-3-oxopiperazine-1-carboxamide | 383.1 | 384.2 | SFC: OJ-H Co-solvent: 30% EtOH with 0.05% DEA peak 4 |
| 42A | 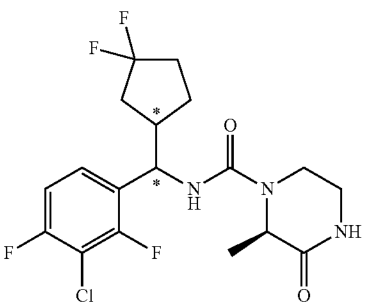 [SMILES: C[C@@H]1C(=O)NCCN1C(=O)NC(c1ccc(F)c(Cl)c1F)C1CCC(F)(F)C1] | (2R)-N-((R or S)-(3-choro-2,4-difluoro-phenyl)((R or S)-3,3-difluorocyclopentyl)-methyl)-2-methyl-3-oxopiperazine-1-carboxamide | 421.1 | 422.1 | SFC: OJ-H Co-solvent: 30% (MeOH + 0.1% $NH_3H_2O$) peak 1 |

TABLE 5-continued

The following examples were prepared according to the synthetic procedure for Examples 36A, 36B, 36C and 36D, using the appropriate starting materials and reagents

| Example | Compound | Name | Calc'd $[M + H]^+$ | Observed $[M + H]^+$ | Conditions |
|---|---|---|---|---|---|
| 42B | 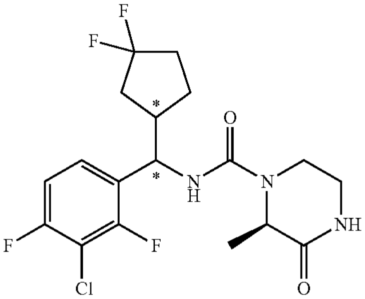 [SMILES: C[C@@H]1C(=O)NCCN1C(=O)NC(c1ccc(F)c(Cl)c1F)C1CCC(F)(F)C1] | (2R)-N-((R or S)-(3-chloro-2,4-difluoro-phenyl)((S or R)-3,3-difluorocyclopentyl)-methyl)-2-methyl-3-oxopiperazine-1-carboxamide | 421.1 | 422.1 | SFC: OJ-H Co-solvent: 30% (MeOH + 0.1% $NH_3H_2O$) peak 2 |
| 42C | 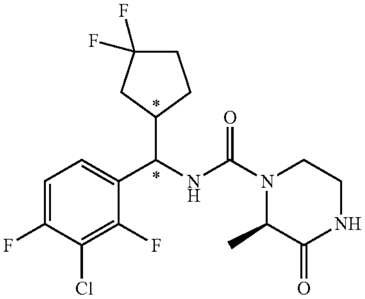 [SMILES: C[C@@H]1C(=O)NCCN1C(=O)NC(c1ccc(F)c(Cl)c1F)C1CCC(F)(F)C1] | (2R)-N-((S or R)-(3-chloro-2,4-difluoro-phenyl)((R or S)-(3,3-difluorocyclopentyl)-methyl)-2-methyl-3-oxopiperazine-1-carboxamide | 421.1 | 422.1 | SFC: OJ-H Co-solvent: 30% (MeOH + 0.1% $NH_3H_2O$) peak 3 |
| 42D | 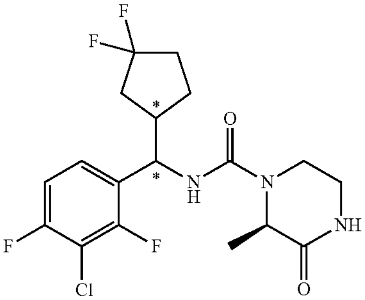 [SMILES: C[C@@H]1C(=O)NCCN1C(=O)NC(c1ccc(F)c(Cl)c1F)C1CCC(F)(F)C1] | (2R)-N-((S or R)-(3-chloro-2,4-difluoro-phenyl)((S or R)-3,3-difluorocyclopentyl)-methyl)-2-methyl-3-oxopiperazine-1-carboxamide | 421.1 | 422.1 | SFC: OJ-H Co-solvent: 30% (MeOH + 0.1% $NH_3H_2O$) Peak 4 |
| 43A | 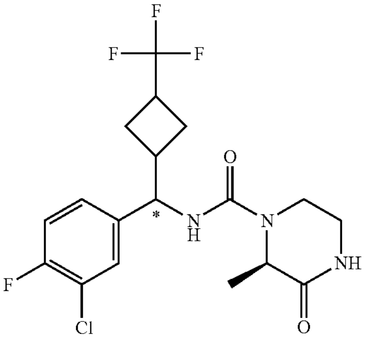 [SMILES: C[C@@H]1C(=O)NCCN1C(=O)NC(c1ccc(F)c(Cl)c1)C1CC(C(F)(F)F)C1] | (2R)-N-((R or S)-(3-chloro-4-fluorophenyl)-(trans-3-(trifluoro-methyl)-cyclobutyl)-methyl)-2-methyl-3-oxopiperazine-1-carboxamide | 421.1 | 422.0 | SFC: OJ-3 Co-solvent: 5%-40% EtOH with 0.05% DEA peak 1 |

TABLE 5-continued

| The following examples were prepared according to the synthetic procedure for Examples 36A, 36B, 36C and 36D, using the appropriate starting materials and reagents | | | | | |
|---|---|---|---|---|---|
| Example | Compound | Name | Calc'd $[M + H]^+$ | Observed $[M + H]^+$ | Conditions |
| 43B | 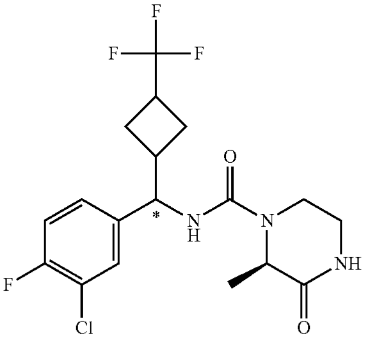 [SMILES: C[C@@H]1C(=O)NCCN1C(=O)NC(c1ccc(F)c(Cl)c1)C1CC(C(F)(F)F)C1] | (2R)-N-((R or S)-(3-chloro-4-fluorophenyl)-(cis-3-(trifluoromethyl)-cyclobutyl)methyl)-2-methyl-3-oxopiperazine-1-carboxamide | 421.1 | 422.0 | SFC: OJ-3 Co-solvent: 5%-40% EtOH with 0.05% DEA peak 2 |
| 43C | 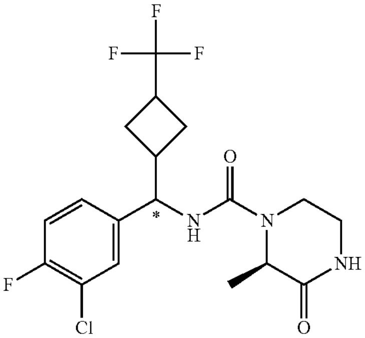 [SMILES: C[C@@H]1C(=O)NCCN1C(=O)NC(c1ccc(F)c(Cl)c1)C1CC(C(F)(F)F)C1] | (2R)-N-((S or R)-(3-chloro-4-fluorophenyl)-(trans-3-(trifluoro-methyl)-cyclobutyl)-methyl)-2-methyl-3-oxopiperazine-1-carboxamide | 421.1 | 422.0 | SFC: OJ-3 Co-solvent: 5%-40% EtOH with 0.05% DEA peak 3 2nd SFC: AS-3 Co-solvent: 5%-40% EtOH with 0.05% DEA Peak 1 |
| 43D | 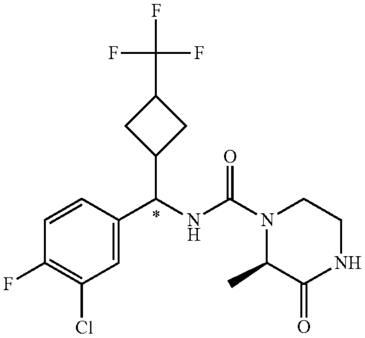 [SMILES: C[C@@H]1C(=O)NCCN1C(=O)NC(c1ccc(F)c(Cl)c1)C1CC(C(F)(F)F)C1] | (2R)-N-((S or R)-(3-chloro-4-fluorophenyl)-(cis-3-(trifluoromethyl)-cyclobutyl)methyl)-2-methyl-3-oxopiperazine-1-carboxamide | 421.1 | 422.0 | SFC: OJ-3 Co-solvent: 5%-40% EtOH with 0.05% DEA peak 3 2nd SFC: AS-3 Co-solvent: 5%-40% EtOH with 0.05% DEA Peak 2 |

Examples 44A, 44B, 44C and 44D (2R)-N-((R or S)-(3-chloro-4-fluorophenyl)(cis-3-(2,2,2-trifluoroethoxy)cyclobutyl)methyl)-2-methyl-3-oxopiperazine-1-carboxamide (44A), (2R)-N-((S or R)-(3-chloro-4-fluorophenyl)(cis-3-(2,2,2-trifluoroethoxy)cyclobutyl)methyl)-2-methyl-3-oxopiperazine-1-carboxamide (44B), (2R)-N-((R or S)-(3-chloro-4-fluorophenyl)(trans-3-(2,2,2-trifluoroethoxy)cyclobutyl)methyl)-2-methyl-3-oxopiperazine-1-carboxamide (44C) and (2R)-N-((S or R)-(3-chloro-4-fluorophenyl)(trans-3-(2,2,2-trifluoroethoxy)cyclobutyl)methyl)-2-methyl-3-oxopiperazine-1-carboxamide (44D)

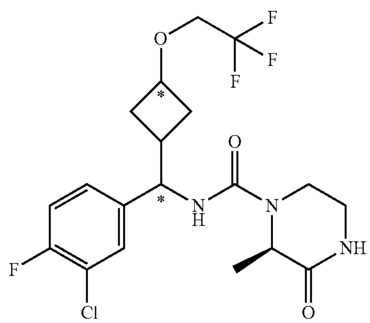 [SMILES: C[C@@H]1C(=O)NCCN1C(=O)NC(c1ccc(F)c(Cl)c1)C1CC(OCC(F)(F)F)C1]

Step 1: benzyl 3-(2,2,2-trifluoroethoxy)cyclobutane-1-carboxylate To a suspension of NaH (0.389 g, 9.72 mmol) in THF (10 mL) was added benzyl 3-hydroxycyclobutane-1-carboxylate (1.67 g, 8.10 mmol) at 0° C. for 10 minutes. Then 2,2,2-trifluoroethyl trifluoromethanesulfonate (1.231 mL, 8.91 mmol) was added and the mixture was stirred at 20° C. for 16 hours. The reaction was quenched with saturated aqueous $NH_4Cl$ and extracted with ethyl acetate (3×10 mL). The combined organic layers were washed with brine (10 mL), dried over $Na_2SO_4$, filtered and evaporated under reduced pressure. The resulting residue was purified by Prep-TLC (silica gel, ethyl acetate/pet. ether=1/10, v/v) to give the title compound. $^1H$ NMR (500 MHz, $CDCl_3$) δ 7.35-7.38 (m, 5H), 5.14-5.16 (m, 2H), 4.34 (q, J=6.5 Hz, 1H), 3.70-3.78 (m, 2H), 3.06-3.14 (m, 1H), 2.51-2.63 (m, 2H), 2.29-2.38 (m, 2H).

Step 2: 3-(2,2,2-trifluoroethoxy)cyclobutane-1-carboxylic acid To a solution of benzyl 3-(2,2,2-trifluoroethoxy)cyclobutane-1-carboxylate (550 mg, 1.908 mmol) in MeOH (10 mL) was added Pd/C (203 mg) under a $N_2$ atmosphere. The reaction mixture was degassed and backfilled with $H_2$ (three times), and the reaction was stirred under $H_2$ (15 psi) at 20° C. for 12 hours. Then the catalyst was filtered off and the filtrate was concentrated under reduced pressure to give the title compound. $^1H$ NMR (500 MHz, $CDCl_3$) δ 10.05 (br s, 1H), 4.35 (q, J=6.5 Hz, 1H), 3.66-3.85 (m, 2H), 3.01-3.17 (m, 1H), 2.56-2.64 (m, 2H), 2.31-2.45 (m, 2H).

Step 3: N-methoxy-N-methyl-3-(2,2,2-trifluoroethoxy)cyclobutane-1-carboxamide To a solution of 3-(2,2,2-trifluoroethoxy)cyclobutane-1-carboxylic acid (370 mg, 1.867 mmol) in DCM (5 mL) was added CDI (303 mg, 1.867 mmol) at 20° C. The mixture was stirred for 1 hour, then TEA (0.521 mL, 3.73 mmol) and N,O-dimethylhydroxylamine hydrochloride (182 mg, 1.867 mmol) were added. The reaction mixture was stirred at 20° C. for another 12 hours, followed by the addition of water (10 mL). The reaction mixture was extracted with DCM (3×5 mL). The combined organic layers were dried over $Na_2SO_4$, filtered and the filtrate was evaporated under reduced pressure to give the title compound. LRMS m/z (M-16): calculated 241.1, observed 242.1.

Step 4: (3-chloro-4-fluorophenyl)(3-(2,2,2-trifluoroethoxy)cyclobutyl)methanone To a solution of 4-bromo-2-chloro-1-fluorobenzene in THF (2 mL) was added isopropylmagnesium chloride in THF (2 M, 1.741 mL, 3.48 mmol) at 0° C. The reaction mixture was stirred at 20° C. for 1 hour, followed by the addition of a mixture of N-methoxy-N-methyl-3-(2,2,2-trifluoroethoxy)-cyclobutane-1-carboxamide (420 mg crude) in THF (1 mL). The reaction was stirred at 20° C. for 2 hours, then quenched with saturated aqueous $NH_4Cl$ (5 mL) and extracted with EtOAc (3×5 mL). The combined organic layers were dried by $Na_2SO_4$, filtered and the solvent was evaporated under reduced pressure. The resulting residue was purified by flash silica gel chromatography (ISCO®; 12 g SepaFlash® Silica Flash Column, eluent of 4% ethyl acetate/pet. ether) to give the title compound. $^1H$ NMR (400 MHz, $CD_3OD$) δ 8.02-8.08 (m, 1H), 7.88-7.96 (m, 1H), 7.37 (t, J=8.8 Hz, 1H), 4.09-4.24 (m, 1H), 3.96-4.09 (m, 1H), 3.86 (q, J=9.2 Hz, 2H), 2.56-2.64 (m, 2H), 2.37-2.48 (m, 2H).

Step 5: (3-chloro-4-fluorophenyl)(3-(2,2,2-trifluoroethoxy)cyclobutyl)methanamine To a mixture of (3-chloro-4-fluorophenyl)(3-(2,2,2-trifluoroethoxy)cyclobutyl)methanone (250 mg, 0.805 mmol), $NH_4OAc$ (930 mg, 12.07 mmol) in EtOH (3 mL) was added $NaBH_3CN$ (76 mg, 1.207 mmol) at 20° C. The mixture was stirred under microwave (Biotage Initiator) at 130° C. for 10 minutes. Then the reaction mixture was concentrated to remove most of the EtOH, treated with 2 N NaOH until pH>12, and extracted with EtOAc (3×5 mL). The combined organic layers were dried over $Na_2SO_4$, filtered, and the filtrate was concentrated under reduced pressure to give the title compound. LRMS m/z (M+H): calculated 311.1, observed 312.0.

Step 6: (2R)-N-((3-chloro-4-fluorophenyl)(cis-3-(2,2,2-trifluoroethoxy)cyclobutyl)methyl)-2-methyl-3-oxopiperazine-1-carboxamide (isomer A) and (2R)-N-((3-chloro-4-fluorophenyl)(trans-3-(2,2,2-trifluoroethoxy)cyclobutyl)methyl)-2-methyl-3-oxopiperazine-1-carboxamide (isomer B) A mixture of CDI (260 mg, 1.604 mmol) and (3-chloro-4-fluorophenyl)(3-(2,2,2-trifluoroethoxy)cyclobutyl)methanamine (250 mg crude) in DMF (3 mL) was stirred at 20° C. for 1 hour. Then (R)-3-methylpiperazin-2-one (101 mg, 0.882 mmol) was added. The resulting mixture was stirred at 20° C. for 2 hours. Then the solid was filtered off and the filtrate was purified by reverse phase HPLC (58:42 to 28:72; water (0.1% TFA):MeCN (0.1% TFA)) to give two isomers: First eluted isomer, (2R)-N-((3-chloro-4-fluorophenyl)(cis-3-(2,2,2-trifluoroethoxy)cyclobutyl)methyl)-2-methyl-3-oxopiperazine-1-carboxamide (isomer A).

LRMS m/z (M+H): calculated 451.1, observed 452.2. Second eluted isomer, (2R)-N-((3-chloro-4-fluorophenyl)(trans-3-(2,2,2-trifluoroethoxy) cyclobutyl)methyl)-2-methyl-3-oxopiperazine-1-carboxamide (isomer B). LRMS m/z (M+H): calculated 451.1, observed 452.2.

Step 7: Examples 44A, 44B, 44C and 44D Isomer A (150 mg, 0.332 mmol) was resolved by SFC (AS-H column, 30% (EtOH+0.1% $NH_3H_2O$) co-solvent) to give Examples 44A (first eluted fraction) and 44B (second eluted fraction).

Example 44A: LRMS m/z (M+H): calculated 451.1, observed 452.2. $^1H$ NMR δ (ppm) (500 MHz, CD3OD-d4): 7.40-7.46 (m, 1H), 7.23-7.31 (m, 1H), 7.17 (t, J=8.5 Hz, 1H), 4.62-4.68 (m, 1H), 4.48-4.53 (m, 1H), 3.95-4.04 (m, 2H), 3.82 (q, J=9.0 Hz, 2H), 3.32-3.38 (m, 1H), 3.17-3.29

(m, 2H), 2.48-2.55 (m, 1H), 2.19-2.29 (m, 1H), 2.11-2.18 (m, 1H), 1.76-1.82 (m, 1H), 1.63-1.70 (m, 1H), 1.36-1.42 (m, 3H).

Example 44B: LRMS m/z (M+H): calculated 451.1, observed 452.2. $^1$H NMR δ (ppm) (500 MHz, CD3OD-d4): 7.40-7.46 (m, 1H), 7.23-7.31 (m, 1H), 7.17 (t, J=8.5 Hz, 1H), 4.62-4.68 (m, 1H), 4.56 (q, J=7.2 Hz, 1H), 4.01-4.07 (m, 1H), 3.96-4.01 (m, 1H), 3.82 (q, J=9.0 Hz, 2H), 3.32-3.36 (m, 1H), 3.17-3.27 (m, 2H), 2.48-2.55 (m, 1H), 2.20-2.27 (m, 1H), 2.09-2.19 (m, 1H), 1.76-1.83 (m, 1H), 1.65-1.72 (m, 1H), 1.37-1.43 (m, 3H).

Isomer B (100 mg, 0.221 mmol) was resolved by SFC (OJ-H column, 20% (EtOH+0.1% $NH_3H_2O$) co-solvent) to give examples 44C (first eluted fraction) and 44D (second eluted fraction).

Example 44C: LRMS m/z (M+H): calculated 451.1, observed 452.2. $^1$H NMR δ (ppm) (500 MHz, CD30D-d4): δ 7.42-7.48 (m, 1H), 7.24-7.62 (m, 1H), 7.15-7.20 (m, 1H), 4.64-4.70 (m, 1H), 4.54 (q, J=7.0 Hz, 1H), 4.27 (q, J=6.0 Hz, 1H), 4.00-4.07 (m, 1H), 3.82 (q, J=9.0 Hz, 2H), 3.32-3.35 (m, 1H), 3.17-3.26 (m, 2H), 2.66-2.75 (m, 1H), 2.21 (t, J=6.5 Hz, 2H), 1.91-2.01 (m, 2H), 1.36-1.42 (m, 3H).

Example 44D: LRMS m/z (M+H): calculated 451.1, observed 452.2. $^1$H NMR δ (ppm) (500 MHz, CD3OD-d4): δ 7.41-7.47 (m, 1H), 7.23-7.31 (m, 1H), 7.16-7.21 (m, 1H), 4.66-4.72 (m, 1H), 4.48-4.53 (m, 1H), 4.26 (q, J=6.0 Hz, 1H), 3.98-4.04 (m, 1H), 3.81 (q, J=9.0 Hz, 2H), 3.32-3.36 (m, 1H), 3.15-3.27 (m, 2H), 2.67-2.75 (m, 1H), 2.21 (t, J=6.5 Hz, 2H), 1.90-2.01 (m, 2H), 1.34-1.40 (m, 3H).

Examples 45A and 45B

N-((R)-(5-chloro-6-(trifluoromethyl)pyridin-2-yl)(trans-4-(trifluoromethyl)cyclohexyl)methyl)-3-oxopiperazine-1-carboxamide and N-((S)-(5-chloro-6-(trifluoromethyl)pyridin-2-yl)(trans-4-(trifluoromethyl)cyclohexyl)methyl)-3-oxopiperazine-1-carboxamide

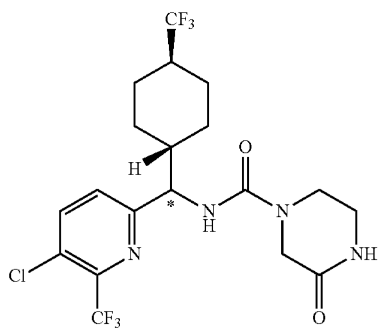

Step 1: 3-chloro-2-(trifluoromethyl)-6-vinylpyridine To a mixture of 3,6-dichloro-2-(trifluoromethyl)pyridine (2 g, 9.26 mmol), potassium trifluoro(vinyl)borate (1.861 g, 13.89 mmol) and $K_2CO_3$ (2.56 g, 18.52 mmol) in THF (30 mL) and water (3 mL) was added $Pd(dppf)Cl_2$ (0.339 g, 0.463 mmol) at 20° C. under $N_2$. The mixture was stirred at 80° C. for 12 hours. Then water (3 mL) was added and the mixture was extracted with DCM (3×15 mL). The combined organic layers were dried over $Na_2SO_4$, filtered and the filtrate was concentrated under vacuum to give the title compound. LRMS m/z (M+H): calculated 207.5, observed 208.0.

Step 2: 5-chloro-6-(trifluoromethyl)picolinaldehyde A mixture of 3-chloro-2-(trifluoromethyl)-6-vinylpyridine (1.922 g, 9.26 mmol), NMO (2.169 g, 18.52 mmol) and $OSO_4$ (4.63 mL, 0.463 mmol) in THF (10 mL) and water (5 mL) was stirred at 20° C. for 12 hours. Then $NaIO_4$ (5.94 g, 27.8 mmol) was added and the mixture was stirred at 20° C. for additional 2 hours. Then water (60 mL) was added, and the mixture was extracted with DCM (3×40 mL). The combined organic layers were dried over $Na_2SO_4$, filtered and the filtrate was concentrated under vacuum to give the title compound. LRMS m/z (M+H): calculated 209.6, observed 210.0.

Step 3: (5-chloro-6-(trifluoromethyl)pyridin-2-yl)(4-(trifluoromethyl)cyclohexyl)methanone To a solution of 5-chloro-6-(trifluoromethyl)picolinaldehyde (600 mg crude), 4-methyl-N'-(4-(trifluoromethyl)cyclohexylidene) benzenesulfonohydrazide (1915 mg, 5.73 mmol) in dioxane (20 mL) was added $Cs_2CO_3$ (1866 mg, 5.73 mmol) at 15° C. Then the reaction was heated to 100° C. for 12 hours, filtered, and the filtrate was concentrated. The resulting residue was purified by flash silica gel chromatography (ISCO®; 20 g SepaFlash® Silica Flash Column, eluent of 10% ethyl acetate/pet. ether) to give the title compound. $^1$H NMR (400 MHz, CDCl3) δ 8.12-8.18 (m, 1H), 7.98-8.04 (m, 1H), 4.02 (t, J=3.6 Hz, 1H), 2.06-2.20 (m, 5H), 1.72-1.77 (m, 4H).

Step 4: (5-chloro-6-(trifluoromethyl)pyridin-2-yl)(4-(trifluoromethyl)cyclohexyl)methanamine To a mixture of (5-chloro-6-(trifluoromethyl)pyridin-2-yl)(4-(trifluoromethyl)cyclohexyl) methanone (130 mg, 0.361 mmol), and $NH_4OAc$ (417.89 mg, 5.42 mmol) in EtOH (2 mL) was added $NaBH_3CN$ (34.07 mg, 0.542 mmol) at 20° C. The reaction mixture was stirred under microwave (Biotage Initiator) at 130° C. for 10 minutes, then concentrated to remove most of the EtOH, treated with 2 N NaOH until pH>12, and extracted with EtOAc (3×5 mL). The combined organic layers were dried over $Na_2SO_4$, filtered, and the filtrate was concentrated under reduced pressure to give the title compound. LRMS m/z (M+H): calculated 360.1, observed 361.1.

Step 5: N-((5-chloro-6-(trifluoromethyl)pyridin-2-yl)(trans-4-(trifluoromethyl)cyclohexyl) methyl)-3-oxopiperazine-1-carboxamide A mixture of CDI (90 mg, 0.554 mmol) and (5-chloro-6-(trifluoromethyl)pyridin-2-yl)(4-(trifluoromethyl)cyclohexyl)methanamine (100 mg crude) in DMF (1.5 mL) was stirred at 20° C. for 1 hour. Then piperazin-2-one (30.5 mg, 0.305 mmol) was added. The reaction mixture was stirred at 20° C. for 1 hour, then the solid was filtered off and the filtrate was purified by prep-HPLC (53:47 to 23:67; water (0.1% TFA):MeCN (0.1% TFA)) to give two isomers: First eluted isomer, N-((5-chloro-6-(trifluoromethyl)pyridin-2-yl)(trans-4-(trifluoromethyl)cyclohexyl) methyl)-3-oxopiperazine-1-carboxamide (trans-isomers). LRMS m/z (M+H): calculated 486.1, observed 487.2. Second eluted isomer, N-((5-chloro-6-(trifluoromethyl)pyridin-2-yl)(cis-4-(trifluoromethyl)cyclohexyl)methyl)-3-oxo-piperazine-1-carboxamide (cis-isomers). LRMS m/z (M+H): calculated 486.1, observed 487.1.

Step 6: Examples 45A and 45B N-((5-chloro-6-(trifluoromethyl)pyridin-2-yl)(trans-4-(trifluoromethyl)cyclohexyl)methyl)-3-oxopiperazine-1-carboxamide (80 mg, 0.164 mmol) was resolved by Chiral-SFC (Column DAICEL CHIRALPAK IC, 30% (EtOH+0.1% $NH_3H_2O$) co-solvent) to give examples 45A (first eluted fraction) and 45B (second eluted fraction).

Example 45A: LRMS m/z (M+H): calculated 486.1, observed 487.2. $^1$H NMR δ (ppm) (500 MHz, CD3OD-d4): 7.99-8.05 (m, 1H), 7.56-7.62 (m, 1H), 4.66-4.72 (m, 1H), 4.05 (s, 2H), 3.57-3.66 (m, 2H), 3.33 (br s, 2H), 2.05-2.13 (m, 2H), 1.87-2.02 (m, 3H), 1.28-1.40 (m, 2H), 1.06-1.27 (m, 3H).

Example 45B: LRMS m/z (M+H): calculated 486.1, observed 487.2. $^1$H NMR δ (ppm) (500 MHz, CD3OD-d4): 7.99-8.05 (m, 1H), 7.56-7.62 (m, 1H), 4.66-4.72 (m, 1H), 4.05 (s, 2H), 3.57-3.66 (m, 2H), 3.33 (br s, 2H), 2.04-2.14 (m, 2H), 1.87-2.02 (m, 3H), 1.27-1.41 (m, 2H), 1.06-1.26 (m, 3H).

TABLE 6

The following Examples were prepared according to the synthetic procedure for Examples 45A and 45B, using the appropriate starting materials and reagents

| Example | Compound | Name | Calc'd [M + H]+ | Observed [M + H]+ | Conditions |
|---|---|---|---|---|---|
| 46A | 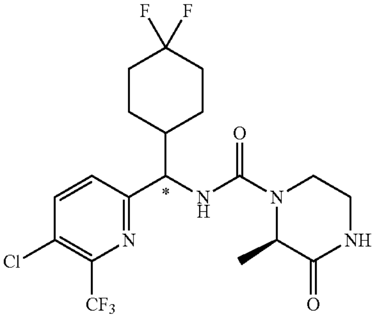 [SMILES: C[C@@H]1C(=O)NCCN1C(=O)NC(c1ccc(Cl)c(C(F)(F)F)n1)C1CCC(F)(F)CC1] | (2R)-N-((R or S)-(5-chloro-6-(trifluoro-methyl)pyridin-2-yl)(4,4-difluoro-cyclohexyl)methyl)-2-methyl-3-oxo-piperazine-1-carboxamide | 468.1 | 469.1 | SFC: AD-H Co-solvent: 20% (IPA + 0.1% $NH_3H_2O$) peak 1 |
| 46B | 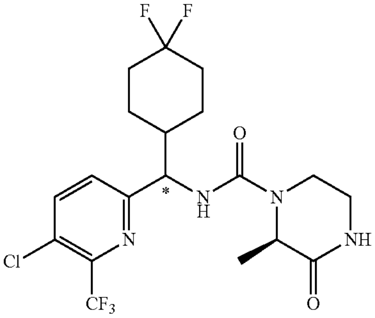 [SMILES: C[C@@H]1C(=O)NCCN1C(=O)NC(c1ccc(Cl)c(C(F)(F)F)n1)C1CCC(F)(F)CC1] | (2R)-N-((S or R)-(5-chloro-6-(trifluoro-methyl)pyridin-2-yl)(4,4-difluoro-cyclohexyl)methyl)-2-methyl-3-oxo-piperazine-1-carboxamide | 468.1 | 469.1 | SFC: AD-H Co-solvent; 20% (IPA + 0.1% $NH_3H_2O$) peak 2 |

Examples 47A, 47B, 47C and 47D (2R)-N-((R or S)-(5-chloro-6-(trifluoromethyl)pyridin-2-yl)(cis-3-(trifluoromethyl)-cyclobutyl)methyl)-2-methyl-3-oxopiperazine-1-carboxamide (47A), (2R)-N-((R or S)-(5-chloro-6-(trifluoromethyl)pyridin-2-yl)(trans-3-(trifluoromethyl)cyclobutyl)methyl)-2-methyl-3-oxopiperazine-1-carboxamide (47B), (2R)-N-((S or R)-(5-chloro-6-(trifluoromethyl)pyridin-2-yl)(trans-3-(trifluoromethyl)cyclobutyl)methyl)-2-methyl-3-oxopiperazine-1-carboxamide (47C) and (2R)-N-((S or R)-(5-chloro-6-(trifluoromethyl)pyridin-2-yl)(cis-3-(trifluoromethyl)-cyclobutyl)methyl)-2-methyl-3-oxopiperazine-1-carboxamide (47D)

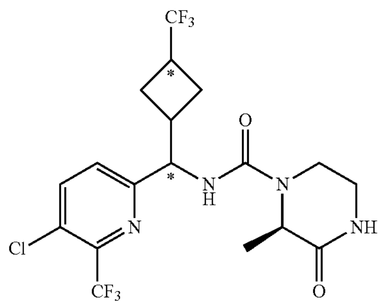 [SMILES: C[C@@H]1C(=O)NCCN1C(=O)NC(c1ccc(Cl)c(C(F)(F)F)n1)C1CC(C(F)(F)F)C1]

Step 1: 6-bromo-3-chloro-2-(trifluoromethyl)pyridine To a solution of 5-chloro-6-(trifluoromethyl)pyridin-2-amine (2 g, 10.18 mmol) and copper(II) bromide (3.41 g, 15.26 mmol) in acetonitrile (20 mL) was added tert-butyl nitrite (2.099 g, 20.35 mmol) at 0° C. The reaction mixture was stirred at 30° C. for 16 hours, then concentrated under reduced pressure, diluted with water (20 mL), and extracted with DCM (3×10 mL). The combined organic layers were washed with brine (20 mL), dried over anhydrous $Na_2SO_4$, and filtered. The filtrate was concentrated under reduced pressure, and the resulting residue was purified by MPLC (ISCO®; 12 g SepaFlash® Silica Flash Column, eluent of 0~8% Pet. ether/EtOAc) to give the title compound. $^1H$ NMR (500 MHz, CDCl3) δ 7.69-7.76 (m, 1H), 7.61-7.67 (m, 1H).

Step 2: (5-chloro-6-(trifluoromethyl)pyridin-2-yl)(3-(trifluoromethyl)cyclobutyl)methanone To a solution of 6-bromo-3-chloro-2-(trifluoromethyl)pyridine (555 mg, 2.131 mmol) in toluene (6 mL) under $N_2$ was added butyllithium in THF (2.5 M, 0.796 mL, 1.989 mmol) at −70° C. The mixture was stirred at −70° C. for 1 hour, then N-methoxy-N-methyl-3-(trifluoromethyl) cyclobutanecarboxamide (300 mg, 1.421 mmol) in toluene (3 mL) was added. The reaction was warmed to 0° C., stirred for 1 hour and quenched with water (20 mL), extracted with DCM (3×10 mL). The combined organic layers were washed with brine (20 mL), dried over $Na_2SO_4$, filtered, and the filtrate was concentrated under reduced pressure. The resulting residue was purified by MPLC (ISCO®; 4 g SepaFlash® Silica Flash Column, eluent of 0~5% petroleum ether/EtOAc) to give the title compound. $^1H$ NMR (500 MHz, CDCl3) δ 8.18-8.23 (m, 1H), 8.03-8.05 (m, 1H), 4.19-4.47 (m, 1H), 2.96-3.10 (m, 1H), 2.51-2.60 (m, 4H).

Step 3: (R,E)-N-((5-chloro-6-(trifluoromethyl)pyridin-2-yl)(3-(trifluoromethyl)cyclobutyl) methylene)-2-methylpropane-2-sulfinamide To a solution of (5-chloro-6-(trifluoromethyl)-pyridin-2-yl)(3-(trifluoromethyl)cyclobutyl) methanone (400 mg, 0.808 mmol) in toluene (6 ml) were added tetraethoxytitanium (369 mg, 1.616 mmol) and (R)-2-methylpropane-2-sulfinamide (196 mg, 1.616 mmol). The mixture was stirred at 105° C. for 1 hour in a microwave and then cooled to RT. The reaction mixture was used as is in the next step without further purification. LRMS m/z (M+H): calculated 434.1, observed 435.1.

Step 4: (R)—N-((5-chloro-6-(trifluoromethyl)pyridin-2-yl)(3-(trifluoromethyl)cyclobutyl)methyl)-2-methylpropane-2-sulfinamide (R,E)-N-((5-chloro-6-(trifluoromethyl) pyridin-2-yl)(3-(trifluoromethyl)cyclobutyl)methylene)-2-methylpropane-2-sulfinamide (300 mg, crude) in toluene (6 ml) was diluted in THF (6 mL) and water (0.05 mL). Then $NaBH_4$ (131 mg, 3.45 mmol) was added and the mixture was stirred at −70° C. for 1 hour. The reaction mixture was slowly warmed to 27° C., and stirred for 15 hours. Then the mixture was diluted with water (10 mL), filtered, and extracted with EtOAc (3×10 mL). The combined organic layers were washed with brine (20 mL), dried over $Na_2SO_4$, filtered and the filtrate was concentrated in vacuo. The resulting residue was purified by Preparative TLC ($SiO_2$, petroleum ether:EtOAc=2:1) to give the title compound. LRMS m/z (M+H): calculated 436.1, observed 437.1.

Step 5: (5-chloro-6-(trifluoromethyl)pyridin-2-yl)(3-(trifluoromethyl)cyclobutyl)methanamine hydrochloride To a solution of (R)—N-((5-chloro-6-(trifluoromethyl)pyridin-2-yl)(3-(trifluoro-methyl)cyclobutyl) methyl)-2-methylpropane-2-sulfinamide (300 mg, 0.549 mmol) in MeOH (3 mL) was added HCl/MeOH (4 N, 3 mL). The mixture was stirred at 27° C. for 1 hour, then concentrated under reduced pressure to give the title compound. LRMS m/z (M+H): calculated 332.1, observed 333.1.

Step 6: Examples 47A, 47B, 47C and 47D To a solution of (5-chloro-6-(trifluoromethyl)pyridin-2-yl)(3-(trifluoromethyl)cyclobutyl) methanamine hydrochloride (180 mg, 0.433 mmol) in DMF (3.5 mL) was added di(1H-imidazol-1-yl)methanone (140 mg, 0.866 mmol). The reaction mixture was stirred at 27° C. for 1 hour, then (R)-3-methylpiperazin-2-one (51.9 mg, 0.455 mmol) was added. The resulting mixture was stirred at 27° C. for 2 hours, then diluted with MeCN (1 mL) and purified by preparative HPLC (62:38 to 32:68; water (0.1% TFA):MeCN (0.1% TFA)) to give a mixture of isomers, which was separated by SFC (OJ-H column, 30% (EtOH+0.1% $NH_3H_2O$) co-solvent) to give first eluted isomer, Examples 47C (second eluted fraction) and 47D (third eluted fraction). The first eluted isomer was further separated by second SFC (OJ-H column, 10-30% (EtOH+0.1% $NH_3H_2O$) co-solvent)) to give Examples 47A (first eluted fraction) and 47B (second eluted fraction).

Example 47A: LRMS m/z (M+H): calculated 472.1, observed 473.0. $^1H$ NMR δ (ppm) (400 MHz, Chloroform-d): 8.01 (d, J=8.8 Hz, 1H), 7.60 (d, J=8.8 Hz, 1H), 4.88 (d, J=10.4 Hz, 1H), 4.50-4.55 (m, 1H), 3.95-4.12 (m, 1H), 3.34-3.41 (m, 1H), 3.19-3.29 (m, 2H), 2.75-2.99 (m, 2H), 2.28-2.37 (m, 1H), 1.96-2.13 (m, 3H), 1.41 (d, J=7.2 Hz, 3H).

Example 47B: LRMS m/z (M+H): calculated 472.1, observed 473.1 $^1H$ NMR δ (ppm) (400 MHz, Chloroform-d): 8.02 (d, J=8.4 Hz, 1H), 7.62 (d, J=8.4 Hz, 1H), 4.98 (d, J=11.2 Hz, 1H), 4.56-4.60 (m, 1H), 4.04-4.07 (m, 1H), 3.31-3.34 (m, 1H), 3.26-3.30 (m, 2H), 2.96-3.26 (m, 2H), 2.30-2.35 (m, 1H), 2.22-2.26 (m, 2H), 2.12-2.18 (m, 1H), 1.40 (d, J=7.2 Hz, 3H).

Example 47C: LRMS m/z (M+H): calculated 472.1, observed 473.0 $^1H$ NMR δ (ppm) (400 MHz, Chloroform-d): 8.01 (d, J=8.8 Hz, 1H), 7.60 (d, J=8.4 Hz, 1H), 4.88 (d, J=10.4 Hz, 1H), 4.50-4.55 (m, 1H), 3.95-4.12 (m, 1H), 3.34-3.41 (m, 1H), 3.19-3.29 (m, 2H), 2.75-2.99 (m, 2H), 2.28-2.37 (m, 1H), 1.96-2.13 (m, 3H), 1.43 (d, J=7.2 Hz, 3H).

Example 47D: LRMS m/z (M+H): calculated 472.1, observed 473.0 $^1H$ NMR δ (ppm) (400 MHz, Chloroform-d): 8.01 (d, J=8.4 Hz, 1H), 7.62 (d, J=8.0 Hz, 1H), 4.97 (d, J=10.4 Hz, 1H), 4.51-4.56 (m, 1H), 4.02-4.05 (m, 1H), 3.32-3.40 (m, 1H), 3.19-3.28 (m, 2H), 2.87-3.08 (m, 2H), 2.30-2.39 (m, 1H), 2.16-2.27 (m, 2H), 2.03-2.13 (m, 1H), 1.41 (d, J=7.2 Hz, 3H).

Examples 48A, 48B, 48C and 48D (2R)-N-((R or S)-1-(3-chloro-4-fluorophenyl)-1-(cis-3-(trifluoromethyl)cyclobutyl)ethyl)-2-methyl-3-oxopiperazine-1-carboxamide (48A), (2R)-N-((R or S)-1-(3-chloro-4-fluorophenyl)-1-(trans-3-(trifluoromethyl)cyclobutyl)ethyl)-2-methyl-3-oxopiperazine-1-carboxamide (48B), (2R)-N-((S or R)-1-(3-chloro-4-fluorophenyl)-1-(cis-3-(trifluoromethyl) cyclobutyl)ethyl)-2-methyl-3-oxopiperazine-1-carboxamide (48C) and (2R)-N-((S or R)-1-(3-chloro-4-fluorophenyl)-1-(trans-3-(trifluoromethyl) cyclobutyl)ethyl)-2-methyl-3-oxopiperazine-1-carboxamide (48D)

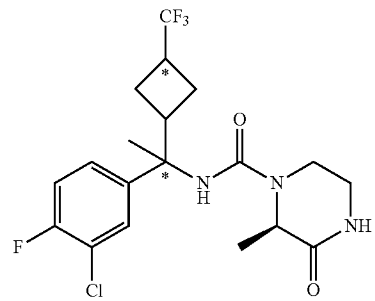 [SMILES: C[C@@H]1C(=O)NCCN1C(=O)NC(C)(c1ccc(F)c(Cl)c1)C1CC(C(F)(F)F)C1]

Step 1: 1-(3-chloro-4-fluorophenyl)-1-(3-(trifluoromethyl)cyclobutyl)ethan-1-ol MeMgBr (68.0 mg, 0.570 mmol) was added to a solution of (3-chloro-4-fluorophenyl) (3-(trifluoromethyl) cyclobutyl)methanone (20 mg, 0.071 mmol) in THF (2.0 mL) at −78° C. The resulting mixture was warmed to 25° C. slowly and stirred at 25° C. for 16 hours. Then the reaction was quenched with saturated aqueous $NH_4Cl$ (5 mL) and extracted with EtOAc (4×8 mL). The combined EtOAc layers were dried over $Na_2SO_4$, filtered and the filtrate was concentrated. The resulting residue was purified by prep-TLC (SiO2, Pet.ether:EtOAc=5:1) to give the title compound. $^1H$ NMR (400 MHz, $CDCl_3$) δ 7.62 (dd, J=2.0, 7.5 Hz, 1H), 7.37-7.48 (m, 1H), 7.26-7.36 (m, 1H), 2.85-2.87 (m, 1H), 2.71-2.81 (m, 1H), 2.41-2.43 (m, 1H), 1.95-2.12 (m, 2H), 1.64-1.66 (m, 1H), 1.38-1.28 (m, 3H).

Step 2: 2-chloro-N-(1-(3-chloro-4-fluorophenyl)-1-(3-(trifluoromethyl)cyclobutyl)ethyl) acetamide 2-chloroacetonitrile (153 mg, 2.022 mmol) was added to a solution of 1-(3-chloro-4-fluorophenyl)-1-(3-(trifluoromethyl)cyclobutyl)ethan-1-ol (60 mg, 0.202 mmol) in TFA (1.5 mL) at 25° C. The resulting mixture was stirred at 25° C. for 16 h, and then concentrated. The resulting residue was purified by prep-HPLC (TFA) to give the title compound. $^1$H NMR (400 MHz, $CDCl_3$) δ 8.15-8.39 (m, 1H), 7.37 (t, J=2.4, 6.4 Hz, 1H), 7.20-7.28 (m, 1H), 7.11-7.19 (m, 1H), 3.92-4.08 (m, 2H), 2.65-3.08 (m, 2H), 1.93-2.31 (m, 4H), 1.62-1.68 (m, 3H).

Step 3: 1-(3-chloro-4-fluorophenyl)-1-(3-(trifluoromethyl)cyclobutyl)ethan-1-amine A mixture of 2-chloro-N-(1-(3-chloro-4-fluorophenyl)-1-(3-(trifluoromethyl)cyclobutyl)ethyl)acetamide (55 mg, 0.148 mmol) and thiourea (13.50 mg, 0.177 mmol) in EtOH (2 mL) and AcOH (0.400 mL) was stirred at 110° C. for 16 hours. Then the mixture was concentrated, and the resulting residue was purified by prep-HPLC (50:50 to 20:80; water (0.1% TFA):MeCN (0.1% TFA)) to give the title compound. LRMS m/z (M+H): calculated 295.1, observed 296.1.

Step 4: (2R)—N-(1-(3-chloro-4-fluorophenyl)-1-(3-(trifluoromethyl)cyclobutyl)ethyl)-2-methyl-3-oxopiperazine-1-carboxamide To a solution of triphosgene (25.07 mg, 0.095 mmol) in $CH_2Cl_2$ (5 mL) was added DIEA (0.124 mL, 0.710 mmol) at 0° C. Then a solution of 1-(3-chloro-4-fluorophenyl)-1-(3-(trifluoromethyl)cyclobutyl)ethan-1-amine (70 mg, 0.237 mmol) in $CH_2Cl_2$ (1 mL) was added. The reaction mixture was stirred at 0° C. for 0.5 hour, then a solution of (R)-3-methylpiperazin-2-one (32.4 mg, 0.284 mmol) in $CH_2Cl_2$ (1 mL) was added. The reaction mixture was stirred at 0° C. for 30 minutes, and then concentrated. The resulting residue was purified by prep-HPLC (80:20 to 50:50; water (0.1% TFA):MeCN (0.1% TFA)) to give the title compound. LRMS m/z (M+H): calculated 435.1, observed 436.1.

Step 5: Examples 48A, 48B, 48C and 48D (2R)—N-(1-(3-chloro-4-fluorophenyl)-1-(3-(trifluoromethyl)cyclobutyl)ethyl)-2-methyl-3-oxopiperazine-1-carboxamide (75 mg, 0.172 mmol) was separated by Chiral SFC (Column: (S,S)-Whelk-O; 5% to 40% of IPA with 0.05% DEA cosolvent) to give Examples 48A (first eluted fraction) and 48B (second eluted fraction). The third eluted fraction which was further separated by second SFC (Column: OD-3, 5-40% EtOH with 0.05% DEA co-solvent) to give Examples 48C (first eluted fraction) and 48D (second eluted fraction).

Example 48A: LRMS m/z (M+H): calculated 435.1, observed 436.1. $^1$H NMR δ (ppm) (500 MHz, Chloroform-d): 7.38 (dd, J=2.5, 7.0 Hz, 1H), 7.26-7.28 (m, 1H), 7.12-7.21 (m, 1H), 4.53-4.65 (m, 1H), 3.95 (d, J=13.0 Hz, 1H), 3.32-3.40 (m, 1H), 3.17-3.28 (m, 2H), 3.13-3.15 (m, 1H), 2.62-2.76 (m, 1H), 2.12-2.34 (m, 3H), 2.06-2.08 (m, 1H), 1.76 (s, 3H), 1.40 (d, J=7.0 Hz, 3H).

Example 48B: LRMS m/z (M+H): calculated 435.1, observed 436.1. $^1$H NMR δ (ppm) (500 MHz, Chloroform-d): 7.37 (dd, J=2.5, 7.0 Hz, 1H), 7.24-7.26 (m, 1H), 7.10-7.20 (m, 1H), 4.55-4.58 (m, 1H), 3.96-3.98 (m, 1H), 3.34-3.45 (m, 1H), 3.20-3.29 (m, 2H), 2.94-3.05 (m, 1H), 2.75-2.89 (m, 1H), 1.98-2.14 (m, 4H), 1.62 (s, 3H), 1.41 (d, J=7.0 Hz, 3H).

Example 48C: LRMS m/z (M+H): calculated 435.1, observed 436.1. $^1$H NMR δ (ppm) (500 MHz, Chloroform-d): 7.37 (dd, J=2.5, 7.0 Hz, 1H), 7.25-7.28 (m, 1H), 7.13-7.19 (m, 1H), 4.53-4.55 (m, 1H), 3.93-4.01 (m, 1H), 3.32-3.41 (m, 1H), 3.15-3.28 (m, 3H), 2.67-2.69 (m, 1H), 2.14-2.32 (m, 3H), 2.04-2.13 (m, 1H), 1.69 (s, 3H), 1.41 (d, J=7.0 Hz, 3H).

Example 48D: LRMS m/z (M+H): calculated 435.1, observed 436.1. $^1$H NMR δ (ppm) (500 MHz, Chloroform-d): 7.36 (dd, J=2.5, 7.0 Hz, 1H), 7.23-7.25 (m, 1H), 7.12-7.18 (m, 1H), 4.54-4.56 (m, 1H), 3.93-4.01 (m, 1H), 3.32-3.41 (m, 1H), 3.19-3.29 (m, 2H), 3.05-3.08 (m, 1H), 2.84-2.86 (m, 1H), 1.93-2.05 (m, 4H), 1.60 (s, 3H), 1.42 (d, J=7.0 Hz, 3H).

Examples 49A and 49B (2R)-N-((R)-(3-fluoro-4-(trifluoromethoxy)phenyl)(trans-3-(trifluoromethyl)cyclobutyl)methyl)-2-methyl-3-oxopiperazine-1-carboxamide and (2R)-N-((S)-(3-fluoro-4-(trifluoromethoxy)phenyl)(trans-3-(trifluoromethyl)cyclobutyl)methyl)-2-methyl-3-oxopiperazine-1-carboxamide

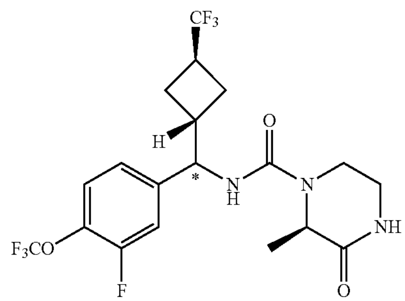 [SMILES: C[C@@H]1C(=O)NCCN1C(=O)NC(c1ccc(OC(F)(F)F)c(F)c1)[C@H]1C[C@H](C(F)(F)F)C1]

Step 1: (3-fluoro-4-(trifluoromethoxy)phenyl)(trans-3-(trifluoromethyl)cyclobutyl)methanone To a mixture of N-methoxy-N-methyl-3-(trifluoromethyl)cyclobutane-1-carboxamide (50 mg, 0.237 mmol) in THF (2 mL) was added (3-fluoro-4-(trifluoromethoxy)phenyl)magnesium bromide (134 mg, 0.474 mmol) at 0° C. The mixture was stirred at 0° C. for 2 hours under $N_2$. Then the reaction was quenched with saturated aqueous $NH_4Cl$ (10 mL) and extracted with EtOAc (3×10 mL). The combined organic layers were washed with brine (20 mL), dried over anhydrous $Na_2SO_4$, filtered and the filtrate was concentrated under reduced pressure. The resulting residue was purified by prep-TLC ($SiO_2$, PE:EtOAc=20:1) to give the title compound. $^1$H NMR (500 MHz, $CD_3CN$) δ 7.73-7.77 (m, 1H), 7.67-7.73 (m, 1H), 7.51-7.42 (m, 1H), 4.05-3.96 (m, 1H), 3.04-2.79 (m, 1H), 2.54-2.47 (m, 2H), 2.46-2.40 (m, 2H).

Step 2: (3-fluoro-4-(trifluoromethoxy)phenyl)(trans-3-(trifluoromethyl)cyclobutyl)methanol TEA (0.147 mL, 1.053 mmol) in DMF (1 mL) was added to a solution of HCOOH (27.0 mg, 0.587 mmol) in DMF (2 mL) at 20° C. The resulting mixture was stirred at 20° C. for 10 min., then (3-fluoro-4-(trifluoromethoxy)phenyl)(trans-3-(trifluoromethyl)cyclobutyl)methanone (60 mg, 0.173 mmol) in DMF (2 mL) was added, followed by the addition of (S,S)-Noyori's catalyst (1.098 mg, 1.726 μmol). The reaction was stirred at 20° C. for 16 hours, then quenched with water (10 mL) and extracted with EtOAc (2×5 mL). The combined EtOAc layers were washed with brine (2×5 mL), dried over $Na_2SO_4$, and filtered. The filtrate was concentrated, and the resulting residue was purified by prep-TLC (PE:EtOAc=5:1) to give the title compound. $^1$H NMR (400 MHz, CDCl3) δ 7.27-7.23 (m, 1H), 7.18 (td, J=1.6, 10.8 Hz, 1H), 7.06-7.10 (m, 1H), 4.66-4.55 (m, 1H), 2.67 (qd, J=7.6, 15.2 Hz, 1H), 2.36-2.22 (m, 2H), 2.19-2.11 (m, 3H).

Step 3: (3-fluoro-4-(trifluoromethoxy)phenyl)(trans-3-(trifluoromethyl)cyclobutyl)methyl methanesulfonate Ms-Cl (0.279 mL, 3.58 mmol) was added to a solution of (3-fluoro-4-(trifluoromethoxy)phenyl)(trans-3-(trifluoromethyl)cyclobutyl)methanol (55 mg, 0.157 mmol) and TEA (0.044 mL, 0.315 mmol) in THF (5 mL) cooled in an ice bath. The reaction was stirred at 20° C. for 2.5 hours, then quenched with brine (10 mL) and extracted with EtOAc (2×5 mL). The combined EtOAc layers were dried over $Na_2SO_4$, and filtered. The filtrate was concentrated to give the title compound.

Step 4: 4-(azido(trans-3-(trifluoromethyl)cyclobutyl) methyl)-2-fluoro-1-(trifluoromethoxy) benzene $NaN_3$ (130 mg, 2.000 mmol) was added to a solution of (3-fluoro-4-(trifluoromethoxy) phenyl)(trans-3-(trifluoromethyl)cyclobutyl)methyl methanesulfonate (60 mg, crude) in DMF (2.5 mL). The reaction was stirred at 80° C. for 16 hours, then quenched with water (5 mL) and extracted with EtOAc (4×5 mL). The combined EtOAc layers were washed with brine (2×10 mL), dried over $Na_2SO_4$, and filtered. The filtrate was concentrated to give the title compound.

Step 5: N-((3-fluoro-4-(trifluoromethoxy)phenyl)(trans-3-(trifluoromethyl)cyclobutyl)methyl)-1,1,1-triphenyl-15-phosphanimine $PPh_3$ (62.4 mg, 0.238 mmol) was added to a solution of 4-(azido(trans-3-(trifluoromethyl)cyclobutyl) methyl)-2-fluoro-1-(trifluoromethoxy) benzene (50 mg, crude) in THF (5 mL) and $H_2O$ (1 mL). The reaction mixture was stirred at 65° C. for 16 hours, then concentrated to give the title compound. LRMS m/z (M+H): calculated 591.2, observed 592.1.

Step 6: (3-fluoro-4-(trifluoromethoxy)phenyl)(trans-3-(trifluoromethyl)cyclobutyl)methanamine NaOH (47.7 mg, 1.192 mmol) was added to a mixture of N-((3-fluoro-4-(trifluoromethoxy) phenyl)(trans-3-(trifluoromethyl)cyclobutyl)methyl)-1,1,1-triphenyl-15-phosphanimine (70.5 mg crude) in MeOH (3 mL). The reaction mixture was stirred at 40° C. for 3 hours, then concentrated under reduced pressure. To the resulting residue was added water (10 mL), and the mixture was extracted with DCM/MeOH (3×5 mL, 10:1). The combined organic layers were dried over $Na_2SO_4$, and filtered. The filtrate was concentrated, and the resulting residue was purified by prep-HPLC (70:30 to 40:60; water (0.1% TFA):MeCN (0.1% TFA)) to give the title compound. LRMS m/z (M+H-17): calculated 331.1, observed 315.0.

Step 7: Examples 49A and 49B A mixture of CDI (34.3 mg, 0.211 mmol) and (3-fluoro-4-(trifluoromethoxy)phenyl) (trans-3-(trifluoromethyl)cyclobutyl)methanamine (35 mg, 0.106 mmol) in DMF (0.5 mL) was stirred at 20° C. for 1 hour. Then (R)-3-methylpiperazin-2-one (14.47 mg, 0.127 mmol) was added. The reaction mixture was stirred at 20° C. for 1 hour, then filtered. The filtrate was purified by Prep-HPLC (51:49 to 31:69; water (0.1% TFA):MeCN (0.1% TFA)) to give a mixture of isomers, which was further separated by SFC (AD-H column, 10% EtOH with 0.1% $NH_3H_2O$ co-solvent) to give examples 49A (first eluted fraction) and 49B (second eluted fraction).

Example 49A: LRMS m/z (M+H): calculated 471.1, observed 472.2. $^1H$ NMR δ (ppm) (500 MHz, CD3CN): 7.36 (t, J=8.0 Hz, 1H), 7.25-7.29 (m, 1H), 7.20 (d, J=8.5 Hz, 1H), 6.35 (br s, 1H), 5.53-5.61 (m, 1H), 4.75-4.79 (m, 1H), 4.32 (q, J=7.0 Hz, 1H), 3.87-3.95 (m, 1H), 3.23-3.30 (m, 1H), 3.08-3.19 (m, 2H), 2.96-3.05 (m, 1H), 2.72-2.81 (m, 1H), 2.27-2.36 (m, 1H), 2.12 (br s, 1H), 1.96-2.02 (m, 2H), 1.31 (d, J=7.0 Hz, 3H).

Example 49B: LRMS m/z (M+H): calculated 471.1, observed 472.1. $^1H$ NMR δ (ppm) (500 MHz, CD3CN): 7.36 (t, J=8.0 Hz, 1H), 7.26-7.30 (m, 1H), 7.17-7.25 (m, 1H), 6.35 (br s, 1H), 5.53-5.61 (m, 1H), 4.76-4.80 (m, 1H), 4.37 (q, J=7.0 Hz, 1H), 3.90-3.98 (m, 1H), 3.19-3.27 (m, 1H), 3.08-3.19 (m, 2H), 2.95-3.06 (m, 1H), 2.71-2.83 (m, 1H), 2.27-2.37 (m, 1H), 2.12-2.16 (m, 1H), 1.98-2.04 (m, 2H), 1.31 (d, J=7.0 Hz, 3H).

TABLE 7

The following examples were prepared according to the synthetic procedure for Examples 49A and 49B, using the appropriate starting materials and reagents

| Example | Compound | Name | Calc'd [M + H]+ | Observed [M + H]+ | Conditions |
|---|---|---|---|---|---|
| 50A | 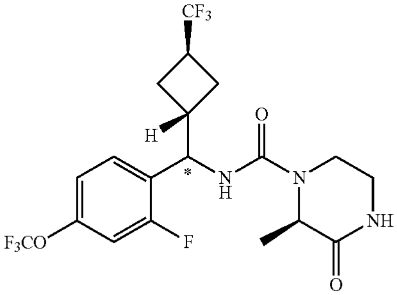 [SMILES: C[C@@H]1C(=O)NCCN1C(=O)NC(c1ccc(OC(F)(F)F)cc1F)[C@H]1C[C@H](C(F)(F)F)C1] | ((2R)-N-((R or S)-(2-fluoro-4-(trifluoro-methoxy)phenyl)(trans-3-(trifluoromethyl)-cyclobutyl)methyl)-2-methyl-3-oxopiperazine-1-carboxamide | 471.1 | 472.1 | SFC: AD-H Co-solvent: 15-40% EtOH peak 1 |
| 50B | 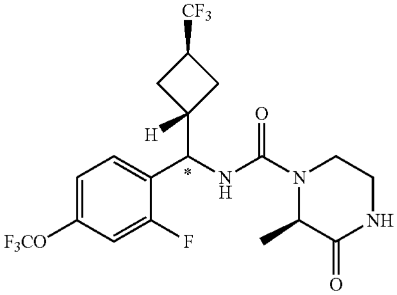 [SMILES: C[C@@H]1C(=O)NCCN1C(=O)NC(c1ccc(OC(F)(F)F)cc1F)[C@H]1C[C@H](C(F)(F)F)C1] | (2R)-N-((S or R)-(2-fluoro-4-(trifluoro-methoxy)phenyl)(trans-3-(trifluoro-methyl)-cyclobutyl)-methyl)-2-methyl-3-oxopiperazine-1-carboxamide | 471.1 | 472.1 | SFC: AD-H Co-solvent: 15-40% EtOH peak 2 |

TABLE 7-continued

| Example | Compound | Name | Calc'd $[M + H]^+$ | Observed $[M + H]^+$ | Conditions |
|---|---|---|---|---|---|
| The following examples were prepared according to the synthetic procedure for Examples 49A and 49B, using the appropriate starting materials and reagents | | | | | |
| 51A | 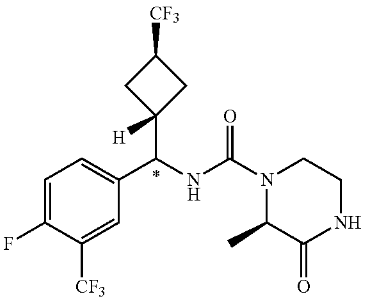 [SMILES: C[C@@H]1C(=O)NCCN1C(=O)NC(c1ccc(F)c(C(F)(F)F)c1)[C@H]1C[C@H](C(F)(F)F)C1] | (2R)-N-((R or S)-(4-fluoro-3-(trifluoro-methyl)phenyl)(trans-3-(trifluoro-methyl)-cyclo-butyl)methyl)-2-methyl-3-oxo-piperazine-1-carboxamide | 455.1 | 456.0 | SFC: OJ-H Co-solvent: 15% EtOH peak 1 |
| 51B | 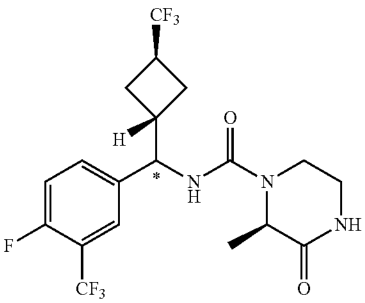 [SMILES: C[C@@H]1C(=O)NCCN1C(=O)NC(c1ccc(F)c(C(F)(F)F)c1)[C@H]1C[C@H](C(F)(F)F)C1] | (2R)-N-((S or R)-(4-fluoro-3-(trifluoro-methyl)phenyl)(trans-3-(trifluoro-methyl)-cyclobutyl)methyl)-2-methyl-3-oxopiperazine-1-carboxamide | 455.1 | 456.0 | SFC: OJ-H Co-solvent: 15% EtOH peak 2 |
| 52A | 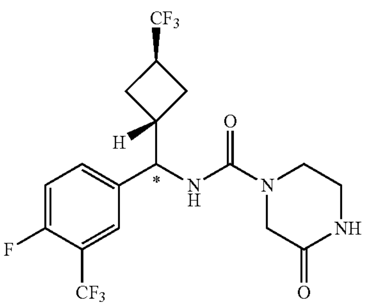 [SMILES: O=C1CN(C(=O)NC(c2ccc(F)c(C(F)(F)F)c2)[C@H]2C[C@H](C(F)(F)F)C2)CCN1] | N-((R or S)-(4-fluoro-3-(trifluoromethyl)phenyl)(trans-3-(trifluoro-methyl)cyclobutyl)-methyl)-3-oxo-piperazine-1-carboxamide | 441.1 | 442.1 | SFC: OJ-H Co-solvent: 20-40% EtOH peak 1 |
| 52B | 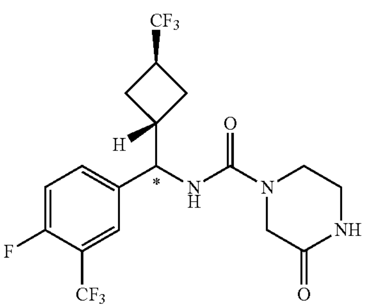 [SMILES: O=C1CN(C(=O)NC(c2ccc(F)c(C(F)(F)F)c2)[C@H]2C[C@H](C(F)(F)F)C2)CCN1] | N-((S or R)-(4-fluoro-3-(trifluoromethyl)phenyl)(trans-3-(trifluoro-methyl)cyclobutyl)-methyl)-3-oxo-piperazine-1-carboxamide | 441.1 | 442.1 | SFC: OJ-H Co-solvent; 20-40% EtOH peak 2 |

TABLE 7-continued

The following examples were prepared according to the synthetic procedure for Examples 49A and 49B, using the appropriate starting materials and reagents

| Example | Compound | Name | Calc'd $[M + H]^+$ | Observed $[M + H]^+$ | Conditions |
|---|---|---|---|---|---|
| 53A | 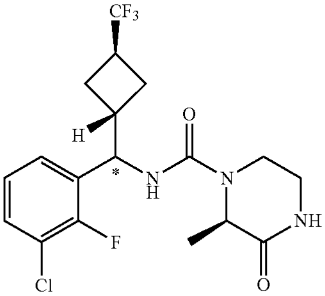 [SMILES: C[C@@H]1C(=O)NCCN1C(=O)NC(c1cccc(Cl)c1F)[C@H]1C[C@H](C(F)(F)F)C1] | (2R)-N-((R or S)-(3-chloro-2-fluorophenyl)-(trans-3-(trifluoro-methyl)cyclobutyl)meth-yl)-2-methyl-3-oxo-piperazine-1-carboxamide | 421.1 | 422.0 | SFC: (S,S)-Whelk-O1 Co-solvent: 5-40% EtOH with 0.05% DEA peak 1 |
| 53B | 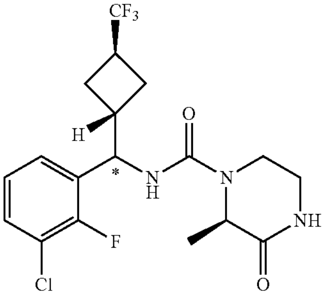 [SMILES: C[C@@H]1C(=O)NCCN1C(=O)NC(c1cccc(Cl)c1F)[C@H]1C[C@H](C(F)(F)F)C1] | (2R)-N-((S or R)-(3-chloro-2-fluorophenyl)-(trans-3-(trifluoro-methyl)cyclobutyl)meth-yl)-2-methyl-3-oxo-piperazine-1-carboxamide | 421.1 | 422.0 | SFC: (S,S)-Whelk-O1 Co-solvent: 5-40% EtOH with 0.05% DEA peak 2 |
| 54A | 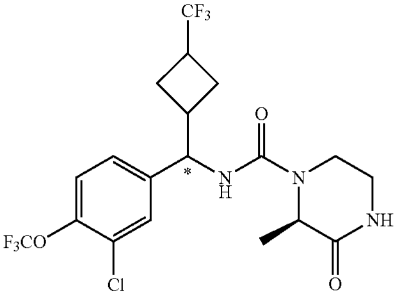 [SMILES: C[C@@H]1C(=O)NCCN1C(=O)NC(c1ccc(OC(F)(F)F)c(Cl)c1)C1CC(C(F)(F)F)C1] | (2R)-N-((R or S)-(3-chloro-4-(trifluoro-methoxy)phenyl)(3-(trifluoromethyl)cyclo-butyl)methyl)-2-methyl-3-oxopiperazine-1-carboxamide | 487.8 | 488.5 | SFC: AS-H Co-solvent: 10% EtOH Peak 1 |
| 54B | 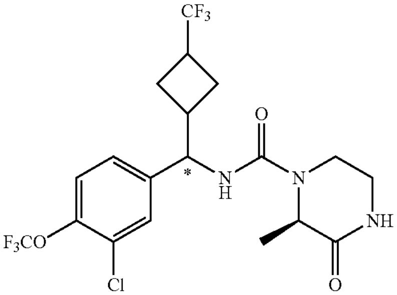 [SMILES: C[C@@H]1C(=O)NCCN1C(=O)NC(c1ccc(OC(F)(F)F)c(Cl)c1)C1CC(C(F)(F)F)C1] | (2R)-N-((S or R)-(3-chloro-4-(trifluoro-methoxy)phenyl)(3-(trifluoromethyl)cyclo-butyl)methyl)-2-methyl-3-oxopiperazine-1-carboxamide | 487.8 | 488.5 | SFC: AS-H Co-solvent: 10% EtOH peak 2 |

Examples 55A and 55B (2R)-2-methyl-3-oxo-N-((trans-4-(trifluoromethyl) cyclohexyl)((R)-2-(trifluoromethyl)thiazol-4-yl) methyl)piperazine-1-carboxamide and (2R)-2-methyl-3-oxo-N-((trans-4-(trifluoromethyl) cyclohexyl)((S)-2-(trifluoromethyl)thiazol-4-yl) methyl)piperazine-1-carboxamide

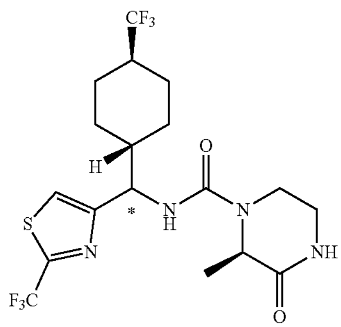 [SMILES: C[C@@H]1C(=O)NCCN1C(=O)NC(c1csc(C(F)(F)F)n1)[C@H]1CC[C@H](C(F)(F)F)CC1]

Step 1: 2-bromothiazole-4-carbaldehyde To a solution of ethyl 2-bromothiazole-4-carboxylate (3.4 g, 14.40 mmol) in THF/$CH_2Cl_2$ (1:1, 30 mL) was added DIBAL-H in toluene (1 M, 43.2 mL, 43.2 mmol) dropwise to maintain the temperature −78° C. After 5 hours at −78° C., the reaction was quenched with MeOH (5 mL), and the resulting mixture was poured into cold HCl (1 N, 20 mL). The aqueous phase was extracted with EtOAc (3×20 mL), and the combined organic layers were dried with $Na_2SO_4$, filtered and concentrated under reduced pressure to give the title compound.

Step 2: (2-bromothiazol-4-yl)(trans-4-(trifluoromethyl) cyclohexyl)methanone To a solution of 2-bromothiazole-4-carbaldehyde (0.689 g, 3.59 mmol) in 1,4-dioxane (20 mL) was added $Cs_2CO_3$ (1.462 g, 4.49 mmol) and 4-methyl-N'-(4-(trifluoromethyl)cyclohexylidene)benzenesulfonohydrazide (1 g, 2.99 mmol). The reaction mixture was stirred at 110° C. for 2 hours, then diluted with water (20 mL) and extracted with EtOAc (3×20 mL). The combined organic layers were washed with brine (20 mL), dried over anhydrous $Na_2SO_4$, filtered and concentrated. The resulting crude product was purified by Preparative TLC ($SiO_2$, petroleum ether/ethyl acetate=10/1) to give the title compound (first eluted isomer). $^1H$ NMR (500 MHz, CD30D) δ 8.24 (s, 1H), 3.52-3.59 (m, 1H), 2.08-2.16 (m, 1H), 2.01-2.04 (m, 2H), 1.59-1.72 (m, 6H).

Step 3: (trans-4-(trifluoromethyl)cyclohexyl)(2-(trifluoromethyl)thiazol-4-yl)methanone A mixture of (2-bromothiazol-4-yl)(trans-4-(trifluoromethyl)cyclohexyl)methanone (50 mg, 0.146 mmol), methyl 2,2-difluoro-2-(fluorosulfonyl)acetate (33.7 mg, 0.175 mmol) and CuI (2.78 mg, 0.015 mmol) in DMF (1 mL) was heated for 10 hours at 100° C. and then concentrated under reduced pressure. The resulting residue was purified by Preparative TLC (pet. ether/ethyl acetate=10/1) to give the title compound. $^1H$ NMR (400 MHz, CDCl3) δ 8.38 (s, 1H), 3.54 (s, 1H), 2.07-2.18 (m, 3H), 1.47-1.57 (m, 6H).

Step 4: (R)-2-methyl-N-((E)-(trans-4-(trifluoromethyl) cyclohexyl)(2-(trifluoromethyl)thiazol-4-yl)methylene)propane-2-sulfinamide To a microwave tube was charged with (trans-4-(trifluoro-methyl)cyclohexyl)(2-(trifluoromethyl) thiazol-4-yl)methanone (200 mg, 0.604 mmol), (R)-2-methylpropane-2-sulfinamide (110 mg, 0.906 mmol), $Ti(OEt)_4$ (275 mg, 1.207 mmol) and toluene (3 ml). The reaction mixture was microwaved at 110° C. for 60 minutes, and then cooled to RT, followed by the addition of water (5 mL) and EtOAc (10 mL). The mixture was stirred for 10 minutes, and then filtered through a Celite® pad. The separated organic layer was dried over $Na_2SO_4$, filtered and concentrated under reduced pressure to give the title compound. LRMS m/z (M+H-17): calculated 434.1, observed 435.0.

Step 5: (R)-2-methyl-N-((trans-4-(trifluoromethyl)cyclohexyl)(2-(trifluoromethyl)thiazol-4-yl)methyl)propane-2-sulfinamide A solution of (R)-2-methyl-N-((E)-(trans-4-(trifluoromethyl)-cyclohexyl)(2-(trifluoromethyl) thiazol-4-yl) methylene)propane-2-sulfinamide (190 mg crude) in THF (2.5 ml) and water (0.01 mL) was cooled to −78° C., followed by the addition of $NaBH_4$ (8.27 mg, 0.219 mmol). The reaction was stirred at −78° C. for 5 minutes, then quenched with saturated aqueous $NaHCO_3$ (6 mL) and extracted with EtOAc (3×10 mL). The combined organic layers were dried over $Na_2SO_4$, filtered and concentrated under reduced pressure to give the title compound. LRMS m/z (M+H−17): calculated 436.1, observed 437.0.

Step 6: (trans-4-(trifluoromethyl)cyclohexyl)(2-(trifluoromethyl)thiazol-4-yl)methanamine hydrochloride A solution of (R)-2-methyl-N-((trans-4-(trifluoromethyl)cyclohexyl)(2-(trifluoromethyl)thiazol-4-yl)methyl)propane-2-sulfinamide (110 mg crude) in HCl-MeOH (3 mL) was stirred at 20° C. for 2 hours. Then the solvent was evaporated under reduced pressure to give the title compound. LRMS m/z (M+H−17): calculated 332.1, observed 333.0

Step 7: Examples 55A and 55B A mixture of CDI (29.3 mg, 0.181 mmol) and (trans-4-(trifluoromethyl)cyclohexyl) (2-(trifluoromethyl)thiazol-4-yl)methanamine hydrochloride (50 mg, 0.090 mmol) in DMF (1 mL) was stirred at 20° C. for 1 hour. Then (R)-3-methylpiperazin-2-one (11.34 mg, 0.099 mmol) was added. The resulting mixture was stirred at 20° C. for 1 hour and then purified by Prep-HPLC (50:50 to 30:70; water (0.1% TFA):MeCN (0.1% TFA)) to give a mixture of isomers which was further separated by SFC ((s,s) WHELK-01, 30% EtOH with 0.1% $NH_3H_2O$ co-solvent) to give examples 55A (first eluted fraction) and 55B (second eluted fraction).

Example 55A: LRMS m/z (M+H): calculated 472.1, observed 473.1. $^1H$ NMR δ (ppm) (500 MHz, CD30D): 7.71 (s, 1H), 4.81 (d, J=9.0 Hz, 1H), 4.55-4.60 (m, 1H), 4.05 (d, J=14.5 Hz, 1H), 3.32-3.33 (m, 1H), 3.20-3.27 (m, 2H), 2.05-2.15 (m, 2H), 1.95-2.04 (m, 2H), 1.91 (d, J=13.0 Hz, 1H), 1.39-1.41 (m, 4H), 1.18-1.30 (m, 2H), 1.11-1.18 (m, 1H), 1.01-1.10 (m, 1H).

Example 55B: LRMS m/z (M+H): calculated 472.1, observed 473.1. $^1H$ NMR δ (ppm) (500 MHz, CD3OD): 7.70 (s, 1H), 4.78 (d, J=9.0 Hz, 1H), 4.51-4.59 (m, 1H), 4.04 (d, J=13.5 Hz, 1H), 3.32-3.33 (m, 1H), 3.18-3.27 (m, 2H), 2.04-2.16 (m, 2H), 1.94-2.03 (m, 2H), 1.87-1.93 (m, 1H), 1.42 (d, J=14.0 Hz, 1H), 1.34-1.39 (m, 3H), 1.28-1.34 (m, 1H), 1.20-1.28 (m, 1H), 1.10-1.18 (m, 1H), 1.01-1.10 (m, 1H).

Examples 56A, 56B, 56C and 56D (2R)-N-((R)-(3-chloro-2,4-difluorophenyl)((3R,6R)-6-(trifluoromethyl)tetrahydro-2H-pyran-3-yl)methyl)-2-methyl-3-oxopiperazine-1-carboxamide, (2R)-N-((R)-(3-chloro-2,4-difluorophenyl)((3S,6S)-6-(trifluoromethyl)tetrahydro-2H-pyran-3-yl)methyl)-2-methyl-3-oxopiperazine-1-carboxamide, (2R)-N-((S)-(3-chloro-2,4-difluorophenyl)((3R,6R)-6-(trifluoromethyl)tetrahydro-2H-pyran-3-yl)methyl)-2-methyl-3-oxopiperazine-1-carboxamide and (2R)-N-((S)-(3-chloro-2,4-difluorophenyl)((3S,6S)-6-(trifluoromethyl)tetrahydro-2H-pyran-3-yl)methyl)-2-methyl-3-oxopiperazine-1-carboxamide

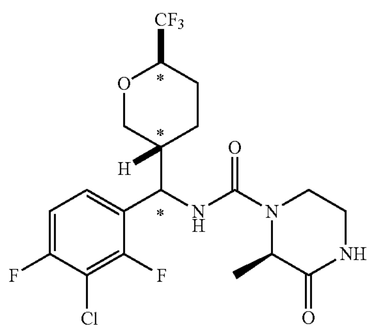 [SMILES: C[C@@H]1C(=O)NCCN1C(=O)NC(c1ccc(F)c(Cl)c1F)[C@H]1CC[C@H](C(F)(F)F)OC1]

Step 1: N-methoxy-N-methyl-6-(trifluoromethyl)tetrahydro-2H-pyran-3-carboxamide To a stirred solution of 6-(trifluoromethyl)tetrahydro-2H-pyran-3-carboxylic acid (300 mg, 1.514 mmol), N,O-dimethyl hydroxylamine hydrochloride (148 mg, 1.514 mmol) and DIPEA (0.80 mL, 4.58 mmol) in DMF (5 mL) was added HATU (864 mg, 2.271 mmol). Then reaction was stirred at 20° C. for 12 hours. Then the reaction mixture was diluted with EtOAc (30 mL), washed with water (2×20 mL), and brine (10 mL). The separated organic layer was dried over anhydrous sodium sulfate, filtered and concentrated under reduced pressure. The resulting residue was purified by pre-TLC (Pet.ether/EtOAc=3:1) to give the title compound. $^1$H NMR (400 MHz, $CDCl_3$) δ 3.95-4.27 (m, 2H), 3.57-3.78 (m, 4H), 3.07-3.29 (m, 3H), 2.74-2.86 (m, 0.4H), 2.42-2.55 (m, 0.6H), 2.09-2.23 (m, 1H), 1.54-1.89 (m, 3H).

Step 2: 6-(trifluoromethyl)tetrahydro-2H-pyran-3-carbaldehyde To a stirred solution of N-methoxy-N-methyl-6-(trifluoromethyl)tetrahydro-2H-pyran-3-carboxamide (300 mg, 1.244 mmol) in $CH_2Cl_2$ (8 mL) was added DIBAL-H in toluene (1 M, 2.487 mL, 2.487 mmol) at 0° C. The reaction was stirred at 0° C. for 3 hours, then quenched with saturated aqueous $NH_4Cl$ solution (10 mL). The mixture was diluted with DCM (20 mL), and washed with brine (10 mL). The separated organic layer was dried over anhydrous sodium sulfate, filtered and the filtrate was concentrated at 0° C. to give the title compound.

Step 3: (R)-2-methyl-N-((E)-(trans-6-(trifluoromethyl)tetrahydro-2H-pyran-3-yl)methylene)-propane-2-sulfinamide To a stirred solution of 6-(trifluoromethyl)tetrahydro-2H-pyran-3-carbaldehyde (140 mg) and (R)-2-methylpropane-2-sulfinamide (121 mg, 0.999 mmol) in THF (3 ml) was added tetraethoxytitanium (877 mg, 3.84 mmol) at 0° C. The reaction was stirred at 20° C. for 12 hours, then poured into brine (10 mL) and diluted with EtOAc (20 mL). The mixture was filtered through a Celite® pad, and the filtrate was washed with brine (5 mL). The organic layer was dried over anhydrous sodium sulfate, filtered and concentrated under reduced pressure to give a residue, which was purified by preparative-TLC (silica, Pet.ether/EtOAc=5:1) to give the title compound. LRMS m/z (M+H): calculated 285.1, observed 286.0.

Step 4: (R)—N-((3-chloro-2,4-difluorophenyl)(trans-6-(trifluoromethyl)tetrahydro-2H-pyran-3-yl)methyl)-2-methylpropane-2-sulfinamide To a stirred solution of (R)-2-methyl-N-((E)-(trans-6-(trifluoromethyl)tetrahydro-2H-pyran-3-yl)methylene)propane-2-sulfinamide (80 mg, 0.280 mmol) in THF (3.0 mL) was added (3-chloro-2,4-difluorophenyl)magnesium bromide (0.701 mL, 0.701 mmol) at 0° C. The reaction was stirred at 0° C. for 3 hours, then quenched with saturated aqueous $NH_4Cl$ solution (5.0 mL) and extracted with EtOAc (2×10 mL). The combined organic layers were dried over anhydrous sodium sulfate, filtered and concentrated under reduced pressure to give the title compound. LRMS m/z (M+H): calculated 433.1, observed 434.0.

Step 6: (3-chloro-2,4-difluorophenyl)(trans-6-(trifluoromethyl)tetrahydro-2H-pyran-3-yl)methanamine hydrochloride The mixture of (R)—N-((3-chloro-2,4-difluorophenyl)(trans-6-(trifluoromethyl)tetrahydro-2H-pyran-3-yl)methyl)-2-methylpropane-2-sulfinamide (120 mg, crude) and HCl/MeOH (1 M, 3 mL) was stirred at 20° C. for 5 hours. Then the solvent was removed under reduced pressure to give the title compound. LRMS m/z (M+H): calculated 329.1, observed 329.9.

Step 7: Examples 56A, 56B, 56C and 56D To a stirred solution of (3-chloro-2,4-difluoro-henyl)(trans-6-(trifluoromethyl)tetrahydro-2H-pyran-3-yl)methanamine hydrochloride (80 mg, 0.243 mmol) in DMF (2.0 ml) was added CDI (87 mg, 0.534 mmol) at 20° C. After the addition was finished, the reaction mixture was stirred at 20° C. for 1 hour, followed by the addition of (R)-3-methylpiperazin-2-one (36.0 mg, 0.315 mmol). The reaction mixture was stirred at 20° C. for 2 hours and then purified by preparative HPLC (62:38 to 42:58; water (0.1% TFA):MeCN (0.1% TFA)) to give isomer A (first eluted fraction) and isomer B (second eluted fraction). Isomer A was further separated by SFC (OJ-H column, 25% EtOH with 0.1% $NH_3H_2O$ co-solvent) to give Examples 56A (first eluted fraction) and 56B (second eluted fraction). Isomer B was further separated by SFC (OJ-H column, 25% EtOH with 0.1% $NH_3H_2O$ co-solvent) to give Examples 56C (first eluted fraction) and 56D (second eluted fraction).

Example 56A: LRMS m/z (M+H): calculated 469.1, observed 470.2. $^1$H NMR δ (ppm) (400 MHz, CD30D): 7.36 (dd, J=8.0, 6.0 Hz, 1H), 7.11 (dd, J=8.0, 1.6 Hz, 1H), 4.75-4.81 (m, 1H), 4.47-4.63 (m, 2H), 4.00 (d, J=13.2 Hz, 1H), 3.76-3.84 (m, 1H), 3.47 (d, J=10.0 Hz, 1H), 3.33 (d, J=3.2 Hz, 1H), 3.17-3.24 (m, 2H), 2.26 (d, J=13.2 Hz, 1H), 2.07-2.17 (m, 1H), 1.85-1.94 (m, 1H), 1.51-1.62 (m, 1H), 1.34-1.48 (m, 4H).

Example 56B: LRMS m/z (M+H): calculated 469.1, observed 470.2. $^1$H NMR δ (ppm) (400 MHz, CD3OD): 7.29-7.38 (m, 1H), 7.11 (t, J=8.8 Hz, 1H), 4.77 (d, J=10.0 Hz, 1H), 4.59 (s, 1H), 4.48 (q, J=6.8 Hz, 1H), 3.99 (d, J=13.2 Hz, 1H), 3.76-3.86 (m, 1H), 3.47 (d, J=10.0 Hz, 1H), 3.34 (d, J=3.6 Hz, 1H), 3.16-3.27 (m, 2H), 2.28 (d, J=13.2 Hz, 1H), 2.07-2.17 (m, 1H), 1.89 (d, J=13.2 Hz, 1H), 1.52-1.63 (m, 1H) 1.28-1.48 (m, 4H).

Example 56C: LRMS m/z (M+H): calculated 469.1, observed 470.2. $^1$H NMR δ (ppm) (400 MHz, CD30D): 7.33-7.40 (m, 1H), 7.08-7.17 (m, 1H), 4.81 (d, J=10.8 Hz, 1H), 4.58 (s, 1H), 4.48-4.56 (m, 1H), 4.32 (d, J=10.8 Hz, 1H), 4.00 (d, J=12.8 Hz, 1H), 3.77-3.86 (m, 1H), 3.34-3.43 (m, 1H), 3.19-3.29 (m, 2H), 2.02-2.15 (m, 1H), 1.79 (d, J=13.6 Hz, 1H), 1.25-1.55 (m, 6H).

Example 56D: LRMS m/z (M+H): calculated 469.1, observed 470.2. $^1$H NMR δ (ppm) (400 MHz, CD3OD): 7.29-7.38 (m, 1H), 7.11 (dd, J=8.8, 1.6 Hz, 1H), 4.78 (d, J=11.2 Hz, 1H), 4.58 (s, 1H), 4.46 (q, J=6.8 Hz, 1H), 4.31 (d, J=11.2 Hz, 1H), 3.97 (d, J=13.6 Hz, 1H), 3.74-3.85 (m, 1H), 3.31-3.39 (m, 1H), 3.16-3.26 (m, 2H), 2.09-2.20 (m, 1H), 1.77 (d, J=11.2 Hz, 1H), 1.15-1.59 (m, 6H).

Examples 57A, 57B, 57C and 57D (2R)-N-(R)-(3-chloro-2,4-difluorophenyl)(trans-2-(trifluoromethyl)cyclopropyl)methyl)-2-methyl-3-oxopiperazine-1-carboxamide, (2R)-N-(R)-(3-chloro-2,4-difluorophenyl)(trans-2-(trifluoromethyl)cyclopropyl)methyl)-2-methyl-3-oxopiperazine-1-carboxamide, (2R)-N-(S)-(3-chloro-2,4-difluorophenyl)(trans-2-(trifluoromethyl)cyclopropyl)methyl)-2-methyl-3-oxopiperazine-1-carboxamide and (2R)-N-(S)-(3-chloro-2,4-difluorophenyl)(trans-2-(trifluoromethyl)cyclopropyl)methyl)-2-methyl-3-oxopiperazine-1-carboxamide

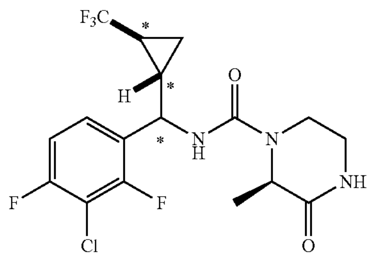 [SMILES: C[C@@H]1C(=O)NCCN1C(=O)NC(c1ccc(F)c(Cl)c1F)[C@H]1C[C@@H]1C(F)(F)F]

Step 1: (E)-4,4,4-trifluoro-N-methoxy-N-methylbut-2-enamide To a solution of (E)-4,4,4-trifluorobut-2-enoic acid (5 g, 35.7 mmol) in DCM (80 ml) were added N-ethyl-N-isopropyl-propan-2-amine (18.70 ml, 107 mmol), EDCI (10.27 g, 53.5 mmol) and N,O-dimethylhydroxylamine hydrochloride (5.22 g, 53.5 mmol). The reaction mixture was stirred at 20° C. for 15 hours, then diluted with water (60 mL) and extracted with DCM (2×40 mL). The combined organic layers were washed with HCl (2 N, 20 mL) and brine (50 mL). The separated organic layer was dried over $Na_2SO_4$, filtered and concentrated under reduced pressure to give the title compound. $^1$H NMR (400 MHz, $CDCl_3$) δ 7.09 (d, J=12.4 Hz, 1H), 6.78-6.86 (m, 1H), 3.77 (s, 3H), 3.30 (s, 3H).

Step 2: trans-N-methoxy-N-methyl-2-(trifluoromethyl)cyclopropane-1-carboxamide To a solution of trimethylsulfoxonium iodide (10.09 g, 45.9 mmol) in DMSO (60 ml) was added sodium hydride (1.835 g, 45.9 mmol). The resulting mixture was stirred at 20° C. for 1 hour, followed by the addition of (E)-4,4,4-trifluoro-N-methoxy-N-methylbut-2-enamide (6 g, 22.93 mmol) in DMSO (30 ml). The reaction mixture was stirred at 20° C. for 1 hour, then diluted with water (20 mL) and extracted with DCM (2×10 mL). The combined organic layers were washed with brine (20 mL), dried over $Na_2SO_4$, filtered and concentrated under reduced pressure. The resulting residue was purified by MPLC (ISCO®; 12 g SepaFlash® Silica Flash Column, eluent of 0~30% petroleum ether/EtOAc gradient) to give the title compound. $^1$H NMR (400 MHz, $CDCl_3$) δ 3.77 (s, 3H), 3.23 (s, 3H), 2.51-2.59 (m, 1H), 2.10-2.16 (m, 1H), 1.34-1.38 (m, 1H), 0.84-0.88 (m, 1H).

Step 3: ((3-chloro-2,4-difluorophenyl)(trans-2-(trifluoromethyl)cyclopropyl)methanone To a solution of isopropylmagnesium chloride (24.25 ml, 48.5 mmol) in THF (24.25 ml) at 0° C. was added 1-bromo-3-chloro-2,4-difluorobenzene (13.24 g, 58.2 mmol). The mixture was stirred at 0° C. for 2.5 hours, then trans-N-methoxy-N-methyl-2-(trifluoromethyl)cyclopropane-1-carboxamide (4.5 g, 19.40 mmol) in THF (30 mL) was added at 0° C. The reaction mixture was stirred at 20° C. for 12 hours, then saturated aqueous $NH_4Cl$ solution (40 mL) was added, and the mixture was diluted with water (20 mL), and extracted with EtOAc (3×40 mL). The combined organic layers were washed with brine (40 mL), dried over anhydrous sodium sulfate, filtered and concentrated under reduced pressure. The resulting residue was purified by MPLC (ISCO®; 12 g SepaFlash® Silica Flash Column, eluent of 0~2% Pet. ether/EtOAc) to give the title compound. $^1$H NMR (400 MHz, $CDCl_3$) δ 7.73-7.77 (m, 1H), 6.96-7.02 (m, 1H), 2.97-3.02 (m, 1H), 2.39-2.43 (m, 1H), 1.56-1.59 (m, 1H), 1.47-1.51 (m, 1H).

Step 4: (R)-N-((Z)-(3-chloro-2,4-difluorophenyl)(trans-2-(trifluoromethyl)cyclopropyl) methylene)-2-methylpropane-2-sulfinamide To a solution of ((3-chloro-2,4-difluorophenyl)-(trans-2-(trifluoromethyl)cyclopropyl)methanone (1 g, 3.51 mmol) in toluene (5 ml) were added (R)-2-methylpropane-2-sulfinamide (0.639 g, 5.27 mmol) and tetraethoxytitanium (1.202 g, 5.27 mmol). The reaction mixture was stirred at 105° C. for 30 minutes in the microwave, then diluted with water (10 mL) and EtOAc (10 mL), and filtered. The filtrate was extracted with EtOAc (2×10 mL). The combined organic layers were washed with brine (20 mL), dried over $Na_2SO_4$, and filtered. The filtrate was concentrated under reduced pressure to give the title compound. $^1$H NMR (400 MHz, $CDCl_3$) δ 7.73-7.77 (m, 1H), 6.96-7.02 (m, 1H), 2.97-3.02 (m, 1H), 2.39-2.43 (m, 1H), 1.56-1.59 (m, 1H), 1.47-1.51 (m, 1H). LRMS m/z (M+H): calculated 387.1, observed 388.0.

Step 5: (R)-N-((S or R)-(3-chloro-2,4-difluorophenyl)(trans-2-(trifluoromethyl)cyclopropyl) methyl)-2-methylpropane-2-sulfinamide (isomer A) and (R)-N-((R or S)-(3-chloro-2,4-difluorophenyl)(trans-2-(trifluoromethyl)cyclopropyl)methyl)-2-methylpropane-2-sulfinamide (isomer B) To a solution of (R)-N-((Z)-(3-chloro-2,4-difluorophenyl)(trans-2-(trifluoromethyl)-cyclopropyl) methylene)-2-methylpropane-2-sulfinamide (1 g, crude) in THF (15 mL) and water (1 mL) was added $NaBH_4$ (0.293 g, 7.74 mmol) at −70° C. The reaction mixture was stirred at −70° C. for 2 hours, then quenched with water (10 ml) and extracted with EtOAc (2×10 mL). The combined organic layers were washed with brine (20 mL), dried over $Na_2SO_4$, filtered and the filtrate was concentrated under reduced pressure. The resulting residue was purified by MPLC (ISCO®; 12 g SepaFlash® Silica Flash Column, eluent of 0~50% petroleum ether/EtOAc) to give isomer A (first eluted fraction) and isomer B (second fraction). Isomer A: LRMS m/z (M+H): calculated 389.1, observed 390.0. Isomer B: LRMS m/z (M+H): calculated 389.1, observed 390.0.

Step 6: ((S or R)-(3-chloro-2,4-difluorophenyl)(trans-2-(trifluoromethyl)cyclopropyl) methanamine hydrochloride (isomer C) A solution of R)-N-((S)-(3-chloro-2,4-difluorophenyl)-(trans-2-(trifluoromethyl)cyclopropyl)methyl)-2-methylpropane-2-sulfinamide (isomer A, 200 mg, 0.513 mmol) in HCl/MeOH (4 N, 3 mL) was stirred at 29° C. for 1 hour. Then the reaction mixture was concentrated under reduced pressure to give the title compound. LRMS m/z (M+H): calculated 285.0, observed 285.9.

Step 7: Examples 57A, 57B, 57C and 57D To a solution of ((S)-(3-chloro-2,4-difluorophenyl)-(trans-2-(trifluoromethyl)cyclopropyl) methanamine hydrochloride (isomer C, 100 mg crude) in DMF (2 ml) were added triethylamine (70.9 mg, 0.700 mmol), and di(1H-imidazol-1-yl)methanone (114 mg, 0.700 mmol). The reaction was stirred at 29° C. for 1 hour, then (R)-3-methylpiperazin-2-one (40.0 mg, 0.350 mmol) was added, and the mixture was stirred at 29° C. for 1 hour. The mixture was then diluted with MeCN (2 mL) and purified by Prep. HPLC (70:30 to 40:60; water (0.1% TFA):MeCN (0.1% TFA)) to give a mixture of isomers, which was further separated by SFC (OJ_H column, 30% EtOH with 0.1% $NH_3H_2O$ co-solvent) to give Examples 57A (first eluted fraction) and 57B (second eluted fraction).

Examples 57C and 57D were prepared according to the synthetic procedure for Examples 57A and 57B using isomer B in step 6. Examples 57C (first eluted fraction) and 57D (second eluted fraction) were separated by SFC (OJ-H column, 30% EtOH with 0.1% $NH_3H_2O$ co-solvent).

Example 57A: LRMS m/z (M+H): calculated 425.1, observed 426.0. $^1$H NMR δ (ppm) (400 MHz, CD30D): 7.45-7.49 (m, 1H), 7.11-7.16 (m, 1H), 4.60-4.63 (m, 1H), 4.51-4.54 (m, 1H), 4.00-4.03 (m, 1H), 3.33-3.36 (m, 1H), 3.25-3.29 (m, 2H), 1.80-1.89 (m, 2H), 1.40 (d, J=7.2 Hz, 3H), 1.01-1.04 (m, 1H), 0.93-1.00 (m, 1H).

Example 57B: LRMS m/z (M+H): calculated 425.1, observed 426.0. $^1$H NMR δ (ppm) (400 MHz, CD3OD): 77.48-7.52 (m, 1H), 7.11-7.16 (m, 1H), 4.55-4.62 (m, 2H), 4.03-4.07 (m, 1H), 3.34-3.36 (m, 1H), 3.20-3.27 (m, 2H), 1.77-1.87 (m, 2H), 1.43 (d, J=7.2 Hz, 3H), 1.03-1.06 (m, 1H), 0.96-1.02 (m, 1H).

Example 57C: LRMS m/z (M+H): calculated 425.1, observed 426.0. $^1$H NMR δ (ppm) (400 MHz, CD30D): 7.43-7.46 (m, 1H), 7.11-7.16 (m, 1H), 4.52-4.60 (m, 2H), 4.00-4.03 (m, 1H), 3.33-3.36 (m, 1H), 3.24-3.27 (m, 2H), 1.72-1.76 (m, 2H), 1.41 (d, J=7.2 Hz, 3H), 1.06-1.14 (m, 2H).

Example 57D: LRMS m/z (M+H): calculated 425.1, observed 426.0. $^1$H NMR δ (ppm) (400 MHz, CD30D): 7.42-7.45 (m, 1H), 7.11-7.16 (m, 1H), 4.50-4.56 (m, 2H), 4.02-4.05 (m, 1H), 3.33-3.36 (m, 1H), 3.24-3.28 (m, 2H), 1.73-1.79 (m, 2H), 1.40 (d, J=6.8 Hz, 3H), 1.07-1.14 (m, 2H).

Examples 58A, 58B, 58C and 58D (2R)-N-((R or S)-(3-chloro-2,4-difluorophenyl)(cis-3-(trifluoromethyl)cyclopentyl)methyl)-2-methyl-3-oxopiperazine-1-carboxamide (58A), (2R)-N-((R or S)-(3-chloro-2,4-difluorophenyl)(cis-3-(trifluoromethyl)cyclopentyl)methyl)-2-methyl-3-oxopiperazine-1-carboxamide (58B), (2R)-N-((R or S)-(3-chloro-2,4-difluorophenyl)(trans-3-(trifluoromethyl)cyclopentyl)methyl)-2-methyl-3-oxopiperazine-1-carboxamide (58C) and (2R)-N-((R or S)-(3-chloro-2,4-difluorophenyl)(trans-3-(trifluoromethyl)cyclopentyl)methyl)-2-methyl-3-oxopiperazine-1-carboxamide (58D)

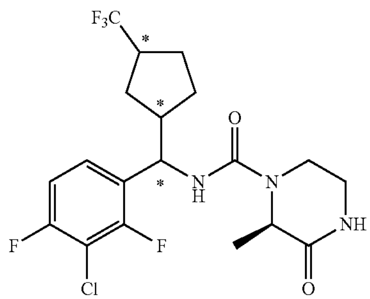 [SMILES: C[C@@H]1C(=O)NCCN1C(=O)NC(c1ccc(F)c(Cl)c1F)C1CCC(C(F)(F)F)C1]

Step 1: N-methoxy-N-methyl-3-(trifluoromethyl)cyclopentane-1-carboxamide To a solution of CDI (1602 mg, 9.88 mmol) in DCM (10 mL) was added 3-(trifluoromethyl)cyclopentane-1-carboxylic acid (900 mg, 4.94 mmol) at 20° C. The mixture was stirred for 1 h. Then DIEA (2.59 mL, 14.82 mmol) and N,O-dimethyl hydroxylamine hydrochloride (578 mg, 5.93 mmol) were added, and the resulting mixture was stirred at 20° C. for another 2 h. Water (20 mL) was added, and the mixture was extracted with DCM (3×10 mL). The combined organic fractions were washed with brine (10 mL), dried over $Na_2SO_4$, filtered and the filtrate was evaporated under reduced pressure. The resulting crude product was purified by flash silica gel chromatography (ISCO®; 12 g SepaFlash® Silica Flash Column, eluent of 24% petroleum ether/ethyl acetate) to give the title compound. $^1$H NMR (400 MHz, $CDCl_3$) δ 3.67 (s, 3H), 3.17 (s, 2H), 3.12-3.23 (m, 4H), 2.51-2.69 (m, 1H), 1.89-2.16 (m, 4H).

Step 2: (3-chloro-2,4-difluorophenyl)(3-(trifluoromethyl)cyclopentyl)methanon To a solution of 1-bromo-3-chloro-2,4-difluorobenzene (3.28 g, 14.43 mmol) in THF (10 mL) was added isopropyl magnesium chloride (6.35 mL, 12.70 mmol) at 0° C. The reaction mixture was stirred for 2 h, then N-methoxy-N-methyl-3-(trifluoromethyl)cyclopentane-1-carboxamide (1.3 g, 5.77 mmol) in THF (6 mL) was added. The reaction was stirred at 0° C. for 12 hours, then quenched with saturated aqueous $NH_4Cl$ (20 mL) and extracted with ethyl acetate (3×10 mL). The combined organic layers were washed with brine (20 mL), dried over $Na_2SO_4$, and filtered. The filtrate was evaporated under reduced pressure, and the resulting crude product was purified by flash silica gel chromatography (ISCO®; 12 g SepaFlash® Silica Flash Column, Eluent of 1% petroleum ether/ethyl acetate) to give the title compound. $^1$H NMR (500 MHz, $CDCl_3$) δ 7.76-7.83 (m, 1H), 7.06-7.12 (m, 1H), 3.61-3.70 (m, 1H), 2.68-2.80 (m, 1H), 2.20-2.29 (m, 1H), 2.07-2.14 (m, 1H), 1.92-2.05 (m, 3H), 1.83-1.91 (m, 1H).

Step 3: (3-chloro-2,4-difluorophenyl)(3-(trifluoromethyl)cyclopentyl)methanol $Et_3N$ (2.140 mL, 15.35 mmol) in DMF (5 mL) was added to a solution of formic acid (0.338 mL, 8.96 mmol) in DMF (5 mL) at 25° C. The resulting mixture was stirred at 25° C. for 10 minutes. Then (3-chloro-2,4-difluorophenyl)(3-(trifluoromethyl)cyclopentyl)methanone (1 g, 2.56 mmol) in DMF (5.00 mL) was added to the mixture, followed by the addition of (s,s)-n-(p-toluenesulfonyl)-1,2-diphenylethanediamine (chloro) (p-cymene) ruthenium (ii) (0.016 g, 0.026 mmol). The reaction was stirred at 25° C. for 16 hours, then quenched with water (6 mL) and extracted with EtOAc (4×6 mL). The combined EtOAc layers were dried over $Na_2SO_4$, and filtered. The filtrate was concentrated under reduced pressure, and the resulting crude product was purified by flash silica gel chromatography (ISCO®; 12 g SepaFlash® Silica Flash Column, eluent of 34% petroleum ether/ethyl acetate) to give the title compound. $^1$H NMR (400 MHz, $CDCl_3$) δ 7.42-7.54 (m, 1H), 7.30 (t, J=8.8 Hz, 1H), 5.54-5.68 (m, 1H), 4.54-4.81 (m, 1H), 2.70-2.95 (m, 1H), 2.21-2.23 (m, 1H), 1.27-1.94 (m, 6H).

Step 4: (3-chloro-2,4-difluorophenyl)(3-(trifluoromethyl)cyclopentyl)methyl methanesulfonate Ms-Cl (0.297 mL, 3.81 mmol) was added to a solution of (3-chloro-2,4-difluorophenyl)(3-(trifluoromethyl)cyclopentyl)methanol (800 mg, 2.54 mmol) and $Et_3N$ (0.709 mL, 5.08 mmol) in THF (12 mL) cooled in an ice bath. The reaction was stirred at 15° C. for 2 hours, then quenched with brine (50 mL) and extracted with EtOAc (4×10 mL). The combined EtOAc layers were dried over $Na_2SO_4$, filtered, and the filtrate was concentrated to give the title compound. $^1H$ NMR (400 MHz, $CDCl_3$) δ 7.30-7.40 (m, 1H), 7.01-7.13 (m, 1H), 5.58-5.67 (m, 1H), 3.68 (s, 1H), 2.85-2.87 (m, 3H), 2.48-2.78 (m, 2H), 1.79-1.95 (m, 2H), 1.60-1.77 (m, 2H), 1.31-1.49 (m, 1H).

Step 5: 1-(azido(3-(trifluoromethyl)cyclopentyl)methyl)-3-chloro-2,4-difluorobenzen Sodium azide (99 mg, 1.528 mmol) was added to a solution of (3-chloro-2,4-difluorophenyl)(3-(trifluoromethyl)cyclopentyl)methyl methanesulfonate (200 mg, 0.509 mmol) in DMF (2.5 mL). The reaction was stirred at 50° C. for 16 hours, then quenched with water (15 mL) and extracted with EtOAc (4×10 mL). The combined EtOAc layers were washed with brine (2×5 mL), dried over $Na_2SO_4$, filtered, and the filtrate was concentrated to give the title compound. $^1H$ NMR (400 MHz, $CDCl_3$) δ 7.23-7.32 (m, 1H), 7.00-7.08 (m, 1H), 4.59-4.70 (m, 1H), 2.54-2.76 (m, 1H), 2.27-2.43 (m, 1H), 1.91-2.07 (m, 1H), 1.46-1.84 (m, 4H), 1.29-1.45 (m, 1H).

Step 6: (3-chloro-2,4-difluorophenyl)(3-(trifluoromethyl)cyclopentyl)methanamine $PPh_3$ (174 mg, 0.662 mmol) was added to a solution of 1-(azido(3-(trifluoromethyl)cyclopentyl)methyl)-3-chloro-2,4-difluorobenzene (150 mg, 0.442 mmol) in THF (2.5 mL) and $H_2O$ (0.5 mL). The reaction was stirred at 65° C. for 16 hours, then cooled to room temperature, followed by the addition of water (20 mL). The mixture was extracted with ethyl acetate (3×10 mL). The combined organic layers were washed with brine (20 mL), dried over $Na_2SO_4$, filtered, and the solvent was evaporated under reduced pressure. The resulting residue was purified by reverse phase HPLC (75:25 to 55:45; water (0.1% TFA): MeCN (0.1% TFA)), followed by lyophilization to give the title compound. LRMS m/z (M+H): calculated 313.1, observed 314.1.

Step 7: Examples 58A, 58 B, 58C and 58D A mixture of (3-chloro-2,4-difluorophenyl)(3-(trifluoromethyl)cyclopentyl)methanamine (80 mg, 0.255 mmol), CDI (41.4 mg, 0.255 mmol) and DIEA (0.045 mL, 0.255 mmol) in DMF (1 mL) was stirred at 20° C. for 1 hour, then (R)-3-methylpiperazin-2-one (29.1 mg, 0.255 mmol) in DMF (0.5 mL) was added. The resulting mixture was stirred at 20° C. for 1 hour, and then purified by reverse phase HPLC (50:50 to 20:80; water (0.1% TFA):MeCN (0.1% TFA)) followed by lyophilization to give four fractions: First eluted fraction gave example 58A; Second eluted fraction was further separated by SFC (AS-H column, 15-35% (0.1% $NH_3H_2O$+EtOH) as cosolvent) to give example 58B; Third eluted fraction gave example 58C; Fourth eluted fraction was further separated by SFC (AS-H column, 15-35% (0.1% $NH_3H_2O$+EtOH) as cosolvent) to give Example 58D.

Example 58A: LRMS m/z (M+H): calculated 453.1, observed 454.1. $^1H$ NMR δ (ppm) (400 MHz, CD30D): 7.30-7.42 (m, 1H), 7.10 (t, J=8.8 Hz, 1H), 4.84 (s, 1H), 4.40-4.55 (m, 1H), 3.99-4.01 (m, 1H), 3.31-3.37 (m, 1H), 3.15-3.28 (m, 2H), 2.63-2.79 (m, 1H), 2.42-2.58 (m, 1H), 1.99-2.11 (m, 1H), 1.80-1.97 (m, 2H), 1.50-1.64 (m, 2H), 1.37 (d, J=7.2 Hz, 3H), 1.21-1.33 (m, 1H). Example 58B: LRMS m/z (M+H): calculated 453.1, observed 454.1. $^1H$ NMR δ (ppm) (400 MHz, CD30D): 7.29-7.43 (m, 1H), 7.04-7.15 (m, 1H), 4.84-4.86 (m, 1H), 4.49 (q, J=7.2 Hz, 1H), 4.0-4.03 (m, 1H), 3.31-3.38 (m, 1H), 3.15-3.28 (m, 2H), 2.69-2.86 (m, 1H), 2.41-2.56 (m, 1H), 2.21-2.32 (m, 1H), 1.74-1.90 (m, 2H), 1.27-1.53 (m, 6H). Example 58C: LRMS m/z (M+H): calculated 453.1, observed 454.1. $^1H$ NMR δ (ppm) (400 MHz, CD30D): 7.33-7.40 (m, 1H), 7.11 (t, J=8.4 Hz, 1H), 4.83 (d, J=10.8 Hz, 1H), 4.49 (d, J=6.4 Hz, 1H), 3.99-4.02 (m, 1H), 3.34-3.36 (m, 1H), 3.16-3.27 (m, 2H), 2.74-2.88 (m, 1H), 2.47-2.61 (m, 1H), 2.00-2.16 (m, 2H), 1.66-1.78 (m, 1H), 1.44-1.57 (m, 3H), 1.37 (d, J=7.2 Hz, 3H). Example 58D: LRMS m/z (M+H): calculated 453.1, observed 454.1. $^1H$ NMR δ (ppm) (400 MHz, CD30D): 7.29-7.42 (m, 1H), 7.10 (t, J=8.4 Hz, 1H), 4.82 (d, J=10.8 Hz, 1H), 4.49 (q, J=7.2 Hz, 1H), 3.99-4.02 (m 1H), 3.32-3.38 (m, 1H), 3.17-3.28 (m, 2H), 2.86-2.90 (m, 1H), 2.52-2.54 (m, 1H), 2.05-2.15 (m, 1H), 1.93-2.04 (m, 1H), 1.73-1.84 (m, 1H), 1.57-1.70 (m, 1H), 1.45 (br s, 1H), 1.37 (d, J=7.2 Hz, 3H), 1.28 (br s, 1H).

Intermediate 1

(S)-(3-chloro-2,4-difluorophenyl)(trans-3-(trifluoromethyl)cyclobutyl)methanamine hydrochloride

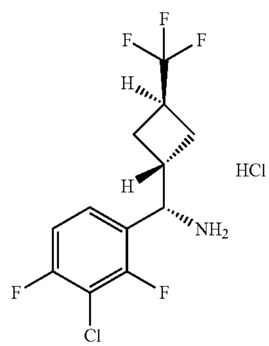 [SMILES: N[C@H](c1ccc(F)c(Cl)c1F)[C@H]1C[C@@H](C(F)(F)F)C1 ; Cl]

Step 1: (R)-N-((S)-(3-chloro-2,4-difluorophenyl)(trans-3-(trifluoromethyl)cyclobutyl)methyl)-2-methylpropane-2-sulfinamide To a solution of (R,E)-N-((3-chloro-2,4-difluorophenyl)(3-(trifluoromethyl)cyclobutyl) methylene)-2-methylpropane-2-sulfinamide (8.0 g, 20 mmol, see preparation in step 2 for Examples 20A-20D) in THF (80 mL) at −78° C. under an inert atmosphere of $N_2$ was added DIBAL-H (50 mL, 50 mmol, 1M) dropwise. The reaction mixture was stirred at −78° C. for 2 hours. An aqueous solution of $NH_4Cl$ (50 mL) was added at −78° C., then the mixture was warmed to 40° C. After 20 minutes the mixture was filtered through a pad of Celite™ and the filtrate was rinsed with ethyl acetate (5×50 mL). The resulting mixture was extracted with ethyl acetate. The combined organic layers were washed with brine, dried over $Na_2SO_4$, filtered and concentrated under reduced pressure. The resulting residue was purified by silica gel chromatography (1-17% ethyl acetate/petroleum ether) to give the title compound.

Step 2: (S)-(3-chloro-2,4-difluorophenyl)(trans-3-(trifluoromethyl)cyclobutyl)methanamine hydrochloride To a solution of (R)-N-((S)-(3-chloro-2,4-difluorophenyl)(trans-3-(trifluoromethyl)-cyclobutyl)-methyl)-2-methyl propane-2-sulfinamide (63 g, 0.16 mol) in $CH_2Cl_2$ (0.63 L) at 0° C. was added HCl in ethyl acetate (4 M, 0.26 L, 3.1 mol). The reaction mixture was stirred at 0° C. for 2 hours and then concentrated under reduced pressure. The resulting residue was treated with methyl tert-butyl ether (100 mL), stirred 20 minutes at 25° C. and filtered to give the title compound.

Intermediate 2

(S)-(3-chloro-2,4-difluorophenyl)(trans-3-(trifluoromethyl)cyclobutyl)methanamine

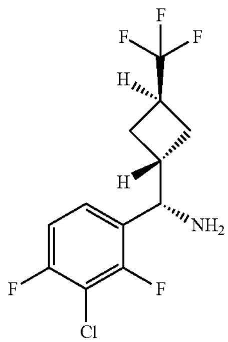 [SMILES: N[C@H](c1ccc(F)c(Cl)c1F)[C@H]1C[C@@H](C(F)(F)F)C1]

(S)-(3-chloro-2,4-difluorophenyl)(trans-3-(trifluoromethyl)cyclobutyl)methanamine The free base (S)-(3-chloro-2,4-difluorophenyl)(trans-3-(trifluoromethyl)-cyclobutyl)-methanamine is formed by washing a solution of (S)-(3-chloro-2,4-difluorophenyl)(trans-3-(trifluoromethyl)-cyclobutyl)methanamine hydrochloride in an organic solvent such as ethyl acetate with a basic aqueous solution such as potassium carbonate, sodium bicarbonate or sodium hydroxide. The resulting organic layer is dried over $Na_2SO_4$, filtered and concentrated under reduced pressure to give (S)-(3-chloro-2,4-difluorophenyl)(trans-3-(trifluoromethyl)-cyclobutyl)methanamine.

Intermediate 3

(S)-(3-chloro-2,4-difluorophenyl)(trans-3-(trifluoromethyl)cyclobutyl)methanamine oxalate

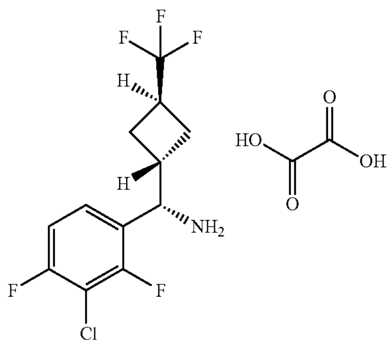 [SMILES: N[C@H](c1ccc(F)c(Cl)c1F)[C@H]1C[C@@H](C(F)(F)F)C1 ; O=C(O)C(=O)O]

To a solution of (S)-(3-chloro-2,4-difluorophenyl)(trans-3-(trifluoromethyl)cyclobutyl)-methanamine (0.50 g, 1.7 mmol) in THF (1.5 mL) at 25° C. was added a solution of oxalic acid (0.15 g, 1.7 mmol) in THF (1.5 mL). After 12 hours, the resulting mixture was filtered to give the title compound.

Example 59A and 59B (R or S)-N-((S)-(3-chloro-2,4-difluorophenyl)((trans)-3-(trifluoromethyl)cyclobutyl)methyl)-2-methyl-3-oxopiperazine-5,5,6,6-d4-1-carboxamide (59A) and (S or R)-N-((S)-(3-chloro-2,4-difluorophenyl)((trans)-3-(trifluoromethyl)cyclobutyl)methyl)-2-methyl-3-oxopiperazine-5,5,6,6-d4-1-carboxamide (59B)

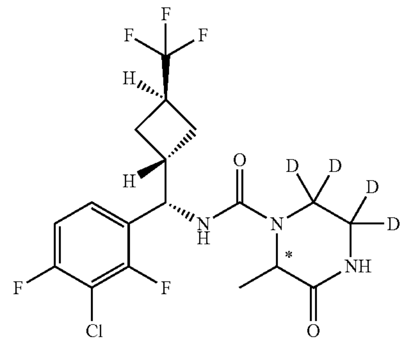 [SMILES: [2H]C1([2H])NC(=O)C(C)N(C(=O)N[C@H](c2ccc(F)c(Cl)c2F)[C@H]2C[C@@H](C(F)(F)F)C2)C1([2H])[2H]]

Step 1: methyl (S)-2-bromopropanoate To a solution of (S)-2-bromopropanoic acid (4.0 g, 26 mmol) in MeOH (25 ml) and DCM (50 ml) at 15° C. was added (diazomethyl) trimethylsilane (45 ml, 90 mmol, 2 M in hexane). The resulting mixture was stirred at 15° C. for 1 hour and then concentrated under reduced pressure to give the title compound which was used in the next step without further purification. 1H NMR (500 MHz, $CDCl_3$) δ (ppm): 4.39 (q, J=7.0 Hz, 1H), 3.79 (s, 3H), 1.84 (d, J=7.0 Hz, 3H).

Step 2: 3-methylpiperazin-2-one-5,5,6,6-d4 To a solution of ethane-d4-1,2-diamine (0.30 g, 4.7 mmol) in dioxane (5.5 mL) at 15° C. were added sodium hydrogencarbonate (0.59 g, 7.0 mmol) and (S)-2-bromopropanoate (0.39 g, 2.3 mmol). The mixture was stirred at 15° C. for 1 hour, then at 50° C. for 24 hours. Then the mixture was concentrated under reduced pressure, and the resulting residue was purified by silica gel chromatography, eluting with 10/1/0.1 DCM/MeOH/$NH_3 \cdot H_2O$ to give the title compound. 1H NMR (500 MHz, CD3OD) δ (ppm): 3.40-3.42 (m, 1H), 1.33-13.35 (m, 3H).

Step 3: Example 59 A mixture of CDI (0.38 g, 2.3 mmol) and (S)-(3-chloro-2,4-difluorophenyl)-((trans)-3-(trifluoromethyl)cyclobutyl)methanamine oxalate (Intermediate 3, 0.35 g, 1.2 mmol) in DMF (4 mL) was stirred at 25° C. for 5 minutes, then 3-methylpiperazin-2-one-5,5,6,6-d4 (0.19 g, 1.6 mmol) was added. The resulting mixture was stirred at 25° C. for 30 minutes, and then filtered. The filtrate was purified by reverse phase HPLC (Phenomenex Synergi C18 column, 65:35 to 35:65; water containing 10 mM $NH_4HCO_3$:acetonitrile) to give a residue, that was further separated by SFC (Daicel Chiralpak AD-H column, 20% IPA as cosolvent) to give Examples 59A (first eluted peak) and 59B (second eluted peak).

Example 59A: LRMS m/z (M+H): calculated 444.1, observed 444.1. 1H NMR (400 MHz, CD3OD) δ (ppm): 7.29-7.35 (m, 1H), 7.08-7.12 (m, 1H), 5.08 (d, J=11.2 Hz, 1H), 4.46-4.52 (m, 1H), 3.01-3.05 (m, 1H), 2.90 (s, 1H), 2.24-2.38 (m, 1H), 2.20-2.22 (m, 1H), 1.94-2.04 (m, 2H), 1.37 (d, J=8.8 Hz, 3H).

Example 59B: LRMS m/z (M+H): calculated 444.1, observed 444.2. 1H NMR (400 MHz, CD3OD) δ (ppm):

7.31-7.35 (m, 1H), 7.08-7.12 (m, 1H), 5.10 (d, J=11.5 Hz, 1H), 4.52 (q, J=7.0 Hz, 1H), 3.00-3.08 (m, 1H), 2.81-2.95 (m, 1H), 2.34-2.40 (m, 1H), 2.16-2.27 (m, 1H), 2.00-2.09 (m, 1H), 1.91-2.00 (m, 1H), 1.38 (d, J=7.0 Hz, 3H).

Examples 60A and 60B (2R)-N-((1(R or S))-(4-fluoro-3-(trifluoromethyl) phenyl)-trans-(6-(trifluoromethyl)tetrahydro-2H-pyran-3-yl)methyl)-2-methyl-3-oxopiperazine-1-carboxamide (60A) and (2R)-N-((1(R or S))-(4-fluoro-3-(trifluoromethyl)phenyl)-trans-(6-(trifluoromethyl)tetrahydro-2H-pyran-3-yl)methyl)-2-methyl-3-oxopiperazine-1-carboxamide (60B)

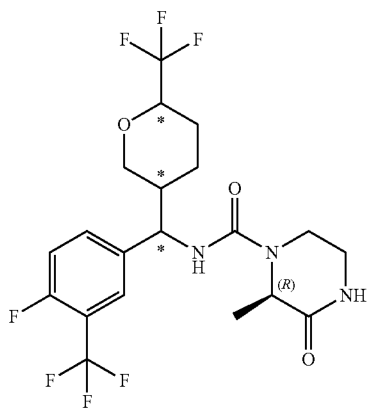

Step 1: (R)—N-((5-fluoro-6-(trifluoromethyl)pyridin-2-yl)(6-(trifluoromethyl)tetrahydro-2H-pyran-3-yl)methyl)-2-methylpropane-2-sulfinamide To a solution of 6-bromo-3-fluoro-2-(trifluoromethyl)-pyridine (0.26 g, 1.1 mmol) in dry THF (5 mL) at 0° C. was added dropwise iPrMgCl (0.50 ml, 1.0 mmol). The mixture was stirred at 0° C. for 25 minutes and then transferred dropwise to a 0° C. solution of (R)-2-methyl-N-((E)-(6-(trifluoromethyl)tetrahydro-2H-pyran-3-yl)methylene)propane-2-sulfinamide (0.15 g, 0.53 mmol) in dry THF (8 ml). The resulting mixture was gradually allowed to warm to rt and then stirred for 18 h. Then water was added and the resulting mixture was extracted with EtOAc (3×10 mL). The combined organic layers were dried over $Na_2SO_4$, filtered and evaporated under reduced pressure. The resulting crude residue was purified by reverse phase HPLC (85:15 to 5:95; water containing 0.1% TFA: acetonitrile containing 0.1% TFA) to give the title compound. LRMS m/z (M+H): calculated 451.1, observed 451.3.

Step 2: (5-fluoro-6-(trifluoromethyl)pyridin-2-yl)-trans-(6-(trifluoromethyl)tetrahydro-2H-pyran-3-yl)methanamine hydrochloride To a stirred solution of a trans mixture (R)—N-((5-fluoro-6-(trifluoromethyl)pyridin-2-yl)(6-(trifluoromethyl)tetrahydro-2H-pyran-3-yl)methyl)-2-methylpropane-2-sulfinamide (0.20 g, 0.44 mmol) in MeOH (5 ml) at 20° C. was added HCl (2.2 ml, 6.7 mmol). The resulting mixture was stirred at 20° C. for 1 hour. Then the solvent was evaporated under reduced pressure, and the resulting crude residue was purified by reverse phase HPLC (90:10 to 5:95; water containing 0.1% TFA:acetonitrile containing 0.1% TFA) to give the title compound. LRMS m/z (M+H): calculated 347.1, observed 347.3.

Step 3: Examples 60A and 60B To a stirred solution of (5-fluoro-6-(trifluoromethyl)pyridin-2-yl)(6-(trifluoromethyl)tetrahydro-2H-pyran-3-yl)methanamine hydrochloride (13 mg, 0.035 mmol) in DMF (1 ml) at 20° C. was added CDI (7.1 mg, 0.044 mmol). The mixture was stirred at 20° C. for 30 minutes, and then (R)-3-methylpiperazin-2-one (4.0 mg, 0.035 mmol) was added. The resulting mixture was stirred at 20° C. for 2 hours and then purified by reverse phase HPLC (95:5 to 5:95; water containing 0.1% TFA:acetonitrile containing 0.1% TFA) to give a mixture of isomers, which was further separated by SFC (Chiral ART Cellulose-SJ column, 3 cm×25 cm, 5 um, 10% MeOH (0.1% DEA) @ 80 g/min and 100 Bar) to give Examples 60A (first eluted peak) and 60B (second eluted peak).

Example 60A: LRMS m/z (M+H): calculated 486.4, observed 487.4. $^1$H NMR (500 MHz, Methanol-d4) δ (ppm): 7.86-7.77 (m, 1H), 7.68 (dd, J=8.6, 3.5 Hz, 1H), 4.71 (d, J=10.0 Hz, 1H), 4.52 (q, J=6.7, 6.3 Hz, 1H), 4.29 (d, J=10.7 Hz, 1H), 4.02 (d, J=13.4 Hz, 1H), 3.80 (d, J=6.7 Hz, 1H), 3.48-3.37 (m, 2H), 3.27-3.15 (m, 2H), 2.97 (d, J=7.3 Hz, 1H), 2.34-2.23 (m, 1H), 1.78 (d, J=12.9 Hz, 1H), 1.52-1.44 (m, 1H), 1.41-1.35 (m, 4H).

Example 60B: LRMS m/z (M+H): calculated 486.4, observed 487.4. $^1$H NMR (500 MHz, Methanol-d4) δ (ppm): 7.87-7.76 (m, 1H), 7.68 (dd, J=8.7, 3.5 Hz, 1H), 4.76 (d, J=9.2 Hz, 1H), 4.54 (q, J=7.0 Hz, 1H), 4.08-4.01 (m, 1H), 3.85-3.75 (m, 1H), 3.66-3.55 (m, 1H), 3.38-3.32 (m, 2H), 3.29-3.19 (m, 2H), 2.33-2.23 (m, 1H), 2.15 (d, J=13.0 Hz, 1H), 1.93-1.84 (m, 1H), 1.58 (qd, J=13.0, 3.8 Hz, 1H), 1.46 (td, J=12.5, 3.6 Hz, 1H), 1.41 (d, J=7.1 Hz, 3H).

Example 61

(S)-N-((S)-(3-chloro-2,4-difluorophenyl)((trans)-3-(trifluoromethyl)cyclobutyl)methyl)-2-(fluoromethyl)-3-oxopiperazine-2-d-1-carboxamide

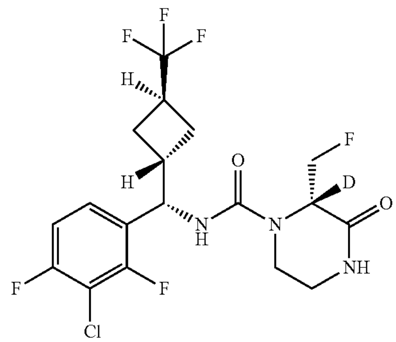 [SMILES: [2H][C@@]1(CF)C(=O)NCCN1C(=O)N[C@H](c1ccc(F)c(Cl)c1F)[C@H]1C[C@@H](C(F)(F)F)C1]

To a solution of (S)-(3-chloro-2,4-difluorophenyl) ((trans)-3-(trifluoromethyl)-cyclobutyl)-methanamine oxalate (Intermediate 3, 50 mg, 0.17 mmol) in DMF (1 ml) at 25° C. was added CDI (54 mg, 0.33 mmol). The mixture was stirred at 25° C. for 30 minutes, and then (S)-3-(fluoromethyl)piperazin-2-one-3-d (27 mg, 0.20 mmol) was added. The reaction mixture was stirred at 25° C. for 1 hour, then purified by reverse phase HPLC (Boston Green ODS column, (58:42 to 28:72; water (0.1% TFA):MeCN) to give the title compound. LRMS m/z (M+Na): calculated 481.1, observed 481.0. $^1$H NMR δ (ppm) (400 MHz, Chloroform-d): 7.28-7.32 (m, 1H), 7.07-7.12 (m, 1H), 5.08 (d, J=11.2 Hz, 1H), 4.91 (dd, J=48.0, 9.2 Hz, 1H), 4.65 (dd, J=48.0, 10.0 Hz, 1H), 4.03-4.07 (m, 1H), 3.27-3.33 (m, 1H), 2.85-

2.87 (m, 1H), 2.37-2.38 (m, 1H), 2.23-2.24 (m, 1H), 2.02-2.04 (m, 1H), 1.94-1.98 (m, 2H).

Example 62A, 62B, 62C, 62D (R)-N-((R or S)-(3-chloro-2,4-difluorophenyl)((R or S)-chroman-3-yl)methyl)-2-methyl-3-oxopiperazine-1-carboxamide (62A), (R)-N-((R or S)-(3-chloro-2,4-difluorophenyl)((S or R)-chroman-3-yl)methyl)-2-methyl-3-oxopiperazine-1-carboxamide (62B), (R)-N-((S or R)-(3-chloro-2,4-difluorophenyl)((R or S)-chroman-3-yl)methyl)-2-methyl-3-oxopiperazine-1-carboxamide (62C), (R)-N-((S or R)-(3-chloro-2,4-difluorophenyl)((S or R)-chroman-3-yl)methyl)-2-methyl-3-oxopiperazine-1-carboxamide (62D)

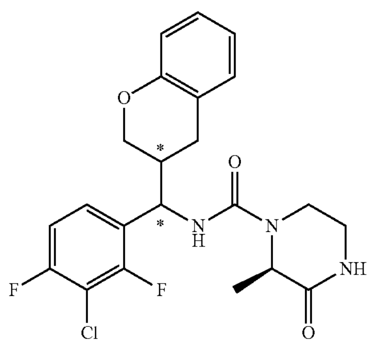 [SMILES: C[C@@H]1C(=O)NCCN1C(=O)NC(c1ccc(F)c(Cl)c1F)C1COc2ccccc2C1]

Step 1: N-methoxy-N-methylchromane-3-carboxamide To a solution chromane-3-carboxylic acid (1.0 g, 5.6 mmol) in DMF (20 ml) at 0° C. were added DIEA (2.9 ml, 17 mmol) and HATU (4.3 g, 11 mmol). The resulting mixture was stirred at 0° C. for 30 minutes, then N,O-dimethylhydroxylamine hydrochloride (0.82 g, 8.4 mmol) was added. The resulting mixture was stirred at 20° C. for 2 hours. Then the solvent was removed under reduced pressure and the resulting residue was dissolved in water (20 mL) and EtOAc (15 mL). The organic layer was separated, and the aqueous layer was extracted with EtOAc (10 ml×3). The combined organic layers were washed with brine, dried over anhydrous $Na_2SO_4$, filtered and concentrated under reduced pressure. The resulting residue was purified by silica gel chromatography, eluting with 50% EtOAc/hexane to give the title compound. LRMS m/z (M+H): calculated 222.1, observed 222.3.

Step 2: (3-chloro-2,4-difluorophenyl)(chroman-3-yl) methanone To a solution of 1-bromo-3-chloro-2,4-difluorobenzene (0.99 g, 4.3 mmol) in THF (4 ml) at 0° C. was added i-PrMgCl (2 M in THF, 2.0 ml, 4.1 mmol). The mixture was warmed to 18° C. and stirred for 2 h. To the reaction mixture was added a solution of N-methoxy-N-methylchromane-3-carboxamide (0.30 g, 1.4 mmol) in THF (2 ml) at 18° C. The reaction was stirred at 18° C. for 2 h, then quenched with saturated $NH_4Cl$ solution (10 mL) and extracted with EtOAc (10 mL×2). The combined organic layers were washed with brine (15 mL), dried over anhydrous sodium sulfate, filtered and concentrated under reduced pressure. The resulting residue was purified by preparative TLC (eluting with petroleum ether/ethyl acetate=10/1) to give the title compound. LRMS m/z (M+H): calculated 309.0, observed 309.2.

Step 3: (3-chloro-2,4-difluorophenyl)(chroman-3-yl) methanamine Ammonia acetate (0.64 g, 8.3 mmol) and $NaBH_3CN$ (69 mg, 1.1 mmol) were added to a solution of (3-chloro-2,4-difluoro-phenyl)(chroman-3-yl)methanone (0.17 g, 0.55 mmol) in EtOH (3 ml) and acetic acid (0.6 ml) in a microwave vial. The reaction mixture was stirred and heated at 130° C. for 10 minutes in a microwave reactor. The reaction mixture was concentrated to remove most of the EtOH, treated with 2 N NaOH until the pH>10. The mixture was then extracted with EtOAc (2×20 mL). The combined organic layers were dried over $Na_2SO_4$, filtered, and concentrated under reduced pressure to give the title compound. LRMS m/z (M+H): calculated 310.1, observed 310.2.

Step 4: Example 62A, 62B, 62C, 62D To a solution of (3-chloro-2,4-difluorophenyl)(chroman-3-yl)methanamine (0.15 g) in DMF (1 ml) at 18° C. was added CDI (157 mg, 0.969 mmol). The resulting mixture was stirred at 18° C. for 10 minutes, then a solution of (R)-3-methylpiperazin-2-one (66 mg, 0.58 mmol) in DMF (0.5 ml) was added. The reaction mixture was stirred at 18° C. for 1 h and then purified by reverse phase HPLC (Boston Green ODS, (70:30 to 40:60; water (0.1% TFA):MeCN), to give 2 peaks, which were further purified by reverse phase HPLC (Phenomenex Synergi C18, 57:43 to 37:63 water (0.1% TFA):MeCN) to give the title compounds.

Example 62A: LRMS m/z (M+H): calculated 450.1, observed 450.1. 1H NMR (500 MHz, METHANOL-d4) δ (ppm): 7.38-7.44 (m, 1H), 7.02-7.18 (m, 4H), 6.80-6.85 (m, 1H), 6.72 (d, J=8.09 Hz, 1H), 4.95-5.00 (m, 1H), 4.52 (q, J=7.02 Hz, 1H), 4.02 (br d, J=13.58 Hz, 1H), 3.88 (br d, J=9.61 Hz, 1H), 3.69 (dd, J=7.48, 10.83 Hz, 1H), 3.32-3.37 (m, 1H), 3.19-3.27 (m, 2H), 3.10 (br dd, J=5.19, 16.33 Hz, 1H), 2.80 (dd, J=7.40, 16.40 Hz, 1H), 2.59 (dt, J=2.75, 7.63 Hz, 1H), 1.38 (d, J=7.02 Hz, 3H).

Example 62B: LRMS m/z (M+H): calculated 450.1, observed 450.2. 1H NMR (500 MHz, METHANOL-d4) δ (ppm): 7.35-7.41 (m, 1H), 7.09-7.15 (m, 2H), 7.04 (t, J=7.78 Hz, 1H), 6.90 (d, J=7.48 Hz, 1H), 6.73-6.81 (m, 2H), 5.00 (dd, J=8.16, 10.76 Hz, 1H), 4.56 (q, J=7.07 Hz, 1H), 4.40 (br d, J=10.83 Hz, 1H), 3.97-4.08 (m, 2H), 3.34 (br d, J=3.51 Hz, 1H), 3.19-3.29 (m, 3H), 2.56-2.63 (m, 1H), 2.47-2.54 (m, 1H), 2.35-2.43 (m, 1H), 2.35-2.43 (m, 1H), 1.40 (d, J=7.02 Hz, 3H).

Example 62C: LRMS m/z (M+H): calculated 450.1, observed 450.1. 1H NMR (500 MHz, METHANOL-d4) δ (ppm): 7.35 (dt, J=6.18, 8.20 Hz, 1H), 7.13 (dt, J=1.53, 8.62 Hz, 1H), 7.04 (t, J=7.63 Hz, 1H), 6.89 (br d, J=7.17 Hz, 1H), 6.73-6.81 (m, 2H), 4.98 (br d, J=10.99 Hz, 1H), 4.50 (q, J=6.97 Hz, 1H), 4.39-4.44 (m, 1H), 3.98-4.07 (m, 2H), 3.33-3.37 (m, 1H), 3.16-3.28 (m, 3H), 2.61 (br d, J=2.44 Hz, 1H), 2.47-2.53 (m, 1H), 2.35-2.43 (m, 1H), 1.38 (d, J=7.02 Hz, 3H)

Example 62D: LRMS m/z (M+H): calculated 450.1, observed 450.2. 1H NMR (500 MHz, METHANOL-d4) δ (ppm): 7.42 (dt, J=6.10, 8.24 Hz, 1H), 7.14 (dt, J=1.53, 8.62 Hz, 1H), 7.02-7.09 (m, 2H), 6.83 (dt, J=0.99, 7.44 Hz, 1H), 6.73 (d, J=8.09 Hz, 1H), 4.98 (d, J=10.83 Hz, 1H), 4.55 (q, J=7.02 Hz, 1H), 3.98-4.07 (m, 1H), 3.89 (dd, J=1.37, 10.99 Hz, 1H), 3.69 (dd, J=7.55, 10.91 Hz, 1H), 3.32-3.36 (m, 1H), 3.18-3.27 (m, 2H), 3.09 (dd, J=5.19, 16.33 Hz, 1H), 2.81 (dd, J=7.48, 16.33 Hz, 1H), 2.52-2.63 (m, 1H), 1.42 (d, J=7.02 Hz, 3H).

Example 63A and 63B (R or S)-N-((S)-(3-chloro-2,4-difluorophenyl)((trans)-3-(trifluoromethyl)cyclobutyl)methyl)-3-oxo-2-(trifluoromethyl)piperazine-1-carboxamide (63A) and (S or R)-N-((S)-(3-chloro-2,4-difluoro-phenyl)((trans)-3-(trifluoromethyl)cyclobutyl)methyl)-3-oxo-2-(trifluoromethyl)piperazine-1-carboxamide (63B)

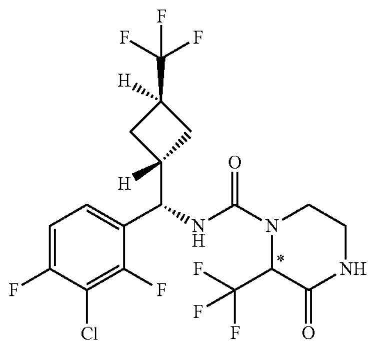 [SMILES: O=C1NCCN(C(=O)N[C@H](c2ccc(F)c(Cl)c2F)[C@H]2C[C@@H](C(F)(F)F)C2)C1C(F)(F)F]

Step 1: ethyl 2-(((benzyloxy)carbonyl)amino)-3,3,3-trifluoropropanoate To a solution of ethyl 2-amino-3,3,3-trifluoropropanoate hydrochloride (0.50 g, 2.4 mmol) and $NaHCO_3$ (0.37 g, 9.6 mmol) in DCM (3 ml) and water (2 ml) at 0° C. was added benzyl chloroformate (0.41 ml, 2.9 mmol). The reaction mixture stirred for 12 hours at 20° C., then the mixture was diluted with water and extracted with EtOAc. The combined organic layers were washed with water, brine, dried over anhydrous $Na_2SO_4$, filtered, and concentrated under reduced pressure. The resulting residue was purified by flash silica gel chromatography, eluting with 30% ethyl acetate/petroleum ether to give the title compound. LRMS m/z (M+H): calculated 306.1, observed 306.2.

Step 2: benzyl (3-((2,2-dimethoxyethyl)amino)-1,1,1-trifluoro-3-oxopropan-2-yl)carbamate To a solution of 2,2-dimethoxyethan-1-amine (0.52 g, 4.9 mmol) in DCM (6.5 ml) at 0° C. was added trimethylaluminum (2.5 ml, 4.9 mmol). The reaction mixture was stirred for 10 minutes at 0° C., then a solution of ethyl 2-(((benzyloxy)carbonyl)amino)-3,3,3-trifluoropropanoate (0.50 g, 1.6 mmol) in DCM (6.5 ml) was added. The reaction mixture was stirred for 3 hours at 20° C., then quenched with 0.1N HCl (10 ml) and extracted with $CH_2Cl_2$ (2×10 mL). The combined organic layers were dried over anhydrous $Na_2SO_4$, filtered and concentrated to give the title compound. LRMS m/z ($M-OCH_3$): calculated 333.1, observed 333.2.

Step 3: benzyl 3-oxo-2-(trifluoromethyl)-3,4-dihydropyrazine-1(2H)-carboxylate To a solution of TFA (3.5 ml) and water (1.5 ml) at 5° C. was added benzyl(3-((2,2-dimethoxyethyl)amino)-1,1,1-trifluoro-3-oxopropan-2-yl)carbamate (0.60 g). The reaction mixture was stirred at 20° C. for 12 h. Then the mixture was slowly added to stirring cooled (5° C.) saturated aqueous $Na_2CO_3$ (20 mL) to keep the pH>8. The mixture was then extracted with EtOAc (20 mL×2). The combined organic layers were dried over by $Na_2SO_4$, filtered and concentrated. The resulting residue was purified by silica gel chromatography, eluting with petroleum ether/ethyl acetate from 1/1 to 0/1 to give the title compound. $^1H$ NMR (400 MHz, CD30D) δ (ppm): 7.30-7.44 (m, 5H), 6.32-6.43 (m, 1H), 5.55-5.74 (m, 1H), 5.14-5.28 (m, 2H), 4.66-4.76 (m, 1H), 3.68-3.85 (m, 2H).

Step 4: 3-(trifluoromethyl)piperazin-2-one A solution of benzyl 3-oxo-2-(trifluoromethyl)-3,4-dihydropyrazine-1(2H)-carboxylate (0.16 g, 0.53 mmol) in MeOH (8 ml) was pumped through an H-Cube™ flow hydrogenator (30° C. at 1 MPa) fitted with a 5 mol % Pd/C catalyst column at a flow rate of 1 ml/min. The eluted phase was concentrated under reduced pressure to give title compound. $^1H$ NMR (500 MHz, $CD_3OD$) δ 4.03-4.08 (m, 2H), 3.07-3.09 (m, 2H), 2.90-3.02 (m, 2H).

Step 5: Examples 63A and 63B To a stirred solution of (S)-(3-chloro-2,4-difluorophenyl)-((trans)-3-(trifluoromethyl)cyclobutyl)methanamine oxalate (Intermediate 3, 50 mg, 0.17 mmol) in DMF (0.5 ml) at 20° C. was added di(1H-imidazol-1-yl)methanone (60 mg, 0.37 mmol). The reaction mixture was stirred at 20° C. for 10 minutes, then 3-(trifluoromethyl)piperazin-2-one (51 mg, 0.30 mmol) was added. The mixture was stirred at 20° C. for 0.5 hours, and then purified by reverse phase HPLC (59:41 to 39:61; water containing 0.1% TFA:acetonitrile) to give a mixture of isomers, which was further separated by SFC (DAICEL CHIRALPAK AD-H, 250 mm×30 mm, 5 um, 20% IPA) to give Examples 63A (first eluted peak) and 63B (second eluted peak).

Example 63A: LRMS m/z (M+H): calculated 494.1, observed 494.1. $^1H$ NMR (400 MHz, $CD_3OD$) δ (ppm): 7.25-7.38 (m, 1H), 7.10 (d, J=8.8 Hz, 1H), 5.30 (q, J=8.4 Hz, 1H), 5.12 (d, J=11.2 Hz, 1H), 4.04 (d, J=12.8 Hz, 1H), 3.32-3.45 (m, 3H), 2.97-3.14 (m, 1H), 2.92 (s, 1H), 2.38 (s, 1H), 2.15-2.30 (m, 1H), 1.89-2.11 (m, 2H).

Example 63B: LRMS m/z (M+H): calculated 494.1, observed 494.1. $^1H$ NMR (400 MHz, $CD_3OD$) δ (ppm): 7.29-7.37 (m, 1H), 7.22 (d, J=6.8 Hz, 1H), 7.04-7.16 (m, 1H), 5.26-5.38 (m, 1H), 5.03-5.12 (m, 1H), 4.06 (d, J=10.4 Hz, 1H), 3.31-3.43 (m, 3H), 3.03 (s, 1H), 2.89 (s, 1H), 2.36 (s, 1H), 2.15-2.27 (m, 1H), 1.94-2.08 (m, 2H).

Example 64

(R)-N-((S)-(3-chloro-2,4-difluorophenyl)((trans)-3-(trifluoromethyl)cyclobutyl)methyl)-2-(hydroxymethyl)-3-oxopiperazine-1-carboxamide

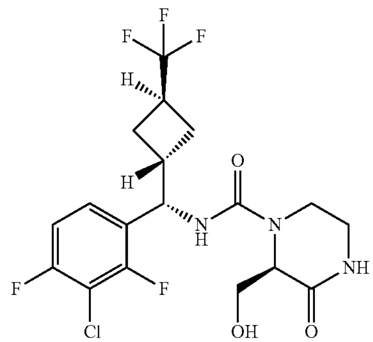 [SMILES: O=C1NCCN(C(=O)N[C@H](c2ccc(F)c(Cl)c2F)[C@H]2C[C@@H](C(F)(F)F)C2)[C@@H]1CO]

Step 1: Benzyl (R)-(1-((2,2-dimethoxyethyl)amino)-3-hydroxy-1-oxopropan-2-yl)carbamate To a solution of ((benzyloxy)carbonyl)-D-serine (3.0 g, 13 mmol), 2,2-dimethoxyethanamine (2.0 g, 19 mmol) and 4-methylmorpholine (2.2 ml, 20 mmol) in MeCN (30 ml) at 15° C. was added propylphosphonic anhydride (16 g, 25 mmol, 50% in EtOAc solution). The reaction mixture was stirred at 15° C. for 30 minutes, then the reaction mixture was quenched with brine (20 mL) and extracted with EtOAc (20 mL×3). The combined organic layers were washed with aqueous HCl (20 mL, 1 N), saturated aqueous $NaHCO_3$ (80 mL), dried over $Na_2SO_4$, and filtered. The filtrate was concentrated under reduced pressure to give the title compound, which was used in the next step without further purification.

Step 2: benzyl (R)-2-(hydroxymethyl)-3-oxo-3,4-dihydropyrazine-1(2H)-carboxylate To a mixture of TFA (7.0 ml) and water (3.0 ml) at 5° C. was added benzyl (R)-(1-((2,2-dimethoxy-ethyl)amino)-3-hydroxy-1-oxopropan-2-yl)carbamate (1.5 g). The reaction was stirred at 15° C. for 12 h, then the reaction mixture was added slowly to stirring cooled (5° C.) saturated aqueous $Na_2CO_3$ (20 mL) to keep the pH>8. The mixture was extracted with EtOAc (20 mL×2). The combined organic layers were dried over by $Na_2SO_4$, filtered and concentrated under reduced pressure. The resulting residue was purified by silica gel chromatography, eluting with 50-100% ethyl acetate/petroleum ether gradient to give the title compound. $^1H$ NMR (400 MHz, $CD_3OD$) δ (ppm): 7.25-7.47 (m, 5H), 6.28-6.44 (m, 1H), 5.54-5.77 (m, 1H), 5.18-5.28 (m, 2H), 4.65-4.77 (m, 1H), 3.68-3.86 (m, 2H).

Step 3: (R)-3-(hydroxymethyl)piperazin-2-one A solution of benzyl (R)-2-(hydroxymethyl)-3-oxo-3,4-dihydropyrazine-1(2H)-carboxylate (0.50 g, 1.9 mmol) in MeOH (8 ml) was pumped through an H-Cube™ flow hydrogenator (30° C. at 1 MPa) fitted with a 5 mol % Pd/C catalyst column at a flow rate of 1 ml/min. The eluted phase was concentrated under reduced pressure to give the title compound. $^1H$ NMR (400 MHz, $CD_3OD$) δ (ppm): 3.89-3.97 (m, 1H), 3.77-3.86 (m, 1H), 3.47 (d, J=9.6 Hz, 1H), 3.34-3.43 (m, 1H), 3.28 (t, J=3.6 Hz, 1H), 3.19 (d, J=12.8 Hz, 1H), 2.90-3.12 (m, 1H).

Step 4: Example 64 To a stirred solution of (S)-(3-chloro-2,4-difluorophenyl)((1r,3S)-3-(trifluoromethyl)cyclobutyl) methanamine oxalate (Intermediate 3, 30 mg, 0.10 mmol) in DMF (1 ml) at 20° C. was added di(1H-imidazol-1-yl) methanone (24 mg, 0.15 mmol). The reaction mixture was stirred at 20° C. for 10 minutes, then (R)-3-(hydroxymethyl) piperazin-2-one (17 mg, 0.13 mmol) was added. The reaction mixture was stirred at 20° C. for 30 minutes, then filtered and purified by reverse phase HPLC (Phenomenex Synergi C18, eluting 60:40 to 40:60; water containing 0.10% TFA:acetonitrile) to give the title compound. LRMS m/z (M+H): calculated 456.1, observed 456.1. $^1H$ NMR (400 MHz, $CD_3OD$) δ (ppm): 7.32 (d, J=12.4 Hz, 1H), 7.09 (d, J=8.8 Hz, 1H), 5.04 (d, J=10.8 Hz, 1H), 4.46 (d, J=9.6 Hz, 1H), 4.00-4.08 (m, 1H), 3.90-4.00 (m, 2H), 3.32-3.44 (m, 2H), 3.23-3.29 (m, 1H), 2.92-3.11 (m, 1H), 2.78-2.91 (m, 1H), 2.30-2.43 (m, 1H), 2.15-2.28 (m, 1H), 1.90-2.12 (m, 2H).

Example of a Pharmaceutical Composition

As a specific embodiment of an oral pharmaceutical composition, a 100 mg potency tablet is composed of 100 mg of any one of the Examples, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

Biological Assays

Qube® Assay Experimental Procedure

Compounds were tested on human NaV1.8 and NaV1.5 channels stably expressed in human embryo kidney (HEK) 293 cells. Sodium current measurements on Qube® were conducted as follows: automated 384-well patch-clamp assays on the Qube® platform (Sophion Biosciences) were used to measure the inhibition of sodium flow through human NaV1.8 and NaV1.5 channels. Whole-cell voltage-clamp recordings were performed in QChips® (Sophion Biosciences) at room temperature. NaV1.8 current measurements on Qube® were obtained as follows: NaV1.8 currents were elicited with a 10 second 1 Hertz (Hz) pulse train from a holding potential of −90 millivolts (mV), delivered to the cells once per minute in the control condition (DMSO only) and after compound addition. The 1 hertz pulse train stimulation consisted of ten test pulses to 10 millivolt (mV) for 20 milliseconds (ms), each of which was followed by a 980 millisecond repolarization to −67 millivolts. At the end of the 10 second pulse train stimulation, a 5 second hyperpolarization step to −100 millivolt (mV) was used to recover NaV1.8 from fast inactivation. The peak currents elicited by the 1st and 10th test pulses were used to determine $IC_{50}$ values for resting inhibition and inactivated state inhibition. NaV1.5 current measurements on Qube® were obtained as follows: NaV1.5 currents were elicited with a 20 second 3 Hertz pulse train in the control condition (DMSO only) and after compound addition. The pulse train consisted of sixty 20 millisecond test pulses to 0 millivolt from a holding potential of −80 millivolt (mV). The average peak currents elicited by the last 3 test pulses were used to determine IC50 values for NaV1.5 inhibition.

The following buffers were used for the Qube® recordings: External buffer for NaV1.8 Qube® recording: 150 NaCl, 2 CaCl2, 5 KCl, 1 Mg Cl2, 10 HEPES, 12 Dextrose; External buffer for Qube® NaV1.5 recording: 120 N-Methyl-D-Glucamine, 40 NaCl, 1 KCl, 2.7 CaCl2, 5 HEPES, 0.5 MgCl2; and Internal buffer for Qube® recording: 120 CsF, 30 CsCl, 10 EGTA, 5 HEPES, 5 NaF, 2 MgCl2.

For all Qube® experiments offline analysis was used to determine percent inhibition as a function of drug concentration. $IC_{50}$ values were determined by fitting to the Hill equation. The compounds of structural formula I have Nav1.8 $IC_{50}$ values in the Qube® Assay of less than 5 micromolar. Specific $IC_{50}$ values of the compounds of Examples 1A-58D in the Qube® Assay are listed in Table I.

TABLE I $IC_{50}$ values (nM) for Examples in the Nav1.8 Qube ® Assay

| Example | $IC_{50}$ (nM) | Example | $IC_{50}$ (nM) |
|---|---|---|---|
| 1A | 3.5 | 36B | 74.61 |
| 1B | 183.1 | 36C | 58.1 |
| 2A | 65.5 | 36D | 3.99 |
| 2B | 410 | 37A | 108.5 |
| 3A | 14.8 | 37B | 145.1 |
| 3B | 148.2 | 37C | 27.19 |
| 4A | 89.3 | 37D | 1.99 |
| 4B | 287.8 | 38A | 145.5 |
| 5A | 40.9 | 38B | 158.4 |
| 5B | 4.2 | 38C | 87.1 |
| 6A | 232.1 | 38D | 17.9 |
| 6B | 35.4 | 39A | 816.2 |
| 7A | 112.3 | 39B | 915.9 |
| 7B | 11.7 | 39C | 48.5 |
| 8A | 244.4 | 39D | 8.1 |
| 8B | 13.2 | 40A | 11730 |
| 9A | 46.8 | 40B | 14460 |
| 9B | 0.8 | 40C | 362.3 |
| 10A | 311 | 40D | 108.5 |
| 10B | 3.87 | 41A | 31.6 |
| 11A | 870.5 | 41B | 1180 |
| 11B | 4.14 | 41C | 143 |

TABLE I-continued

| IC$_{50}$ values (nM) for Examples in the Nav1.8 Qube ® Assay | | | |
|---|---|---|---|
| Example | IC$_{50}$ (nM) | Example | IC$_{50}$ (nM) |
| 12A | 342.9 | 41D | 1064 |
| 12B | 11.5 | 42A | 321.1 |
| 13A | 13.4 | 42B | 2832 |
| 13B | 726 | 42C | 24.1 |
| 14A | 18.5 | 42D | 20.1 |
| 14B | 359.3 | 43A | 39.6 |
| 15A | 28.3 | 43B | 26.4 |
| 15B | 553 | 43C | 3.2 |
| 16A | 366 | 43D | 21.9 |
| 16B | 935.9 | 44A | 90.5 |
| 17A | 1630 | 44B | 335.2 |
| 17B | 136.1 | 44C | 172.5 |
| 18A | 4.1 | 44D | 22.74 |
| 18B | 6.87 | 45A | 283.4 |
| 18C | 91.6 | 45B | 5.27 |
| 18D | 83.5 | 46A | 342.6 |
| 19A | 5.75 | 46B | 23.7 |
| 19B | 3.23 | 47A | 11.36 |
| 19C | 15.69 | 47B | 61.84 |
| 19D | 10.03 | 47C | 2.66 |
| 20A | 1.37 | 47D | 36.55 |
| 20B | 191.1 | 48A | 4366 |
| 20C | 9.02 | 48B | 904.1 |
| 20D | 115.9 | 48C | 312 |
| 21A | 1.08 | 48D | 515.3 |
| 21B | 2.87 | 49A | 4.46 |
| 21C | 59.72 | 49B | 84.56 |
| 21D | 128.1 | 50A | 389.2 |
| 22A | 2.90 | 50B | 9.01 |
| 22B | 5.89 | 51A | 117.5 |
| 22C | 84.49 | 51B | 3.03 |
| 22D | 85.18 | 52A | 319.8 |
| 23 | 1.16 | 52B | 11.84 |
| 24A | 2629 | 53A | 538.5 |
| 24B | 29.1 | 53B | 9.06 |
| 25A | 10.37 | 54A | 1.70 |
| 25B | 652.1 | 54B | 4.18 |
| 26 | 6.82 | 55A | 494.1 |
| 27A | 0.80 | 55B | 26.29 |
| 27B | 106.9 | 57C | 566 |
| 28A | 2.65 | 57D | 11.96 |
| 28B | 191 | 58A | 9.23 |
| 29A | 8.91 | 58B | 5.65 |
| 29B | 66.45 | 58C | 5.10 |
| 30A | 280.7 | 58D | 6.03 |
| 30B | 3.12 | 59A | 2.6 |
| 31A | 0.74 | 59B | 44 |
| 31B | 70.98 | 60A | 10.1 |
| 32A | 570.6 | 60B | 51.2 |
| 32B | 3.93 | 61 | 0.7 |
| 33A | 135.4 | 62A | 3.2 |
| 33B | 3587 | 62B | 358.1 |
| 34A | 600.8 | 62C | 488.2 |
| 34B | 47.14 | 62D | 0.8 |
| 35A | 6.08 | 63A | 1.8 |
| 35B | 48.6 | 63B | 9.1 |
| 36A | 55.74 | 64 | 3.2 |

The scope of the claims should not be limited by the preferred embodiments set forth in the examples, but should be given the broadest interpretation consistent with the description as a whole.

While the invention has been described and illustrated with reference to certain particular embodiments thereof, those skilled in the art will appreciate that various adaptations, changes, modifications, substitutions, deletions, or additions of procedures and protocols may be made without departing from the scope of the invention. For example, effective dosages other than the particular dosages as set forth herein above may be applicable as a consequence of variations in responsiveness of the mammal being treated for any of the indications with the compounds of structural formula I indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of structural formula I.

What is claimed is:

1. A compound of structural Formula I:

(I)

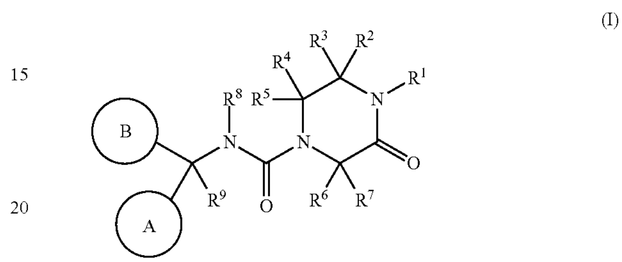

or a pharmaceutically acceptable salt thereof, wherein

A is selected from:

(1) phenyl, (2) pyridine, and (3) thiazole, wherein phenyl, pyridine and thiazole are substituted with one to five substituents selected from $R^a$;

B is selected from:

(1) cyclobutane, (2) cyclopentane, (3) cyclohexane, (4) bicyclo[3.2.1]octane, (5) bicyclo[3.1.0]hexane, (6) bicyclo[2.2.2]octane, (7) spiro[2.5]octane, (8) bicyclo[1.1.1]pentane, (9) spiro[3.3]heptane,

(10) spiro[2.3]hexane,

(11) spiro[2.2]pentane,

(12) piperidine,

(13) tetrahydropyran, and

(14) chromane, wherein cyclopentane, cyclohexane, bicyclo[3.2.1]octane, bicyclo[3.1.0]hexane, bicyclo[2.2.2]octane, spiro[2.5]octane, bicyclo[1.1.1]pentane, spiro[3.3]heptane, spiro[2.3]hexane, spiro[2.2]pentane, piperidine, tetrahydropyran, and chromane are unsubstituted or substituted with one to six substituents selected from $R^b$, and wherein cyclobutane is substituted with one to six substituents selected from $R^b$;

$R^1$ is hydrogen;

$R^2$ is selected from:

(1) hydrogen, (2) deuterium, (3) —$C_{1-6}$alkyl, (4) —$C_{2-6}$alkenyl, (5) —$C_{2-6}$alkynyl, (6) —$C_{3-6}$cycloalkyl, (7) —$C_{2-6}$cycloheteroalkyl, (8) —$C_{1-6}$alkyl-O—$C_{1-6}$alkyl, (9) —$(CH_2)_sC(O)R^j$,

(10) —$(CH_2)_sC(O)NR^eR^j$,

(11) —$(CH_2)_sNR^eC(O)R^j$,

(12) —$(CH_2)_sNR^eC(O)OR^j$,

(13) —$(CH_2)_sNR^eC(O)N(R^e)_2$,
(14) —$(CH_2)_sNR^eC(O)NR^eR^j$,
(15) —$(CH_2)_sNR^eS(O)_mR^j$,
(16) —$(CH_2)_sNR^eS(O)_mN(R^e)_2$,
(17) —$(CH_2)_sNR^eS(O)_mNR^eR^j$, and
(18) —$(CH_2)SNR^eR^j$, wherein each $CH_2$, alkyl, alkenyl, alkynyl, cycloalkyl, and cycloheteroalkyl is unsubstituted or substituted with one to five substituents selected from $R^d$, wherein $R^2$ and $R^3$ and the carbon atoms they are connected to can form a —$C_{3-5}$cycloalkyl ring, and wherein $R^2$ and $R^4$ and the carbon atoms they are connected to can form a —$C_{3-5}$cycloalkyl ring;

$R^3$ is selected from:
(1) hydrogen,
(2) deuterium,
(3) —$C_{1-6}$alkyl,
(4) —$C_{2-6}$alkenyl,
(5) —$C_{2-6}$alkynyl,
(6) —$C_{3-6}$cycloalkyl,
(7) —$C_{2-6}$cycloheteroalkyl,
(8) —$C_{1-6}$alkyl-O—$C_{1-6}$alkyl,
(9) —$(CH_2)_sC(O)R^j$,
(10) —$(CH_2)_sC(O)NR^eR^j$,
(11) —$(CH_2)_sNR^eC(O)R^j$,
(12) —$(CH_2)_sNR^eC(O)OR^j$,
(13) —$(CH_2)_sNR^eC(O)N(R^e)_2$,
(14) —$(CH_2)_sNR^eC(O)NR^eR^j$,
(15) —$(CH_2)_sNR^eS(O)_mR^j$,
(16) —$(CH_2)_sNR^eS(O)_mN(R^e)_2$,
(17) —$(CH_2)_sNR^eS(O)_mNR^eR^j$, and
(18) —$(CH_2)SNR^eR^j$, wherein each $CH_2$, alkyl, alkenyl, alkynyl, cycloalkyl, and cycloheteroalkyl is unsubstituted or substituted with one to five substituents selected from $R^d$;

$R^4$ is selected from:
(1) hydrogen,
(2) deuterium,
(3) —$C_{1-6}$alkyl,
(4) —$C_{2-6}$alkenyl,
(5) —$C_{2-6}$alkynyl,
(6) —$C_{3-6}$cycloalkyl,
(7) —$C_{2-6}$cycloheteroalkyl,
(8) —$C_{1-6}$alkyl-O—$C_{1-6}$alkyl,
(9) —$(CH_2)_sC(O)R^j$,
(10) —$(CH_2)_sC(O)NR^eR^j$,
(11) —$(CH_2)_sNR^eC(O)R^j$,
(12) —$(CH_2)_sNR^eC(O)OR^j$,
(13) —$(CH_2)_sNR^eC(O)N(R^e)_2$,
(14) —$(CH_2)_sNR^eC(O)NR^eR^j$,
(15) —$(CH_2)_sNR^eS(O)_mR^j$,
(16) —$(CH_2)_sNR^eS(O)_mN(R^e)_2$,
(17) —$(CH_2)_sNR^eS(O)_mNR^eR^j$, and
(18) —$(CH_2)_sNR^eR^j$, wherein each $CH_2$, alkyl, alkenyl, alkynyl, cycloalkyl, and cycloheteroalkyl is unsubstituted or substituted with one to five substituents selected from $R^f$, and wherein $R^4$ and $R^5$ and the carbon atoms they are connected to can form a —$C_{3-5}$cycloalkyl ring;

$R^5$ is selected from:
(1) hydrogen,
(2) deuterium,
(3) —$C_{1-6}$alkyl,
(4) —$C_{2-6}$alkenyl,
(5) —$C_{2-6}$alkynyl,
(6) —$C_{3-6}$cycloalkyl,
(7) —$C_{2-6}$cycloheteroalkyl,
(8) —$C_{1-6}$alkyl-O—$C_{1-6}$alkyl,
(9) —$(CH_2)_sC(O)R^j$,
(10) —$(CH_2)_sC(O)NR^eR^j$,
(11) —$(CH_2)_sNR^eC(O)R^j$,
(12) —$(CH_2)_sNR^eC(O)OR^j$,
(13) —$(CH_2)_sNR^eC(O)N(R^e)_2$,
(14) —$(CH_2)_sNR^eC(O)NR^eR^j$,
(15) —$(CH_2)_sNR^eS(O)_mR^j$,
(16) —$(CH_2)_sNR^eS(O)_mN(R^e)_2$,
(17) —$(CH_2)_sNR^eS(O)_mNR^eR^j$, and
(18) —$(CH_2)SNR^eR^j$, wherein each $CH_2$, alkyl, alkenyl, alkynyl, cycloalkyl, and cycloheteroalkyl is unsubstituted or substituted with one to five substituents selected from $R^f$, and wherein $R^5$ and $R^7$ and the carbon atoms they are attached to may form a 4-, 5- or 6-membered saturated ring;

$R^6$ is selected from:
(1) hydrogen,
(2) deuterium,
(3) —$C_{1-6}$alkyl,
(4) —$C_{2-6}$alkenyl,
(5) —$C_{2-6}$alkynyl,
(6) —$C_{3-6}$cycloalkyl,
(7) —$C_{2-6}$cycloheteroalkyl,
(8) —$C_{1-6}$alkyl-O—$C_{1-6}$alkyl,
(9) —$(CH_2)_sC(O)R^j$,
(10) —$(CH_2)_sC(O)NR^eR^j$,
(11) —$(CH_2)_sNR^eC(O)R^j$,
(12) —$(CH_2)_sNR^eC(O)OR^j$,
(13) —$(CH_2)_sNR^eC(O)N(R^e)_2$,
(14) —$(CH_2)_sNR^eC(O)NR^eR^j$,
(15) —$(CH_2)_sNR^eS(O)_mR^j$,
(16) —$(CH_2)_sNR^eS(O)_mN(R^e)_2$,
(17) —$(CH_2)_sNR^eS(O)_mNR^eR^j$, and
(18) —$(CH_2)SNR^eR^j$, wherein each $CH_2$, alkyl, alkenyl, alkynyl, cycloalkyl, and cycloheteroalkyl is unsubstituted or substituted with one to five substituents selected from $R^g$, and wherein $R^6$ and $R^7$ and the carbon atoms they are connected to can form a —$C_{3-5}$cycloalkyl ring;

$R^7$ is selected from:
(1) hydrogen,
(2) deuterium,
(3) —$C_{1-6}$alkyl,
(4) —$C_{2-6}$alkenyl,
(5) —$C_{2-6}$alkynyl,
(6) —$C_{3-6}$cycloalkyl,
(7) —$C_{2-6}$cycloheteroalkyl,
(8) —$C_{1-6}$alkyl-O—$C_{1-6}$alkyl,
(9) —$(CH_2)_sC(O)R^j$,
(10) —$(CH_2)_sC(O)NR^eR^j$,
(11) —$(CH_2)_sNR^eC(O)R^j$,
(12) —$(CH_2)_sNR^eC(O)OR^j$,
(13) —$(CH_2)_sNR^eC(O)N(R^e)_2$,
(14) —$(CH_2)_sNR^eC(O)NR^eR^j$,
(15) —$(CH_2)_sNR^eS(O)_mR^j$,
(16) —$(CH_2)_sNR^eS(O)_mN(R^e)_2$,
(17) —$(CH_2)_sNR^eS(O)_mNR^eR^j$, and
(18) —$(CH_2)SNR^eR^j$, wherein each $CH_2$, alkyl, alkenyl, alkynyl, cycloalkyl, and cycloheteroalkyl is unsubstituted or substituted with one to five substituents selected from $R^g$;

$R^8$ is selected from:
(1) hydrogen,
(2) —$C_{1-6}$alkyl,
(3) —$C_{3-6}$cycloalkyl, and
(4) —$C_{2-6}$cycloheteroalkyl, wherein each alkyl, cycloalkyl and cycloheteroalkyl is unsubstituted or substituted with one to five substituents selected from halogen;

$R^9$ is selected from:

(1) hydrogen, (2) —$C_{1-6}$alkyl, (3) —$C_{2-6}$alkenyl, and (4) —$C_{2-6}$alkynyl, wherein each alkyl, alkenyl and alkynyl is unsubstituted or substituted with one to five substituents selected from halogen;

each $R^a$ is independently selected from:

(1) CN, (2) halogen, (3) —$S(O)_2C_{1-6}$alkyl, (4) —$C_{1-6}$alkyl, (5) —$C_{2-6}$alkenyl, (6) —$C_{2-6}$alkynyl, (7) —$C_{3-6}$cycloalkyl, (8) —$C_{2-6}$cycloheteroalkyl, (9) aryl,

(10) heteroaryl,

(11) —$C_{1-6}$alkyl-aryl,

(12) —$C_{1-6}$alkyl-heteroaryl,

(13) —$C_{1-6}$alkyl-$C_{3-6}$cycloalkyl,

(14) —$C_{1-6}$alkyl-$C_{2-6}$cycloheteroalkyl,

(15) —$C_{2-6}$alkenyl-$C_{3-6}$cycloalkyl,

(16) —$C_{2-6}$alkenyl-$C_{2-6}$cycloheteroalkyl,

(17) —$C_{2-6}$alkenyl-aryl,

(18) —$C_{2-6}$alkenyl-heteroaryl,

(19) —$C_{2-6}$alkynyl-$C_{3-6}$cycloalkyl,

(20) —$C_{2-6}$alkynyl$C_{2-6}$cycloheteroalkyl,

(21) —$C_{2-6}$alkynyl-aryl,

(22) —$C_{2-6}$alkynyl-heteroaryl,

(23) —OH,

(24) —$(CH_2)_p$—O—$C_{1-6}$alkyl,

(25) —$(CH_2)_p$—O—$C_{2-6}$alkenyl,

(26) —$(CH_2)_p$—O—$C_{2-6}$alkynyl,

(27) —$(CH_2)_p$—O—$C_{3-6}$cycloalkyl,

(28) —$(CH_2)_p$—O—$C_{2-6}$cycloheteroalkyl,

(29) —$(CH_2)_p$—O-aryl,

(30) —$(CH_2)_p$—O-heteroaryl,

(31) —$OC_{1-6}$alkyl-$C_{3-6}$cycloalkyl,

(32) —$OC_{1-6}$alkyl-$C_{2-6}$cycloheteroalkyl,

(33) —$OC_{1-6}$alkyl-aryl,

(34) —$OC_{1-6}$alkyl-heteroaryl,

(35) —$S(O)_rR^h$,

(36) —$C_{1-6}$alkyl-$S(O)_rR^h$,

(37) —$N(R^k)_2$,

(38) —$C(O)R^L$, and

(39) —$NR^kR^L$, wherein $R^a$ is unsubstituted or substituted with one to six substituents selected from halogen, $CF_3$, OH, $C_{1-6}$alkyl, and —$OC_{1-6}$alkyl, provided that CN, halogen and OH are unsubstituted;

each $R^b$ is independently selected from the group consisting of:

(1) F, (2) Cl, (3) —$CH_3$, (4) —$CF_3$, (5) —$CH_2CF_3$, (6) —$CH(CH_3)CF_3$, (7) —$CF_2CH_3$, (8) =$CH_2$, (9) cyclopropyl,

(10) —$OCH_3$,

(11) —$OCF_3$,

(12) —$OCHF_2$, and

(13) —$OCH_2CF_3$, wherein cyclopropyl is unsubstituted or substituted with one to five substituents selected from F, Cl, $CF_3$, $OCF_3$, CN, $CH_2CF_3$, $CF_2CH_3$, —$CH_3$, and O—$CH_3$;

$R^d$ is selected from:

(1) —$C_{1-6}$alkyl, (2) OH, (3) halogen, and (4) —$OC_{1-6}$alkyl, wherein alkyl is unsubstituted or substituted with one to three halogens;

$R^e$ is selected from:

(1) hydrogen, and (2) $C_{1-6}$alkyl;

$R^f$ is selected from:

(1) —$C_{1-6}$alkyl, (2) OH, (3) halogen, and (4) —$OC_{1-6}$alkyl, wherein alkyl is unsubstituted or substituted with one to three halogens;

$R^g$ is selected from:

(1) —$C_{1-6}$alkyl, (2) OH, (3) halogen, and (4) —$OC_{1-6}$alkyl, wherein alkyl is unsubstituted or substituted with one to three halogens;

$R^h$ is selected from:

(1) hydrogen, (2) $C_{1-6}$alkyl, (3) $C_{3-6}$cycloalkyl, (4) aryl, and (5) heteroaryl;

$R^j$ is selected from:

(1) hydrogen, (2) $C_{1-6}$alkyl, (3) $C_{3-6}$alkenyl, (4) $C_{3-6}$alkynyl, (5) $C_{3-6}$cycloalkyl, (6) $C_{2-5}$cycloheteroalkyl, (7) aryl, and (8) heteroaryl;

$R^k$ is selected from:

(1) hydrogen, and (2) $C_{1-6}$alkyl;

$R^L$ is selected from:

(1) hydrogen, (2) $C_{1-6}$alkyl, (3) $C_{3-6}$cycloalkyl, (4) aryl, and (5) heteroaryl;

m is independently selected from 0, 1 and 2;

p is independently selected from 0, 1, 2 and 3;

r is independently selected from 0, 1 and 2; and s is independently selected from 0, 1, 2, 3, 4, 5, and 6.

2. The compound according to claim 1 wherein A is selected from:

(1) phenyl, and (2) pyridine, wherein phenyl and pyridine are substituted with one to four substituents selected from $R^a$; or a pharmaceutically acceptable salt thereof.

3. The compound according to claim 1 wherein B is selected from:

(1) cyclobutane,
(2) cyclopentane,
(3) cyclohexane,
(4) bicyclo[3.2.1]octane,
(5) bicyclo[3.1.0]hexane,
(6) bicyclo[2.2.2]octane,
(7) spiro[2.5]octane,
(8) bicyclo[1.1.1]pentane,
(9) spiro[3.3]heptane,
(10) spiro[2.3]hexane,
(11) spiro[2.2]pentane,
(12) piperidine, and
(13) tetrahydropyran, wherein cyclopentane, cyclohexane, bicyclo[3.2.1]octane, bicyclo[3.1.0]hexane, bicyclo[2.2.2]octane, spiro[2.5]octane, bicyclo[1.1.1]pentane, spiro[3.3]heptane, spiro[2.3]hexane, spiro[2.2]pentane, piperidine, and tetrahydropyran are unsubstituted or substituted with one to six substituents selected from $R^b$, and wherein cyclobutane is substituted with one to six substituents selected from $R^b$;

or a pharmaceutically acceptable salt thereof.

4. The compound according to claim 1 wherein B is selected from:
(1) cyclobutane,
(2) cyclohexane, and
(3) tetrahydropyran, wherein cyclobutane is substituted with one to six substituents selected from $R^b$, and cyclohexane and tetrahydropyran are unsubstituted or substituted with one to six substituents selected from $R^b$; or a pharmaceutically acceptable salt thereof.

5. The compound according to claim 1 wherein $R^2$ is selected from:
(1) hydrogen,
(2) deuterium,
(3) —$C_{1-6}$alkyl, and
(4) —$C_{3-6}$cycloalkyl, wherein each alkyl and cycloalkyl is unsubstituted or substituted with one to five substituents selected from $R^d$;

$R^3$ is selected from:
(1) hydrogen,
(2) deuterium,
(3) —$C_{1-6}$alkyl, and
(4) —$C_{3-6}$cycloalkyl, wherein each alkyl and cycloalkyl is unsubstituted or substituted with one to five substituents selected from $R^d$;

$R^4$ is selected from:
(1) hydrogen,
(2) deuterium,
(3) —$C_{1-6}$alkyl, and
(4) —$C_{3-6}$cycloalkyl, wherein each alkyl and cycloalkyl is unsubstituted or substituted with one to five substituents selected from $R^f$;

$R^5$ is selected from:
(1) hydrogen,
(2) deuterium,
(3) —$C_{1-6}$alkyl, and
(4) —$C_{3-6}$cycloalkyl, wherein alkyl and cycloalkyl is unsubstituted or substituted with one to five substituents selected from $R^f$;

or a pharmaceutically acceptable salt thereof.

6. The compound according to claim 1 wherein $R^2$ is selected from:
(1) hydrogen,
(2) —$C_{1-6}$alkyl, and
(3) —$C_{3-6}$cycloalkyl, wherein each alkyl and cycloalkyl is unsubstituted or substituted with one to five substituents selected from $R^d$;

$R^3$ is selected from:
(1) hydrogen,
(2) —$C_{1-6}$alkyl, and
(3) —$C_{3-6}$cycloalkyl, wherein each alkyl and cycloalkyl is unsubstituted or substituted with one to five substituents selected from $R^d$;

$R^4$ is selected from:
(1) hydrogen,
(2) —$C_{1-6}$alkyl, and
(3) —$C_{3-6}$cycloalkyl, wherein each alkyl and cycloalkyl is unsubstituted or substituted with one to five substituents selected from $R^f$;

$R^5$ is selected from:
(1) hydrogen,
(2) —$C_{1-6}$alkyl, and
(3) —$C_{3-6}$cycloalkyl, wherein alkyl and cycloalkyl is unsubstituted or substituted with one to five substituents selected from $R^f$;

$R^6$ is selected from:
(1) hydrogen,
(2) —$C_{1-6}$alkyl, and
(3) —$C_{3-6}$cycloalkyl, wherein alkyl and cycloalkyl is unsubstituted or substituted with one to five substituents selected from $R^g$; and $R^7$ is selected from:
(1) hydrogen,
(2) —$C_{1-6}$alkyl, and
(3) —$C_{3-6}$cycloalkyl, wherein alkyl, and cycloalkyl is unsubstituted or substituted with one to five substituents selected from $R^g$;

or a pharmaceutically acceptable salt thereof.

7. The compound according to claim 1 wherein $R^8$ is selected from:
(1) hydrogen, and
(2) —$C_{1-6}$alkyl, wherein alkyl is unsubstituted or substituted with one to five substituents selected from halogen; and $R^9$ is selected from:
(1) hydrogen, and
(2) —$C_{1-6}$alkyl, wherein alkyl is unsubstituted or substituted with one to five substituents selected from halogen;

or a pharmaceutically acceptable salt thereof.

8. The compound according to claim 1 wherein $R^1$ is hydrogen;

$R^2$, $R^3$, $R^4$ and $R^5$ are each independently deuterium or hydrogen;

$R^6$ and $R^7$ are each independently $CH_3$ or hydrogen; and $R^8$ and $R^9$ are hydrogen;

or a pharmaceutically acceptable salt thereof.

9. The compound according to claim 1 wherein $R^1$, $R^2$, $R^3$, $R^4$, $R^5$, $R^6$, $R^7$, $R^8$ and $R^9$ are hydrogen;

or a pharmaceutically acceptable salt thereof.

10. The compound according to claim 1 wherein each $R^a$ is independently selected from:
(1) CN,
(2) halogen,
(3) —$S(O)_2C_{1-6}$alkyl,
(4) —$C_{1-6}$alkyl, (5) —$C_{2-6}$alkenyl,
(6) —$C_{3-6}$cycloalkyl,
(7) —$C_{2-6}$cycloheteroalkyl,
(8) aryl,
(9) heteroaryl,
(10) —OH,
(11) —O—$C_{1-6}$alkyl,
(12) —O—$C_{3-6}$cycloalkyl, and
(13) —O—$C_{2-6}$cycloheteroalkyl, wherein $R^a$ is unsubstituted or substituted with one to six substituents selected from halogen, $CF_3$, OH, $C_{1-6}$alkyl, and —$OC_{1-6}$alkyl, provided that CN, halogen and OH are unsubstituted; or a pharmaceutically acceptable salt thereof.

11. The compound according to claim 1 wherein each $R^a$ is independently selected from:
(1) halogen,
(2) —$C_{1-6}$alkyl, and
(3) —O—$C_{1-6}$alkyl, wherein $R^a$ is unsubstituted or substituted with one to six substituents selected from halogen, $CF_3$, OH, $C_{1-6}$alkyl, and —$OC_{1-6}$alkyl, provided that halogen is unsubstituted; or a pharmaceutically acceptable salt thereof.

12. The compound according to claim 1 wherein each $R^a$ is independently selected from:
(1) halogen, and
(2) —$C_{1-6}$alkyl, wherein each alkyl is unsubstituted or substituted with one to six substituents selected from halogen, $CF_3$, OH, $C_{1-6}$alkyl, and —$OC_{1-6}$alkyl, provided that halogen is unsubstituted; or a pharmaceutically acceptable salt thereof.

13. The compound according to claim 1 wherein each $R^b$ is independently selected from the group consisting of:
(1) F,
(2) Cl,
(3) —$CH_3$,
(4) —$CF_3$,
(5) —$CH_2CF_3$,
(6) —$CH(CH_3)CF_3$,
(7) =$CH_2$,
(8) cyclopropyl,
(9) —$OCH_3$,
(10) —$OCHF_2$, and
(11) —$OCH_2CF_3$, wherein cyclopropyl is unsubstituted or substituted with one to five substituents selected from F, Cl, $CF_3$, $OCF_3$, CN, $CH_2CF_3$, $CF_2CH_3$, —$CH_3$, and O—$CH_3$;

or a pharmaceutically acceptable salt thereof.

14. The compound according to claim 1 wherein each $R^b$ is independently selected from:
(1) F,
(2) Cl,
(3) —$CH_3$,
(4) —$CF_3$,
(5) —$CH_2CF_3$,
(6) —$CH(CH_3)CF_3$, and
(7) —$CF_2CH_3$;

or a pharmaceutically acceptable salt thereof.

15. The compound according to claim 1 wherein

A is selected from:
(1) phenyl,
(2) pyridine, and
(3) thiazole, wherein phenyl, pyridine and thiazole are substituted with one to five substituents selected from $R^a$;

B is selected from:
(1) cyclobutane,
(2) cyclopentane,
(3) cyclohexane,
(4) bicyclo[3.2.1]octane,
(5) bicyclo[3.1.0]hexane,
(6) bicyclo[2.2.2]octane,
(7) spiro[2.5]octane,
(8) bicyclo[1.1.1]pentane,
(9) spiro[3.3]heptane,
(10) spiro[2.3]hexane,
(11) spiro[2.2]pentane
(12) piperidine,
(13) tetrahydropyran, and
(14) chromane, wherein cyclopentane, cyclohexane, bicyclo[3.2.1]octane, bicyclo[3.1.0]hexane, bicyclo[2.2.2]octane, spiro[2.5]octane, bicyclo[1.1.1]pentane, spiro[3.3]heptane, spiro[2.3]hexane, spiro[2.2]pentane, piperidine, tetrahydropyran, and chromane are unsubstituted or substituted with one to six substituents selected from $R^b$, and wherein cyclobutane is substituted with one to six substituents selected from $R^b$;

$R^1$ is hydrogen;

$R^2$ is selected from:
(1) hydrogen,
(2) deuterium,
(3) —$C_{1-6}$alkyl, and
(4) —$C_{3-6}$cycloalkyl, wherein each alkyl and cycloalkyl is unsubstituted or substituted with one to five substituents selected from $R^d$;

$R^3$ is selected from:
(1) hydrogen,
(2) deuterium,
(3) —$C_{1-6}$alkyl, and
(4) —$C_{3-6}$cycloalkyl, wherein each alkyl and cycloalkyl is unsubstituted or substituted with one to five substituents selected from $R^d$;

$R^4$ is selected from:
(1) hydrogen,
(2) deuterium,
(3) —$C_{1-6}$alkyl, and
(4) —$C_{3-6}$cycloalkyl, wherein each alkyl and cycloalkyl is unsubstituted or substituted with one to five substituents selected from $R^f$;

$R^5$ is selected from:
(1) hydrogen,
(2) deuterium,
(3) —$C_{1-6}$alkyl, and
(4) —$C_{3-6}$cycloalkyl, wherein alkyl and cycloalkyl is unsubstituted or substituted with one to five substituents selected from $R^f$;

$R^6$ is selected from:
(1) hydrogen,
(2) —$C_{1-6}$alkyl, and
(3) —$C_{3-6}$cycloalkyl, wherein alkyl and cycloalkyl is unsubstituted or substituted with one to five substituents selected from $R^g$;

$R^7$ is selected from:
(1) hydrogen,
(2) —$C_{1-6}$alkyl, and
(3) —$C_{3-6}$cycloalkyl, wherein alkyl, and cycloalkyl is unsubstituted or substituted with one to five substituents selected from $R^g$;

$R^8$ is selected from:
(1) hydrogen, and
(2) —$C_{1-6}$alkyl,
wherein alkyl is unsubstituted or substituted with one to five substituents selected from halogen;
$R^9$ is selected from:
(1) hydrogen, and
(2) —$C_{1-6}$alkyl,
wherein alkyl is unsubstituted or substituted with one to five substituents selected from halogen;
$R^a$ is independently selected from:
(1) CN,
(2) halogen,
(3) —$S(O)_2C_{1-6}$alkyl,
(4) —$C_{1-6}$alkyl,
(5) —$C_{2-6}$alkenyl,
(6) —$C_{3-6}$cycloalkyl,
(7) —$C_{2-6}$cycloheteroalkyl,
(8) aryl,
(9) heteroaryl,
(10) —OH,
(11) —O—$C_{1-6}$alkyl,
(12) —O—$C_{3-6}$cycloalkyl, and
(13) —O—$C_{2-6}$cycloheteroalkyl,
wherein $R^a$ is unsubstituted or substituted with one to six substituents selected from halogen, $CF_3$, OH, $C_{1-6}$alkyl, and —$OC_{1-6}$alkyl, provided that CN, halogen and OH are unsubstituted; and
each $R^b$ is independently selected from the group consisting of:
(1) F,
(2) Cl,
(3) —$CH_3$,
(4) —$CF_3$,
(5) —$CH_2CF_3$,
(6) —$CH(CH_3)CF_3$,
(7) —$CF_2CH_3$,
(8) =$CH_2$,
(9) cyclopropyl,
(10) —$OCH_3$,
(11) —$OCF_3$,
(12) —$OCHF_2$, and
(13) —$OCH_2CF_3$,
wherein cyclopropyl is unsubstituted or substituted with one to five substituents selected from F, Cl, $CF_3$, $OCF_3$, CN, $CH_2CF_3$, $CF_2CH_3$, —$CH_3$, and O—$CH_3$;
or a pharmaceutically acceptable salt thereof.

16. The compound according to claim 1 wherein
A is selected from:
(1) phenyl,
(2) pyridine, and
(3) thiazole,
wherein phenyl, pyridine and thiazole are substituted with one to five substituents selected from $R^a$;
B is selected from:
(1) cyclobutane,
(2) cyclopentane,
(3) cyclohexane,
(4) bicyclo[3.2.1]octane,
(5) bicyclo[3.1.0]hexane,
(6) bicyclo[2.2.2]octane,
(7) spiro[2.5]octane,
(8) bicyclo[1.1.1]pentane,
(9) spiro[3.3]heptane,
(10) spiro[2.3]hexane,
(11) spiro[2.2]pentane
(12) piperidine, and
(13) tetrahydropyran,
wherein cyclopentane, cyclohexane, bicyclo[3.2.1]octane, bicyclo[3.1.0]hexane, bicyclo[2.2.2]octane, spiro[2.5]octane, bicyclo[1.1.1]pentane, spiro[3.3]heptane, spiro[2.3]hexane, spiro[2.2]pentane, piperidine, and tetrahydropyran are unsubstituted or substituted with one to six substituents selected from $R^b$, and wherein cyclobutane is substituted with one to six substituents selected from $R^b$;
$R^1$ is hydrogen;
$R^2$ is selected from:
(1) hydrogen,
(2) —$C_{1-6}$alkyl, and
(3) —$C_{3-6}$cycloalkyl,
wherein each alkyl and cycloalkyl is unsubstituted or substituted with one to five substituents selected from $R^d$;
$R^3$ is selected from:
(1) hydrogen,
(2) —$C_{1-6}$alkyl, and
(3) —$C_{3-6}$cycloalkyl,
wherein each alkyl and cycloalkyl is unsubstituted or substituted with one to five substituents selected from $R^d$;
$R^4$ is selected from:
(1) hydrogen,
(2) —$C_{1-6}$alkyl, and
(3) —$C_{3-6}$cycloalkyl,
wherein each alkyl and cycloalkyl is unsubstituted or substituted with one to five substituents selected from $R^f$;
$R^5$ is selected from:
(1) hydrogen,
(2) —$C_{1-6}$alkyl, and
(3) —$C_{3-6}$cycloalkyl,
wherein alkyl and cycloalkyl is unsubstituted or substituted with one to five substituents selected from $R^f$;
$R^6$ is selected from:
(1) hydrogen,
(2) —$C_{1-6}$alkyl, and
(3) —$C_{3-6}$cycloalkyl,
wherein alkyl and cycloalkyl is unsubstituted or substituted with one to five substituents selected from $R^g$;
$R^7$ is selected from:
(1) hydrogen,
(2) —$C_{1-6}$alkyl, and
(3) —$C_{3-6}$cycloalkyl,
wherein alkyl, and cycloalkyl is unsubstituted or substituted with one to five substituents selected from $R^g$;
$R^8$ is selected from:
(1) hydrogen, and
(2) —$C_{1-6}$alkyl, wherein alkyl is unsubstituted or substituted with one to five substituents selected from halogen;
$R^9$ is selected from:
(1) hydrogen, and
(2) —$C_{1-6}$alkyl,
wherein alkyl is unsubstituted or substituted with one to five substituents selected from halogen;
$R^a$ is independently selected from:
(1) CN,
(2) halogen,
(3) —$S(O)_2C_{1-6}$alkyl,
(4) —$C_{1-6}$alkyl,
(5) —$C_{2-6}$alkenyl,
(6) —$C_{3-6}$cycloalkyl,
(7) —$C_{2-6}$cycloheteroalkyl, (8) aryl,
(9) heteroaryl,
(10) —OH,
(11) —O—$C_{1-6}$alkyl,
(12) —O—$C_{3-6}$cycloalkyl, and
(13) —O—$C_{2-6}$cycloheteroalkyl, wherein $R^a$ is unsubstituted or substituted with one to six substituents selected from halogen, $CF_3$, OH, $C_{1-6}$alkyl, and —$OC_{1-6}$alkyl, provided that CN, halogen and OH are unsubstituted; and each $R^b$ is independently selected from the group consisting of:
(1) F,
(2) Cl,
(3) —$CH_3$,
(4) —$CF_3$,
(5) —$CH_2CF_3$,
(6) —$CH(CH_3)CF_3$,
(7) —$CF_2CH_3$,
(8) =$CH_2$,
(9) cyclopropyl,
(10) —$OCH_3$,
(11) —$OCF_3$,
(12) —$OCHF_2$, and
(13) —$OCH_2CF_3$, wherein cyclopropyl is unsubstituted or substituted with one to five substituents selected from F, Cl, $CF_3$, $OCF_3$, CN, $CH_2CF_3$, $CF_2CH_3$, —$CH_3$, and O—$CH_3$;

or a pharmaceutically acceptable salt thereof.

17. The compound according to claim 1 wherein
A is selected from:
(1) phenyl, and
(2) pyridine, wherein phenyl and pyridine are substituted with one to four substituents selected from $R^a$;

B is selected from:
(1) cyclobutane,
(2) cyclopentane,
(3) cyclohexane,
(4) bicyclo[3.2.1]octane,
(5) bicyclo[3.1.0]hexane,
(6) bicyclo[2.2.2]octane,
(7) spiro[2.5]octane,
(8) bicyclo[1.1.1]pentane,
(9) spiro[3.3]heptane,
(10) spiro[2.3]hexane,
(11) spiro[2.2]pentane,
(12) piperidine,
(13) tetrahydropyran, and
(14) chromane, wherein cyclopentane, cyclohexane, bicyclo[3.2.1]octane, bicyclo[3.1.0]hexane, bicyclo[2.2.2]octane, spiro[2.5]octane, bicyclo[1.1.1]pentane, spiro[3.3]heptane, spiro[2.3]hexane, spiro[2.2]pentane, piperidine, tetrahydropyran, and chromane are unsubstituted or substituted with one to six substituents selected from $R^b$, and wherein cyclobutane is substituted with one to six substituents selected from $R^b$;

$R^1$ is hydrogen;

$R^2$, $R^3$, $R^4$ and $R^5$ are each independently deuterium or hydrogen;

$R^6$ and $R^7$ are $CH_3$ or hydrogen;

$R^8$ and $R^9$ are hydrogen;

each $R^a$ is independently selected from:
(1) halogen,
(2) —$C_{1-6}$alkyl, and
(3) —O—$C_{1-6}$alkyl, wherein $R^a$ is unsubstituted or substituted with one to six substituents selected from halogen, $CF_3$, OH, $C_{1-6}$alkyl, and —$OC_{1-6}$alkyl, provided that halogen is unsubstituted; and each $R^b$ is independently selected from the group consisting of:
(1) F,
(2) Cl,
(3) —$CH_3$,
(4) —$CF_3$,
(5) —$CH_2CF_3$,
(6) —$CH(CH_3)CF_3$,
(7) =$CH_2$,
(8) cyclopropyl,
(9) —$OCH_3$,
(10) —$OCHF_2$, and
(11) —$OCH_2CF_3$, wherein cyclopropyl is unsubstituted or substituted with one to five substituents selected from F, Cl, $CF_3$, $OCF_3$, CN, $CH_2CF_3$, $CF_2CH_3$, —$CH_3$, and O—$CH_3$;

or a pharmaceutically acceptable salt thereof.

18. The compound according to claim 1 wherein
A is selected from:
(1) phenyl, and
(2) pyridine, wherein phenyl and pyridine are substituted with one to four substituents selected from $R^a$;

B is selected from:
(1) cyclobutane,
(2) cyclohexane, and
(3) tetrahydropyran, wherein cyclobutane is substituted with one to six substituents selected from $R^b$, and cyclohexane and tetrahydropyran are unsubstituted or substituted with one to six substituents selected from $R^b$, $R^1$, $R^2$, $R^3$, $R^4$, $R^5$, $R^6$, $R^7$, $R^8$ and $R^9$ are hydrogen;

each $R^a$ is independently selected from:
(1) halogen,
(2) —$C_{1-6}$alkyl, and
(3) —O—$C_{1-6}$alkyl, wherein $R^a$ is unsubstituted or substituted with one to six substituents selected from halogen, $CF_3$, OH, $C_{1-6}$alkyl, and —$OC_{1-6}$alkyl, provided that halogen is unsubstituted; and each $R^b$ is independently selected from the group consisting of:
(1) F,
(2) Cl,
(3) —$CH_3$,
(4) —$CF_3$,
(5) —$CH_2CF_3$,
(6) —$CH(CH_3)CF_3$,
(7) =$CH_2$,
(8) cyclopropyl,
(9) —$OCH_3$,
(10) —$OCHF_2$, and
(11) —$OCH_2CF_3$, wherein cyclopropyl is unsubstituted or substituted with one to five substituents selected from F, Cl, $CF_3$, $OCF_3$, CN, $CH_2CF_3$, $CF_2CH_3$, —$CH_3$, and O—$CH_3$;

or a pharmaceutically acceptable salt thereof.

19. A pharmaceutical composition comprising a compound of claim 1, or a pharmaceutically acceptable salt thereof, and a pharmaceutically acceptable carrier.

20. A method of treating a disorder that is responsive to the inhibition of $Na_v1.8$ channel activity in a patient in need thereof comprising administration of a therapeutically effective amount of a compound according to claim 1, or a pharmaceutically acceptable salt thereof, wherein the disorder is selected from: a pain disorder, a cough disorder, an acute itch disorder and a chronic itch disorder.

21. The method of claim 20 wherein the disorder is a pain disorder.

22. The method of claim 20 wherein the disorder is selected from: acute pain, inflammatory pain, neuropathic pain, chronic pain, osteoarthritis, peripheral neuropathy, acute pain due to fractures, musculoskeletal damage, pancreatitis and renal colic, pre-operative pain, peri-operative pain, post-operative pain, diabetic neuropathy, chronic lower back pain, pain resulting from chemotherapy, bone and joint pain, myofascial pain, muscular injury, fibromyalgia, shoulder tendonitis, and bursitis.

23. A compound of structural Formula I:

(I)

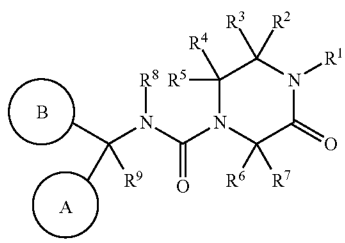

or a pharmaceutically acceptable salt thereof, wherein

A is selected from:
(1) phenyl,
(2) pyridine, and
(3) thiazole, wherein phenyl, pyridine and thiazole are substituted with one to five substituents selected from $R^a$;

B is selected from:
(1) cyclobutane,
(2) cyclopentane,
(3) cyclohexane,
(4) bicyclo[3.2.1]octane,
(5) bicyclo[3.1.0]hexane,
(6) bicyclo[2.2.2]octane,
(7) spiro[2.5]octane,
(8) bicyclo[1.1.1]pentane,
(9) spiro[3.3]heptane,
(10) spiro[2.3]hexane,
(11) spiro[2.2]pentane,
(12) piperidine,
(13) tetrahydropyran, and
(14) chromane, wherein cyclopentane, cyclohexane, bicyclo[3.2.1]octane, bicyclo[3.1.0]hexane, bicyclo[2.2.2]octane, spiro[2.5]octane, bicyclo[1.1.1]pentane, spiro[3.3]heptane, spiro[2.3]hexane, spiro[2.2]pentane, piperidine, tetrahydropyran, and chromane are unsubstituted or substituted with one to six substituents selected from $R^b$, and wherein cyclobutane is substituted with one to six substituents selected from $R^b$;

$R^1$ is hydrogen;

$R^2$ is selected from:
(1) hydrogen,
(2) $—C_{1-6}$alkyl,
(3) $—C_{2-6}$alkenyl,
(4) $—C_{2-6}$alkynyl,
(5) $—C_{3-6}$cycloalkyl,
(6) $—C_{2-6}$cycloheteroalkyl,
(7) $—C_{1-6}$alkyl-O$—C_{1-6}$alkyl,
(8) $—(CH_2)_sC(O)R^j$,
(9) $—(CH_2)_sC(O)NR^eR^j$,
(10) $—(CH_2)_sNR^eC(O)R^j$,
(11) $—(CH_2)_sNR^eC(O)OR^j$,
(12) $—(CH_2)_sNR^eC(O)N(R^e)_2$,
(13) $—(CH_2)_sNR^eC(O)NR^eR^j$,
(14) $—(CH_2)_sNR^eS(O)_mR^j$,
(15) $—(CH_2)_sNR^eS(O)_mN(R^e)_2$,
(16) $—(CH_2)_sNR^eS(O)_mNR^eR^j$, and
(17) $—(CH_2)SNR^eR^j$, wherein each $CH_2$, alkyl, alkenyl, alkynyl, cycloalkyl, and cycloheteroalkyl is unsubstituted or substituted with one to five substituents selected from $R^d$, wherein $R^2$ and $R^3$ and the carbon atoms they are connected to can form a $—C_{3-5}$cycloalkyl ring, and wherein $R^2$ and $R^4$ and the carbon atoms they are connected to can form a $—C_{3-5}$cycloalkyl ring;

$R^3$ is selected from:
(1) hydrogen,
(2) $—C_{1-6}$alkyl,
(3) $—C_{2-6}$alkenyl,
(4) $—C_{2-6}$alkynyl,
(5) $—C_{3-6}$cycloalkyl,
(6) $—C_{2-6}$cycloheteroalkyl,
(7) $—C_{1-6}$alkyl-O$—C_{1-6}$alkyl,
(8) $—(CH_2)_sC(O)R^j$,
(9) $—(CH_2)_sC(O)NR^eR^j$,
(10) $—(CH_2)_sNR^eC(O)R^j$,
(11) $—(CH_2)_sNR^eC(O)OR^j$,
(12) $—(CH_2)_sNR^eC(O)N(R^e)_2$,
(13) $—(CH_2)_sNR^eC(O)NR^eR^j$,
(14) $—(CH_2)_sNR^eS(O)_mR^j$,
(15) $—(CH_2)_sNR^eS(O)_mN(R^e)_2$,
(16) $—(CH_2)_sNR^eS(O)_mNR^eR^j$, and
(17) $—(CH_2)SNR^eR^j$, wherein each $CH_2$, alkyl, alkenyl, alkynyl, cycloalkyl, and cycloheteroalkyl is unsubstituted or substituted with one to five substituents selected from $R^d$;

$R^4$ is selected from:
(1) hydrogen,
(2) $—C_{1-6}$alkyl,
(3) $—C_{2-6}$alkenyl,
(4) $—C_{2-6}$alkynyl,
(5) $—C_{3-6}$cycloalkyl,
(6) $—C_{2-6}$cycloheteroalkyl,
(7) $—C_{1-6}$alkyl-O$—C_{1-6}$alkyl,
(8) $—(CH_2)_sC(O)R^j$,
(9) $—(CH_2)_sC(O)NR^eR^j$,
(10) $—(CH_2)_sNR^eC(O)R^j$,
(11) $—(CH_2)_sNR^eC(O)OR^j$,
(12) $—(CH_2)_sNR^eC(O)N(R^e)_2$,
(13) $—(CH_2)_sNR^eC(O)NR^eR^j$,
(14) $—(CH_2)_sNR^eS(O)_mR^j$,
(15) $—(CH_2)_sNR^eS(O)_mN(R^e)_2$,
(16) $—(CH_2)_sNR^eS(O)_mNR^eR^j$, and
(17) $—(CH_2)SNR^eR^j$, wherein each $CH_2$, alkyl, alkenyl, alkynyl, cycloalkyl, and cycloheteroalkyl is unsubstituted or substituted with one to five substituents selected from $R^f$, and wherein $R^4$ and $R^5$ and the carbon atoms they are connected to can from a $—C_{3-5}$cycloalkyl ring;

$R^5$ is selected from:
(1) hydrogen,
(2) $—C_{1-6}$alkyl,
(3) $—C_{2-6}$alkenyl,
(4) $—C_{2-6}$alkynyl, (5) —$C_{3-6}$cycloalkyl,
(6) —$C_{2-6}$cycloheteroalkyl,
(7) —$C_{1-6}$alkyl-O—$C_{1-6}$alkyl,
(8) —$(CH_2)_sC(O)R^j$,
(9) —$(CH_2)_sC(O)NR^eR^j$,
(10) —$(CH_2)_sNR^eC(O)R^j$,
(11) —$(CH_2)_sNR^eC(O)OR^j$,
(12) —$(CH_2)_sNR^eC(O)N(R^e)_2$,
(13) —$(CH_2)_sNR^eC(O)NR^eR^j$,
(14) —$(CH_2)_sNR^eS(O)_mR^j$,
(15) —$(CH_2)_sNR^eS(O)_mN(R^e)_2$,
(16) —$(CH_2)_sNR^eS(O)_mNR^eR^j$, and
(17) —$(CH_2)SNR^eR^j$, wherein each $CH_2$, alkyl, alkenyl, alkynyl, cycloalkyl, and cycloheteroalkyl is unsubstituted or substituted with one to five substituents selected from $R^f$, and wherein $R^5$ and $R^7$ and the carbon atoms they are attached to may form a 4-, 5- or 6-membered saturated ring;

$R^6$ is selected from:
(1) hydrogen,
(2) —$C_{1-6}$alkyl,
(3) —$C_{2-6}$alkenyl,
(4) —$C_{2-6}$alkynyl,
(5) —$C_{3-6}$cycloalkyl,
(6) —$C_{2-6}$cycloheteroalkyl,
(7) —$C_{1-6}$alkyl-O—$C_{1-6}$alkyl,
(8) —$(CH_2)_sC(O)R^j$,
(9) —$(CH_2)_sC(O)NR^eR^j$,
(10) —$(CH_2)_sNR^eC(O)R^j$,
(11) —$(CH_2)_sNR^eC(O)OR^j$,
(12) —$(CH_2)_sNR^eC(O)N(R^e)_2$,
(13) —$(CH_2)_sNR^eC(O)NR^eR^j$,
(14) —$(CH_2)_sNR^eS(O)_mR^j$,
(15) —$(CH_2)_sNR^eS(O)_mN(R^e)_2$,
(16) —$(CH_2)_sNR^eS(O)_mNR^eR^j$, and
(17) —$(CH_2)SNR^eR^j$, wherein each $CH_2$, alkyl, alkenyl, alkynyl, cycloalkyl, and cycloheteroalkyl is unsubstituted or substituted with one to five substituents selected from $R^g$, and wherein $R^6$ and $R^7$ and the carbon atoms they are connected to can from a —$C_{3-5}$cycloalkyl ring;

$R^7$ is selected from:
(1) hydrogen,
(2) —$C_{1-6}$alkyl,
(3) —$C_{2-6}$alkenyl,
(4) —$C_{2-6}$alkynyl,
(5) —$C_{3-6}$cycloalkyl,
(6) —$C_{2-6}$cycloheteroalkyl,
(7) —$C_{1-6}$alkyl-O—$C_{1-6}$alkyl,
(8) —$(CH_2)_sC(O)R^j$,
(9) —$(CH_2)_sC(O)NR^eR^j$,
(10) —$(CH_2)_sNR^eC(O)R^j$,
(11) —$(CH_2)_sNR^eC(O)OR^j$,
(12) —$(CH_2)_sNR^eC(O)N(R^e)_2$,
(13) —$(CH_2)_sNR^eC(O)NR^eR^j$,
(14) —$(CH_2)_sNR^eS(O)_mR^j$,
(15) —$(CH_2)_sNR^eS(O)_mN(R^e)_2$,
(16) —$(CH_2)_sNR^eS(O)_mNR^eR^j$, and
(17) —$(CH_2)SNR^eR^j$, wherein each $CH_2$, alkyl, alkenyl, alkynyl, cycloalkyl, and cycloheteroalkyl is unsubstituted or substituted with one to five substituents selected from $R^g$;

$R^8$ is selected from:
(1) hydrogen,
(2) —$C_{1-6}$alkyl,
(3) —$C_{3-6}$cycloalkyl, and
(4) —$C_{2-6}$cycloheteroalkyl, wherein each alkyl, cycloalkyl and cycloheteroalkyl is unsubstituted or substituted with one to five substituents selected from halogen;

$R^9$ is selected from:
(1) hydrogen,
(2) —$C_{1-6}$alkyl,
(3) —$C_{2-6}$alkenyl, and
(4) —$C_{2-6}$alkynyl, wherein each alkyl, alkenyl and alkynyl is unsubstituted or substituted with one to five substituents selected from halogen;

each $R^a$ is independently selected from:
(1) CN,
(2) halogen,
(3) —$S(O)_2C_{1-6}$alkyl,
(4) —$C_{1-6}$alkyl,
(5) —$C_{2-6}$alkenyl,
(6) —$C_{2-6}$alkynyl,
(7) —$C_{3-6}$cycloalkyl,
(8) —$C_{2-6}$cycloheteroalkyl,
(9) aryl,
(10) heteroaryl,
(11) —$C_{1-6}$alkyl-aryl,
(12) —$C_{1-6}$alkyl-heteroaryl,
(13) —$C_{1-6}$alkyl-$C_{3-6}$cycloalkyl,
(14) —$C_{1-6}$alkyl-$C_{2-6}$cycloheteroalkyl,
(15) —$C_{2-6}$alkenyl-$C_{3-6}$cycloalkyl,
(16) —$C_{2-6}$alkenyl-$C_{2-6}$cycloheteroalkyl,
(17) —$C_{2-6}$alkenyl-aryl,
(18) —$C_{2-6}$alkenyl-heteroaryl,
(19) —$C_{2-6}$alkynyl-$C_{3-6}$cycloalkyl,
(20) —$C_{2-6}$alkynyl$C_{2-6}$cycloheteroalkyl,
(21) —$C_{2-6}$alkynyl-aryl,
(22) —$C_{2-6}$alkynyl-heteroaryl,
(23) —OH,
(24) —$(CH_2)_p$—O—$C_{1-6}$alkyl,
(25) —$(CH_2)_p$—O—$C_{2-6}$alkenyl,
(26) —$(CH_2)_p$—O—$C_{2-6}$alkynyl,
(27) —$(CH_2)_p$—O—$C_{3-6}$cycloalkyl,
(28) —$(CH_2)_p$—O—$C_{2-6}$cycloheteroalkyl,
(29) —$(CH_2)_p$—O-aryl,
(30) —$(CH_2)_p$—O-heteroaryl,
(31) —$OC_{1-6}$alkyl-$C_{3-6}$cycloalkyl,
(32) —$OC_{1-6}$alkyl-$C_{2-6}$cycloheteroalkyl,
(33) —$OC_{1-6}$alkyl-aryl,
(34) —$OC_{1-6}$alkyl-heteroaryl,
(35) —$S(O)_rR^h$,
(36) —$C_{1-6}$alkyl-$S(O)_rR^h$,
(37) —$N(R^k)_2$,
(38) —C(O) $R^L$, and
(39) —$NR^kR^L$, wherein $R^a$ is unsubstituted or substituted with one to six substituents selected from halogen, $CF_3$, OH, $C_{1-6}$alkyl, and —$OC_{1-6}$alkyl, provided that CN, halogen and OH are unsubstituted;

each $R^b$ is independently selected from the group consisting of:
(1) F,
(2) Cl,
(3) —$CH_3$,
(4) —$CF_3$,
(5) —$CH_2CF_3$,
(6) —$CH(CH_3)CF_3$,
(7) —$CF_2CH_3$,
(8) =$CH_2$,
(9) cyclopropyl,
(10) —$OCH_3$,

(11) $-OCF_3$,
(12) $-OCHF_2$, and
(13) $-OCH_2CF_3$, wherein cyclopropyl is unsubstituted or substituted with one to five substituents selected from F, Cl, $CF_3$, $OCF_3$, CN, $CH_2CF_3$, $CF_2CH_3$, $-CH_3$, and O—$CH_3$;

$R^d$ is selected from:
(1) $-C_{1-6}$alkyl,
(2) OH,
(3) halogen, and
(4) $-OC_{1-6}$alkyl, wherein alkyl is unsubstituted or substituted with one to three halogens;

$R^e$ is selected from:
(1) hydrogen, and
(2) $C_{1-6}$alkyl;

$R^f$ is selected from:
(1) $-C_{1-6}$alkyl,
(2) OH,
(3) halogen, and
(4) $-OC_{1-6}$alkyl, wherein alkyl is unsubstituted or substituted with one to three halogens;

$R^g$ is selected from:
(1) $-C_{1-6}$alkyl,
(2) OH,
(3) halogen, and
(4) $-OC_{1-6}$alkyl, wherein alkyl is unsubstituted or substituted with one to three halogens;

$R^h$ is selected from:
(1) hydrogen,
(2) $C_{1-6}$alkyl,
(3) $C_{3-6}$cycloalkyl,
(4) aryl, and
(5) heteroaryl;

$R^i$ is selected from:
(1) hydrogen,
(2) $C_{1-6}$alkyl,
(3) $C_{3-6}$alkenyl,
(4) $C_{3-6}$alkynyl,
(5) $C_{3-6}$cycloalkyl,
(6) $C_2$-5cycloheteroalkyl,
(7) aryl, and
(8) heteroaryl;

$R^k$ is selected from:
(1) hydrogen, and
(2) $C_{1-6}$alkyl;

$R^L$ is selected from:
(1) hydrogen,
(2) $C_{1-6}$alkyl,
(3) $C_{3-6}$cycloalkyl,
(4) aryl, and
(5) heteroaryl;

m is independently selected from 0, 1 and 2;
p is independently selected from 0, 1, 2 and 3;
r is independently selected from 0, 1 and 2; and
s is independently selected from 0, 1, 2, 3, 4, 5, and 6.

24. A compound selected from:
(1) N-((R)-3-chloro-4-fluorophenyl)(trans-4-(trifluoromethyl)cyclohexyl)methyl)-3-oxopiperazine-1-carboxamide;
(2) N-((S)-3-chloro-4-fluorophenyl)(trans-4-(trifluoromethyl)cyclohexyl)methyl)-3-oxopiperazine-1-carboxamide;
(3) N-((R)-(3-chloro-4-fluorophenyl)(8,8-difluorobicyclo[3.2.1]octan-3-yl)methyl)-3-oxopiperazine-1-carboxamide;
(4) N-((S)-(3-chloro-4-fluorophenyl)(8,8-difluorobicyclo[3.2.1]octan-3-yl)methyl)-3-oxopiperazine-1-carboxamide;
(5) (2R)-N-((R)-(3-chloro-4-fluorophenyl)(8,8-difluorobicyclo[3.2.1]octan-3-yl)-methyl)-2-methyl-3-oxopiperazine-1-carboxamide;
(6) (2R)-N-((S)-(3-chloro-4-fluorophenyl)(8,8-difluorobicyclo[3.2.1]octan-3-yl)methyl)-2-methyl-3-oxopiperazine-1-carboxamide;
(7) N-((R)-(4-chlorophenyl)(trans-4-(trifluoromethyl)cyclohexyl)methyl)-3-oxopiperazine-1-carboxamide;
(8) N-((R)-(4-chlorophenyl)(trans-4-(trifluoromethyl)cyclohexyl)methyl)-3-oxopiperazine-1-carboxamide;
(9) N-((S)-(4-chlorophenyl)(trans-4-(trifluoromethyl)cyclohexyl)methyl)-3-oxopiperazine-1-carboxamide;
(10) (2R)-N-((R)-(3-chloro-4-fluorophenyl)(trans-4-(trifluoromethyl)-cyclohexyl)-methyl)-2-methyl-3-oxopiperazine-1-carboxamide;
(11) (2R)-N-((S)-(3-chloro-4-fluorophenyl)(trans-4-(trifluoromethyl)-cyclohexyl)-methyl)-2-methyl-3-oxopiperazine-1-carboxamide;
(12) (R)-2-methyl-3-oxo-N-((R)-(trans-4-(trifluoromethyl)cyclohexyl)(3,4,5-trifluorophenyl)methyl) piperazine-1-carboxamide;
(13) (R)-2-methyl-3-oxo-N-((S)-(trans-4-(trifluoromethyl)cyclohexyl)(3,4,5-trifluorophenyl)methyl) piperazine-1-carboxamide;
(14) (2R)-N-((R)-(3-chloro-4-fluorophenyl)((1R,3s,5S)-6,6-difluorobicyclo-[3.1.0]hexan-3-yl)methyl)-2-methyl-3-oxopiperazine-1-carboxamide;
(15) (2R)-N-((S)-(3-chloro-4-fluorophenyl)((1R,3s,5S)-6,6-difluorobicyclo-[3.1.0]hexan-3-yl)methyl)-2-methyl-3-oxopiperazine-1-carboxamide;
(16) (2R)-N-((R)-(3,4-difluorophenyl)(trans-4-(trifluoromethyl)cyclohexyl)-methyl)-2-methyl-3-oxopiperazine-1-carboxamide;
(17) (2R)-N-((S)-(3,4-difluorophenyl)(trans-4-(trifluoromethyl)cyclohexyl)-methyl)-2-methyl-3-oxopiperazine-1-carboxamide;
(18) (2R)-N-((R)-(3-chloro-2,4-difluorophenyl)(trans-4-(trifluoromethyl)cyclohexyl)-methyl)-2-methyl-3-oxopiperazine-1-carboxamide;
(19) (2R)-N-((S)-(3-chloro-2,4-difluorophenyl)(trans-4-(trifluoromethyl)cyclohexyl)-methyl)-2-methyl-3-oxopiperazine-1-carboxamide;
(20) N-((R)-(3-chloro-2,4-difluorophenyl)(trans-4-(trifluoromethyl)cyclohexyl)-methyl)-3-oxopiperazine-1-carboxamide;
(21) N-((S)-(3-chloro-2,4-difluorophenyl)(trans-4-(trifluoromethyl)cyclohexyl)-methyl)-3-oxopiperazine-1-carboxamide;
(22) (R)-N-((R)-(3-chloro-2,4-difluorophenyl)((1R,3s,5S)-6,6-difluorobicyclo-[3.1.0]hexan-3-yl)methyl)-2-methyl-3-oxopiperazine-1-carboxamide;
(23) (R)-N-((S)-(3-chloro-2,4-difluorophenyl)((1R,3s,5S)-6,6-difluorobicyclo-[3.1.0]hexan-3-yl)methyl)-2-methyl-3-oxopiperazine-1-carboxamide;
(24) N-((R)-(3-chloro-4-fluorophenyl)(4-(trifluoromethyl) bicyclo[2.2.2]octan-1-yl)methyl)-3-oxopiperazine-1-carboxamide;
(25) N-((S)-(3-chloro-4-fluorophenyl)(4-(trifluoromethyl) bicyclo[2.2.2]octan-1-yl)methyl)-3-oxopiperazine-1-carboxamide;

(26) (2R)-N-((R)-(3-chloro-2,4-difluorophenyl)(4,4-difluorocyclohexyl)methyl)-2-methyl-3-oxopiperazine-1-carboxamide;

(27) (2R)-N-((S)-(3-chloro-2,4-difluorophenyl)(4,4-difluorocyclohexyl)methyl)-2-methyl-3-oxopiperazine-1-carboxamide;

(28) (2R)-N-((R)-(3-chloro-4-fluorophenyl)(4,4-difluorocyclohexyl)methyl)-2-methyl-3-oxopiperazine-1-carboxamide;

(29) (2R)-N-((S)-(3-chloro-4-fluorophenyl)(4,4-difluorocyclohexyl)methyl)-2-methyl-3-oxopiperazine-1-carboxamide;

(30) (2R)-N-((R)-(3-chloro-4-fluorophenyl)(1-(2,2,2-trifluoroethyl) piperidin-4-yl)-methyl)-2-methyl-3-oxopiperazine-1-carboxamide;

(31) (2R)-N-((S)-(3-chloro-4-fluorophenyl)(1-(2,2,2-trifluoroethyl) piperidin-4-yl)-methyl)-2-methyl-3-oxopiperazine-1-carboxamide;

(32) (2R)-N-((R)-(4-chlorophenyl)(1-(2,2,2-trifluoroethyl) piperidin-4-yl)methyl)-2-methyl-3-oxopiperazine-1-carboxamide;

(33) (2R)-N-((S)-(4-chlorophenyl)(1-(2,2,2-trifluoroethyl) piperidin-4-yl)methyl)-2-methyl-3-oxopiperazine-1-carboxamide;

(34) N-((R)-(3-chloro-4-fluorophenyl)(1-(2,2,2-trifluoroethyl) piperidin-4-yl)methyl)-3-oxopiperazine-1-carboxamide;

(35) N-((S)-(3-chloro-4-fluorophenyl)(1-(2,2,2-trifluoroethyl) piperidin-4-yl)methyl)-3-oxopiperazine-1-carboxamide;

(36) (2R)-N-((R)-(3-chloro-4-fluorophenyl)(1-(R)-(1,1,1-trifluoropropan-2-yl)-piperidin-4-yl)methyl)-3-oxopiperazine-1-carboxamide;

(37) (2R)-N-((R)-(3-chloro-4-fluorophenyl)(1-(S)-(1,1,1-trifluoropropan-2-yl) piperidin-4-yl)methyl)-3-oxopiperazine-1-carboxamide;

(38) (2R)-N-((S)-(3-chloro-4-fluorophenyl)(1-(R)-(1,1,1-trifluoropropan-2-yl) piperidin-4-yl)methyl)-3-oxopiperazine-1-carboxamide;

(39) (2R)-N-((S)-(3-chloro-4-fluorophenyl)(1-(S)-(1,1,1-trifluoropropan-2-yl) piperidin-4-yl)methyl)-3-oxopiperazine-1-carboxamide;

(40) (2R)-N-((R)-(3-chloro-4-fluorophenyl)(trans-1,1-difluorospiro[2.5]octan-6-yl)methyl)-2-methyl-3-oxopiperazine-1-carboxamide;

(41) (2R)-N-((S)-(3-chloro-4-fluorophenyl)(trans-1,1-difluorospiro[2.5]octan-6-yl)methyl)-2-methyl-3-oxopiperazine-1-carboxamide;

(42) (2R)-N-((R)-(3-chloro-4-fluorophenyl)(cis-1,1-difluorospiro[2.5]octan-6-yl)methyl)-2-methyl-3-oxopiperazine-1-carboxamide;

(43) (2R)-N-((S)-(3-chloro-4-fluorophenyl)(cis-1,1-difluorospiro[2.5]octan-6-yl)methyl)-2-methyl-3-oxopiperazine-1-carboxamide;

(44) (R)-N-((S)-(3-chloro-2,4-difluorophenyl)(trans-3-(trifluoromethyl)cyclobutyl)-methyl)-2-methyl-3-oxopiperazine-1-carboxamide;

(45) (R)-N-((R)-(3-chloro-2,4-difluorophenyl)(trans-3-(trifluoromethyl)cyclobutyl)-methyl)-2-methyl-3-oxopiperazine-1-carboxamide;

(46) (R)-N-((S)-(3-chloro-2,4-difluorophenyl)(cis-3-(trifluoromethyl)cyclobutyl)-methyl)-2-methyl-3-oxopiperazine-1-carboxamide;

(47) (R)-N-((R)-(3-chloro-2,4-difluorophenyl)(cis-3-(trifluoromethyl)cyclobutyl)-methyl)-2-methyl-3-oxopiperazine-1-carboxamide;

(48) (2R)-N-((R)-(3-chloro-2,4-difluorophenyl)(trans-3-cyclopropylcyclobutyl)-methyl)-2-methyl-3-oxopiperazine-1-carboxamide;

(49) (2R)-N-((R)-(3-chloro-2,4-difluorophenyl)(cis-3-cyclopropylcyclobutyl)methyl)-2-methyl-3-oxopiperazine-1-carboxamide;

(50) (2R)-N-((S)-(3-chloro-2,4-difluorophenyl)(trans-3-cyclopropylcyclobutyl)-methyl)-2-methyl-3-oxopiperazine-1-carboxamide;

(51) (2R)-N-((S)-(3-chloro-2,4-difluorophenyl)(cis-3-cyclopropylcyclobutyl)methyl)-2-methyl-3-oxopiperazine-1-carboxamide;

(52) (2R)-N-((R)-(3-chloro-2,4-difluorophenyl)(trans-1,1-difluorospiro[2.3]hexan-5-yl)methyl)-2-methyl-3-oxopiperazine-1-carboxamide;

(53) (2R)-N-((R)-(3-chloro-2,4-difluorophenyl)(cis-1,1-difluorospiro[2.3]hexan-5-yl)methyl)-2-methyl-3-oxopiperazine-1-carboxamide;

(54) (2R)-N-((S)-(3-chloro-2,4-difluorophenyl)(trans-1,1-difluorospiro[2.3]hexan-5-yl)methyl)-2-methyl-3-oxopiperazine-1-carboxamide;

(55) (2R)-N-((S)-(3-chloro-2,4-difluorophenyl)(cis-1,1-difluorospiro[2.3]hexan-5-yl)methyl)-2-methyl-3-oxopiperazine-1-carboxamide;

(56) (2R)-N-((R)-(3-chloro-2,4-difluorophenyl)(6,6-difluorospiro[3.3]heptan-2-yl)methyl)-2-methyl-3-oxopiperazine-1-carboxamide;

(57) 2R)-N-((S)-(3-chloro-2,4-difluorophenyl)(6,6-difluorospiro[3.3]heptan-2-yl)methyl)-2-methyl-3-oxopiperazine-1-carboxamide;

(58) (2R)-N-((R)-(3-chloro-2,4-difluorophenyl)(3,3-difluorocyclobutyl)methyl)-2-methyl-3-oxopiperazine-1-carboxamide;

(59) (2R)-N-((S)-(3-chloro-2,4-difluorophenyl)(3,3-difluorocyclobutyl)methyl)-2-methyl-3-oxopiperazine-1-carboxamide;

(60) (2R)-N-((R)-(3-chloro-2,4-difluorophenyl)(3-methylenecyclobutyl)methyl)-2-methyl-3-oxopiperazine-1-carboxamide;

(61) (2R)-N-((S)-(3-chloro-2,4-difluorophenyl)(3-methylenecyclobutyl)methyl)-2-methyl-3-oxopiperazine-1-carboxamide;

(62) N-((S)-(3-chloro-2,4-difluorophenyl)(trans-3-(trifluoromethyl)cyclobutyl)-methyl)-3-oxopiperazine-1-carboxamide;

(63) (R)-N-((S)-(3-chloro-2,4-difluorophenyl)(trans-3-(trifluoromethyl)cyclobutyl)-methyl)-2-cyclopropyl-3-oxopiperazine-1-carboxamide;

(64) (S)-N-((S)-(3-chloro-2,4-difluorophenyl)(trans-3-(trifluoromethyl)cyclobutyl)-methyl)-2-cyclopropyl-3-oxopiperazine-1-carboxamide;

(65) (2R)-N-((R)-(3-chloro-2,4-difluorophenyl)(spiro[2.3]hexan-5-yl)methyl)-2-methyl-3-oxopiperazine-1-carboxamide;

(66) (2R)-N-((S)(3-chloro-2,4-difluorophenyl)(spiro[2.3]hexan-5-yl)methyl)-2-methyl-3-oxopiperazine-1-carboxamide;

(67) (2R)-N-((R)-(3-chloro-2,4-difluorophenyl)(trans-3-(difluoromethyl)cyclobutyl)-methyl)-2-methyl-3-oxopiperazine-1-carboxamide;

(68) (2R)-N-((S)-(3-chloro-2,4-difluorophenyl)(trans-3-(difluoromethyl)cyclobutyl)-methyl)-2-methyl-3-oxopiperazine-1-carboxamide;

(69) (2R)-N-((R)-(3-chloro-2,4-difluorophenyl)(3-(trifluoromethyl) bicyclo[1.1.1]pentan-1yl)methyl)-2-methyl-3-oxopiperazine-1-carboxamide;

(70) (2R)-N-((S)-(3-chloro-2,4-difluorophenyl)(3-(trifluoromethyl) bicyclo-[1.1.1]pentan-1-yl)methyl)-2-methyl-3-oxopiperazine-1-carboxamide;

(71) (2R)-N-((R)-(3-chloro-2,4-difluorophenyl)(3,3-dimethylcyclobutyl)methyl)-2-methyl-3-oxopiperazine-1-carboxamide;

(72) (2R)-N-((S)-(3-chloro-2,4-difluorophenyl)(3,3-dimethylcyclobutyl)methyl)-2-methyl-3-oxopiperazine-1-carboxamide;

(73) N-((R)-(3-chloro-2,4-difluorophenyl)(3,3-dimethylcyclobutyl)methyl)-3-oxopiperazine-1-carboxamide;

(74) N-((S)-(3-chloro-2,4-difluorophenyl)(3,3-dimethylcyclobutyl)methyl)-3-oxopiperazine-1-carboxamide;

(75) (2R)-N-((R)-(3,3-dimethylcyclobutyl)(6-(trifluoromethyl)pyridin-3-yl)methyl)-2-methyl-3-oxopiperazine-1-carboxamide;

(76) (2R)-N-((S)-(3,3-dimethylcyclobutyl)(6-(trifluoromethyl)pyridin-3-yl)methyl)-2-methyl-3-oxopiperazine-1-carboxamide;

(77) N-((R)-(3-chloro-4-fluorophenyl)(3-(trifluoromethyl) bicyclo[1.1.1]pentan-1-yl)methyl)-3-oxopiperazine-1-carboxamide;

(78) N-((S)-(3-chloro-4-fluorophenyl)(3-(trifluoromethyl) bicyclo[1.1.1]pentan-1-yl)methyl)-3-oxopiperazine-1-carboxamide;

(79) (2R)-N-((R)-(3-chloro-4-fluorophenyl)(3-(trifluoromethyl) bicyclo[1.1.1]pentan-1-yl)methyl)-2-methyl-3-oxopiperazine-1-carboxamide;

(80) (2R)-N-((S)-(3-chloro-4-fluorophenyl)(3-(trifluoromethyl) bicyclo[1.1.1]pentan-1-yl)methyl)-2-methyl-3-oxopiperazine-1-carboxamide;

(81) (2R)-N-((R)-(4-fluoro-3-methylphenyl)(trans-4-(trifluoromethyl)cyclohexyl)-methyl)-2-methyl-3-oxopiperazine-1-carboxamide;

(82) (2R)-N-((S)-(4-fluoro-3-methylphenyl)(trans-4-(trifluoromethyl)cyclohexyl)-methyl)-2-methyl-3-oxopiperazine-1-carboxamide;

(83) (2R)-N-((R)-(4-fluoro-3-methylphenyl)(cis-4-(trifluoromethyl)cyclohexyl)-methyl)-2-methyl-3-oxopiperazine-1-carboxamide;

(84) (2R)-N-((S)-(4-fluoro-3-methylphenyl)(cis-4-(trifluoromethyl)cyclohexyl)-methyl)-2-methyl-3-oxopiperazine-1-carboxamide;

(85) (2R)-N-((R)-(4-chloro-3-(difluoromethyl)phenyl) (cis-4-(trifluoromethyl) cyclohexyl)methyl)-2-methyl-3-oxopiperazine-1-carboxamide;

(86) (2R)-N-((R)-(4-chloro-3-(difluoromethyl)phenyl) (trans-4-(trifluoromethyl) cyclohexyl)methyl)-2-methyl-3-oxopiperazine-1-carboxamide;

(87) (2R)-N-((S)-(4-chloro-3-(difluoromethyl)phenyl) (cis-4-(trifluoromethyl) cyclohexyl)methyl)-2-methyl-3-oxopiperazine-1-carboxamide;

(88) (2R)-N-((S)-(4-chloro-3-(difluoromethyl)phenyl) (trans-4-(trifluoromethyl) cyclohexyl)methyl)-2-methyl-3-oxopiperazine-1-carboxamide;

(89) (2R)-N-((R)-(3-chloro-4-fluorophenyl)(trans-3-(difluoromethoxy)cyclobutyl)-methyl)-2-methyl-3-oxopiperazine-1-carboxamide;

(90) (2R)-N-((R)-(3-chloro-4-fluorophenyl)(cis-3-(difluoromethoxy)cyclobutyl)-methyl)-2-methyl-3-oxopiperazine-1-carboxamide;

(91) (2R)-N-((S)-(3-chloro-4-fluorophenyl)(cis-3-(difluoromethoxy)cyclobutyl)-methyl)-2-methyl-3-oxopiperazine-1-carboxamide;

(92) (2R)-N-((S)-(3-chloro-4-fluorophenyl)(trans-3-(difluoromethoxy)cyclobutyl)-methyl)-2-methyl-3-oxopiperazine-1-carboxamide;

(93) (2R)-N-((R)-(3-chloro-2,4-difluorophenyl)(trans-3-(difluoromethoxy)cyclobutyl)-methyl)-2-methyl-3-oxopiperazine-1-carboxamide;

(94) (2R)-N-((R)-(3-chloro-2,4-difluorophenyl)(cis-3-(difluoromethoxy)cyclobutyl)-methyl)-2-methyl-3-oxopiperazine-1-carboxamide;

(95) (2R)-N-((S)-(3-chloro-2,4-difluorophenyl)(cis-3-(difluoromethoxy)cyclobutyl)-methyl)-2-methyl-3-oxopiperazine-1-carboxamide;

(96) (2R)-N-((S)-(3-chloro-2,4-difluorophenyl)(trans-3-(difluoromethoxy)cyclobutyl)-methyl)-2-methyl-3-oxopiperazine-1-carboxamide;

(97) (2R)-N-((R)-(3-chloro-2,4-difluorophenyl)(trans-3-methoxycyclobutyl)methyl)-2-methyl-3-oxopiperazine-1-carboxamide;

(98) (2R)-N-((R)-(3-chloro-2,4-difluorophenyl)(cis-3-methoxycyclobutyl)methyl)-2-methyl-3-oxopiperazine-1-carboxamide;

(99) (2R)-N-((S)-(3-chloro-2,4-difluorophenyl)(cis-3-methoxycyclobutyl)methyl)-2-methyl-3-oxopiperazine-1-carboxamide;

(100) (2R)-N-((S)-(3-chloro-2,4-difluorophenyl)(trans-3-methoxycyclobutyl)methyl)-2-methyl-3-oxopiperazine-1-carboxamide;

(101) (2R)-N-((R)-(3-chloro-2,4-difluorophenyl)((R)-spiro[2.2]pentan-1-yl)methyl)-2-methyl-3-oxopiperazine-1-carboxamide;

(102) (2R)-N-((R)-(3-chloro-2,4-difluorophenyl)((S)-spiro[2.2]pentan-1-yl)methyl)-2-methyl-3-oxopiperazine-1-carboxamide;

(103) (2R)-N-((S)-(3-chloro-2,4-difluorophenyl)(R)-spiro[2.2]pentan-1-yl)methyl)-2-methyl-3-oxopiperazine-1-carboxamide;

(104) (2R)-N-((S)-(3-chloro-2,4-difluorophenyl)((S)-spiro[2.2]pentan-1-yl)methyl)-2-methyl-3-oxopiperazine-1-carboxamide;

(105) (2R)-N-((R)-(3-chloro-2,4-difluorophenyl)((R)-3,3-difluorocyclopentyl)methyl)-2-methyl-3-oxopiperazine-1-carboxamide;

(106) (2R)-N-((R)-(3-chloro-2,4-difluorophenyl)((S)-3,3-difluorocyclopentyl)methyl)-2-methyl-3-oxopiperazine-1-carboxamide;

(107) (2R)-N-((S)-(3-chloro-2,4-difluorophenyl)((R)-(3,3-difluorocyclopentyl)methyl)-2-methyl-3-oxopiperazine-1-carboxamide;

(108) (2R)-N-((S)-(3-chloro-2,4-difluorophenyl)((S)-3,3-difluorocyclopentyl)methyl)-2-methyl-3-oxopiperazine-1-carboxamide;

(109) (2R)-N-((R)-(3-chloro-4-fluorophenyl)(trans-3-(trifluoromethyl)cyclobutyl)-methyl)-2-methyl-3-oxopiperazine-1-carboxamide;

(110) (2R)-N-((R)-(3-chloro-4-fluorophenyl)(cis-3-(trifluoromethyl)cyclobutyl)-methyl)-2-methyl-3-oxopiperazine-1-carboxamide;

(111) (2R)-N-((S)-(3-chloro-4-fluorophenyl)(trans-3-(trifluoromethyl)cyclobutyl)-methyl)-2-methyl-3-oxopiperazine-1-carboxamide;

(112) (2R)-N-((S)-(3-chloro-4-fluorophenyl)(cis-3-(trifluoromethyl)cyclobutyl)methyl)-2-methyl-3-oxopiperazine-1-carboxamide;

(113) (2R)-N-((R)-(3-chloro-4-fluorophenyl)(cis-3-(2,2,2-trifluoroethoxy)cyclobutyl)-methyl)-2-methyl-3-oxopiperazine-1-carboxamide;

(114) (2R)-N-((S)-(3-chloro-4-fluorophenyl)(cis-3-(2,2,2-trifluoroethoxy)cyclobutyl)-methyl)-2-methyl-3-oxopiperazine-1-carboxamide;

(115) (2R)-N-((R)-(3-chloro-4-fluorophenyl)(trans-3-(2,2,2-trifluoroethoxy)-cyclobutyl)-methyl)-2-methyl-3-oxopiperazine-1-carboxamide;

(116) (2R)-N-((S)-(3-chloro-4-fluorophenyl)(trans-3-(2,2,2-trifluoroethoxy)cyclobutyl)-methyl)-2-methyl-3-oxopiperazine-1-carboxamide;

(117) N-((R)-(5-chloro-6-(trifluoromethyl)pyridin-2-yl)(trans-4-(trifluoromethyl)-cyclohexyl) methyl)-3-oxopiperazine-1-carboxamide;

(118) N-((S)-(5-chloro-6-(trifluoromethyl)pyridin-2-yl)(trans-4-(trifluoromethyl)cyclo-hexyl)methyl)-3-oxopiperazine-1-carboxamide;

(119) (2R)-N-((R)-(5-chloro-6-(trifluoromethyl)pyridin-2-yl)(4,4-difluorocyclohexyl)-methyl)-2-methyl-3-oxopiperazine-1-carboxamide;

(120) (2R)-N-((S)-(5-chloro-6-(trifluoromethyl)pyridin-2-yl)(4,4-difluorocyclohexyl)-methyl)-2-methyl-3-oxopiperazine-1-carboxamide;

(121) (2R)-N-((R or S)-(5-chloro-6-(trifluoromethyl)pyridin-2-yl)(cis-3-(trifluoromethyl)-cyclobutyl)methyl)-2-methyl-3-oxopiperazine-1-carboxamide;

(122) (2R)-N-((R or S)-(5-chloro-6-(trifluoromethyl)pyridin-2-yl)(trans-3-(trifluoro-methyl)-cyclobutyl) methyl)-2-methyl-3-oxopiperazine-1-carboxamide;

(123) (2R)-N-((S or R)-(5-chloro-6-(trifluoromethyl)pyridin-2-yl)(trans-3-(trifluoro-methyl)-cyclobutyl) methyl)-2-methyl-3-oxopiperazine-1-carboxamide;

(124) (2R)-N-((S or R)-(5-chloro-6-(trifluoromethyl)pyridin-2-yl)(cis-3-(trifluoro-methyl)-cyclobutyl)methyl)-2-methyl-3-oxopiperazine-1-carboxamide;

(125) (2R)-N-((R or S)-1-(3-chloro-4-fluorophenyl)-1-(cis-3-(trifluoromethyl)-cyclobutyl)-ethyl)-2-methyl-3-oxopiperazine-1-carboxamide;

(126) (2R)-N-((R or S)-1-(3-chloro-4-fluorophenyl)-1-(trans-3-(trifluoromethyl)-cyclobutyl)-ethyl)-2-methyl-3-oxopiperazine-1-carboxamide;

(127) (2R)-N-((S or R)-1-(3-chloro-4-fluorophenyl)-1-(cis-3-(trifluoromethyl)-cyclobutyl)-ethyl)-2-methyl-3-oxopiperazine-1-carboxamide;

(128) (2R)-N-((S or R)-1-(3-chloro-4-fluorophenyl)-1-(trans-3-(trifluoromethyl)-cyclobutyl)-ethyl)-2-methyl-3-oxopiperazine-1-carboxamide;

(129) (2R)-N-((R)-(3-fluoro-4-(trifluoromethoxy) phenyl)(trans-3-(trifluoromethyl)-cyclo-butyl)methyl)-2-methyl-3-oxopiperazine-1-carboxamide;

(130) (2R)-N-((S)-(3-fluoro-4-(trifluoromethoxy) phenyl)(trans-3-(trifluoromethyl)-cyclo-butyl)methyl)-2-methyl-3-oxopiperazine-1-carboxamide;

(131) ((2R)-N-((R)-(2-fluoro-4-(trifluoromethoxy) phenyl)(trans-3-(trifluoromethyl)-cyclo-butyl)-methyl)-2-methyl-3-oxopiperazine-1-carboxamide;

(132) (2R)-N-((S)-(2-fluoro-4-(trifluoromethoxy) phenyl)(trans-3-(trifluoromethyl)-cyclo-butyl)methyl)-2-methyl-3-oxopiperazine-1-carboxamide;

(133) (2R)-N-((R)-(4-fluoro-3-(trifluoromethyl)phenyl)(trans-3-(trifluoromethyl)cyclo-butyl)methyl)-2-methyl-3-oxopiperazine-1-carboxamide;

(134) (2R)-N-((S)-(4-fluoro-3-(trifluoromethyl)phenyl)(trans-3-(trifluoromethyl)-cyclo-butyl)methyl)-2-methyl-3-oxopiperazine-1-carboxamide;

(135) N-((R)-(4-fluoro-3-(trifluoromethyl)phenyl)(trans-3-(trifluoro methyl)-cyclobutyl)-methyl)-3-oxopiperazine-1-carboxamide;

(136) N-((S)-(4-fluoro-3-(trifluoromethyl)phenyl)(trans-3-(trifluoro methyl)cyclobutyl)-methyl)-3-oxopiperazine-1-carboxamide;

(137) (2R)-N-((R)-(3-chloro-2-fluorophenyl)(trans-3-(trifluoromethyl)cyclobutyl)-methyl)-2-methyl-3-oxopiperazine-1-carboxamide;

(138) (2R)-N-((S)-(3-chloro-2-fluorophenyl)(trans-3-(trifluoromethyl)cyclobutyl)-methyl)-2-methyl-3-oxopiperazine-1-carboxamide;

(139) (2R)-N-((R)-(3-chloro-4-(trifluoromethoxy) phenyl)(3-(trifluoromethyl)cyclobutyl)-methyl)-2-methyl-3-oxopiperazine-1-carboxamide;

(140) (2R)-N-((S)-(3-chloro-4-(trifluoromethoxy) phenyl)(3-(trifluoromethyl)cyclobutyl)-methyl)-2-methyl-3-oxopiperazine-1-carboxamide;

(141) (2R)-2-methyl-3-oxo-N-((trans-4-(trifluoromethyl) cyclohexyl)((R)-2-(trifluoro-methyl) thiazol-4-yl) methyl) piperazine-1-carboxamide;

(142) (2R)-2-methyl-3-oxo-N-((trans-4-(trifluoromethyl) cyclohexyl)((S)-2-(trifluoro-methyl) thiazol-4-yl) methyl) piperazine-1-carboxamide;

(143) (2R)-N-((R)-(3-chloro-2,4-difluorophenyl)((3R,6R)-6-(trifluoromethyl)-tetrahydro-2H-pyran-3-yl) methyl)-2-methyl-3-oxopiperazine-1-carboxamide;

(144) (2R)-N-((R)-(3-chloro-2,4-difluorophenyl)((3S,6S)-6-(trifluoromethyl)-tetrahydro-2H-pyran-3-yl) methyl)-2-methyl-3-oxopiperazine-1-carboxamide;

(145) (2R)-N-((S)-(3-chloro-2,4-difluorophenyl)((3R,6R)-6-(trifluoromethyl)-tetrahydro-2H-pyran-3-yl) methyl)-2-methyl-3-oxopiperazine-1-carboxamide;

(146) (2R)-N-((S)-(3-chloro-2,4-difluorophenyl)((3S,6S)-6-(trifluoromethyl)-tetrahydro-2H-pyran-3-yl) methyl)-2-methyl-3-oxopiperazine-1-carboxamide;

(147) (2R)-N-(R)-(3-chloro-2,4-difluorophenyl)(trans-2-(trifluoromethyl)cyclopropyl)-methyl)-2-methyl-3-oxopiperazine-1-carboxamide;

(148) (2R)-N-(R)-(3-chloro-2,4-difluorophenyl)(trans-2-(trifluoromethyl)cyclopropyl)-methyl)-2-methyl-3-oxopiperazine-1-carboxamide;

(149) (2R)-N-(S)-(3-chloro-2,4-difluorophenyl)(trans-2-(trifluoromethyl)cyclopropyl)-methyl)-2-methyl-3-oxopiperazine-1-carboxamide;

(150) (2R)-N-(S)-(3-chloro-2,4-difluorophenyl)(trans-2-(trifluoromethyl)cyclopropyl)-methyl)-2-methyl-3-oxopiperazine-1-carboxamide;

(151) (2R)-N-((R or S)-(3-chloro-2,4-difluorophenyl)(cis-3-(trifluoromethyl)-cyclopentyl)-methyl)-2-methyl-3-oxopiperazine-1-carboxamide;

(152) (2R)-N-((R or S)-(3-chloro-2,4-difluorophenyl)(cis-3-(trifluoromethyl)-cyclopentyl)-methyl)-2-methyl-3-oxopiperazine-1-carboxamide;

(153) (2R)-N-((R or S)-(3-chloro-2,4-difluorophenyl)(trans-3-(trifluoromethyl)-cyclopentyl)-methyl)-2-methyl-3-oxopiperazine-1-carboxamide; and (154) (2R)-N-((R or S)-(3-chloro-2,4-difluorophenyl)(trans-3-(trifluoromethyl)cyclopentyl)-methyl)-2-methyl-3-oxopiperazine-1-carboxamide;

or a pharmaceutically acceptable salt thereof.

25. A compound selected from:

(1) (2R)-N-((1 (R or S))-(4-fluoro-3-(trifluoromethyl) phenyl)-trans-(6-(trifluoromethyl)-tetrahydro-2H-pyran-3-yl)methyl)-2-methyl-3-oxopiperazine-1-carboxamide;

(2) (2R)-N-((1 (R or S))-(4-fluoro-3-(trifluoromethyl) phenyl)-trans-(6-(trifluoromethyl)-tetrahydro-2H-pyran-3-yl)methyl)-2-methyl-3-oxopiperazine-1-carboxamide;

(3) (S)-N-((S)-(3-chloro-2,4-difluorophenyl)((1r,3S)-3-(trifluoromethyl)cyclobutyl)-methyl)-2-(fluoromethyl)-3-oxopiperazine-2-d-1-carboxamide;

(4) (R)-N-((R)-(3-chloro-2,4-difluorophenyl)((R)-chroman-3-yl)methyl)-2-methyl-3-oxopiperazine-1-carboxamide;

(5) (R)-N-((S)-(3-chloro-2,4-difluorophenyl)((R)-chroman-3-yl)methyl)-2-methyl-3-oxopiperazine-1-carboxamide;

(6) (R)-N-((R)-(3-chloro-2,4-difluorophenyl)((S)-chroman-3-yl)methyl)-2-methyl-3-oxopiperazine-1-carboxamide;

(7) (R)-N-((S)-(3-chloro-2,4-difluorophenyl)((S)-chroman-3-yl)methyl)-2-methyl-3-oxopiperazine-1-carboxamide;

(8) (R)-N-((S)-(3-chloro-2,4-difluorophenyl)((1r,3S)-3-(trifluoromethyl)cyclobutyl)-methyl)-3-oxo-2-(trifluoromethyl) piperazine-1-carboxamide;

(9) (S)-N-((S)-(3-chloro-2,4-difluorophenyl)((1r,3S)-3-(trifluoromethyl)cyclobutyl)-methyl)-3-oxo-2-(trifluoromethyl) piperazine-1-carboxamide; and

(10) (R)-N-((S)-(3-chloro-2,4-difluorophenyl)((1r,3S)-3-(trifluoromethyl)cyclobutyl)-methyl)-2-(hydroxymethyl)-3-oxopiperazine-1-carboxamide;

or a pharmaceutically acceptable salt thereof.

26. A compound selected from:

(1) (R)-N-((S)-(3-chloro-2,4-difluorophenyl) ((trans)-3-(trifluoromethyl)cyclobutyl)methyl)-2-methyl-3-oxopiperazine-5,5,6,6-d4-1-carboxamide;

(2) (S)-N-((S)-(3-chloro-2,4-difluorophenyl) ((trans)-3-(trifluoromethyl)cyclobutyl)methyl)-2-methyl-3-oxopiperazine-5,5,6,6-d4-1-carboxamide;

(3) N-((R)-3-chloro-4-fluorophenyl)(trans-4-(trifluoromethyl)cyclohexyl)methyl)-3-oxopiperazine-1-carboxamide;

(4) N-((S)-(3-chloro-2,4-difluorophenyl)(trans-3-(trifluoromethyl)cyclobutyl)methyl)-3-oxopiperazine-1-carboxamide;

(5) (2R)-N-((S)-(5-chloro-6-(trifluoromethyl)pyridin-2-yl)(trans-3-(trifluoromethyl)-cyclobutyl)methyl)-2-methyl-3-oxopiperazine-1-carboxamide;

(6) (2R)-N-((R)-(5-chloro-6-(trifluoromethyl)pyridin-2-yl)(trans-3-(trifluoromethyl)-cyclobutyl)methyl)-2-methyl-3-oxopiperazine-1-carboxamide; and (7) (2R)-N-((S)-(3-chloro-2,4-difluorophenyl)((3S,6S)-6-(trifluoromethyl)tetrahydro-2H-pyran-3-yl)methyl)-2-methyl-3-oxopiperazine-1-carboxamide;

or a pharmaceutically acceptable salt thereof.

27. The compound of claim 26 which is (R)-N-((S)-(3-chloro-2,4-difluorophenyl) ((trans)-3-(trifluoromethyl)cyclobutyl)methyl)-2-methyl-3-oxopiperazine-5,5,6,6-d4-1-carboxamide; or a pharmaceutically acceptable salt thereof.

28. The compound of claim 26 which is(S)-N-((S)-(3-chloro-2,4-difluorophenyl) ((trans)-3-(trifluoromethyl)cyclobutyl)methyl)-2-methyl-3-oxopiperazine-5,5,6,6-d4-1-carboxamide; or a pharmaceutically acceptable salt thereof.

29. The compound of claim 26 which is N-((R)-3-chloro-4-fluorophenyl)(trans-4-(trifluoromethyl)cyclohexyl) methyl)-3-oxopiperazine-1-carboxamide; or a pharmaceutically acceptable salt thereof.

30. The compound of claim 26 which is N-((S)-(3-chloro-2,4-difluorophenyl)(trans-3-(trifluoromethyl)cyclobutyl) methyl)-3-oxopiperazine-1-carboxamide; or a pharmaceutically acceptable salt thereof.

31. The compound of claim 26 which is (2R)-N-((S)-(5-chloro-6-(trifluoromethyl)pyridin-2-yl)(trans-3-(trifluoromethyl)-cyclobutyl)methyl)-2-methyl-3-oxopiperazine-1-carboxamide; or a pharmaceutically acceptable salt thereof.

32. The compound of claim 26 which is (2R)-N-((R)-(5-chloro-6-(trifluoromethyl)pyridin-2-yl)(trans-3-(trifluoromethyl)-cyclobutyl)methyl)-2-methyl-3-oxopiperazine-1-carboxamide; or a pharmaceutically acceptable salt thereof.

33. The compound of claim 26 which is (2R)-N-((S)-(3-chloro-2,4-difluorophenyl)((3S,6S)-6-(trifluoromethyl)tetrahydro-2H-pyran-3-yl)methyl)-2-methyl-3-oxopiperazine-1-carboxamide; or a pharmaceutically acceptable salt thereof.

34. A pharmaceutical composition comprising a compound of claim 26, or a pharmaceutically acceptable salt thereof, and a pharmaceutically acceptable carrier.

35. A compound which is (R)-N-((S)-(3-chloro-2,4-difluorophenyl)(trans-3-(trifluoromethyl)cyclobutyl)methyl)-2-methyl-3-oxopiperazine-1-carboxamide.

36. A compound which is (R)-N-((S)-(3-chloro-2,4-difluorophenyl) ((trans)-3-(trifluoromethyl)cyclobutyl) methyl)-2-methyl-3-oxopiperazine-5,5,6,6-d4-1-carboxamide.

37. A compound which is(S)-N-((S)-(3-chloro-2,4-difluorophenyl) ((trans)-3-(trifluoromethyl)cyclobutyl)methyl)-2-methyl-3-oxopiperazine-5,5,6,6-d4-1-carboxamide.

38. A compound which is N-((R)-3-chloro-4-fluorophenyl)(trans-4-(trifluoromethyl)cyclohexyl)methyl)-3-oxopiperazine-1-carboxamide.

39. A compound which is N-((S)-(3-chloro-2,4-difluorophenyl)(trans-3-(trifluoromethyl)cyclobutyl)methyl)-3-oxopiperazine-1-carboxamide.

40. A compound which is (2R)-N-((S)-(5-chloro-6-(trifluoromethyl)pyridin-2-yl)(trans-3-(trifluoromethyl)cyclobutyl)methyl)-2-methyl-3-oxopiperazine-1-carboxamide.

41. A compound which is (2R)-N-((R)-(5-chloro-6-(trifluoromethyl)pyridin-2-yl)(trans-3-(trifluoromethyl)cyclobutyl)methyl)-2-methyl-3-oxopiperazine-1-carboxamide.

42. A compound which is (2R)-N-((S)-(3-chloro-2,4-difluorophenyl)((3S,6S)-6-(trifluoromethyl)tetrahydro-2H-pyran-3-yl)methyl)-2-methyl-3-oxopiperazine-1-carboxamide.

43. A compound which is

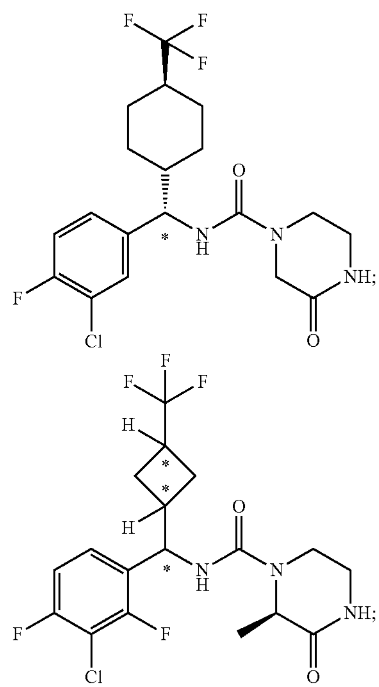

-continued
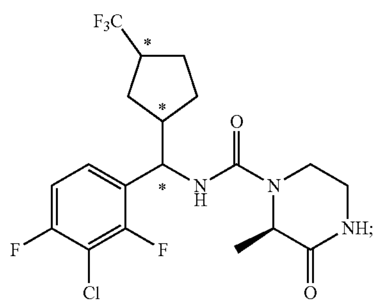
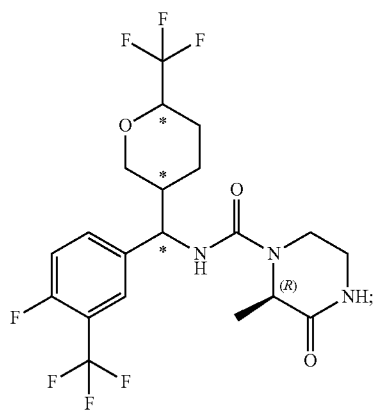
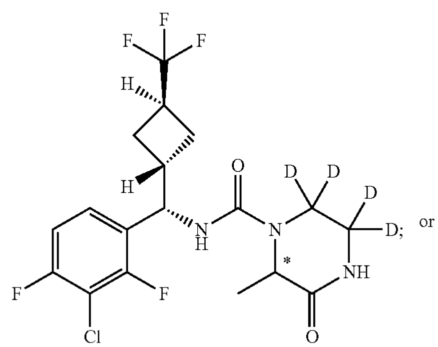
or
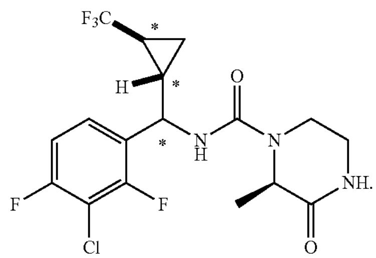
44. The compound of claim 43 which is
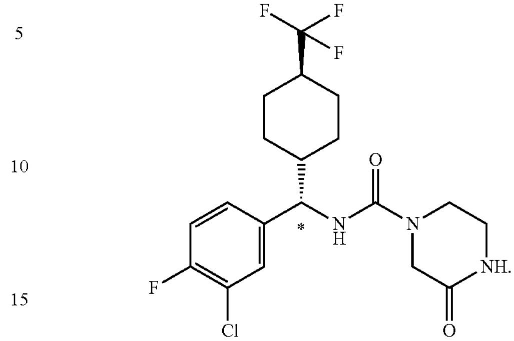
45. The compound of claim 43 which is
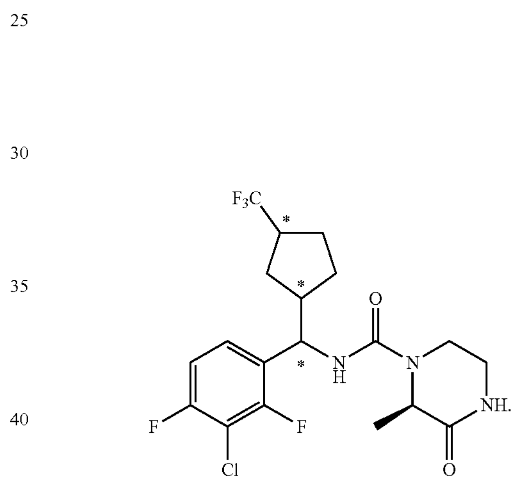
46. The compound of claim 43 which is
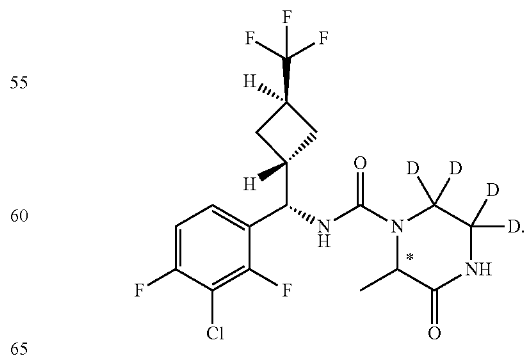

47. The compound of claim 43 which is
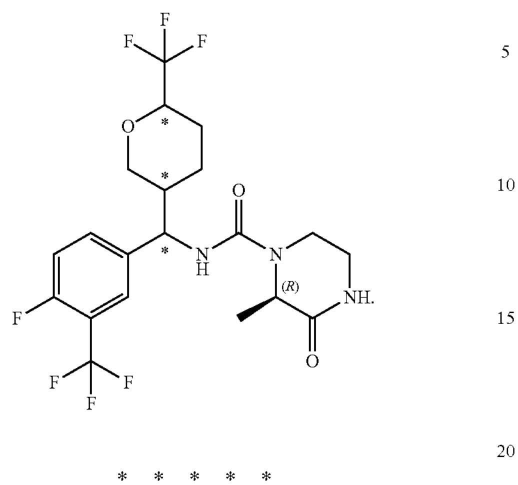
* * * * *